(12) United States Patent
Leban et al.

(10) Patent No.: US 8,354,436 B2
(45) Date of Patent: Jan. 15, 2013

(54) IL17 AND IFN-GAMMA INHIBITION FOR THE TREATMENT OF AUTOIMMUNE INFLAMMATION

(75) Inventors: Johann Leban, Planegg-Martinsried (DE); Stefan Tasler, Seefeld (DE); Wael Saeb, Planegg-Martinsried (DE); Carine Chevrier, Munich (DE)

(73) Assignee: 4SC Discovery GmbH, Planegg-Martinsried (DE)

( * ) Notice: Subject to any disclaimer, the term of this patent is extended or adjusted under 35 U.S.C. 154(b) by 0 days.

(21) Appl. No.: 13/360,063

(22) Filed: Jan. 27, 2012

(65) Prior Publication Data

US 2012/0196862 A1    Aug. 2, 2012

Related U.S. Application Data

(60) Provisional application No. 61/437,080, filed on Jan. 28, 2011.

(30) Foreign Application Priority Data

Jan. 28, 2011    (EP) .................................. 11152512

(51) Int. Cl.
| | |
|---|---|
| A61K 31/4406 | (2006.01) |
| A61K 31/4402 | (2006.01) |
| A61K 31/4409 | (2006.01) |
| A61K 31/4155 | (2006.01) |
| C07D 413/14 | (2006.01) |
| C07D 285/12 | (2006.01) |
| C07D 271/10 | (2006.01) |
| C07D 263/10 | (2006.01) |
| C07D 261/10 | (2006.01) |

(52) U.S. Cl. ........ 514/341; 514/363; 514/364; 514/365; 514/374; 514/378; 546/268.7; 546/269.1; 546/272.1; 548/136; 548/143; 548/202; 548/235; 548/247

(58) Field of Classification Search .................. None
See application file for complete search history.

(56) References Cited

OTHER PUBLICATIONS

Gao et al. Pain, 149 (2010), pp. 33-49.*

* cited by examiner

*Primary Examiner* — Joseph K. McKane
*Assistant Examiner* — Alicia L Otton
(74) *Attorney, Agent, or Firm* — Millen, White, Zelano & Branigan, P.C.

(57) ABSTRACT

The present invention relates to compounds of the general formula (I), and the pharmaceutically acceptable salt or solvate thereof, as anti-inflammatory and immunomodulatory agents.

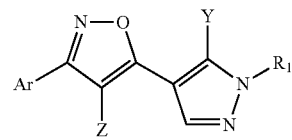

formula (I)

20 Claims, No Drawings

IL17 AND IFN-GAMMA INHIBITION FOR THE TREATMENT OF AUTOIMMUNE INFLAMMATION

This application claims the benefit of the filing date of U.S. Provisional Application Ser. No. 61/437,080 filed 2011 Jan. 28, which is incorporated by reference herein.

The IL-17 family of cytokines has been associated with the pathogenesis of autoimmune diseases and is generally blamed for the pathogenic symptoms of autoimmune inflammation. Overexpression of IL-17 is a hallmark for autoimmune diseases like rheumatoid arthritis, systemic lupus erythematomatosus, inflammatory bowel disease, multiple sclerosis, and psoriasis (Yao Z et. al., J Immunol, 155(12), 1995, 5483-6. Chang S H, et. al., Cytokine, 46, 2009, 7-11; Hisakata Yamada et. al., Journal of Inflamm. Res., 3, 2010, 33-44)).

The IL-17 cytokine family comprises six members, out of which IL-17A and IL-17F are the best characterized. IL-17A and IL-17F exist as homo- as well as as heterodimers (IL-17AA, IL-17AF, IL-17FF). IL-17A and IL-17F are clearly associated with inflammation (Gaffen S H, Cytokine, 43, 2008, 402-407; Torchinsky M B et al., Cell. Mol. Life. Sci., 67, 2010, 1407-1421).

The secretion of IL-17 is predominantly caused by a specific subtype of T helper cells termed TH-17 cells. IL-23, TGFβ and IL-6 were shown to be important factors leading to conversion of naïve CD4+ T-cells to TH17 cells. It was also reported that TGFβ and IL-6 potently induce in synergy TH17 differentiation. Important transcription factors for the secretion of IL-17 from TH17 cells are RORγt and STAT3 (Ivanov, I et. al. Cell 126, 2006, 1121-1133). IL-17 induces pro-inflammatory cytokines (IL-6, TNF-α and IL-1b) and Chemokines (CXCL1,GCP-2,CXCL8 or IL-8,CINC,MCP-1). It increases the production of nitric oxide prostaglandin E2 and matrix-metalloproteinases. As a consequence of these events neutrophil infiltration, tissue damage and chronic inflammation occurs (PECK A et. al., Clin Immunol., 132(3), 2009, 295-304).

Before the recognition of the importance of IL-17 in autoimmune inflammation, IFN-gamma derived from TH1 cells was believed to be an important cytokine that drives autoimmune disorders (Takayanagi H et. al. Nature, 408, 2000, 600-605. Huang W. et. al. Arthritis Res. Ther., 5, 2002, R49-R59) The secretion of IFN-gamma is a key feature of the TH1 effector cell lineage and the secretion is regulated by the transcription factors T-bet and STAT4 (Bluestone J A et. al. Nat Rev Immunol, 11, 2009, 811-6). Infiltration of activated T-cells and elevation of M-CSF, IL-10 and TNF support this notion (Yamanda H et. al. Ann. Rheu. Dis., 67, 2008, 1299-1304; Kotake S et. al. Eur. J. Immunol, 35, 2005, 3353-3363).

Recently, a more complex situation was proposed, where hybrid TH17/TH1 cells induced by IL-23 and IL-6 in concert with IL-1 secrete IL-17 and IFN-gamma. These cells are under the control of the transcription factors RORγt and T-bet, confirming the notion, that these are true hybrids of TH1 and TH17 cells. It was also demonstrated that these double producing cells are the pathogenic species in IBD and EAE (Buonocore S et. al. Nature, 464, 2010, 1371-5; Ghoreshi K. et. al. Nature, 467, 2010, 967-971).

Compounds which target and suppress both IL-17 and IFN-gamma are predisposed for the treatment of autoimmune disorders.

The effectiveness of blocking IL-17 signaling as therapeutic treatment in autoimmune diseases has already been proven in clinical trials with e.g. monoclonal antibodies against IL-17A (AIN457, secukinumab; Ly2439821, ixekizumab; RG4934) and/or the IL-17 receptor IL-17RA (AMG827, brodalumab). Positive results have been reported for the treatment of rheumatoid arthritis, psoriasis and uveitis (Hueber W et al., Sci. Transl. Med., 2, 2010, 52ra72, DOI: 10.1126/scitranslmed.3001107; van den Berg W B et al., Nat. Rev. Rheumatol., 5, 2009, 549-553), ankylosing spondylitis and spondyloarthritides (Song I-H et al., Curr. Opin. Rheumatol., 23, 2011, 346-351). Secukinumab is currently under investigation in clinical trials for psoriatic arthritis, Behcet disease, uveitits, inflammatory bowel disease, Crohn's disease, multiple sclerosis (Kopf M et al., Nat. Rev. Drug Disc., 9, 2010, 703-718; Song I-H et al., Curr. Opin. Rheumatol., 23, 2011, 346-351). Brodalumab, Ixekizumab and RG4934 are currently in clinical trials for the treatment of rheumatoid arthritis, psoriasis and/or psoriatic arthritis (Kopf M et al., Nat. Rev. Drug Disc., 9, 2010, 703-718; clinicaltrials.gov; *Medicines in development for skin diseases*, 2011, published by PhRMA, www.phrma.com).

With regard to blocking of IFN-gamma signaling as therapeutic treatment in autoimmune diseases, the IFN-gamma-specific monoclonal antibody AMG811 is currently under clinical investigations for the treatment of systemic lupus erythematosus (Kopf M et al., Nat. Rev. Drug Disc., 9, 2010, 703-718).

The present invention relates to a compound of formula (I)

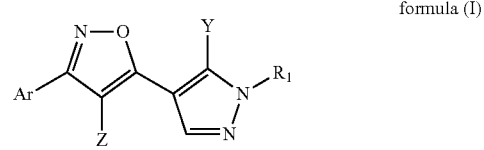

formula (I)

and the pharmaceutically acceptable salt or solvate thereof, wherein $R^1$ is aryl, heteroaryl, cycloalkyl, heterocyclyl or alkyl, which can be substituted by one or more substituents R'

Ar is aryl, cycloalkyl, heterocyclyl or heteroaryl, which can be substituted by one or more substituents R';

Z is aryl, heteroaryl, cycloalkyl or heterocyclyl, which can be substituted by one or more subtituents R';

Y is H, halogen, haloalkyl, alkyl or an alkylester, which can be substituted by one or more substituents R';

R' independently represents H, —CO$_2$R", —CONHR", —CR"O, —SO$_2$N(R")$_2$, —SO$_2$NHR", —NR"—CO-haloalkyl, —NO$_2$, —NR"—SO$_2$-haloalkyl, —NR"—SO$_2$-alkyl, —SO$_2$-alkyl, —NR"—CO-alkyl, —CN, alkyl, cycloalkyl, aminoalkyl, alkylamino, alkoxy, —OH, —SH, alkylthio, hydroxyalkyl, hydroxyalkylamino, halogen, haloalkyl, haloalkoxy, amino, heterocyclyl, aryl, haloaryl, haloarylalkyl, arylalkyl or heteroaryl;

R" independently represents H, haloalkyl, hydroxyalkyl, amino, alkoxy, —N=C(R')$_2$, —NR'—CO—R', —CR'O, —CO$_2$R', alkyl, cycloalkyl, aryl, haloaryl, haloarylalkyl, heteroaryl, heterocyclyl, arylalkyl or aminoalkyl, which are optionally substituted by one or more substituents R'.

The present invention further relates to a compound of formula (I)

formula (I)

and the pharmaceutically acceptable salt or solvate thereof, wherein
$R^1$ is aryl, heteroaryl, cycloalkyl, heterocyclyl or alkyl, which can be substituted by one or more substituents R'
Ar is aryl, cycloalkyl, heterocyclyl or heteroaryl, which can be substituted by one or more substituents R';
Z is aryl, heteroaryl, cycloalkyl or heterocyclyl, which can be substituted by one or more substituents R';
Y is H, halogen, haloalkyl or alkyl, which can be substituted by one or more substituents R';
R' independently represents H, —CO$_2$R", —CONHR", —CR"O, —SO$_2$N(R")$_2$, —SO$_2$NHR", —NR"—CO-haloalkyl, —NO$_2$, —NR"—SO$_2$-haloalkyl, —NR"—SO$_2$-alkyl, —SO$_2$-alkyl, —NR"—CO-alkyl, —CN, alkyl, cycloalkyl, aminoalkyl, alkylamino, alkoxy, —OH, —SH, alkylthio, hydroxyalkyl, hydroxyalkylamino, halogen, haloalkyl, haloalkoxy, amino, heterocyclyl, aryl, haloaryl, haloarylalkyl, arylalkyl or heteroaryl;
R" independently represents H, haloalkyl, hydroxyalkyl, amino, alkoxy, —N=C(R')$_2$, —NR'—CO—R', —CR'O, —CO$_2$R', alkyl, cycloalkyl, aryl, haloaryl, haloarylalkyl, heteroaryl, heterocyclyl, arylalkyl or aminoalkyl, which are optionally substituted by one or more substituents R'.

In a preferred embodiment, the present invention relates to a compound of formula (I) and the pharmaceutically acceptable salt or solvate thereof,
wherein
$R^1$ is aryl, which can be substituted by one or more substituents R'

In a more preferred embodiment, the present invention relates to a compound of formula (I) and the pharmaceutically acceptable salt or solvate thereof,
wherein
$R^1$ is heteroaryl, which can be substituted by one or more substituents R'

In a more preferred embodiment, the present invention relates to a compound of formula (I) and the pharmaceutically acceptable salt or solvate thereof,
wherein
Ar is aryl, which can be substituted by one or more substituents R'

In a more preferred embodiment, the present invention relates to a compound of formula (I) and the pharmaceutically acceptable salt or solvate thereof,
wherein
Ar is heteroaryl, which can be substituted by one or more substituents R'

In a more preferred embodiment, the present invention relates to a compound of formula (I) and the pharmaceutically acceptable salt or solvate thereof,
wherein
Z is aryl, which can be substituted by one or more substituents R'

In a more preferred embodiment, the present invention relates to a compound of formula (I) and the pharmaceutically acceptable salt or solvate thereof,
wherein
Z is heteroaryl, which can be substituted by one or more substituents R'

In a more preferred embodiment, the present invention relates to a compound of formula (I) and the pharmaceutically acceptable salt or solvate thereof,
wherein
Z is heterocyclyl, which can be substituted by one or more substituents R'

In a more preferred embodiment, the present invention relates to a compound of formula (I) and the pharmaceutically acceptable salt or solvate thereof,
wherein
Z is cycloalkyl, which can be substituted by one or more substituents R'

In a more preferred embodiment, the present invention relates to a compound of formula (I) and the pharmaceutically acceptable salt or solvate thereof,
wherein
Y is halogen, which can be substituted by one or more substituents R'

In a more preferred embodiment, the present invention relates to a compound of formula (I) and the pharmaceutically acceptable salt or solvate thereof,
wherein
Y is haloalkyl, which can be substituted by one or more substituents R'

In a more preferred embodiment, the present invention relates to a compound of formula (I) and the pharmaceutically acceptable salt or solvate thereof,
wherein
Y is alkyl, which can be substituted by one or more substituents R'

In another preferred embodiment, the present invention relates to a compound of formula (I) and the pharmaceutically acceptable salt or solvate thereof,
wherein
$R^1$ is aryl, heteroaryl, cycloalkyl, heterocyclyl or alkyl, which can be substituted by one or more substituents R'
Ar is aryl or heteroaryl, which can be substituted by one or more substituents R';
Z is aryl, heteroaryl, cycloalkyl or heterocyclyl, which can be substituted by one or more substituents R';
Y is H, halogen, haloalkyl or alkyl, which can be substituted by one or more substituents R';
R' independently represents H, —CO$_2$R", —CONHR", —CR"O, —SO$_2$N(R")$_2$, —SO$_2$NHR", —NR"—CO-haloalkyl, —NO$_2$, —NR"—SO$_2$-haloalkyl, —NR"—SO$_2$-alkyl, —SO$_2$-alkyl, —NR"—CO-alkyl, —CN, alkyl, cycloalkyl, aminoalkyl, alkylamino, alkoxy, —OH, —SH, alkylthio, hydroxyalkyl, hydroxyalkylamino, halogen, haloalkyl, haloalkoxy, amino, heterocyclyl, aryl, haloaryl, haloarylalkyl, arylalkyl or heteroaryl;
R" independently represents H, haloalkyl, hydroxyalkyl, amino, alkoxy, —N=C(R')$_2$, —NR'—CO—R', —CR'O, —CO$_2$R', alkyl, cycloalkyl, aryl, haloaryl, haloarylalkyl, heteroaryl, heterocyclyl, arylalkyl or aminoalkyl, which are optionally substituted by one or more substituents R';

In another preferred embodiment, the present invention relates to a compound of formula (I) and the pharmaceutically acceptable salt or solvate thereof, wherein
$R^1$ is aryl or heteroaryl, which can be substituted by one or more substituents R'

Ar is aryl or heteroaryl, which can be substituted by one or more substituents R';
Z is aryl, cycloalkyl, heterocyclyl or heteroaryl, which can be substituted by one or more substituents R';
Y is H, halogen, haloalkyl, alkyl, which can be substituted by one or more substituents R';
R' independently represents H, —CO$_2$R", —CONHR", —CR"O, —SO$_2$N(R")$_2$, —SO$_2$NHR", —NR"—CO-haloalkyl, —NO$_2$, —NR"—SO$_2$-haloalkyl, —NR"—SO$_2$-alkyl, —SO$_2$-alkyl, —NR"—CO-alkyl, —CN, alkyl, cycloalkyl, aminoalkyl, alkylamino, alkoxy, —OH, —SH, alkylthio, hydroxyalkyl, hydroxyalkylamino, halogen, haloalkyl, haloalkoxy, amino, heterocyclyl, aryl, haloaryl, haloarylalkyl, arylalkyl or heteroaryl;
R" independently represents H, haloalkyl, hydroxyalkyl, amino, alkoxy, —N═C(R')$_2$, —NR'—CO—R', —CR'O, —CO$_2$R', alkyl, cycloalkyl, aryl, haloaryl, haloarylalkyl, heteroaryl, heterocyclyl, arylalkyl or aminoalkyl, which are optionally substituted by one or more substituents R';

In another preferred embodiment, the present invention relates to a compound of formula (I) and the pharmaceutically acceptable salt or solvate thereof, wherein
R$^1$ is aryl, which can be substituted by one or more substituents R'
Ar is aryl or heteroaryl, which can be substituted by one or more substituents R';
Z is aryl, cycloalkyl, heterocyclyl or heteroaryl, which can be substituted by one or more substituents R';
Y is H, halogen, haloalkyl, or alkyl, which can be substituted by one or more substituents R';
R' independently represents H, —CO$_2$R", —CONHR", —CR"O, —SO$_2$N(R")$_2$, —SO$_2$NHR", —NR"—CO-haloalkyl, —NO$_2$, —NR"—SO$_2$-haloalkyl, —NR"—SO$_2$-alkyl, —SO$_2$-alkyl, —NR"—CO-alkyl, —CN, alkyl, cycloalkyl, aminoalkyl, alkylamino, alkoxy, —OH, —SH, alkylthio, hydroxyalkyl, hydroxyalkylamino, halogen, haloalkyl, haloalkoxy, amino, heterocyclyl, aryl, haloaryl, haloarylalkyl, arylalkyl or heteroaryl;
R" independently represents H, haloalkyl, hydroxyalkyl, amino, alkoxy, —N═C(R')$_2$, —NR'—CO—R', —CR'O, —CO$_2$R', alkyl, cycloalkyl, aryl, haloaryl, haloarylalkyl, heteroaryl, heterocyclyl, arylalkyl or aminoalkyl, which are optionally substituted by one or more substituents R';

In another preferred embodiment, the present invention relates to a compound of formula (I) and the pharmaceutically acceptable salt or solvate thereof, wherein
R$^1$ is heteroaryl, which can be substituted by one or more substituents R'
Ar is aryl or heteroaryl, which can be substituted by one or more substituents R';
Z is aryl, cycloalkyl, heterocyclyl or heteroaryl, which can be substituted by one or more substituents R';
Y is H, halogen, haloalkyl, or alkyl, which can be substituted by one or more substituents R';
R' independently represents H, —CO$_2$R", —CONHR", —CR"O, —SO$_2$N(R")$_2$, —SO$_2$NHR", —NR"—CO-haloalkyl, —NO$_2$, —NR"—SO$_2$-haloalkyl, —NR"—SO$_2$-alkyl, —SO$_2$-alkyl, —NR"—CO-alkyl, —CN, alkyl, cycloalkyl, aminoalkyl, alkylamino, alkoxy, —OH, —SH, alkylthio, hydroxyalkyl, hydroxyalkylamino, halogen, haloalkyl, haloalkoxy, amino, heterocyclyl, aryl, haloaryl, haloarylalkyl, arylalkyl or heteroaryl;
R" independently represents H, haloalkyl, hydroxyalkyl, amino, alkoxy, —N═C(R')$_2$, —NR'—CO—R', —CR'O, —CO$_2$R', alkyl, cycloalkyl, aryl, haloaryl, haloarylalkyl, heteroaryl, heterocyclyl, arylalkyl or aminoalkyl, which are optionally substituted by one or more substituents R';

In another preferred embodiment, the present invention relates to a compound of formula (I) and the pharmaceutically acceptable salt or solvate thereof, wherein
R$^1$ is aryl or heteroaryl, which can be substituted by one or more substituents R'
Ar is aryl or heteroaryl, which can be substituted by one or more substituents R';
Z is aryl, cycloalkyl, heterocyclyl or heteroaryl, which can be substituted by one or more substituents R';
Y is H, halogen, haloalkyl, or alkyl, which can be substituted by one or more substituents R';
R' independently represents H, —CO$_2$R", —CONHR", —CR"O, —SO$_2$N(R")$_2$, —SO$_2$NHR", —CN, alkyl, cycloalkyl, aminoalkyl, alkoxy, —OH, hydroxyalkyl, halogen, haloalkyl, haloalkoxy, amino, heterocyclyl, aryl, haloaryl, haloarylalkyl, arylalkyl or heteroaryl;
R" independently represents H, haloalkyl, hydroxyalkyl, amino, alkoxy, —N═C(R')$_2$, —NR'—CO—R', —CR'O, —CO$_2$R', alkyl, cycloalkyl, aryl, haloaryl, haloarylalkyl, heteroaryl, heterocyclyl, arylalkyl or aminoalkyl, which are optionally substituted by one or more substituents R'

In another preferred embodiment, the present invention relates to a compound of formula (I) and the pharmaceutically acceptable salt or solvate thereof,
wherein
R$^1$ is aryl or heteroaryl, which can be substituted by one or more substituents R';
Ar is aryl or heteroaryl, which can be substituted by one or more substituents R';
Z is aryl, cycloalkyl, heterocyclyl or heteroaryl, which can be substituted by one or more substituents R';
Y is H, halogen, haloalkyl, or alkyl, which can be substituted by one or more substituents R';
R' independently represents H, —CO$_2$R", —SO$_2$N(R")$_2$, —SO$_2$NHR", —CN, alkyl, alkoxy, —OH, hydroxyalkyl, halogen, haloalkyl, haloalkoxy, heterocyclyl, aryl, haloaryl, haloarylalkyl, arylalkyl or heteroaryl;
R" independently represents H, haloalkyl, hydroxyalkyl, amino, alkoxy, —N═C(R')$_2$, —NR'—CO—R', —CR'O, —CO$_2$R', alkyl, cycloalkyl, aryl, haloaryl, haloarylalkyl, heteroaryl, heterocyclyl, arylalkyl or aminoalkyl, which are optionally substituted by one or more substituents R'

In another preferred embodiment, the present invention relates to a compound of formula (I) and the pharmaceutically acceptable salt or solvate thereof,
wherein
R$^1$ is aryl or heteroaryl, which can be substituted by one or more substituents R';
Ar is aryl or heteroaryl, which can be substituted by one or more substituents R';
Z is aryl, cycloalkyl, heterocyclyl or heteroaryl, which can be substituted by one or more substituents R';
Y is H, halogen, haloalkyl, or alkyl, which can be substituted by one or more substituents R';
R' independently represents H, —CO$_2$R", —CONHR", —CR"O, —SO$_2$N(R")$_2$, —SO$_2$NHR", —CN, alkyl, alkoxy, —OH, halogen, haloalkyl or haloalkoxy;
R" independently represents H, haloalkyl, hydroxyalkyl, amino, alkoxy, —N═C(R')$_2$, —NR'—CO—R', —CR'O, —CO$_2$R', alkyl, cycloalkyl, aryl, haloaryl, haloarylalkyl, heteroaryl, heterocyclyl, arylalkyl or aminoalkyl, which are optionally substituted by one or more substituents R'

In another preferred embodiment, the present invention relates to a compound of formula (I) and the pharmaceutically acceptable salt or solvate thereof, wherein
R¹ is aryl, or heteroaryl, which can be substituted by one or more substituents R';
Ar is aryl or heteroaryl, which can be substituted by one or more substituents R';
Z is aryl, cycloalkyl, heterocyclyl or heteroaryl, which can be substituted by one or more substituents R';
Y is H, halogen, haloalkyl, or alkyl, which can be substituted by one or more substituents R';
R' independently represents H, —CO₂R", —CONHR", —CR"O, —SO₂N(R")₂, —SO₂NHR", —CN, alkyl, alkoxy, —OH, halogen, haloalkyl or haloalkoxy;
R" independently represents H, haloalkyl, or alkyl, which can be substituted by one or more substituents R';

In another preferred embodiment, the present invention relates to a compound of formula (I) and the pharmaceutically acceptable salt or solvate thereof,
wherein
R¹ is aryl, which can be substituted by one or more substituents R';
Ar is aryl, which can be substituted by one or more substituents R';
Z is aryl, cycloalkyl, heterocyclyl or heteroaryl, which can be substituted by one or more substituents R';
Y is H, halogen, haloalkyl, or alkyl, which can be substituted by one or more substituents R';
R' independently represents H, —CO₂R", —CONHR", —CR"O, —CN, alkyl, alkoxy, —OH, halogen, haloalkyl or haloalkoxy;
R" independently represents H, haloalkyl, or alkyl, which can be substituted by one or more substituents R';
wherein
an aryl group denotes an aromatic group having five to fifteen carbon atoms, which may be substituted by one or more substituents R', and may be fused to another aromatic ring; the aryl group is preferably a phenyl group, -o-C₆H₄—R', -m-C₆H₄—R', -p-C₆H₄—R', 1-naphthyl, 2-naphthyl, 1-anthracenyl or 2-anthracenyl;
a heteroaryl group denotes a 5- or 6-membered heterocyclic group which contains at least one heteroatom like O, N, S. This heterocyclic group can be fused to another aromatic ring. For example, this group can be selected from a thiadiazole, thiazol-2-yl, thiazol-4-yl, thiazol-5-yl, isothiazol-3-yl, isothiazol-4-yl, isothiazol-5-yl, oxazol-2-yl, oxazol-4-yl, oxazol-5-yl, isooxazol-3-yl, isooxazol-4-yl, isooxazol-5-yl, 1,2,4-oxadiazol-3-yl, 1,2,4-oxadiazol-5-yl, 1,2,5-oxadiazol-3-yl, benzooxazol-2-yl, benzooxazol-4-yl, benzooxazol-5-yl, benzoisooxazol-3-yl, benzoisooxazol-4-yl, benzoisooxazol-5-yl, 1,2,5-oxadiazol-4-yl, 1,3,4,-oxadiazol-2-yl, 1,2,4-thiadiazol-3-yl, 1,2,4-thiadiazol-5-yl, 1,3,4-thiadiazol-2-yl, isothiazol-3-yl, isothiazol-4-yl, isothiazol-5-yl, benzoisothiazol-3-yl, benzoisothiazol-4-yl, benzoisothiazol-5-yl, 1,2,5-thiadiazol-3-yl, 1-imidazolyl, 2-imidazolyl, 1,2,5-thiadiazol-4-yl, 4-imidazolyl, benzoimidazol-4-yl, 1-pyrrolyl, 2-pyrrolyl, 3-pyrrolyl, 2-furanyl, 3-furanyl, 2-thienyl, 3-thienyl, 2-pyridyl, 3-pyridyl, 4-pyridyl, 2-pyranyl, 3-pyranyl, 4-pyranyl, 2-pyrimidinyl, 4-pyrimidinyl, 5-pyrimidinyl, pyrid-2-yl, pyrid-3-yl, pyrid-4-yl, pyrid-5-yl, pyrid-6-yl, 3-pyridazinyl, 4-pyridazinyl, 2-pyrazinyl, 1-pyrazolyl, 3-pyrazolyl, 4-pyrazolyl, 1,2,3-triazol-4-yl, 1,2,3-triazol-5-yl, 1,2,4-triazol-3-yl, 1,2,4-triazol-5-yl, 1H-tetrazol-2-yl, 1H-tetrazol-3-yl, tetrazolyl, acridyl, phenazinyl, carbazolyl, phenoxazinyl, indolizine, 2-indolyl, 3-indolyl, 4-indolyl, 5-indolyl, 6-indolyl, 7-indolyl, 1-isoindolyl, 3-isoindolyl, 4-isoindolyl, 5-isoindolyl, 6-isoindolyl, 7-isoindolyl, 2-indolinyl, 3-indolinyl, 4-indolinyl, 5-indolinyl, 6-indolinyl, 7-indolinyl, benzo[b]furanyl, benzofurazane, benzothiofurazane, benzotriazol-1-yl, benzotriazol-4-yl, benzotriazol-5-yl, benzotriazol-6-yl, benzotriazol-7-yl, benzotriazine, benzo[b]thiophenyl, benzimidazolyl, benzothiazolyl, quinazolinyl, quinoxazolinyl, cinnoline, quinolinyl, tetrahydroquinolinyl, isoquinolinyl, or tetrahydroisoquinolinyl, purine, phthalazine, pteridine, thiatetraazaindene, thiatriazaindene, isothiazolopyrazine, 6-pyrimidinyl, 2,4-dimethoxy-6-pyrimidinyl, benzimidazol-2-yl, 1H-benzimidazolyl, benzimidazol-4-yl, benz-imidazol-5-yl, benzimidazol-6-yl, benzimidazol-7-yl, tetrazole, tetrahydro-thieno[3,4-d]imidazol-2-one, pyrazolo[5,1-c][1,2,4]triazine, isothiazolopyrimidine, pyrazolotriazine, pyrazolopyrimidine, imidazopyridazine, imidazopyrimidine, imidazopyridine, imidazolotriazine, triazolotriazine, triazolopyridine, triazolopyrazine, triazolopyrimidine, or triazolopyridazine group. This heterocyclic group can be substituted by one or more substituents R', wherein R' is as defined above;
a heterocyclyl group denotes a 3 to 8-membered heterocyclic non-aromatic group which contains at least one heteroatom selected from O, N, and S, wherein the heterocyclyl group may be fused to another non-aromatic ring and may be substituted by one or more substituents R', wherein R' is as defined above; the $C_3$-$C_8$-heterocyclyl residue may be selected from the group consisting of morpholine-4-yl, piperazinyl, isoxazolidine-2-yl, 1-alkylpiperazine-4-yl, pyrrolidinyl, pyrrolidino, piperidinyl, piperidino, piperazinyl, piperazino, morpholinyl, morpholino, thiomorpholinyl, thiomorpholino, tetrahydrofuranyl, tetrahydrothiofuranyl, tetrahydropyranyl, and pyranyl;

To keep the definitions as short as possible, in the following paragraphs "alkyl" is to be understood to encompass alkyl, alkenyl and alkynyl.

In the context of the present invention, an alkyl group, if not stated otherwise, denotes a linear or branched $C_1$-$C_6$-alkyl, preferably a linear or branched chain of one to five carbon atoms; an alkenyl group, if not stated otherwise, denotes a linear or branched $C_2$-$C_6$-alkenyl; and an alkynyl group, if not stated otherwise, denotes a linear or branched $C_2$-$C_6$-alkynyl group, which may be substituted by one or more substituents R'.

The $C_1$-$C_6$-alkyl, $C_2$-$C_6$-alkenyl and $C_2$-$C_6$-alkynyl residue may be selected from the group consisting of —CH₃, —C₂H₅, —CH=CH₂, —C≡CH, —C₃H₇, —CH(CH₃)₂, —CH₂—CH=CH₂, —C(CH₃)=CH₂, —CH=CH—CH₃, —C≡C—CH₃, —CH₂—C≡CH, —C₄H₉, —CH₂—CH(CH₃)₂, —CH(CH₃)—C₂H₅, —C(CH₃)₃, —C₅H₁₁, —C₆H₁₃, —C(R')₃, —C₂(R')₅, —CH₂—C(R')₃, —C₃(R')₇, —C₂H₄—C(R')₃, —C₂H₄—CH=CH₂, —CH=CH—C₂H₅, —CH=C(CH₃)₂, —CH₂—CH=CH—CH₃, —CH=CH—CH=CH₂, —C₂H₄—C≡CH, —C≡C—C₂C₅, —CH₂—C≡C—CH₃, —C≡C—CH=CH₂, —CH=CH—C≡CH, —C≡C—C≡CH, —C₂H₄—CH(CH₃)₂, —CH(CH₃)—C₃H₇, —CH₂—CH(CH₃)—C₂H₅, —CH(CH₃)—CH(CH₃)₂, —C(CH₃)₂—C₂H₅, —CH₂—C(CH₃)₃, —C₃H₆—CH=CH₂, —CH=CH—C₃H₇, —C₂H₄—CH=CH—CH₃, —CH₂—CH=CH—C₂H₅, —CH₂—CH=CH—CH=CH₂, —CH=CH—CH=CH—CH₃, —CH=CH—CH₂—CH=CH₂, —C(CH₃)=CH—CH=CH₂, —CH=C(CH₃)—CH=CH₂, —CH=CH—C(CH₃)=CH₂, —CH₂—CH=C(CH₃)₂, C(CH₃)=C(CH₃)₂, —C₃H₆—C≡CH, —C≡C—C₃H₇, —C₂H₄—C≡C—CH₃, —CH₂—C≡C—C₂H₅, —CH₂—C≡C—CH=CH₂, —CH₂—CH=CH—C≡CH, —CH₂—C≡C—C≡CH, —C≡C—CH₂—CH=CH₂, —CH=CH—C≡C—CH₃, —C≡C—C≡C—CH₃, —C≡C—CH₂—C≡CH, —CH=CH—CH₂—C≡CH, —C≡C—CH₂—C≡CH, —C(CH₃)=CH—CH=CH₂, —CH=C(CH₃)—CH=CH₂, —CH=CH—C(CH$_3$)=CH$_2$, —C(CH$_3$)=CH—C≡CH, —CH=C(CH$_3$)—C≡CH, —C≡C—C(CH$_3$)=CH$_2$, —C$_3$H$_6$—CH(CH$_3$)$_2$, —C$_2$H$_4$—CH(CH$_3$)—C$_2$H$_5$, —CH(CH$_3$)—C$_4$H$_9$, —CH$_2$—CH(CH$_3$)—C$_3$H$_7$, —CH(CH$_3$)—CH$_2$—CH(CH$_3$)$_2$, —CH(CH$_3$)—CH(CH$_3$)—C$_2$H$_5$, —CH$_2$—CH(CH$_3$)—CH(CH$_3$)$_2$, —CH$_2$—C(CH$_3$)$_2$—C$_2$H$_5$, —C(CH$_3$)$_2$—C$_3$C$_7$, —C(CH$_3$)$_2$—CH(CH$_3$)$_2$, —C$_2$H$_4$—C(CH$_3$)$_3$, —CH(CH$_3$)—C(CH$_3$)$_3$, —C$_4$H$_8$—CH=CH$_2$, —CH=CH—C$_4$H$_9$, —C$_3$H$_6$—CH=CH—CH$_3$, —CH$_2$—CH=CH—C$_3$H$_7$, —C$_2$H$_4$—CH=CH—C$_2$H$_5$, —CH$_2$—C(CH$_3$)=C(CH$_3$)$_2$, —C$_2$H$_4$—CH=C(CH$_3$)$_2$, —C$_4$-C$_8$—C≡CH, —C≡C—C$_4$H$_9$, —C$_3$H$_6$—C≡C—CH$_3$, —CH$_2$—C≡C—C$_3$C$_7$, and —C$_2$H$_4$—C≡C—C$_2$H$_5$, an arylalkyl group denotes a linear or branched C$_1$-C$_6$-alkyl substituted with at least one aryl group as defined herein. Exemplary arylalkyl groups include benzyl, phenylethyl, 4-hydroxybenzyl, 3-fluorobenzyl, 2-fluorophenylethyl, and the like. This arylalkyl group can be substituted by one or more substituents R', wherein R' is as defined above;

a cycloalkyl group denotes a non-aromatic ring system containing three to eight carbon atoms, preferably four to eight carbon atoms, wherein one or more of the carbon atoms in the ring may be substituted by a group E, E being O, S, SO, SO$_2$, N, or NR", R" being as defined above; the C$_3$-C$_8$-cycloalkyl residue may be selected from the group consisting of -cyclo-C$_3$H$_5$, -cyclo-C$_4$H$_7$, -cyclo-C$_5$H$_9$, -cyclo-C$_6$H$_{11}$, -cyclo-C$_7$H$_{13}$, -cyclo-C$_8$H$_{15}$, morpholine-4-yl, piperazinyl, and 1-alkylpiperazine-4-yl. This cycloalkyl group can be substituted by one or more substituents R', wherein R' is as defined above;

where used, the term "carbocycloalkyl" specifies a non-aromatic ring system comprising three to eight carbon atoms, preferably four to eight carbon atoms, more preferably five to seven carbon atoms, and most preferably six carbons atoms, i.e. a cyclohexyl ring. The carbocycloalkyl group comprises no heteroatoms in the ring. This carbocycloalkyl group can be substituted by one or more substituents R', wherein R' is as defined above; where used, the term "heterocycloalkyl" specifies a cycloalkyl group as defined above, wherein one or more of the carbon atoms in the ring are substituted by O, S, SO, SO$_2$, N, or NR", R" being as defined above. Preferred heterocycloalkyl or heterocyclyl are morpholine-4-yl, piperazinyl, and 1-alkylpiperazine-4-yl.

an alkoxy group denotes an O-alkyl group, the alkyl group being as defined above; the alkoxy group is preferably a methoxy, ethoxy, isopropoxy, t-butoxy or pentoxy group;

an alkylthio group denotes a S-alkyl group, the alkyl group being as defined above;

a haloalkyl group denotes a alkyl group as defined above substituted by one or more halogen atoms, preferably substituted by one to five halogen atoms, the haloalkyl group is preferably a —C(R$^{10}$)$_3$, —CR$^{10}$(R$^{10'}$)$_2$, —CR$^{10}$(R$^{10'}$)R$^{10''}$, —C$_2$(R$^{10}$)$_5$, —CH$_2$—C(R$^{10}$)$_3$, —C(R$^{10'}$)$_2$—CH(R$^{10}$)$_2$, —CH$_2$—CR$^{10}$(R$^{10'}$)$_2$, —CH$_2$—CR$^{10}$(R$^{10'}$)R$^{10''}$, —C$_3$(R$^{10}$)$_7$, or —C$_2$H$_4$—C(R$^{10}$)$_3$, wherein R$^{10}$, R$^{10'}$, R$^{10''}$ represent F, Cl, Br or I, preferably F; more preferably, haloalkyl is CF$_3$.

a haloaryl group denotes a aryl group as defined above substituted by one or more halogen atoms, preferably substituted by one to five halogen atoms;

a haloarylalkyl group denotes a linear or branched C$_1$-C$_6$-alkyl substituted with at least one haloaryl group as defined herein;

a hydroxyalkyl group denotes a HO-alkyl group, the alkyl group being as defined above;

a haloalkoxy group denotes an alkoxy group as defined above substituted by one or more halogen atoms, preferably substituted by one to five halogen atoms, the haloalkoxy group is preferably a —OC(R$^{10}$)$_3$, —OCR$^{10}$(R$^{10'}$)$_2$, —OCR$^{10}$(R$^{10'}$)R$^{10''}$, —OC$_2$(R$^{10}$)$_5$, —OCH$_2$—C(R$^{10}$)$_3$, —OCH$_2$—CR$^{10}$(R$^{10'}$)$_2$, —OCH$_2$—CR$^{10}$(R$^{10'}$)R$^{10''}$, —OC$_3$(R$^{10}$)$_7$ or —OC$_2$H$_4$—C(R$^{10}$)$_3$, wherein R$^{10}$, R$^{10'}$, R$^{10''}$ represent F, Cl, Br or I, preferably F;

a hydroxyalkylamino group denotes a (HO-alkyl)$_2$-N— group or HO-alkyl-NH— group, the alkyl group being as defined above;

an alkylamino group denotes a HN-alkyl or N-dialkyl group, the alkyl group being as defined above;

a halo or halogen group denotes fluorine, chlorine, bromine, or iodine; preferably chlorine or fluorine;

Compounds having infinite chains consisting for instance of repeating R' and R" units and the like are not encompassed by this invention. Thus, the longest chain allowed in each side chain R$^1$, Ar, Z and Y of the compounds according to the invention are three coupled substituents R' and/or R", e.g. R' substituted with R" further substituted with R' or the like;

This is to be understood such that oligomeric or polymeric side chains comprising more repeating R' and/or R" units as above outlined are not within the scope of the present invention.

Constituents which are optionally substituted as stated herein may be substituted, unless otherwise noted, at any chemically possible position.

In the embodiments of the present invention, Ar is preferably not

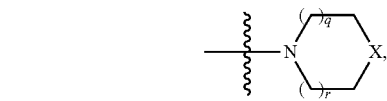

which may be optionally substituted and wherein X is N or C and wherein q and r may independently be 0 or 1; furthermore, in the embodiments of the present invention Ar is preferably other than optionally substituted carbocycloalkyl, more preferably other than optionally substituted cyclobutyl. Thus, preferably, the aforementioned groups are excluded by disclaimer from the definition of Ar.

In the embodiments of the present invention, R' is preferably not CONHR" and/or R" is preferably not heteroaryl. Thus, preferably, the aforementioned groups are excluded by disclaimer from the definition of Ar.

In preferred embodiments of the present invention, Z is selected from the group comprising aryl and heteroaryl, which can be substituted by one or more substituents R';

more preferably Z is phenyl or heteroaryl, which can be substituted by one or more substituents R';

even more preferably Z is selected from the group comprising phenyl, tetrazolyl, thiazolyl, 1,3,4-oxadiazolyl, oxazolyl, 1,3,4-thiadiazolyl, furanyl, and thiophenyl, which can be substituted by one or more substituents R';

even more preferably Z is selected from the group comprising phenyl, tetrazolyl, thiazolyl, 1,3,4-oxadiazolyl, oxazolyl, 1,3,4-thiadiazolyl, furanyl, and thiophenyl, which can be substituted by one or more substituents R';

wherein in the aforementioned preferred embodiments relating to group Z, R' is preferably selected from the group comprising C$_{1-4}$alkyl, C$_{1-4}$haloalkyl, hydrogen, hydroxyl, C$_{1-4}$alkoxy, and C$_{1-4}$alkoxycarbonyl, more preferably methyl, trifluoromethyl, hydrogen, hydroxyl, methoxy, and methoxycarbonyl and ethoxyoxycarbonyl;

yet even more preferably Z is selected from the group comprising 1H-tetrazol-5-yl, 4-methylthiazol-2-yl, thiazol-2-yl, 5-(trifluoromethyl)-1,3,4-oxadiazol-2-yl, 5-methyl-1,3,4-oxadiazol-2-yl, 1,3,4-oxadiazol-2-yl, oxazol-5-yl, 4-hydroxy-thiazol-2-yl, 4-methoxy-thiazol-2-yl, 5-methyl-1,3,4-thiadiazol-2-yl, 1,3,4-thiadiazol-2-yl, furan-3-yl, furan-2-yl, thiophen-3-yl, phenyl, 4-methoxycarbonyl-thiazol-2-yl, and 4-ethoxycarbonyl-thiazol-2-yl;

most preferably Z is selected from the group comprising 4-methylthiazol-2-yl, thiazol-2-yl, 5-(trifluoromethyl)-1,3,4-oxadiazol-1-yl, 5-methyl-1,3,4-oxadiazol-1-yl, 1,3,4-oxadiazol-1-yl, oxazol-5-yl, 4-methoxy-thiazol-2-yl, 5-methyl-1,3,4-thiadiazol-2-yl, 1,3,4-thiadiazol-2-yl, furan-3-yl, furan-2-yl, thiophen-3-yl, phenyl, and 4-methoxycarbonyl-thiazol-2-yl.

In preferred embodiments of the present invention, $R^1$ is selected from the group comprising aryl which is optionally substituted by one or more substituents R', heteroaryl which is optionally substituted by one or more substituents R', cycloalkyl which is optionally substituted by one or more substituents R', and $C_{1-4}$alkyl optionally substituted by a group selected from the group comprising trifluoromethyl, hydroxyl, methoxy, tetrahydropyranyl, morpholinyl, pyridyl, pyridinyl, fluorophenyl and tetrahydrofuranyl;

in other preferred embodiments of the present invention, $R^1$ is selected from the group comprising aryl which is optionally substituted by one or more substituents R', heteroaryl which is optionally substituted by one or more substituents R', cycloalkyl which is optionally substituted by one or more substituents R', and $C_{1-4}$alkyl optionally substituted by a group selected from the group comprising trifluoromethyl, methoxy, tetrahydropyranyl, morpholinyl, pyridyl and tetrahydrofuranyl;

more preferably $R^1$ is selected from the group comprising phenyl which is optionally substituted by one or more substituents R', pyridyl which is optionally substituted by one or more substituents R', pyrimidyl which is optionally substituted by one or more substituents R', thienyl which is optionally substituted by one or more substituents R', thiazolyl which is optionally substituted by one or more substituents R', 1,1-dioxo-tetrahydrothienyl, 2,2,2-trifluoroethyl, isopropyl, isobutyl, 2-piperidin-4-ylethyl, 2-hydroxyethyl, 2-methoxyethyl, tetrahydropyran-4-ylmethyl, 2-morpholinoethyl, pyridin-2-ylmethyl, 2-fluorophenylmethyl, 6-ethoxypyrimidin-4-ylmethyl and tetrahydrofuran-2-ylmethyl;

more preferably $R^1$ is selected from the group comprising phenyl which is optionally substituted by one or more substituents R', pyridyl which is optionally substituted by one or more substituents R', pyrimidyl which is optionally substituted by one or more substituents R', thienyl which is optionally substituted by one or more substituents R', 1,1-dioxo-tetrahydrothienyl, 2,2,2-trifluoroethyl, isopropyl, isobutyl, 2-methoxyethyl, tetrahydropyran-4-ylmethyl, 2-morpholinoethyl, pyridin-2-ylmethyl and tetrahydrofuran-2-ylmethyl;

even more preferably $R^1$ is selected from the group comprising phenyl which is optionally substituted by one or more substituents individually selected from trifluoromethyl, fluorine, chlorine, bromine, iodine, nitro, $NH_2$, —CN, —NHCO—$C_{1-4}$-alkyl, methoxy, $C_{1-4}$-alkyl, —$SO_2NH_2$, or —$SO_2NH$—$C_{1-4}$-alkyl; pyridyl which is optionally substituted by one or more of the aforementioned substituents for phenyl; pyrimidyl which is optionally substituted by one or more of the aforementioned substituents for phenyl; thienyl which is optionally substituted by one substituent —COO—$C_{1-4}$alkyl; thiazolyl which is optionally substituted by one substituent selected from —COO—$C_{1-4}$alkyl or fluorophenyl; 1,1-dioxo-tetrahydrothienyl, 2,2,2-trifluoroethyl, isopropyl, isobutyl, 2-piperidin-4-ylethyl, 2-hydroxyethyl, 2-methoxyethyl, tetrahydropyran-4-ylmethyl, 2-morpholinoethyl, pyridin-2-ylmethyl, 2-fluorophenylmethyl, 6-ethoxypyrimidin-4-ylmethyl and tetrahydrofuran-2-ylmethyl;

even more preferably $R^1$ is selected from the group comprising phenyl which is optionally substituted by one or more substituents individually selected from trifluoromethyl, fluorine, chlorine, bromine, nitro, $NH_2$, —CN, —NHCO—$C_{1-4}$-alkyl, methoxy, $C_{1-4}$-alkyl, —$SO_2NH_2$, or —$SO_2NH$—$C_{1-4}$-alkyl; pyridyl which is optionally substituted by one or more of the aforementioned substituents for phenyl; pyrimidyl which is optionally substituted by one or more of the aforementioned substituents for phenyl; thienyl which is optionally substituted by one substituent —COO—$C_{1-4}$alkyl; 1,1-dioxo-tetrahydrothienyl, 2,2,2-trifluoroethyl, isopropyl, isobutyl, 2-methoxyethyl, tetrahydropyran-4-ylmethyl, 2-morpholinoethyl, pyridin-2-ylmethyl and tetrahydrofuran-2-ylmethyl;

yet even more preferably $R^1$ is selected from the group comprising phenyl which is optionally substituted by one or more substituents individually selected from trifluoromethyl, fluorine, chlorine, bromine, iodine, nitro, $NH_2$, —CN, —NHCO—$C_{1-4}$-alkyl, methoxy, $C_{1-4}$-alkyl, —$SO_2NH_2$, or —$SO_2NH$—$C_{1-4}$-alkyl; pyrimidyl which is optionally substituted by one or more substituents selected from methyl, methoxy or trifluoromethyl; thienyl substituted by one substituent —COO-methyl, thiazolyl which is optionally substituted by one substituent selected from —COO-ethyl or 4-fluorophenyl, 1,1-dioxo-tetrahydrothienyl, 2,2,2-trifluoroethyl, isopropyl, isobutyl, 2-piperidin-4-ylethyl, 2-hydroxyethyl, 2-methoxyethyl, tetrahydropyran-4-ylmethyl, 2-morpholinoethyl, pyridin-2-ylmethyl, 2-fluorophenylmethyl, 6-ethoxypyrimidin-4-ylmethyl and tetrahydrofuran-2-ylmethyl; 1,1-dioxo-tetrahydrothienyl, 2,2,2-trifluoroethyl, isopropyl, isobutyl, 2-methoxyethyl, tetrahydropyran-4-ylmethyl, 2-morpholinoethyl, pyridin-2-ylmethyl and tetrahydrofuran-2-ylmethyl;

yet even more preferably $R^1$ is selected from the group comprising phenyl which is optionally substituted by one or more substituents individually selected from fluorine, chlorine, bromine, nitro, $NH_2$, —CN, —NHCO—$C_{1-4}$-alkyl, methoxy, t-butyl, —$SO_2NH_2$, or —$SO_2NH$-isopropyl; pyridyl; pyrimidyl which is optionally substituted by one or more substituents selected from methyl or trifluoromethyl; thienyl which is optionally substituted by one substituent —COO-methyl, 1,1-dioxo-tetrahydrothienyl, 2,2,2-trifluoroethyl, isopropyl, isobutyl, 2-methoxyethyl, tetrahydropyran-4-ylmethyl, 2-morpholinoethyl, pyridin-2-ylmethyl and tetrahydrofuran-2-ylmethyl;

yet even more preferably $R^1$ is selected from the group comprising phenyl, 2-fluorophenyl, 2-methoxyphenyl, 2-chlorophenyl, 2-bromophenyl, 2-iodophenyl, 2-nitrophenyl, 2-cyanophenyl, 2-aminophenyl, 4-trifluoromethoxyphenyl, 4-methylsulfonylphenyl, 4-chlorophenyl; 4-fluorophenyl, 4-tertbutylphenyl, 4-nitrophenyl, 4-cyanophenyl, 3-trifluoromethylphenyl, 3-fluorophenyl, 3-chlorophenyl, 3-cyanophenyl, 4-acetamido-phenyl, 3-acetamido-phenyl, 2-acetamido-phenyl, 3-aminosulfonyl-phenyl, 3-(isopropylamino)sulfonyl-phenyl, 3-nitrophenyl, 3-aminophenyl, 2,4-difluorophenyl, 2,4-dichlorophenyl, 2,6-dichlorophenyl, 2,3-dichlorophenyl, 3-chloro-5-trifluoromethylphenyl, 3,5-difluorophenyl, 3,5-dichlorophenyl, 2,3,5,6-tetrafluorophenyl, 2-pyridyl; 3-pyridyl; 4-pyridyl; 4-trifluoromethyl-pyrimid-2-yl, 6-ethoxy)-pyrimid-4-yl, 2,6-dimethyl-pyrimid-4-yl, 2-methoxycarbonyl-thien-3-yl, 4-ethoxycarbonyl-thiazol-2-yl, 4-(4-fluorophenyl)thiazol-2-yl, 1,1-dioxo-tetrahydrothienyl, 2,2,2-trifluoroethyl, isopropyl, isobutyl, 2-piperidin-4-ylethyl, 2-hydroxyethyl, 2-methoxyethyl, tetrahydropyran-4-ylmethyl, 2-morpholinoethyl, pyridin-2-ylmethyl, 2-fluorophenylmethyl, 6-ethoxypyrimidin-4-ylmethyl and tetrahydrofuran-2-ylmethyl; 1,1-dioxo-tetrahydrothienyl, 2,2,2-trifluoroethyl, isopropyl, isobutyl, 2-methoxyethyl, tetrahydropyran-4-ylmethyl, 2-morpholinoethyl, pyridin-2-ylmethyl and tetrahydrofuran-2-ylmethyl;

yet even more preferably $R^1$ is selected from the group comprising phenyl, 2-fluorophenyl, 2-methoxyphenyl, 2-chlorophenyl, 2-bromophenyl, 2-nitrophenyl, 2-aminophenyl, 4-fluorophenyl, 4-tertbutylphenyl, 3-fluorophenyl, 3-chlorophenyl, 3-cyanophenyl, 3-acetamido-phenyl, 2-acetamidophenyl, 3-aminosulfonyl-phenyl, 3-(isopropylamino)sulfonyl-phenyl, 3-nitrophenyl, 3-aminophenyl, 2,4-difluorophenyl, 3,5-difluorophenyl, 3,5-dichlorophenyl, 2,3,5,6-tetrafluorophenyl, 2-pyridyl; 3-pyridyl; 4-pyridyl; 4-trifluoromethyl-pyrimid-2-yl, 2,6-dimethyl-pyrimid-4-yl, 2-methoxycarbonyl-thien-3-yl, 1,1-dioxo-tetrahydrothienyl, 2,2,2-trifluoroethyl, isopropyl, isobutyl, 2-methoxyethyl, tetrahydropyran-4-yl-methyl, 2-(morpholin-4-yl)-ethyl, and tetrahydrofuran-2-yl-methyl;

yet even more preferably $R^1$ is selected from the group comprising phenyl, 2-fluorophenyl, 2-chlorophenyl, 2-methoxyphenyl, 2-nitrophenyl, 2-aminophenyl, 4-fluorophenyl, 3-fluorophenyl, 3-chlorophenyl, 3-cyanophenyl, 3-acetamido-phenyl, 3-nitrophenyl, 3-aminophenyl, 3,5-difluorophenyl, 3,5-dichlorophenyl, 2-pyridyl; 3-pyridyl; 4-pyridyl; 2-methoxycarbonyl-thien-3-yl, 2,2,2-trifluoroethyl, isobutyl, and tetrahydrofuran-2-yl-methyl;

yet even more preferably $R^1$ is selected from the group comprising phenyl, 2-fluorophenyl, 2-chlorophenyl, 3-fluorophenyl, 3-chlorophenyl, 2-pyridyl; 3-pyridyl and 4-pyridyl.

In preferred embodiments of the present invention, Ar is selected from the group comprising phenyl and pyridyl, which can be substituted by one or more substituents R';

more preferably Ar is selected from the group comprising phenyl and pyridyl, which can be substituted by one or more substituents independently selected from fluorine, methoxy or chlorine;

also more preferably Ar is selected from the group comprising phenyl, 2,6-difluorophenyl, 2-chloro-6-fluorophenyl, 2-chloro-6-methoxyphenyl, 2-fluorophenyl, 3-fluorophenyl, 2-chlorophenyl, 4-chlorophenyl, 4-methoxyphenyl, 2,6-dichlorophenyl, 3,4-dichlorophenyl, 2,4-dichlorophenyl, 3-fluoropyridin-4-yl, 3,5-dichloropyridin-4-yl and 3-chloro-5-fluoropyridin-4-yl;

even more preferably Ar is selected from the group comprising phenyl, 2-chloro-6-fluorophenyl, 2-fluorophenyl, 2-chlorophenyl, 2,6-dichlorophenyl, 2,4-dichlorophenyl, 3-fluoropyridin-4-yl, 3,5-dichloropyridin-4-yl and 3-chloro-5-fluoropyridin-4-yl.

even more preferably Ar is selected from the group comprising 2-chloro-6-fluorophenyl, and 2-chloro-6-methoxyphenyl.

In preferred embodiments of the present invention, Y is selected from the group comprising H, haloalkyl, and alkylester, which can be substituted by one or more substituents R';

more preferably Y is selected from the group comprising H, and haloalkyl which can be substituted by one or more substituents R';

more preferably Y is selected from the group comprising H, pentafluoroethyl, trifluoromethyl and methoxycarbonyl;

even more preferably Y is selected from the group comprising H, trifluoromethyl and methoxycarbonyl;

even more preferably Y is trifluoromethyl.

In preferred embodiments of the present invention, R' is independently selected from the group comprising H, methyl, ethyl, propyl, butyl, isopropyl, tert-butyl, morpholinyl, piperazinyl, cyclohexyl, pyrrolidinyl, $CF_3$, F, Cl, Br, methoxy, tetrahydropyranyl, isoxazolidinyl, nitro, —NH2, acetamido, —$SO_2NH_2$, —$SO_2NHiPr$ and —COO-methyl;

more preferably R' is independently selected from the group comprising H, methyl, ethyl, propyl, butyl, isopropyl, tert-butyl, $CF_3$, F, Cl, methoxy, tetrahydropyranyl, isoxazolidinyl, nitro, —$NH_2$, and —COO-methyl.

In preferred embodiments of the present invention, R" is independently selected from the group comprising H, trifluoromethyl, methoxy, $NH_2$, and methyl.

Particularly preferred compounds of the present invention are the compounds of the below examples of the present invention, more preferably the compounds of below examples 4, 5, 6, 7, 8, 10, 11, 12, 14, 16, 17, B-2, B-3, B-4, B-5, B-6, B-7, B-8, B-9, B-10, B-21, B-22, B-24, B-25, B-26, B-27, and B-30, most preferably the compounds of below examples 4, 5, 7, 8, 16, 17, B-3, B-4, B-5, B-6, B-7, and B-8.

It is apparent that the aforementioned preferred embodiments regarding the residues X, Y, Ar, $R^1$, R' and R" may be combined to yield further, more preferred embodiments. Some examples of such combinations are, without limiting the invention to these particular combinations:

A compound according to the present invention, wherein $R^1$ is selected from the group comprising phenyl which is optionally substituted by one or more substituents individually selected from trifluoromethyl, fluorine, chlorine, bromine, nitro, $NH_2$, —CN, —NHCO—$C_{1-4}$-alkyl, methoxy, $C_{1-4}$-alkyl, —$SO_2NH_2$, or —$SO_2NH$—$C_{1-4}$-alkyl; pyridyl which is optionally substituted by one or more of the aforementioned substituents for phenyl; pyrimidyl which is optionally substituted by one or more of the aforementioned substituents for phenyl; thienyl which is optionally substituted by one substituent —COO—$C_{1-4}$alkyl; 1,1-dioxo-tetrahydrothienyl, 2,2,2-trifluoroethyl, isopropyl, isobutyl, 2-methoxyethyl, tetrahydropyran-4-ylmethyl, 2-morpholinoethyl, pyridin-2-ylmethyl and tetrahydrofuran-2-ylmethyl;

Ar is selected from the group comprising phenyl and pyridyl, which can be substituted by one or more substituents independently selected from fluorine methoxy or chlorine;

Y is selected from the group comprising H, trifluoromethyl and methoxycarbonyl.

A compound according to the present invention, wherein $R^1$ is selected from the group comprising phenyl which is optionally substituted by one or more substituents individually selected from fluorine, chlorine, bromine, nitro, $NH_2$, —CN, —NHCO—$C_{1-4}$-alkyl, methoxy, t-butyl, —$SO_2NH_2$, or —$SO_2NH$-isopropyl; pyridyl; pyrimidyl which is optionally substituted by one or more substituents selected from methyl or trifluoromethyl; thienyl which is optionally substituted by one substituent —COO-methyl, 1,1-dioxo-tetrahydrothienyl, 2,2,2-trifluoroethyl, isopropyl, isobutyl, 2-methoxyethyl, tetrahydropyran-4-ylmethyl, 2-morpholinoethyl, pyridin-2-ylmethyl and tetrahydrofuran-2-ylmethyl;

Ar is selected from the group comprising phenyl, 2,6-difluorophenyl, 2-chloro-6-fluorophenyl, 2-chloro-6-methoxyphenyl, 2-fluorophenyl, 2-chlorophenyl, 2,6-dichlorophenyl, 2,4-dichlorophenyl, 3-fluoropyridin-4-yl, 3,5-dichloropyridin-4-yl and 3,5-difluoropyridin-4-yl;

Z is selected from the group comprising phenyl, tetrazolyl, thiazolyl, 1,3,4-oxadiazolyl, oxazolyl, 1,3,4-thiadiazolyl, furanyl, and thiophenyl, which can be substituted by one or more substituents selected from the group comprising methyl, trifluoromethyl, hydrogen, hydroxyl, methoxy, and methoxycarbonyl and ethoxyoxycarbonyl;

Y is selected from the group comprising H, trifluoromethyl and methoxycarbonyl.

A compound according to the present invention, wherein $R^1$ is selected from the group comprising phenyl, 2-fluorophenyl, 2-methoxyphenyl, 2-chlorophenyl, 2-bromophenyl, 2-nitrophenyl, 2-aminophenyl, 4-fluorophenyl, 4-tertbutylphenyl, 3-fluorophenyl, 3-chlorophenyl, 3-cyanophenyl, 3-acetamido-phenyl, 2-acetamido-phenyl, 3-aminosulfonyl-phenyl, 3-(isopropylamino)sulfonyl-phenyl, 3-nitrophenyl, 3-aminophenyl, 2,4-difluorophenyl, 3,5-difluorophenyl, 3,5-dichlorophenyl, 2,3,5,6-tetrafluorophenyl, 2-pyridyl; 3-pyridyl; 4-pyridyl; 4-trifluoromethyl-pyrimid-2-yl, 2,6-dimethyl-pyrimid-4-yl, 2-methoxycarbonyl-thien-3-yl, 1,1-dioxo-tetrahydrothienyl, 2,2,2-trifluoroethyl, isopropyl, isobutyl, 2-methoxyethyl, tetrahydropyran-4-yl-methyl, 2-(morpholin-4-yl)-ethyl, and tetrahydrofuran-2-yl-methyl;

Ar is selected from the group comprising phenyl, 2-chloro-6-fluorophenyl, 2-fluorophenyl, 2-chlorophenyl, 2,6-dichlorophenyl, 2,4-dichlorophenyl, 3-fluoropyridin-4-yl, 3,5-dichloropyridin-4-yl and 3,5-difluoropyridin-4-yl;

Z is selected from the group comprising 1H-tetrazol-5-yl, 4-methylthiazol-2-yl, thiazol-2-yl, 5-(trifluoromethyl)-1,3,4-oxadiazol-2-yl, 5-methyl-1,3,4-oxadiazol-2-yl, 1,3,4-oxadiazol-2-yl, oxazol-5-yl, 4-hydroxy-thiazol-2-yl, 4-methoxy-thiazol-2-yl, 5-methyl-1,3,4-thiadiazol-2-yl, 1,3,4-thiadiazol-2-yl, furan-3-yl, furan-2-yl, thiophen-3-yl, phenyl, 4-methoxycarbonyl-thiazol-2-yl, and 4-ethoxycarbonyl-thiazol-2-yl;

Y is selected from the group comprising H, trifluoromethyl and methoxycarbonyl.

According to expert's knowledge the compounds of the invention as well as their salts may contain, e.g. when isolated in crystalline form, varying amounts of solvents. Included within the scope of the invention are therefore all solvates and in particular all hydrates of the compounds of formula (I) as well as all solvates and in particular all hydrates of the salts of the compounds of formula (I).

As used herein the terms disease, indication and medical condition are used interchangeably.

The present invention further relates to a method of treatment for a disease or a therapeutic indication in which the inhibition of interleukin-17 (IL-17) and/or Interferon-γ (INF-γ) is beneficial, or for a disease or indication selected from the group consisting of psoriasis, psoriatric arthritis, autoimmune thyroiditis, Grave's disease, rheumatoid arthritis, vitiligo, Crohn's disease, ulcerative colitis, inflammatory bowel disease, ankylosing spondylitis, diabetes type I, multiple sclerosis, celiac disease, systemic lupus erythematosus, uveitis, Behcet disease, atopic dermatitis, Lichen planus, Sjögren's syndrome, spinal disc herniation, acne, Graft-versus-Host-Reaction, Host-versus-Graft-Reaction and osteoarthritis, wherein the method comprises administering to a subject in need thereof an effective amount of a compound of formula (I). Analogously, the present invention further relates to methods as the one described above, which encompass the further embodiments described herein, in particular the preferred compounds, medical uses and compounds for use in medical treatments as described herein.

The present invention further relates to pharmaceutical compositions, kits and kits-of parts comprising the compounds according to the present invention.

The present invention further relates to the use of the compounds according to the present invention for the production of pharmaceutical compositions which are employed for the treatment and/or prophylaxis of the diseases, disorders, illnesses and/or conditions as mentioned herein.

The present invention further relates to the methods and medical uses described herein, encompassing the pharmaceutical compositions as described herein.

The pharmaceutical compositions as described herein comprise one or more of the compounds according to this invention and a pharmaceutically acceptable carrier or diluent.

Additionally, the invention relates to an article of manufacture, which comprises packaging material and a pharmaceutical agent contained within said packaging material, wherein the pharmaceutical agent is therapeutically effective against the medical conditions as described herein, and wherein the packaging material comprises a label or package insert which indicates that the pharmaceutical agent is useful for preventing or treating said medical conditions, and wherein said pharmaceutical agent comprises one or more compounds of formula (I) according to the invention. The packaging material, label and package insert otherwise parallel or resemble what is generally regarded as standard packaging material, labels and package inserts for pharmaceuticals having related utilities.

The pharmaceutical compositions according to this invention are prepared by processes which are known per se and familiar to the person skilled in the art. As pharmaceutical compositions, the compounds of the invention (=active compounds) are either employed as such, or preferably in combination with suitable pharmaceutical auxiliaries and/or excipients, e.g. in the form of tablets, coated tablets, capsules, caplets, suppositories, patches (e.g. as TTS), emulsions, suspensions, gels or solutions, the active compound content advantageously being between 0.1 and 95% and where, by the appropriate choice of the auxiliaries and/or excipients, a pharmaceutical administration form (e.g. a delayed release form or an enteric form) exactly suited to the active compound and/or to the desired onset of action can be achieved.

The person skilled in the art is familiar with auxiliaries, vehicles, excipients, diluents, carriers or adjuvants which are suitable for the desired pharmaceutical formulations, preparations or compositions on account of his/her expert knowledge. In addition to solvents, gel formers, ointment bases and other active compound excipients, for example antioxidants, dispersants, emulsifiers, preservatives, solubilizers, colorants, complexing agents or permeation promoters, can be used.

Depending upon the particular disease, to be treated or prevented, additional therapeutic active agents, which are normally administered to treat or prevent that disease, may optionally be coadministered with the compounds according to the present invention. As used herein, additional therapeutic agents that are normally administered to treat or prevent a particular disease are known as appropriate for the disease being treated.

In a further aspect of the present invention, the compounds according to this invention or the salts of said compounds of formula (I), may be combined with standard therapeutic agents which are commonly used for the treatment of the medical conditions as described herein.

The person skilled in the art is aware on the base of his/her expert knowledge of the total daily dosage(s) and administration form(s) of the additional therapeutic agent(s) coadministered. Said total daily dosage(s) can vary within a wide range. In practicing the present invention and depending on the details, characteristics or purposes of their uses mentioned above, the compounds according to the present invention may be administered in combination therapy separately, sequentially, simultaneously or chronologically staggered (e.g. as combined unit dosage forms, as separate unit dosage forms or a adjacent discrete unit dosage forms, as fixed or nonfixed combinations, as kit-of-parts or as admixtures) with one or more standard therapeutics, in particular art-known chemotherapeutic or target specific anti-cancer agents, such as those mentioned above.

Thus, a further aspect of the present invention is a combination or pharmaceutical composition comprising a first active ingredient, which is a compound according to this invention or a salt thereof, a second active ingredient, which is an art-known standard therapeutic for the medical conditions as described herein, and optionally a pharmacologically acceptable carrier, diluent and/or excipient for sequential; separate, simultaneous or chronologically staggered use in therapy in any order, e.g. to treat, prevent or ameliorate in a patient the medical conditions as described herein.

In this context, the present invention further relates to a combination comprising a first active ingredient, which is at least one compound according to this invention, and a second active ingredient, which is at least one art-known standard therapeutic for the medical conditions as described herein, for separate, sequential, simultaneous or chronologically staggered use in therapy, such as e.g. in therapy of those diseases mentioned herein.

The term "combination" according to this invention may be present as a fixed combination, a non-fixed combination or a kit-of-parts. A "fixed combination" is defined as a combination wherein the said first active ingredient and the said second active ingredient are present together in one unit dosage or in a single entity. One example of a "fixed combination" is a pharmaceutical composition wherein the said first active ingredient and the said second active ingredient are present in admixture for simultaneous administration, such as in a formulation. Another example of a "fixed combination" is a pharmaceutical combination wherein the said first active ingredient and the said second active ingredient are present in one unit without being in admixture.

A "kit-of-parts" is defined as a combination wherein the said first active ingredient and the said second active ingredient are present in more than one unit. One example of a "kit-of-parts" is a combination wherein the said first active ingredient and the said second active ingredient are present separately. The components of the kit-of-parts may be administered separately, sequentially, simultaneously or chronologically staggered.

The first and second active ingredient of a combination or kit-of-parts according to this invention may be provided as separate formulations (i.e. independently of one another), which are subsequently brought together for simultaneous, sequential, separate or chronologically staggered use in combination therapy; or packaged and presented together as separate components of a combination pack for simultaneous, sequential, separate or chronologically staggered use in combination therapy.

The type of pharmaceutical formulation of the first and second active ingredient of a combination or kit-ofparts according to this invention can be similar, i.e. both ingredients are formulated in separate tablets or capsules, or can be different, i.e. suited for different administration forms, such as e.g. one active ingredient is formulated as tablet or capsule and the other is formulated for e.g. intravenous administration.

The amounts of the first and second active ingredients of the combinations, compositions or kits according to this invention may together comprise a therapeutically effective amount for the treatment, prophylaxis or amelioration of a medical condition as described herein A further aspect of the present invention is a method for treating cotherapeutically the medical conditions as described herein, in a patient in need of such treatment comprising administering separately, sequentially, simultaneously, fixed or non-fixed a pharmacologically active and therapeutically effective and tolerable amount of one or more of the compounds according to the present invention and a pharmacologically active and therapeutically effective and tolerable amount of one or more art-known therapeutic agents for the medical conditions as described herein, to said patient.

For the production of the pharmaceutical compositions, the compounds of the invention (=active compounds) are preferably mixed with suitable pharmaceutical auxiliaries and further processed to give suitable pharmaceutical formulations. Suitable pharmaceutical formulations are, for example, powders, emulsions, suspensions, sprays, oils, ointments, fatty ointments, creams, pastes, gels or solutions. The pharmaceutical compositions according to the invention are prepared by processes known per se.

The dosage of the active compounds is carried out in the customary order of magnitude. Topical application forms (such as ointments) thus contain the active compounds in a concentration of, for example, 0.1-99%. The customary dose in the case of systemic therapy (p.o.) is usually between 0.3 and 30 mg/kg per day, (i. v.) is usually between 0.3 and 30 mg/kg/h. The choice of the optimal dosage regime and duration of medication, particularly the optimal dose and manner of administration of the active compounds necessary in each case can be determined by a person skilled in the art on the basis of his/her expert knowledge.

A method for synthesis of the compounds of the formula (I) comprises the step of reacting a nitriloxyde with an acetoacetate, haloalkene or methylcrotonate to obtain a methylisooxazole derivative (Hanson J C et. al. J Chem Soc 1965, 5976-5979, Lasri J et. al. J Heterocyclic Chem, 45, 2008, 1385-1389). Nitriloxydes are obtained from aldehydes by the reaction of hydroxylamine (II) to obtain oximes (Cheng F K et. al. Bioorg Med Chem Lett 2006, 16, 3376. Oximes are reacting with n-Chlorsuccinimide to obtain the corresponding chlorooxime (III) (Balachandran S et. al. Bioorg Med Chen Lett. 19, 2009, 4773-4776).

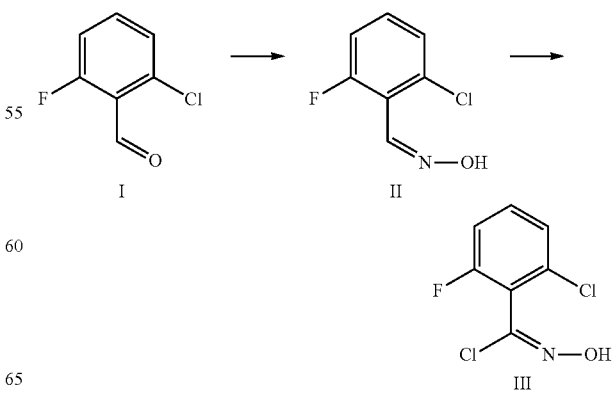

Scheme (1)

The chlorooxime (III) is used in situ to form the nitriloxyde (IV) and a cycloaddition to the appropriate dipolarophile yields the appropriate 3-phenyl-5-methylisoxazole (VI).

Scheme (2)

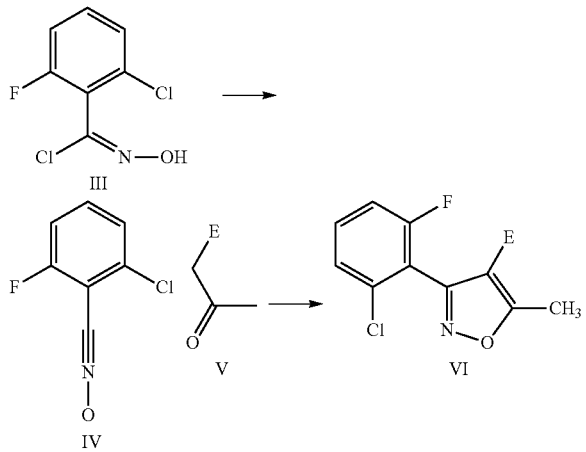

The isooxazole product (VI) can be converted with Bredereck's reagent (VIII) in refluxing toluene to the appropriate enamine (IXa) (Bredereck H et. al. Chem Ber 101, 1968, 41-50). This enamine compound (IXa) is treated with a acid anhydride or an appropriate activated acid (X) to the key intermediate phenyl-dimethylamino-trifluoro-oxobuteneyl-isoxazol (XIa). This intermediate is heated with a substituted hydrazine (XII) to obtain the pyrazol (XX).

Saponification of the ester (XX) (methyl or ethyl) yields the corresponding free acid (XXI), which is converted to the amide (XXII) by coupling reaction with ammoniumhydrochloride, HBTU (2-(1H-benzotriazol-1-yl)-1,1,3,3-tetramethyluronium hexafluorophosphate) and base (DIEPA) in DMA as solvent (Fields C. C. et. al. Peptide Research, Vol. 4, 1991, 95-101). The amide is converted to the thionamide with Lawesson's reagent in dioxane as solvent (Thomsen, I.; Clausen, K.; Scheibye, S.; Lawesson, S.-O., Org. Synth., Coll. Vol. 7, 1990, 372). The thionamide (XIX) is converted to the thiazole (compound 5) with 1,2-dichloro-1-ethoxyethane according to Boedeker, J., Pries, H., Roesch, D., Malewski, G., Journal fuer Praktische Chemie (Leipzig), Volume 317, Issue 6, 1975, 953-8.

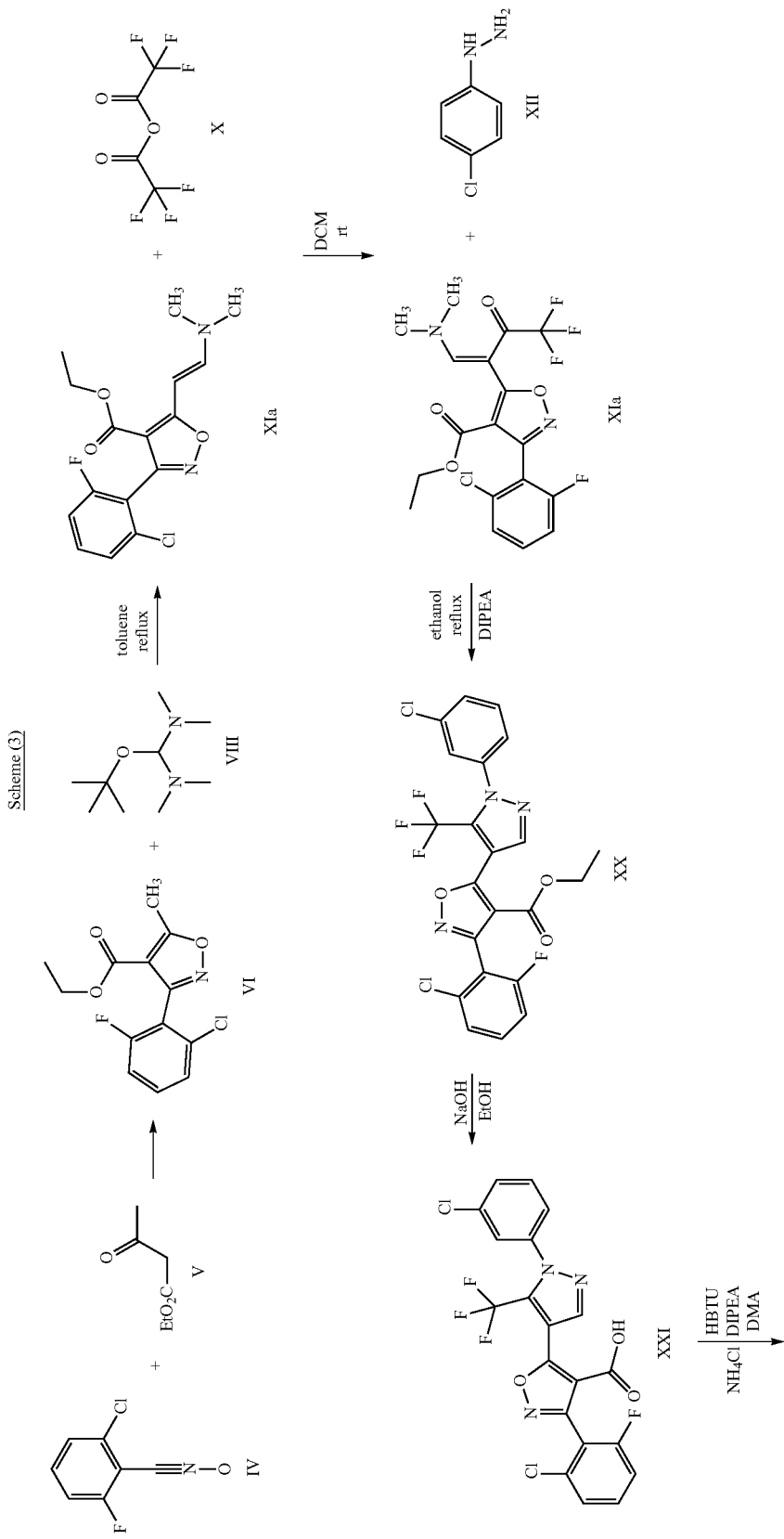

-continued
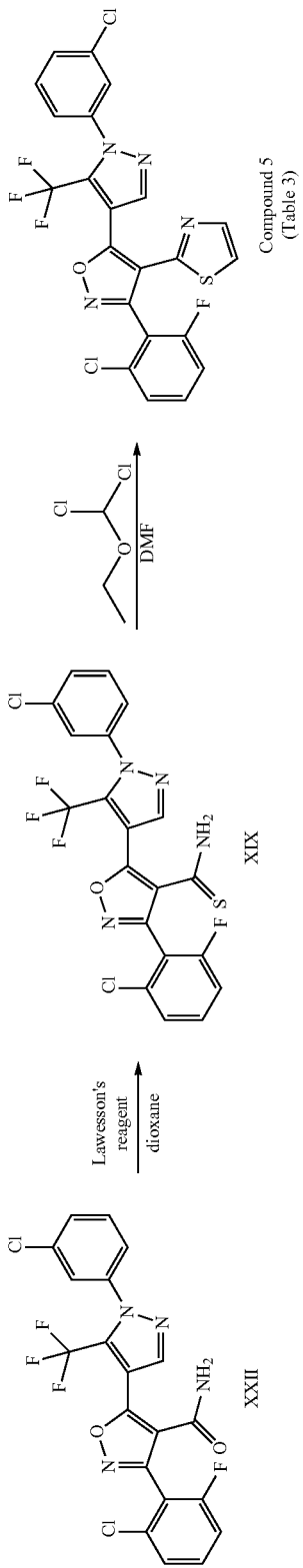

The class of compounds of the present invention is useful for the development of immunomodulatory and anti-inflammatory medicaments or, more generally, for the treatment of diseases where the inhibition of interleukin-17 (IL-17) and/or Interferon-γ (INF-γ) is beneficial.

The compounds of the present invention are also useful for the treatment of diseases which are related to or mediated by inflammatory cytokines, such as psoriasis, psoriatric arthritis, autoimmune thyroiditis, Grave's disease, rheumatoid arthritis, vitiligo, Crohn's disease, ulcerative colitis, inflammatory bowel disease, ankylosing spondylitis, diabetes type I, multiple sclerosis, celiac disease, systemic lupus erythematosus, uveitis, Behcet disease, atopic dermatitis, Lichen planus, Sjögren's syndrome, spinal disc herniation, acne, Graft-versus-Host-Reaction, Host-versus-Graft-Reaction and osteoarthritis

EXAMPLES

The following compounds were purchased:
1. tert-Butoxy-bis(dimethylamino)methan (Apollo Scientific Ltd, UK)
2. Methyl 3-(2-chloro-6-fluorophenyl)-5-methylisoxazole-4-carboxylate (Apollo Scientific Ltd, UK)
3. 3-(2-chloro-6-fluorophenyl)-5-methylisoxazole-4-carbonitrile (Fisher Scientific GmbH, UK)
4. Methylamin hydrochloride (Sigma Aldrich Chemie GmbH, Germany)
5. 2-chloro-6-fluorobenzaldehyde oxime (Fisher Scientific GmbH, UK)
6. N-Chlorosuccinimide, NCS (Acros Organics BVBA, Belgium)
7. Ethyl acetoacetate, Methyl acetoacetate (Sigma Aldrich Chemie GmbH, Germany)
8. Trifluoroacetic anhydride (Sigma Aldrich Chemie GmbH, Germany)
9. 2-(1H-Benzotriazole-1-yl)-1,1,3,3-Tetramethyluronium hexafluorophosphate, HBTU (Iris Biotech GmbH, Germany)
10. Hydroxybenzotriazole, HOBT (Sigma Aldrich Chemie GmbH, Germany)
11. Methyl 3-(2-chloro-6-fluorophenyl)-5-[2-(dimethylamino)-1-(2-ethoxy-2-oxoacetyl)vinyl]-4-isoxazolecarborylate (Key Organics Ltd, UK)
12. 1-(3-dimethylaminopropyl)-3-ethylcarbodiimide hydrochloride, EDC (Sigma Aldrich Chemie GmbH, Germany)
13. Hydrazines (ABCR GmbH & Co. KG, Germany)
14. Solvents generally (Sigma Aldrich Chemie GmbH, Germany)
15. N,N-Diisopropylethylamine, DIPEA (ACROS Organics, Belgium)
16. Ammoniumchlorid p.a. (Sigma Aldrich Chemie GmbH, Germany)
17. 2,4-bis(4-methoxyphenyl)-1,3,2,4-dithiadiphosphetane 2,4-disulfide, Lawesson's Reagent (Sigma Aldrich Chemie GmbH, Germany)
18. 1,2-Dichloroethyl ethyl ether (ABCR GmbH & Co. KG, Germany)
19. Natriumazid (ACROS Organics, Belgium)
20. N,O-Dimethylhydroxylamine (ChemPur GmbH, Germany)
21. Lithium aluminium hydride (Sigma Aldrich Chemie GmbH, Germany)
22. Tosylmethyl isocyanide, TosMIC (ACROS Organics, Belgium)

Synthesis of Compounds of Formula (I)

General Procedure for the Preparation of 5-methylisoxazole-4-carboxylate, exemplarily shown for Ethyl 3-(2-chloro-6-fluorophenyl)-5-methylisoxazole-4-carboxylate

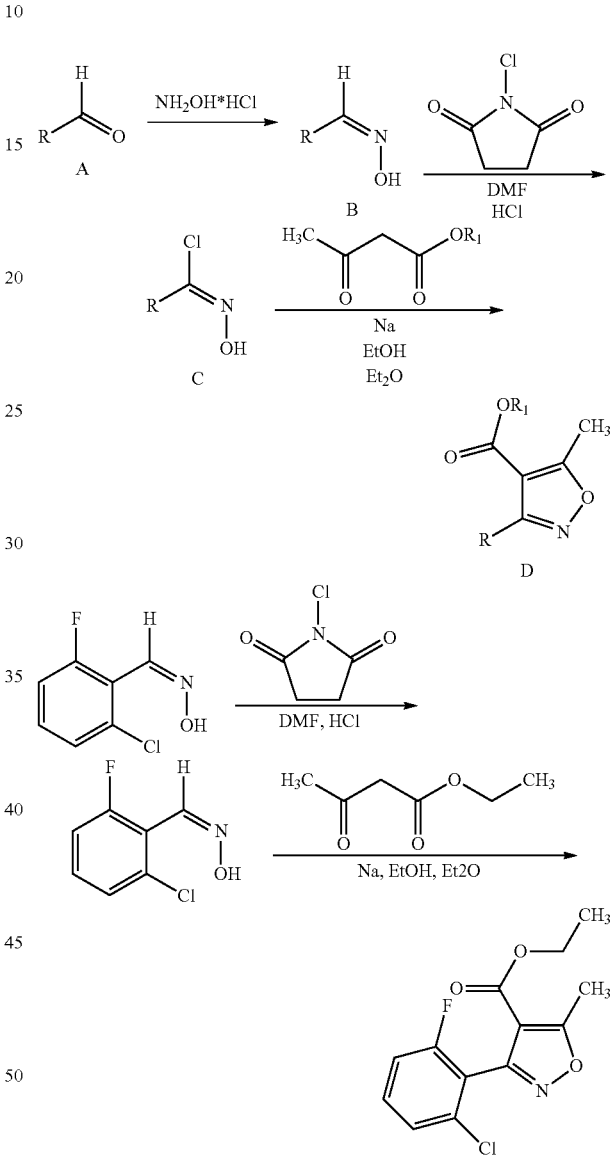

To a stirred mixture of aldehyde A (5 g, 31.5 mmol), ethanol (10 mL), ice and water (30 mL) and hydroxylamine hydrochloride (2.8 g, 40.3 mmol), an aqueous solution of NaOH (3.6 g, 90 mmol in 5 mL of water) was added. The mixture was stirred for an hour and extracted with 40 mL of ether to remove impurities. The aqueous layer was neutralized with HCl and extracted with ether (2×50 mL). Extracts were dried over $Na_2SO_4$ and evaporated to give 5.19 g of oxime B (yield 93%).

To a solution of aldoxime B (2 g, 11.5 mmol) in 10 mL of DMF, 0.23 g (1.72 mmol) of N-chlorosuccinimide (NCS) were added at room temperature. Dry hydrogen chloride was bubbled into the DMF solution until the reaction temperature rose up to 35° C. Then 1.31 g (9.8 mmol) of NCS was added portionwise, the temperature was kept at 35-45° C. The reaction mixture was cooled to room temperature and poured onto 30 mL of ice and extracted with ether. Combined extracts were dried and evaporated to give 2.5 g of hydroxamoyl chloride C as a yellow oil.

A solution of ethyl sodium acetoacetate [from sodium (0.3 g, 13 mmol), dry ethanol (10 mL) and ethyl acetoacetate (1.7 g, 13 mmol)] was added slowly to a stirred solution of the hydroxamoyl chloride C (2.5 g, 12 mmol) in 20 mL of ether at 0-3° C. The mixture was allowed to warm to room temperature overnight, and the solvent was evaporated in vacuo. The residue was taken up with water and ether, the ether extract was evaporated and the product was purified by column chromatography (hexane) to give 2.2 g of the isoxazole derivative D as a colorless oil.

Ethyl 3-(2-chloro-6-fluorophenyl)-5-methylisoxazole-4-carboxylate, oil, yield 67%

Result of LC/MS [M+H]$^+$: 283.95

$^1$H NMR (DMSO-D$_6$, CCl$_4$): 1.06 (3H, t, CH$_3$), 2.78 (3H, s, CH$_3$), 4.09 (2H, q, CH$_2$), 7.26 (1H, t, CH-arom.), 7.39 (1H d, CH-arom.), 7.55 (1H, m, CH-arom.).

Analoguously Prepared:

Ethyl 3-(2,4-dichlorophenyl)-5-methylisoxazole-4-carboxylate, oil, yield 82%

$^1$H NMR (DMSO-D$_6$, CCl$_4$): 1.10 (3H, t, CH$_3$), 2.74 (3H, s, CH$_3$), 4.10 (2H, q, CH$_2$), 7.42 (1H, d, CH-arom.), 7.47 (1H dd, CH-arom.), 7.59 (1H, d, CH— arom.).

Methyl 3-(4-methoxyphenyl)-5-methylisoxazole-4-carboxylate yield 65%

$^1$H NMR (DCCl$_3$): 2.71 (3H, s, CH$_3$), 3.79 (3H, s, OCH$_3$), 3.85 (3H, s, OCH$_3$), 6.97 (2H, AB-syst., CH-arom.), 7.60 (2H AB-syst., CH-arom.).

Methyl 3-isopropyl-5-methylisoxazole-4-carboxylate, oil, yield 64%

$^1$H NMR (DMSO-D$_6$, CCl$_4$): 1.26 (3H, s, CH$_3$), 1.27 (3H, s, CH$_3$), 2.62 (3H, s, CH$_3$), 3.37 (1H, m, CH-i-Pr.), 3.81 (1H s, OCH$_3$).

Synthesis of methyl 3-(2-chloro-6-fluorophenyl)-5-(2-(dimethylamino)vinyl)isoxazole-4-carboxylate

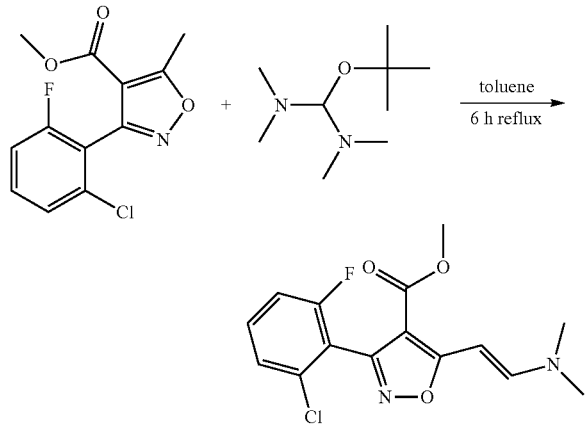

To a solution of 0.1 g (0.3708 mmol) methyl 3-(2-chloro-6-fluorophenyl)-5-methylisoxazole-4-carboxylate in 10 mL dry toluene, 0.15 mL (0.7417 mmol) tert-Butoxy-bis(dimethylamino)methane (Bredereck's reagent) were added. The reaction mixture was heated under reflux for 6 h.

The mixture was concentrated in vacuo and was dried in high vacuum. Petroleum ether was added to the oily residue and crystalline product developed. The product was collected by filtration, and 0.070 g (yield of theory: 58%) of the vinyl isoxazole derivative were obtained.

Result of LC/MS [M+H]$^+$: 325.0; $^1$H NMR (DMSO-d$_6$; CCl$_4$): 3.02 (6H, s, N—CH$_3$), 3.53 (3H, s, CH$_3$), 5.54-5.58 (1H, d, CH), 7.72-7.76 (1H, d, CH), 7.32-7.38 (1H, dd, CH-arom.), 7.44-7.47 (1H, d, CH-arom.), 7.56-7.58 (1H, d, CH-arom.)

Synthesis of methyl 3-(2-chloro-6-fluorophenyl)-5-(1-(dimethylamino)-4,4,4-trifluoro-3-oxobut-1-en-2-yl)isoxazole-4-carboxylate

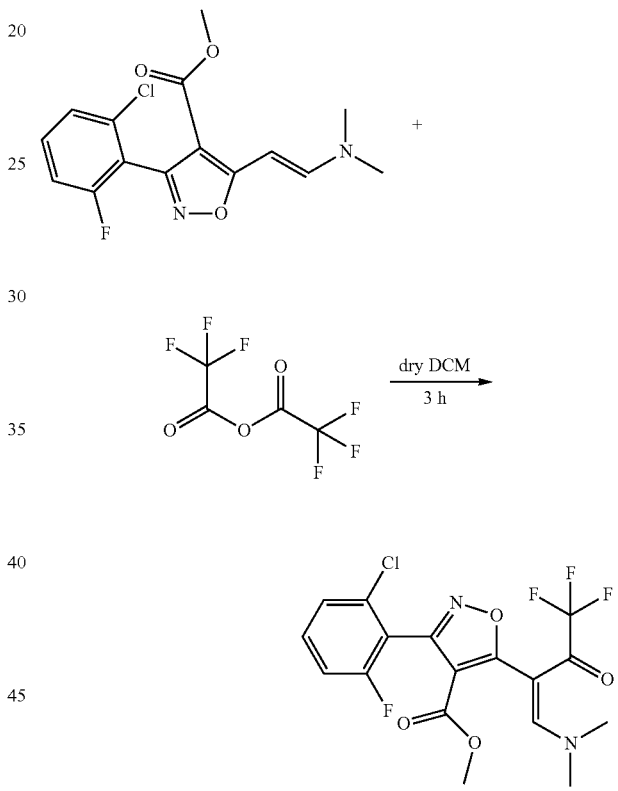

To a solution of 0.5 g (1.5397 mmol) methyl 3-(2-chloro-6-fluorophenyl)-5-[2-(dimethylamino)vinyl]isoxazole-4-carboxylate in 20 mL dry dichloromethane, 0.32 mL (2.309 mmol) trifluoroacetic anhydride were added dropwise under ice-bath cooling. The reaction mixture was stirred for 3 h at room temperature.

Afterwards the mixture was concentrated in vacuo and was dried in high vacuum. The oily residue crystallized from petroleum ether, and the product was collected by filtration to yield 0.604 g (yield of theory: 94%) of the 5-(1-(dimethylamino)-4,4,4-trifluoro-3-oxobut-1-en-2-yl)isoxazole derivative. Result of LC/MS [M+H]$^+$: 420.9; $^1$H NMR (DMSO-d$_6$; CCl$_4$): 2.63 (3H, s, N—CH$_3$), 3.40 (3H, s, N—CH$_3$), 3.59 (3H, s, CH$_3$), 7.40-7.46 (1H, dd, CH-arom.), 7.51-7.55 (1H, d, CH-arom.), 7.64-7.66 (1H, d, CH-arom.), 8.12 (1H, s, CH).

Synthesis of methyl 3-(2-chloro-6-fluorophenyl)-5-(1-(3-chlorophenyl)-5-(trifluoromethyl)-1H-pyrazol-4-yl)isoxazole-4-carboxylate

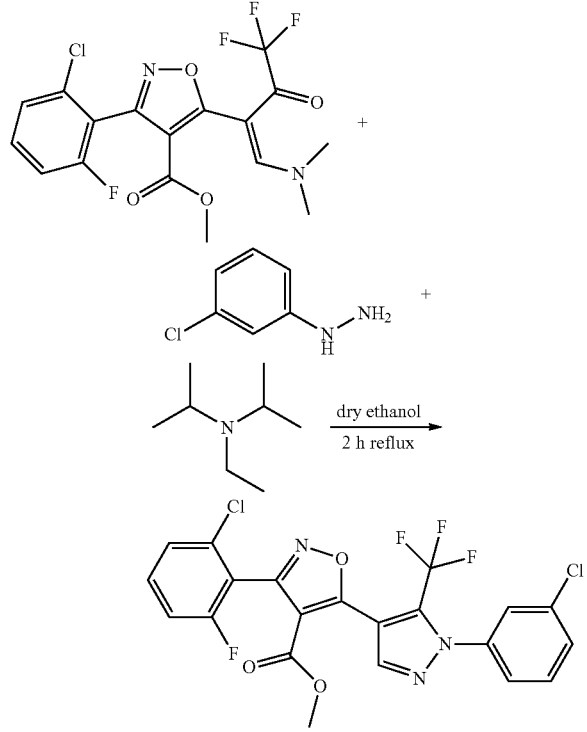

To a solution of 0.5047 g (1.1994 mmol) methyl 3-(2-chloro-6-fluorophenyl)-5-(1-(dimethylamino)-4,4,4-trifluoro-3-oxobut-1-en-2-yl)isoxazole-4-carboxylate in dry ethanol, 0.1790 g (0.9995 mmol) 3-Chlorophenylhydrazine and 0.17 mL (0.9995 mmol) N,N-Diisopropylethylamine (DIPEA) were added. The reaction mixture was heated under reflux for 2 h. The product was isolated by using column chromatography (Petroleum ether:Diethyl ether 80:20), and 0.305 g (yield of theory: 61%) of the pyrazolyl-isoxazole derivative were obtained. Result of LC/MS [M+H]$^+$: 499.9; $^1$H NMR (DMSO-d$_6$; CCl$_4$): 3.66 (3H, s, CH$_3$), 7.45-7.50 (1H, dd, CH-arom.), 7.55-7.58 (1H, d, CH-arom.), 7.65-7.77 (1H, d, CH-arom.), 7.65-7.77 (1H, dd, CH-arom. phenylhydrazine), 7.65-7.77 (1H, d, CH-arom. phenylhydrazine), 7.85 (1H, s, CH-arom phenylhydrazine), 8.56 (1H, s, 1-pyrazole)

Synthesis of (E)-3-(2-chloro-6-fluorophenyl)-5-(2-(dimethylamino)vinyl)isoxazole-4-carbonitrile

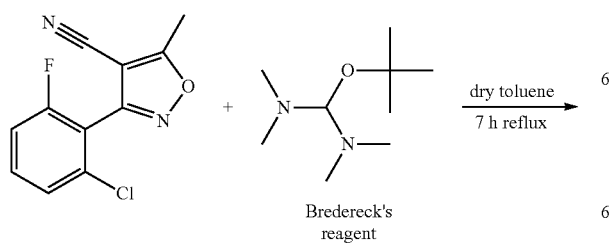

Bredereck's reagent

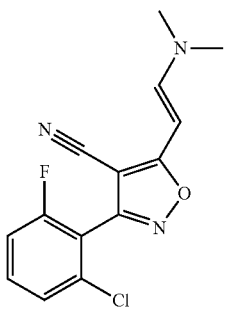

To a solution of 1.5 g (6.3389 mmol) 3-(2-chloro-6-fluorophenyl)-5-methylisoxazole-4-carbonitrile in 100 mL dry toluene, 2.10 g (12.6779 mmol) tert-Butoxy-bis(dimethylamino)methane (Bredereck's reagent) were added. The reaction mixture was heated under reflux for 12 h. The mixture was concentrated in vacuo and was dried in high vacuum. Petroleum ether was added to the crude material to trigger crystallization of the product. The product was collected by filtration, and 1.791 g (yield of theory: 95.9%) of the vinyl isoxazol derivative were obtained. Result of LC/MS MH$^+$: 292.0; $^1$H NMR (DMSO-d$_6$; CCl$_4$): 2.93 (3H, s, N—CH$_3$), 3.17 (3H, s, N—CH$_3$), 5.15-5.20 (1H, d, C$_2$H$_2$), 7.74-7.78 (1H, d, C$_2$H$_2$), 7.45-7.52 (1H, dd, CH-arom.), 7.57-7.59 (1H, d, CH-arom.), 7.65-7.71 (1H, d, CH-arom.)

Synthesis of (Z)-3-(2-chloro-6-fluorophenyl)-5-(1-(dimethylamino)-4,4,4-trifluoro-3-oxobut-1-en-2-yl)isoxazole-4-carbonitrile

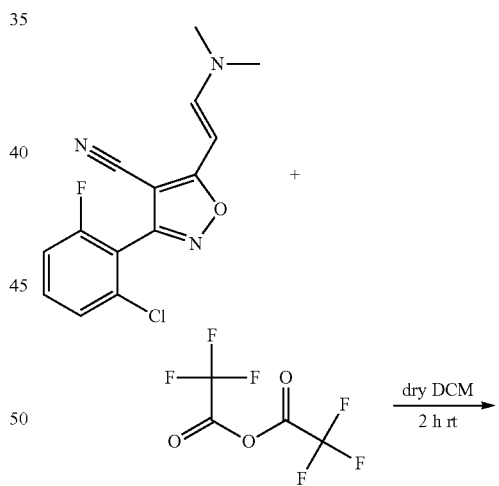

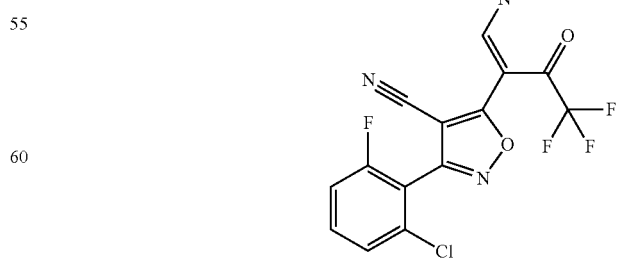

To a solution of 0.5 g (1.714 mmol) (E)-3-(2-chloro-6-fluorophenyl)-5-(2-(dimethylamino)vinyl)isoxazole-4-carbonitrile in 20 mL dry dichloromethane, 0.36 mL (2.571 mmol) trifluoroacetic anhydride were added dropwise under ice-bath cooling. The reaction mixture was stirred for 2 h at r.t. Afterwards the mixture was concentrated in vacuo and was dried in high vacuum. Petroleum ether was added to the crude material to trigger crystallization of the product, which was collected by filtration to obtain 0.625 g (yield of theory: 94%) of the 5-(1-(dimethylamino)-4,4,4-trifluoro-3-oxobut-1-en-2-yl)isoxazole derivative. Result of LC/MS MH$^+$: 388.0; $^1$H NMR (DMSO-d$_6$; CCl$_4$): 2.75 (3H, s, N—CH$_3$), 3.46 (3H, s, N—CH$_3$), 7.53-7.59 (1H, dd, CH-arom.), 7-64-7.67 (1H, d, CH-arom.), 7.73-7.81 (1H, d, CH-arom.), 8.23 (1H, s, CH)

Synthesis of 3-(2-chloro-6-fluorophenyl)-5-(1-(3-chlorophenyl)-5-(trifluoromethyl)-1H-pyrazol-4-yl)isoxazole-4-carbonitrile

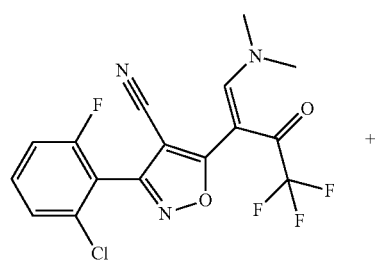

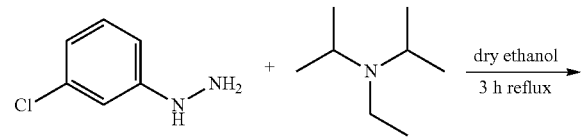

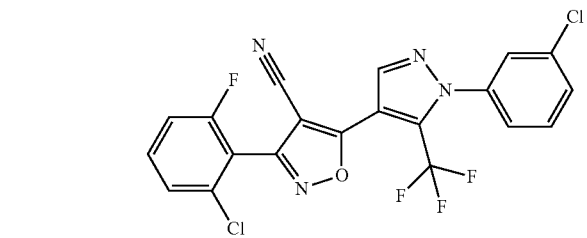

To a solution of 0.1 g (0.2579 mmol) (Z)-3-(2-chloro-6-fluorophenyl)-5-(1-(dimethylamino)-4,4,4-trifluoro-3-oxobut-1-en-2-yl)isoxazole-4-carbonitrile in dry ethanol, 0.0462 g (0.2579 mmol) 3-Chlorophenylhydrazine and 0.78 mL (0.2579 mmol) DIPEA were added. The reaction mixture was heated under reflux for 3 h. The mixture was concentrated in vacuo and was dried in high vacuum. Purification was achieved by using pTLC, and 0.0037 g (yield of theory: 3.0%) of the pyrazolyl-isoxazole derivativewere obtained. Result of LC/MS MH$^+$: 466.9; $^1$H NMR (DMSO-d$_6$; CCl$_4$): 7.73-7.97 (6H, m, CH-arom.), 8.04 (1H, s, CH-arom.), 8.81 (1H, s, CH-pyraz.)

Synthesis of 3-(2-chloro-6-fluorophenyl)-5-(1-(3-chlorophenyl)-5-(trifluoromethyl)-1H-pyrazol-4-yl)-4-(1H-tetrazol-5-yl)isoxazole (Example 3)

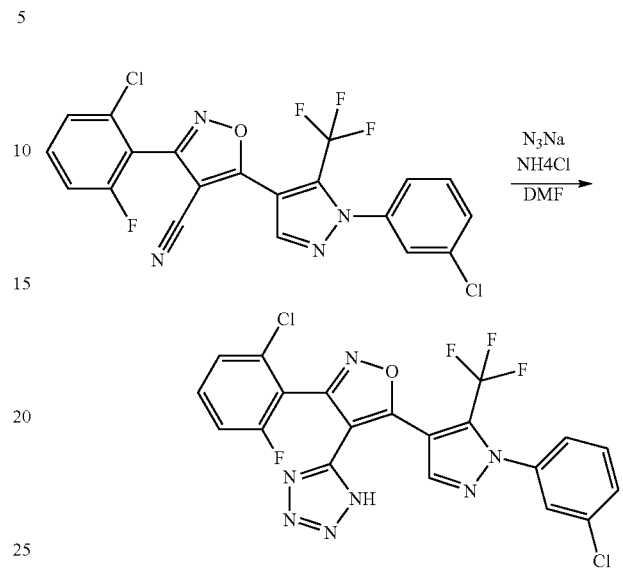

To a solution of 0.115 g (0.246 mmol) cyano-isoxazole in 10 mL dry DMF, 0.080 g (1.231 mmol) sodium azide and 0.065 g (1.231 mmol) ammoniumchloride were added. The mixture was stirred 4 hours at 90° C. The mixture was filtrated, and the filter cake was washed with acetonitrile. The filtrate was evaporated in vacuo. The brown, oily residue was purified by pTLC (petroleum ether:ethylacetate 80:20+5% acetic acid) and dried in vacuum to yield 49 mg (61%) of example 3. Result of LC/MS MH+: 509.71; $^1$H NMR (DMSO-d$_6$; CCl$_4$): 7.42-7.48 (1H, t, CH-arom.), 7.51-7.534 (1H, d, CH-arom.), 7.63-7.55 (4H, m, CH-arom), 7.81 (1H, s, CH-arom.), 8.58 (1H, s CH-pyraz.)

Examples 1 and 2 were Synthesized in Analogy.

Synthesis of 3-(2-chloro-6-fluorophenyl)-5-(1-(3-chlorophenyl)-5-(trifluoromethyl)-1H-pyrazol-4-yl)-4-(thiazol-2-yl)isoxazole (Example 5)

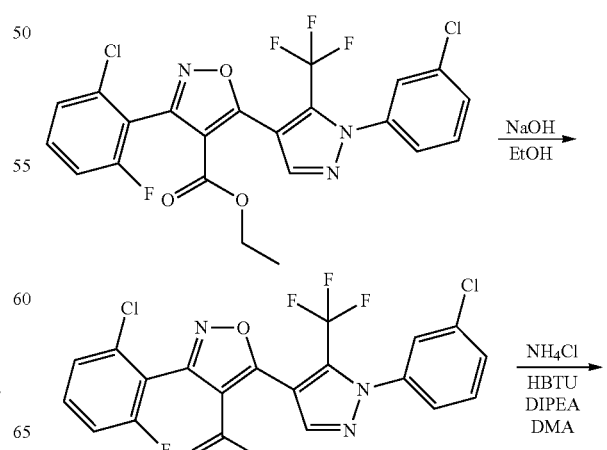

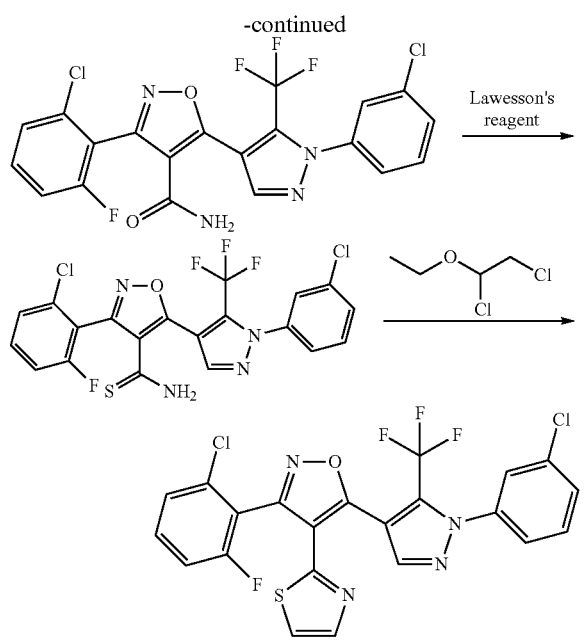

7.13 g (13.86 mmol) of the ethyl ester were dissolved in 150 mL ethanol, and 10 mL NaOH (2.0 mmol) were added. The mixture was heated under reflux for 1 hour. The ethanol was evaporated in vacuum and the basic solution was adjusted to pH 2 by adding hydrochloride acid (10% aq). The acidic solution was extracted with ethyl acetate. The organic layer was dried over anhydrous magnesium sulfate. The solvent was removed in vacuo and the residue was dried in vacuum to yield 6.0 g (89%) of the corresponding carboxylic acid.

To a solution of 6.0 g (12.34 mmol) of the carboxylic acid and 1.98 g (37.021 mmol) ammoniumchlorid in 20 mL dry DMA, 9.36 g (24.681 mmol) HBTU and 6.45 mL (37.021 mmol) DIPEA were added. The mixture was stirred 3 hours at r.t. Ethyl acetate was added to the reaction mixture, and it was washed twice with sodium hydrogen carbonate (5%, aq) and citric acid (5%, aq). The organic layer was dried over anhydrous magnesium sulfate, and the solvent was removed under reduced pressure. The oily residue became solid by drying in vacuum. The solid was washed with petroleum ether, filtrated and dried in vacuum to yield 5.37 g (90%) of the corresponding carboxamide.

To a solution of 5.355 g (11.036 mmol) of the carboxamide in 20 mL dry dioxane, 4.463 g (11.036 mmol) Lawesson's Reagent were added. The mixture was stirred for 4 hours under reflux. Then the solvent was removed in vacuo. The oily residue was purified by column chromatography (petroleum ether:ethylacetate 80:20) to yield 1.716 g (31%) of the respective carbothioamide.

To a solution of 1.022 g (2.039 mmol) of the carbothioamide in 20 mL dry DMF, 0.5 mL (4.077 mmol) 1,2-Dichloroethyl ethyl ether were added. The mixture was stirred 2 hours at 90° C. and then 2 hours at 130° C. The solvent was removed in vacuo, and the oily residue was purified by column chromatography (petroleum ether:ethyacetate 80:20) to yield 180 mg. (17%) of example 5. Result of LC/MS MH+: 524.9; $^1$H NMR (DMSO-$d_6$; $CCl_4$): δ 7.47-7.53 (1H, t, CH-arom.), 7.58-7.60 (1H, d CH-arom.), 7.65-7.66 (1H, d, CH-arom.) 7.65-7.67 (1H, d, CH-arom.), 7.71-7.73 (1H, t, CH-arom.), 7.74-7.75 (1H, d CH-arom.), 7.74-7.75 (1H, s, CH-thiaz.), 7.83 (1H, s, CH-arom), 7.84-7.85 (1H, s, CH-thiaz.), 7.59 (1H, s, CH-pyraz.)

An Alternative Route was Realized for Examples 29 and 30, Exemplarily Shown for 29:

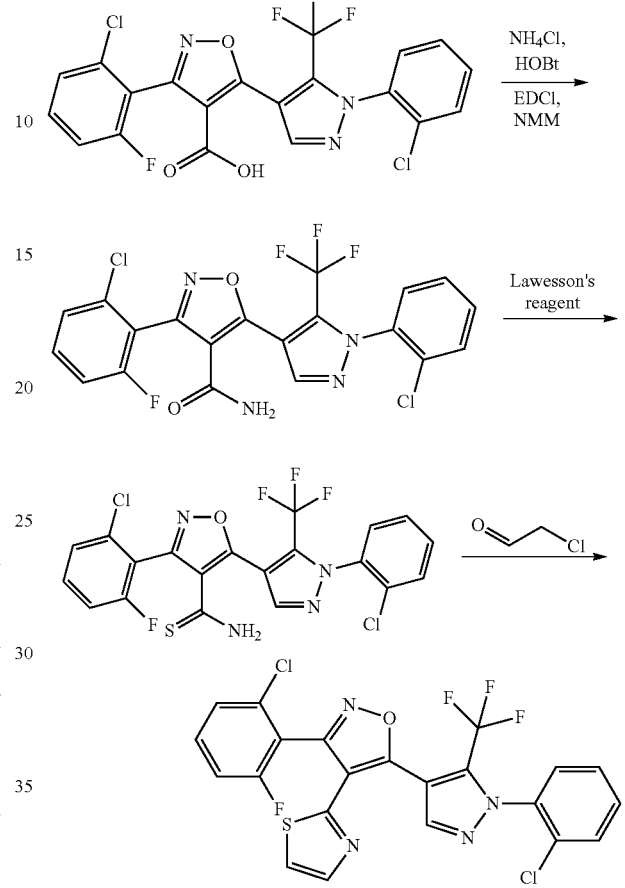

3-(2-chloro-6-fluorophenyl)-5-(1-(2-chlorophenyl)-5-(trifluoromethyl)-1H-pyrazol-4-yl)isoxazole-4-carboxylic acid (100 mg, 0.21 mmol), ammonium chloride (10 mg, 0.21 mmol), HOBt (27.8 mg, 0.21 mmol) and EDCI (38.3 mg, 0.25 mmol) were dissolved in 2 mL dry DMF. N-Methylmorpholine (104.2 µL, 2.1 mmol) was added and the reaction was stirred at room temperature for 72 h. DMF was removed by evaporation. An aqueous solution of aqueous 5% citric acid was added. The precipitate was filtered and dried. The mixture was purified by pTLC ($CH_2Cl_2$/MeOH 95/5) to give 50 mg (yield 50%) of the respective carboxamide.

The Lawesson's reagent step was performed as described within the synthesis of example 5.

To a solution of 3-(2-chloro-6-fluorophenyl)-5-(1-(2-chlorophenyl)-5-(trifluoromethyl)-1H-pyrazol-4-yl)isoxazole-4-carbothioamide (15 mg, 0.03 mmol) in 0.5 mL ethanol was added 2-chloroacetaldehyde (0.046 mL, 0.4 mmol). The mixture was stirred for 48 h at 85° C. The mixture was concentrated, diluted with dichloromethane and washed with water (3×), dried over sodium sulfate, filtered and concentrated under reduced pressure. The resulting oil was purified by pTLC (DCM:MeOH 100:5) to give 10.4 mg of example 29 as a yellow oil (yield 66%). Result of LC/MS MH+: 524.57; $^1$H NMR ($CDCl_3$): δ 7.11 (m, 1H), 7.28 (m, 1H), 7.33-7.42 (m, 6H), 7.52 (m, 1H), 8.37 (s, 1H)

Synthesis of methyl 3-(2-chloro-6-fluorophenyl)-5-(1-(2,4-difluorophenyl)-5-(trifluoromethyl)-1H-pyrazol-4-yl)isoxazole-4-carboxylate (Example 4)

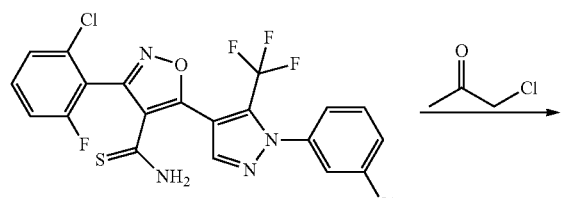

3-(2-chloro-6-fluorophenyl)-5-(1-(3-chlorophenyl)-5-(trifluoromethyl)-1H-pyrazol-4-yl)isoxazole-4-carbothioamide (50.0 mg, 0.100 mmol) and Chloroacetone (0.04 mL 0.5 mmol) were dissolved in 10 mL dry ethanol. The mixture was stirred at r.t. for 4 h. Purification of product was achieved by pTLC (petroleum ether:ethyl acetate 80:20). Drying in high vacuum yielded 20 mg (37%) of example 4 as a colorless oil. Result of LC/MS MH+: 538.76

¹H NMR (DMSO-d₆; CCl₄): 2.32 (s, 1H, CH₃), 6.72 (s, 1H, CH-thiaz.), 7.04-7.52 (m, 7H, arom.), 8.33 (s, 1H, CH-pyraz.);

Synthesis of 4-bromo-3-(2-chloro-6-fluorophenyl)-5-(1-(3-fluorophenyl)-5-(trifluoromethyl)-1H-pyrazol-4-yl)isoxazole

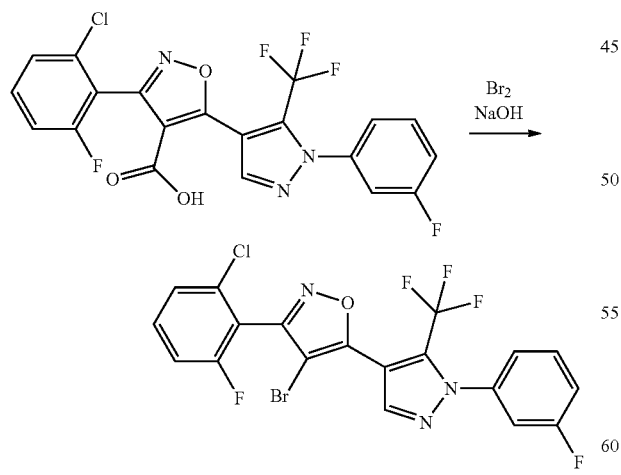

0.32 g (0.70 mmol) of the carboxylic acid were dissolved in aq. NaOH solution (20 mL water+0.115 g NaOH). Bromine (0.34 g, 2.1 mmol) was added slowly and dropwise to this solution at stirring and cooling (0-5° C.). Stirring continued for 2 hours at 0-5° C. and for 2 days at r.t. The precipitate was filtered off and suspended in 5% aq. NaOH solution (10 mL). After 2 hours of stirring solids were filtered off, washed with water and dried in vacuum to yield 0.15 g (0.30 mmol, 42%) of the brominated isoxazole as white crystals. Result of LC/MS MH+: 505.7; ¹H NMR (DMSO-d₆; CCl₄): 7.35-7.48 (m, 4H) 7.52 (d, J=8.28 Hz, 1H) 7.61-7.74 (m, 2H) 8.4 (s, 1H)

Synthesis of methyl 3-(2-chloro-6-fluorophenyl)-5-(1-(3-fluorophenyl)-5-(trifluoromethyl)-1H-pyrazol-4-yl)isothiazole-4-carboxylate (Example 7)

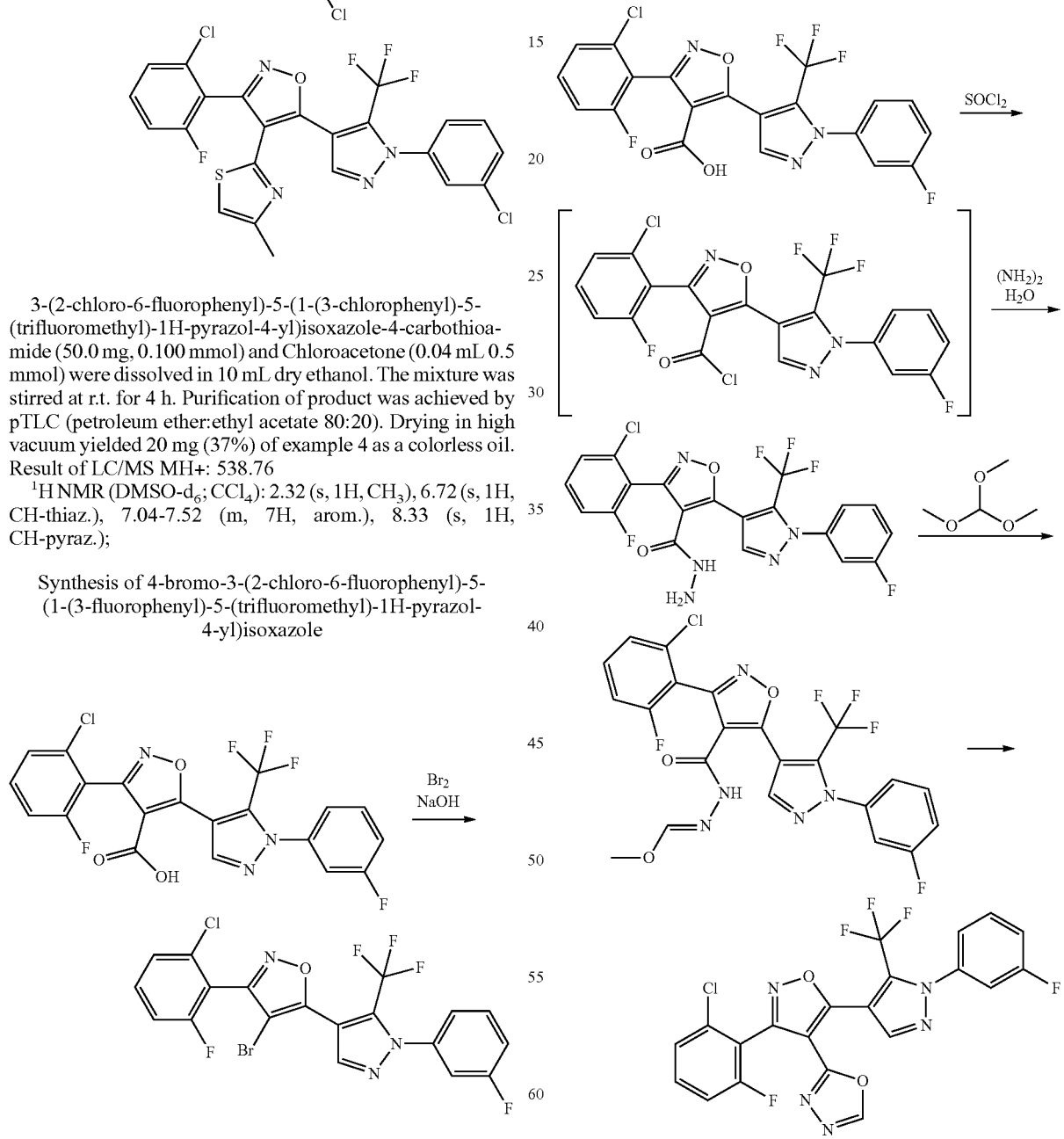

A solution of 102 mg (0.217 mmol) of the carboxylic acid in 8 mL SOCl₂ was refluxed for 3 h. Volatiles were evaporated in vacuum thoroughly. The residue was dissolved in 8 mL absolute dioxane and added dropwise to a stirred mixture of 825 mg N₂H₄*H₂O and 6 mL absolute dioxane. Volatiles were evaporated, some water was added to precipitate an oily pink solid. Water was removed, residue was washed with water, then treated with 5 mL water with 10 drops of AcOH and finally washed with water. The product was partially extracted by boiling heptane (38 mg) and partially extracted by ether with further treating of ethereal solution by heptane (39 mg). The hydrazide was attained in a total yield of 77 mg (73%).

A solution of the hydrazide (125 mg, 0.258 mmol) in 2.0 mL methyl orthoether was heated to boiling temperature and immediately cooled to r.t. Further additional 2 mL of methyl orthoether was added and the solution was refluxed for 1.5 days. Excess orthoether was evaporated, the residue was treated with boiling heptane and evaporated. The residue was purified by column chromatography on silica gel (eluent EtOAc/heptane 1/3 to 1/1), the fraction with pure product was combined and evaporated to give 47 mg (37%) of example 7. Result of LC/MS MH+: 494.8; ¹H NMR (DMSO-d₆; CCl₄): 7.20 (td, J=8.53, 0.75 Hz, 1H) 7.24-7.44 (m, 5H) 7.47-7.59 (m, 2H) 8.35 (s, 1H) 8.40 (s, 1H).

Synthesis of 3-(2-chloro-6-fluorophenyl)-5-(1-(3-chlorophenyl)-5-(trifluoromethyl)-1H-pyrazol-4-yl)-4-(oxazol-5-yl)isoxazole (Example 8)

To a solution of 10.8 g (22.2 mmol) of the carboxylic acid, 2.17 g (1 eq) N,O-Dimethylhydroxylamine and 8.42 g (1 eq) HBTU in DMF, 3.68 mL DIPEA were added. The mixture was stirred overnight at r.t. The solvent was removed in vacuum. The residue was dissolved in ethyl acetate and extracted with sodium hydrogen carbonate (5%, aq) and citric acid (5%, aq). The organic layer was dried over anhydrous magnesium sulfate and the solvent was removed in vacuum. The product was isolated by column chromatoghraphy (6:4 petroleum ether:ethyl acetate). The product resulting Weinreb amide was dried under vacuum to yield 2.28 g (19%).

To an ice-cooled solution of 1.0 g (1.8895 mmol) of the Weinreb amide in dry THF 0.95 mL (0.5 eq=2 eq H) lithiumaluminium hydride were added. After stirring for 30 min, TLC (4:1 petroleum ether:ethyl acetate) shows no more educt. To quench the remaining lithiumaluminium hydride, ice was added carefully to the mixture. For further purification, the solution was diluted with ethyl acetate and extracted three times with sodium hydrogen carbonate (5%, aq) and citric acid (5%, aq). The organic layer was dried over anhydrous magnesium sulfate and the solvent was removed in vacuum. The resulting aldehyde was dried under vacuum to yield 520 mg (58%).

To a solution of 0.5 g (1.0634 mmol) the aldehyde in dry methanol (10 mL), 5 mL sodium methanolate (from 83 mg

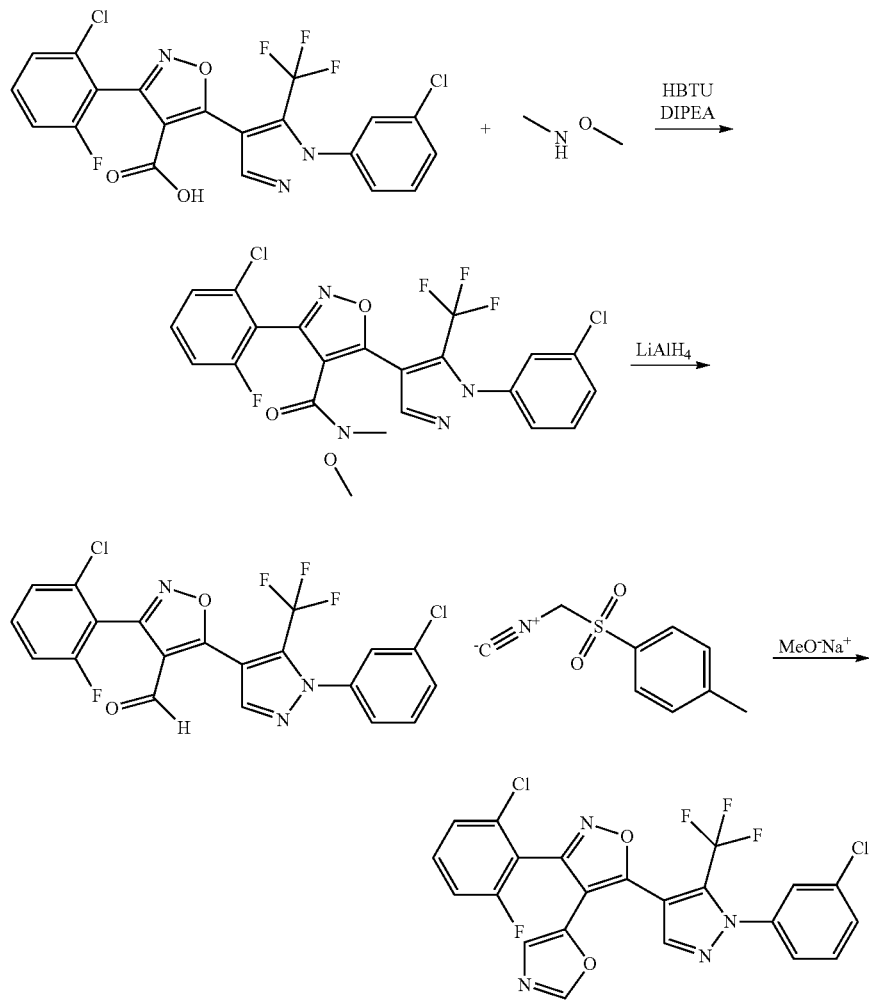

sodium in 5 mL dry methanol) were added carefully under argon. After stirring for 5 min at r.t., 0.25 g (1.2 eq) TosMIC were added stepwise. The mixture was stirred under reflux for 2 hours. The product of example 8 was isolated by preparative HPLC/MS to yield 128 mg (24%). Result of LC/MS MH+: 508.78

¹H NMR (DMSO-d₆; CCl₄): 6.92 (1H, s, CH-oxazole), 7.49-7.78 (6H, m, CH-arom.), 7.87 (1H, s, CH-arom.), 8.41 (1H, s, CH-oxazole.), 8.50 (1H, s, CH-pyraz.)

An Alternative Route was Realized for Examples 28, 32 and 33, Exemplarily Shown for 28:

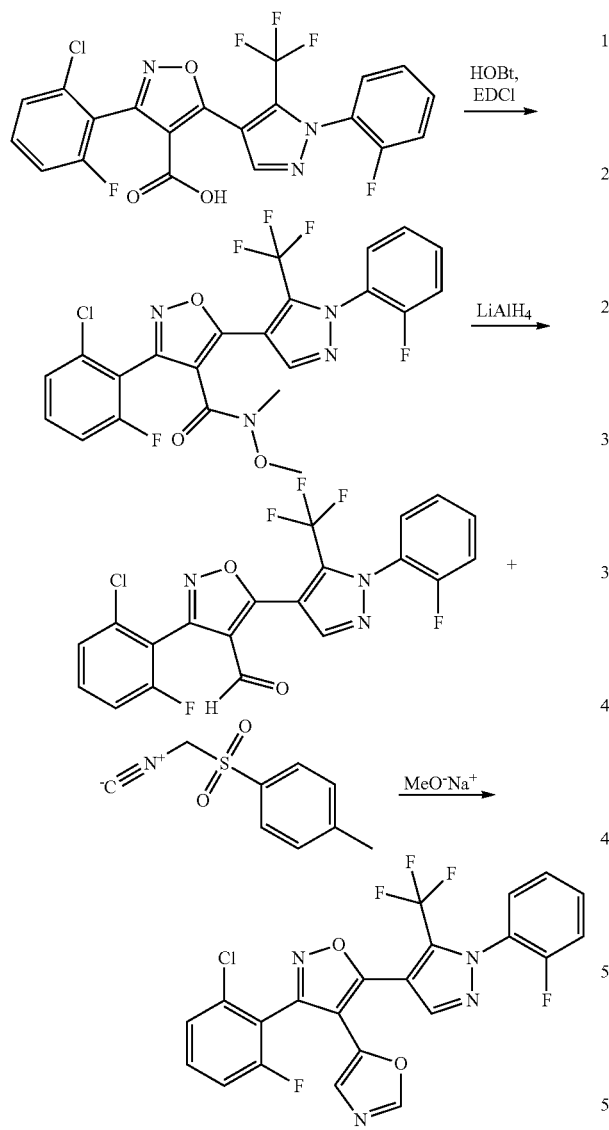

3-(2-chloro-6-fluorophenyl)-5-(1-(2-fluorophenyl)-5-(trifluoromethyl)-1H-pyrazol-4-yl)isoxazole-4-carboxylic acid (0.3 g, 0.64 mmol), N,O-Dimethylhydroxylamine (0.062 g, 0.64 mmol), HOBt (0.082 g, 0.064 mmol) and EDCI (0.118 g, 0.76 mmol) were dissolved in 3 mL dry DMF. N-Methylmorpholine (104 μL, 6.4 mmol) was added and the reaction was stirred at room temperature overnight. DMF was removed by evaporation. An aqueous solution of 5% citric acid was added. The precipitate was filtered and dried. The product was purified by pTLC (PE/EE 7/3) to give the Weinreb amideas an orange solid (149 mg, yield 45%). The subsequent steps were performed as described for the synthesis of example 8.

Within the final step of this synthetic route in similar conversions, byproduct formation was observed in a few cases resulting from a replacement of the aromatic fluoro substituent by methanolate, giving rise to examples 31 and 34.

Synthesis of 2-(3-(2-chloro-6-fluorophenyl)-5-(1-(3-fluorophenyl)-5-(trifluoromethyl)-1H-pyrazol-4-yl)isoxazol-4-yl)thiazol-4-ol (Example 9)

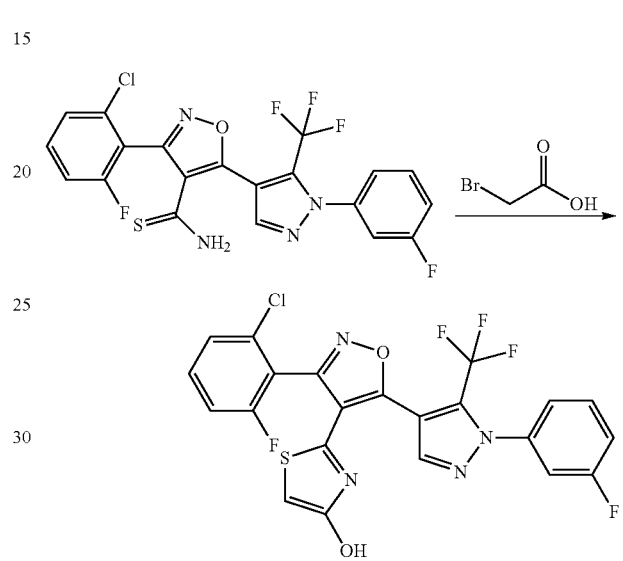

A mixture of 0.145 g (0.03 mmol) of the above thioamide, 0.60 g (0.42 mmol) bromoacetic acid and 5 mL toluene was heated under reflux for 2 h. Then reaction mixture was evaporated in vacuum. Thick oil was washed with water and purified by column chromatography on silica gel, using CCl₄, then CHCl₃/CCl₄ (1:1, v/v) as eluents. Yield of glassy substance of example 9 is 0.063 g (40%). Result of LC/MS MH+: 525.01; ¹H NMR (DMSO-d₆; CCl₄): 7.60-7.94 (7H, m, CH-arom.), 8.62 (1H, s, CH-pyraz.), 8.84 (1H, s, CH-thiazole), 10.81 (1H, s, OH)

Synthesis of 3-(2-chloro-6-fluorophenyl)-5-(1-(3-fluorophenyl)-5-(trifluoromethyl)-1H-pyrazol-4-yl)-4-(4-methoxythiazol-2-yl)isoxazole (Example 10)

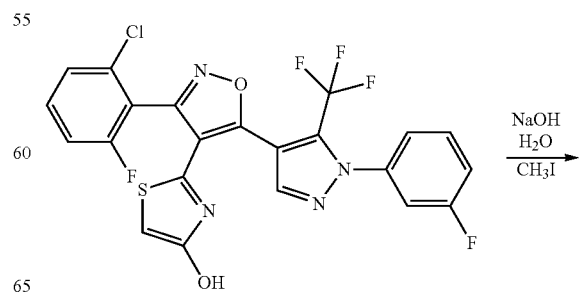

-continued

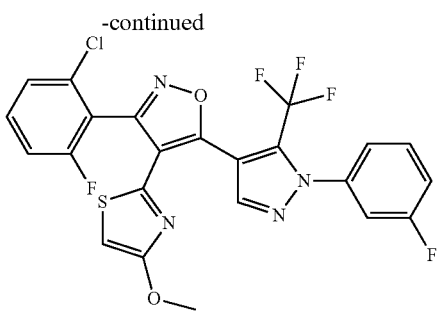

To a stirred solution of 52 mg (0.1 mmol) hydroxyl thiazole (example 9) in 5 ml dioxane were added alternately in small portions 0.140 g (1.0 mmol) of CH$_3$I and a solution of 40 mg (1.0 mmol) NaOH in 1 mL water. The pH has to be kept at 8-9 and the temperature at 40-50° C. Then the reaction mixture was stirred for 1 hour at 40-50° C., diluted with 15 mL water, neutralized with HCl to pH 6-7. Thick oil was extracted with CCl$_4$, dried with MgSO$_4$ and purified by column chromatography on silica gel, using CCl$_4$, then CHCl$_3$/CCl$_4$ (1:1, v/v) as eluents. Yield of glassy substance of example 10 is 20 mg (37%). Result of LC/MS MH+: 539.03; $^1$H NMR (DMSO-d$_6$; CCl$_4$): 3.73 (3H, s, CH$_3$), 6.59 (1H, s, CH-thiazole), 7.52-7.78 (7H, m, CH-arom.), 8.62 (1H, s, CH-pyraz.)

Synthesis of 2-(3-(2-chloro-6-fluorophenyl)-5-(1-(2-fluorophenyl)-5-(trifluoromethyl)-1H-pyrazol-4-yl)isoxazol-4-yl)-5-methyl-1,3,4-oxadiazole (Example 11)

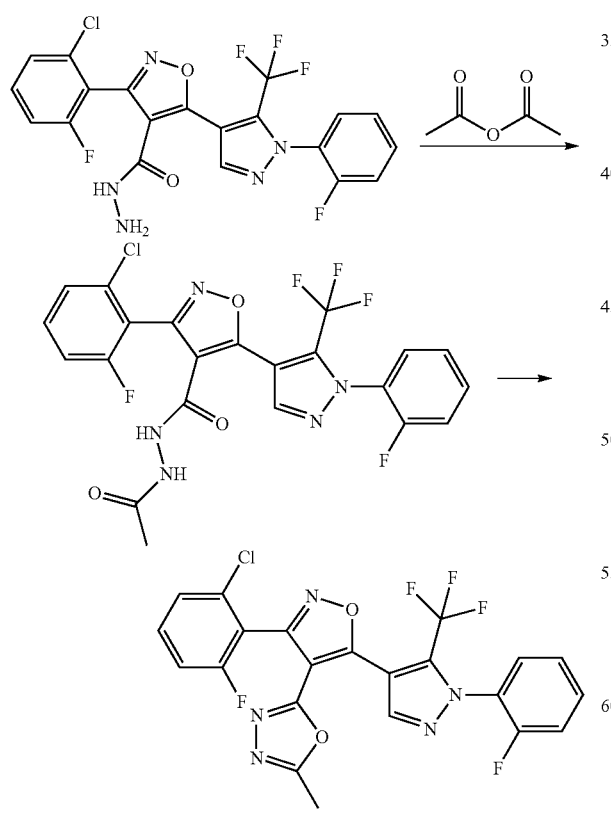

A solution of 3-(2-chloro-6-fluorophenyl)-5-[1-(2-fluorophenyl)-5-(trifluoromethyl)-1H-pyrazol-4-yl)]isoxazole-4-carbohydrazide (66 mg, 0.137 mmol) in acetic anhydride (3.5 g) was kept in a sealed tube at 140° C. for 18 hours. The solvent was removed in vacuum. Residue was re-evaporated with ethanol, and treated with boiling heptane. The concentration and cooling of heptane extract gave a solid. Column chromatography on silica gel (eluent EtOH/heptane, 1/1) gave 40 mg (58%) of colorless powder of example 11. Result of LC/MS MH+: 508.05

$^1$H NMR (400 MHz, METHANOL-d$_4$) δ ppm 2.44 (s, 3H) 7.28-7.35 (m, 1H) 7.41-7.49 (m, 3H) 7.69 (s, 3H) 8.48 (d, J=0.50 Hz, 1H)

Alternatively, the reaction can be performed under microwave irradiation as realized for examples 4, 10, 18, 19 and 26, exemplarily shown for 4.

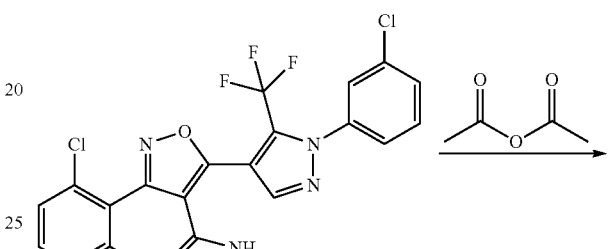

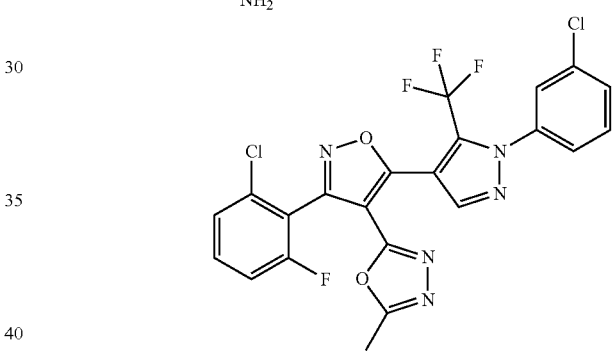

A similar mixture as generated within the synthesis of example 11, consisting of hydrazide in acetic anhydride, was heated under microwave irradiation at 140° C. for 6 h. The mixture was diluted with dichloromethane and washed with water, dried over sodium sulfate, filtered and concentrated under reduced pressure. The product was purified by pTLC (EE/PE 1:1).

Synthesis of N-(3-(4-(3-(2-chloro-6-fluorophenyl)-4-(5-methyl-1,3,4-oxadiazol-2-yl)isoxazol-5-yl)-5-(trifluoromethyl)-1H-pyrazol-1-yl)phenyl)acetamide (Example 11)

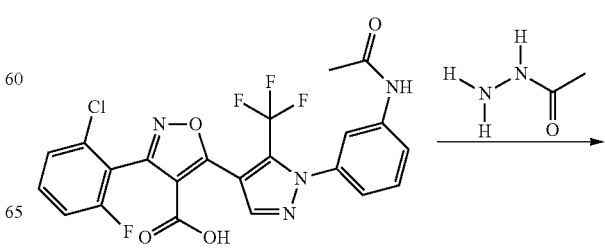

Synthesis of 3-(2-chloro-6-fluorophenyl)-4-(5-methyl-1,3,4-thiadiazol-2-yl)-5-(1-(pyridin-4-yl)-5-(trifluoromethyl)-1H-pyrazol-4-yl)isoxazole (Example 22)

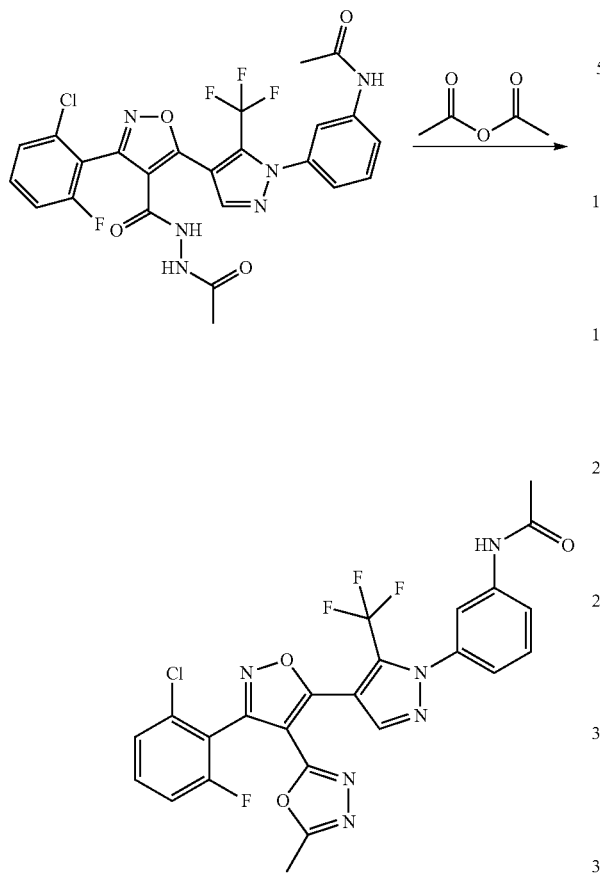

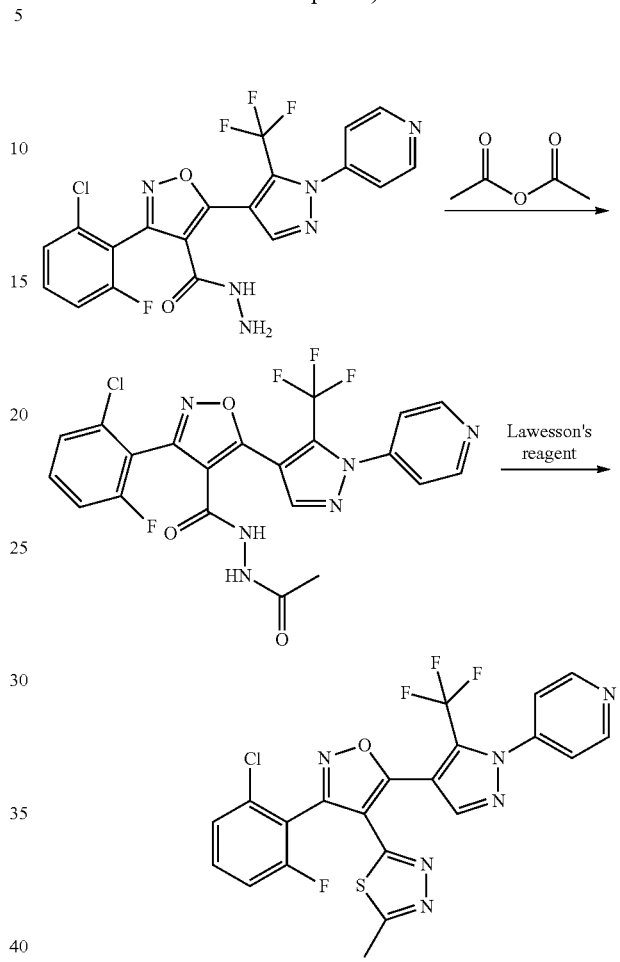

5-(1-(3-acetamidophenyl)-5-(trifluoromethyl)-1H-pyrazol-4-yl)-3-(2-chloro-6-fluorophenyl)isoxazole-4-carboxylic acid (100 mg, 0.196 mmol), acethydrazide (16.0 mg, 0.216 mmol) and HATU (97.1 mg, 0.255 mmol) were dissolved in THF (2.00 mL). DIPEA (268 µL, 0.589 mmol) was added and the resulting mixture was stirred at r.t. for 3.5 h. Additional acethydrazide (160 mg) and HATU (100 mg) were added and stirring was continued at r.t. for 19 h. The reaction mixture was diluted with CH$_2$Cl$_2$ (40 mL) and washed with 1N aq. HCl (1×20 mL) and water (2×20 mL). The combined aqueous layers were re-extracted with CH$_2$Cl$_2$ (20 mL) and the combined organic layers were dried over Na$_2$SO$_4$ and concentrated in vacuo. The residue was purified by pTLC (EtOAc/MeOH=9:1) to give 34 mg of the intermediate as brown oil (yield 31%).

The intermediate N-(3-(4-(4-(2-acetylhydrazinecarbonyl)-3-(2-chloro-6-fluorophenyl)isoxazol-5-yl)-5-(trifluoromethyl)-1H-pyrazol-1-yl)phenyl)acetamide (25.0 mg, 0.044 mmol) was dissolved in acetic acid (1.50 mL). Acetic anhydride (104 µL, 1.1 mmol) was added and the reaction mixture was heated in the microwave to 140° C. for 8 h. The reaction mixture was diluted with water (40 mL) and extracted with CH$_2$Cl$_2$ (3×20 mL). The combined organic layers were washed with water (10 mL), dried over Na$_2$SO$_4$ and concentrated in vacuo. The residue was purified by pTLC (CH$_2$Cl$_2$/MeOH=9:1) to give 2.6 mg of example 11 as a yellow solid (yield 8%). Result of LC/MS MH$^+$: 546.87; $^1$H NMR (MeOD): δ ppm: 2.05 (s, 3H), 2.33 (s, 3H), 7.20 (m, 2H), 7.33-7.61 (m, 4H), 7.93 (s, 1H), 8.39 (s, 1H)

To a solution of 3-(2-chloro-6-fluorophenyl)-5-(1-(pyridin-4-yl)-5-(trifluoromethyl)-1H-pyrazol-4-yl)isoxazole-4-carbohydrazide (0.03 g, 0.06 mmol) in acetic acid (0.03 mL) was added acetic anhydride (0.01 mL, 0.06 mmol). The mixture was stirred at r.t. for 2 h. The mixture was diluted with dichloromethane and washed with water, dried over sodium sulfate, filtered and concentrated under reduced pressure to give 29 mg of the intermediate as a brown oil.

To a solution of N'-acetyl-3-(2-chloro-6-fluorophenyl)-5-(1-(pyridin-4-yl)-5-(trifluoromethyl)-1H-pyrazol-4-yl)isoxazole-4-carbohydrazide (0.029 mg, 0.01 mmol) in dioxane (1.5 mL) was added Lawesson's Reagent (23.1 mg, 0.01 mmol). The mixture was stirred at reflux for 30 min. The mixture was then diluted with dichloromethane and washed with water (3×), dried over sodium sulfate, filtered and concentrated under reduced pressure.

The product was purified by pTLC (CH$_2$Cl$_2$:MeOH 100:5) to give 7.7 mg of example 22 as an oil (yield 26%). Result of LC/MS MH$^+$: 506.69; $^1$H NMR (CDCl$_3$): δ ppm: 2.27 (s, 3H), 7.18 (m, 1H), 7.30 (d, 1H), 7.36 (m, 2H), 7.57 (m, 1H), 8.00 (s, 1H), 8.41 (d, 1H), 8.58 (d, 1H)

Examples 20, 21, 23, 27, and 3 were Synthesized in Analogy to Example 22.

Synthesis of N-(3-(4-(3-(2-chloro-6-fluorophenyl)-4-(5-methyl-1,3,4-thiadiazol-2-yl)isoxazol-5-yl)-5-(trifluoromethyl)-1H-pyrazol-1-yl)phenyl)acetamide (Example 12)

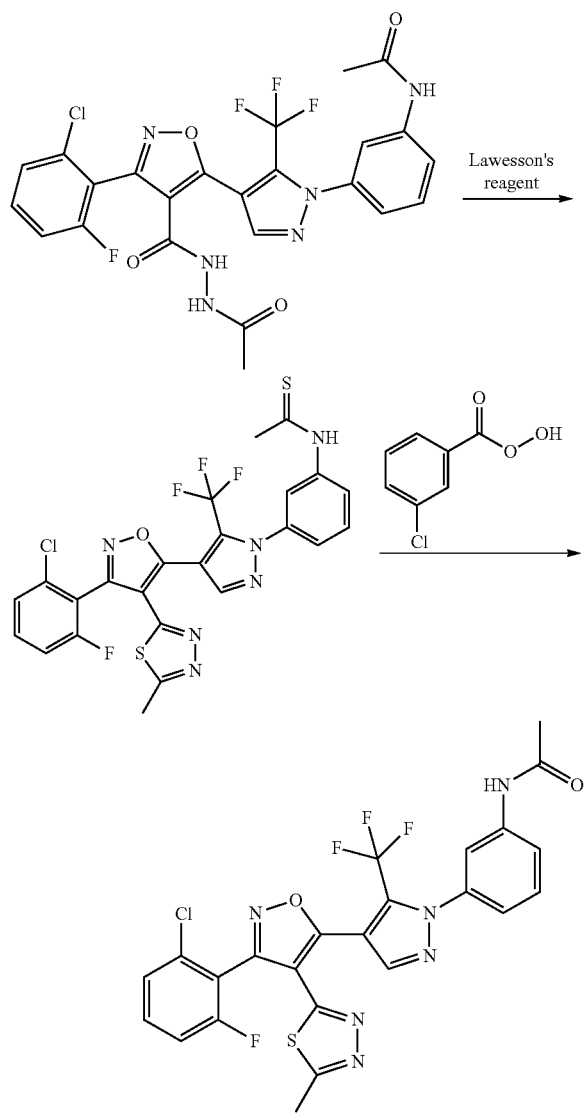

Treatment of N-(3-(4-(4-(2-acetylhydrazinecarbonyl)-3-(2-chloro-6-fluorophenyl)isoxazol-5-yl)-5-(trifluoromethyl)-1H-pyrazol-1-yl)phenyl)acetamide with Lawesson's reagent according to the procedure described for example 22 resulted in the formation of the thiadiazole but simultaneously in the formation of a thioamide at the aryl substituent at the pyrazol ring. For a re-generation of the acetylamino substituent, N-(3-(4-(3-(2-chloro-6-fluorophenyl)-4-(5-methyl-1,3,4-thiadiazol-2-yl)isoxazol-5-yl)-5-(trifluoromethyl)-1H-pyrazol-1-yl)phenyl)ethanethioamide (19.0 mg, 0.032 mmol) was dissolved in CH₂Cl₂ (2.0 mL). 3-Chloroperoxybenzoic acid (70%, 16.2 mg, 0.065 mmol) was added and the resulting mixture was stirred at r.t. for 1 h. The reaction mixture was diluted with sat. Na₂SO₃ (10 mL) and stirred vigorously for 10 min. Satd NaHCO₃ (10 mL) was then added and the mixture was extracted with CH₂Cl₂ (3×15 mL). The combined organic layers were washed with saturated NaHCO₃ (10 mL), dried over Na₂SO₄ and concentrated in vacuo.

The residue was purified by pTLC (CH₂Cl₂/MeOH=95:5) to give 10.2 mg of a yellow solid (yield 37%).

Result of LC/MS MH⁺: 562.75; ¹H NMR (CDCl₃): δ ppm: 2.10 (s, 3H), 2.62 (s, 3H), 7.11 (t, 1H), 7.33 (d, 1H), 7.35-7.48 (m, 2H), 7.65 (m, 3H), 8.21 (s, 1H)

Synthesis of 3-(2-chloro-6-fluorophenyl)-5-(1-(2-fluorophenyl)-5-(trifluoromethyl)-1H-pyrazol-4-yl)-4-(5-methyl-1,3,4-thiadiazol-2-yl)isoxazol (Example 12)

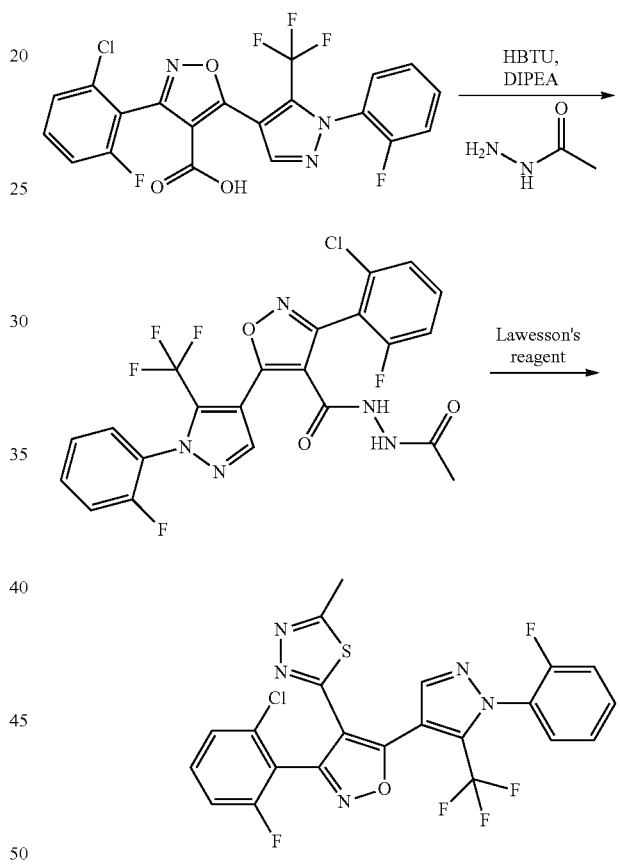

3.44 g (7.3 mmol) of 3-(2-chloro-6-fluorophenyl)-5-(1-(2-fluorophenyl)-5-(trifluoromethyl)-1H-pyrazol-4-yl)isoxazole-4-carboxylic acid were dissolved in 19 ml of DMF. 2.92 g (7.7 mmol) of HBTU and 6.06 ml (36.65 mmol) of DIPEA were added at r.t. After 20 min. stirring at r.t., 1.63 g (22 mmol) of acethydrazine were added and the mixture was stirred at r.t. overnight. The mixture was diluted with ethyl acetate (60 ml) and washed with 60 ml water. The aqueous layer was re-extracted with EE and the combined organic layers were dried over MgSO₄, filtered, and the solvent was removed under reduced pressure. The residue was purified via pTLC (CH₂Cl₂/MeOH 95/5) to give 1.3 g of the intermediate as an orange solid (yield 34%). The thiadiazole formation out of the intermediate was achieved using Lawesson's reagent according to the procedure described for example 22.

Synthesis of 3-(2-chloro-6-fluorophenyl)-5-(1-(3-chlorophenyl)-5-(trifluoromethyl)-1H-pyrazol-4-yl)-4-(1,3,4-thiadiazol-2-yl)isoxazole (Example 8)

Synthesis of 3-(2-chloro-6-fluorophenyl)-5-(1-(3-fluorophenyl)-5-(trifluoromethyl)-1H-pyrazol-4-yl)-4-(furan-3-yl)isoxazole (Example 13)

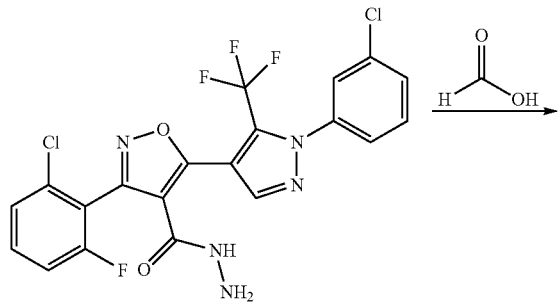

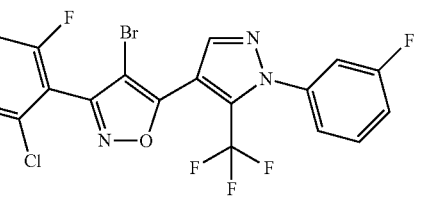

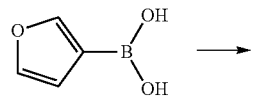

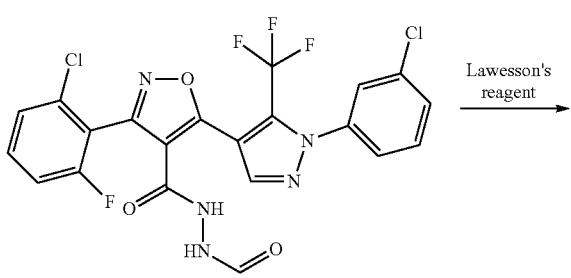

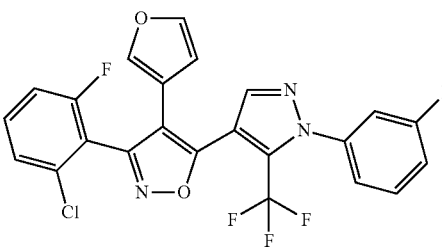

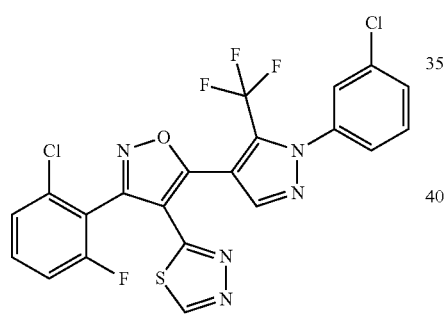

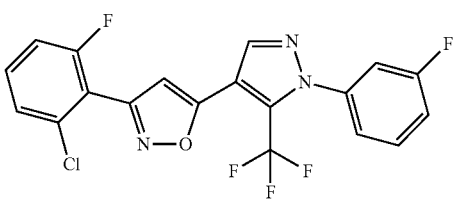

3-(2-chloro-6-fluorophenyl)-5-(1-(3-chlorophenyl)-5-(trifluoromethyl)-1H-pyrazol-4-yl)isoxazole-4-carbohydrazide (85 mg, 0.2 mmol) was treated with formic acid (6.4 µL, 0.2 mmol). The mixture was stirred at r.t. for 72 h. To the reaction mixture was added water, the resulting precipitate was collected, washed with water and dried in vacuum to give 61 mg of the intermediate as a colorless solid. To a solution of the intermediate 3-(2-chloro-6-fluorophenyl)-5-(1-(3-chlorophenyl)-5-(trifluoromethyl)-1H-pyrazol-4-yl)-N'-formylisoxazole-4-carbohydrazide (20 mg, 0.038 mmol) in dioxane (2 mL) was added Lawesson's Reagent (0.033 mL, 0.1 mmol). The mixture was stirred at reflux for 3 h. The mixture was diluted with dichloromethane and washed with water (3×), dried over sodium sulfate, filtered and concentrated under reduced pressure. The product was purified by pTLC (EE/PE 1:1) to give 6 mg of example 8 as a colorless solid (yield 31%). Result of LC/MS MH+: 525.72; $^1$H NMR (MeOD): δ 7.35 (t, 1H), 7.49 (d, 1H), 7.59-7.71 (m, 5H), 8.37 (s, 1H), 9.38 (s, 1H)

The tube was charged with 4-bromo-3-(2-chloro-6-fluorophenyl)-5-(1-(3-fluorophenyl)-5-(trifluoromethyl)-1H-pyrazol-4-yl)isoxazole (30 mg, 0.06 mmol), tetrakis(triphenylphosphine)palladium(0) (0.010 g), 1.5 mL 1,2-Dimethoxyethane and was purged with argon. Then furan-3-ylboronic acid (0.012 g, 0.1 mmol) and an aqueous solution of cesium carbonate (0.05 g in 0.2 mL) were added. The reaction mixture was heated under microwave irradiation to 100° C. for 2 h. The solvent was evaporated and the product was isolated by column chromatography (hexane:ethyl acetate 25:1) to obtain 5 mg (17%) of a yellowish solid of example 13. As a major side reaction, hydrodebromination was observed.

Result of LC/MS MH+: 492.05; $^1$H NMR (CDCl$_3$; CCl$_4$): 6.18 (1H, m, CH-furyl), 7.12-7.53 (9H, m, CH-arom.+CH-furyl), 7.91 (1H, s, CH-pyraz.)

Example 17 was Prepared in Analogy to Example 13.

A similar procedure was applied to the synthesis of examples 14, 6, 7, 9, and 24, only replacing tetrakis(triphenylphosphine)palladium(0) by dichlorobis(triphenylphosphine) palladium (for example 14), and for examples 6, 7, 9 and 24 by also replacing an aqueous solution of cesium carbonate by an aqueous solution of sodium carbonate.

Synthesis of 3-(2-chloro-6-fluorophenyl)-5-(1-(3-fluorophenyl)-5-(trifluoromethyl)-1H-pyrazol-4-yl)-4-(thiophen-3-yl)isoxazole (Example 16)

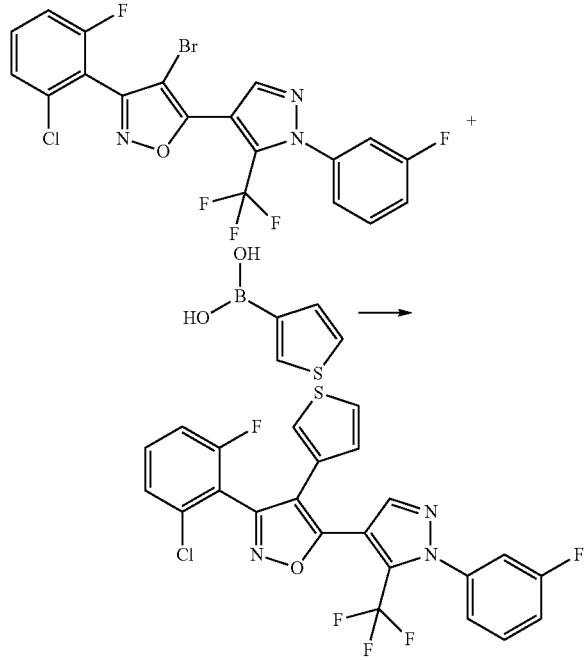

A microwave tube was charged with 4-bromoisoxazole (0.03 g, 0.06 mmol), Pd(PPh$_3$)Cl$_2$ (0.003 g), DME (1.5 mL) and purged with argon. Then 3-thienylboronic acid (0.014 g, 0.1 mmol) and an aqueous solution of Cs$_2$CO$_3$ (0.05 g in 0.2 mL) were added. The reaction mixture was heated under microwave irradiation to 100° C. for 1.5 h. The solvent was evaporated and the resulting mixture was separated by column chromatography (hexane, hexane:EtOAc 50:1, hexane:EtOAc 25:1) to give 0.010 g of the desired product. (yield 33%).; $^1$H NMR (CDCl$_3$): 6.85 (1H, m, CH-thienyl), 7.04 (1H, m, CH-thienyl), 7.11 (1H, m, CH-arom.), 7.24-0.54 (7H, m, CH-arom.+CH-thienyl), 7.80 (1H, s, CH-pyraz).

Synthesis of 2-(3-(2-chloro-6-fluorophenyl)-5-(1-(2-fluorophenyl)-5-(trifluoromethyl)-1H-pyrazol-4-yl)isoxazol-4-yl)-1,3,4-oxadiazole (Example 15)

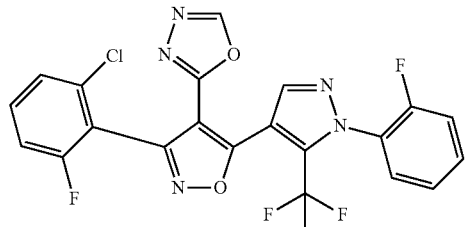

A solution of 3-(2-chloro-6-fluorophenyl)-5-(1-(2-fluorophenyl)-5-(trifluoromethyl)-1H-pyrazol-4-yl)isoxazole-4-carbohydrazide (0.076 g, 0.157 mmol) in 4 g trimethyl orthoformate was kept in a sealed tube at 125° C. for 3 days. The solution was evaporated to dryness and the residue was crystallized from heptane to give 36 mg (46%) of a yellowish solid of example 15. Result of LC/MS MH+: 493.75; $^1$H NMR (methanol-d$_4$; 400 MHz) δ ppm: 7.30-7.35 (1H, m, CH-arom.), 7.42-7.48 (3H, m, CH-arom.), 7.60-7.70 (3H, m, CH-arom.), 8.51 (1H, s, CH-oxadiazole), 8.93 (1H, s, CH-pyraz.)

A Variant of this Procedure was used for the Synthesis of Examples 5, 13, 14, 15, 16, 17; and 25, Exemplarily Shown for 5:

The aforementioned mixture of hydrazide and trimethyl orthoformate (cf. synthesis of example 15) was heated under microwave irradiation to 125° C. for 8 h. The mixture was diluted with dichloromethane and washed with water (3x), dried over sodium sulfate, filtered and concentrated under reduced pressure. The product was purified by pTLC EE/PE 1:1 to give 6 mg of example 5 as white solid (yield 24%).

Synthesis of methyl and ethyl 2-{3-(2-chloro-6-fluorophenyl)-5-[1-(3-fluorophenyl)-5-(trifluoromethyl)-1H-pyrazol-4-yl]isoxazol-4-yl]-1,3-thiazole-4-carboxylate (Examples 1 and 2)

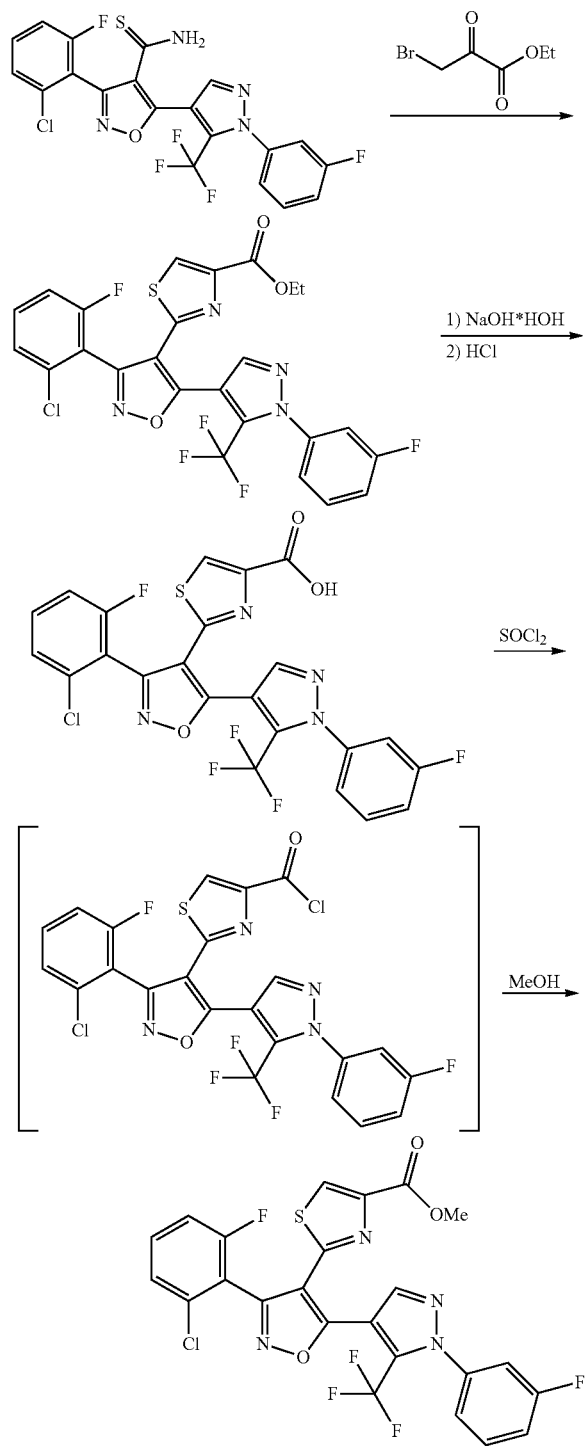

A mixture of the carbothioamide (0.242 g, 0.5 mmol) and ethyl bromopyruvate (0.118 g, 0.6 mmol) was heated under reflux for 3 h in 2 ml of dry dioxane. The reaction mixture was cooled to room temperature and diluted with 20 ml of water. The resulting oil was separated by decantation, dissolved in CCl$_4$, dried with MgSO$_4$. The compound was purified by column chromatography using silica gel and CCl$_4$, then CHCl$_3$ as eluents to give 0.17 g of example 1 as an oil (yield 59%).

$^1$H NMR (DMSO-d$_6$, 400 MHz): δ 8.76 (1H, s, H$_{thiasole}$), 8.50 (1H, s, H$_{pyrasol}$), 7.80...7.53 (7H, m, H$_{arom}$), 4.28 (2H, q, J=7.3 Hz, CH$_2$), 1.27 (3H, t, J=7.3 Hz, Me).

Transesterification of Example 1 into Example 2 was Achieved as Follows:

To a boiling solution of 0.118 g (0.2 mmol) of the ethyl ester in 5 ml ethanol was added a solution of 0.08 g (2 mmol) NaOH in 0.5 ml water. The reaction mixture was heated to reflux for 10 min, then cooled to room temperature, diluted with water acidified to pH 3-4 and concentrated to a volume of 1 ml. The acid was extracted with 10 ml CH$_2$Cl$_2$ and dried over MgSO$_4$. To the solution were added 0.1 ml (1.4 mmol) SOCl$_2$, and the mixture was heated under reflux for 1 h. The mixture was evaporated in vacuum. The residue was taken up in 2 ml of dry methanol and was heated under reflux for 20 min. Then the mixture was concentrated in vacuum and diluted with 10 ml of water. The product was extracted with 10 ml CH$_2$Cl$_2$ and dried over MgSO$_4$. The solution was evaporated in vacuum to give example 2 as a glassy solid (0.063 g, 56%). $^1$NMR (DMSO-d$_6$, 400 MHz): δ 8.72 (1H, s, H$_{thiazole}$), 8.52 (1H, s, H$_{pyrazole}$), 7.82-7.53 (7H, m, H$_{arom}$), 3.82 (3H, s, OMe).

Synthesis of 2-{(3-(2-Chloro-6-fluorophenyl)-5-[1-(3-fluorophenyl)-3-(trifluoromethyl)-1H-pyrazol-4-yl]isoxazol-4-yl}-5-(trifluoromethyl)-1,3,4-oxadiazole (Example 6)

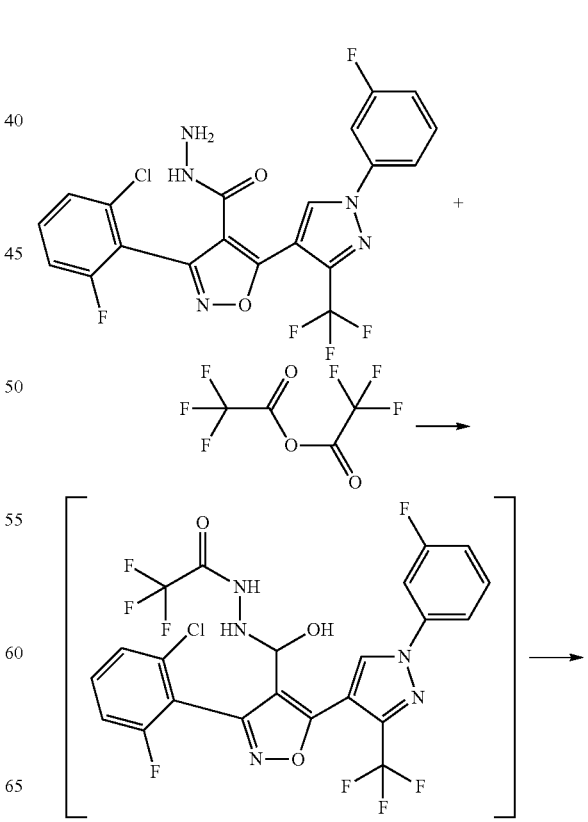

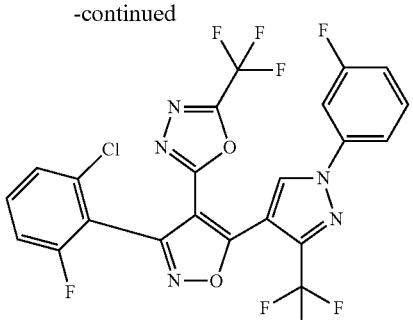

A solution of 3-(2-chloro-6-fluorophenyl)-5-[1-(3-fluorophenyl)-3-(trifluoromethyl)-1H-pyrazol-4-yl]isoxazole-4-carbohydrazide (158 mg, 0.327 mmol) and trifluoroacetic acid anhydride (342 mg, 1.628 mmol) in 9 g of absolute dioxane was heated under refluxe. TLC showed intermediate product which gradually converted into desired 1,3,4-oxadiazole. After heating for 3 days, the mixture was evaporated to dryness The oily residue was extracted with boiling heptane, heptane extracts were combined and evaporated to dryness. Oily residue was purified by column chromatography on silica gel, eluent EtOAc/heptane, 1/2 to yield 18 mg of pure example 6 as a viscous oil (yield 10%). $^1$H NMR (CDCl$_3$; CCl$_4$): δ 7.24 (t, 1H), 7.32 (m, 2H), 7.41 (m 2H), 7.55 (m, 2H), 8.38 (s, 1H)

The Synthesis of Compounds of the Illustrative Examples is Described in the Following:

1. Synthesis of Compounds of Formula (I)

The compounds of formula (I) were obtained through the synthetic route described in scheme (1). Methyl 3-(2-chloro-6-fluorophenyl)-5-methylisoxazole-4-carboxylate was purchased from Apollo Scientific Ltd, Whitefield Rd, Bredbury, Stockport, Cheshire, SK6 2QR. Bredereck's reagent (tert-Butoxy-bis(dimethylamino)methane) was purchased from Apollo Scientific Ltd, Whitefield Rd, Bredbury, Stockport, Cheshire, SK6 2QR. Trifluoroacetic anhydride was purchased from Acros Organics BVBA, Janssen Pharmaceuticalaan 3a, 2440 Geel, Belgium. 3-Chlorophenylhydrazine hydrochloride was purchased from Alfa Aesar, 26 Parkridge Road, Ward Hill, Mass. 01835, USA.

Synthesis of Benzaldoxime Derivatives, Exemplarily Shown for 2-chloro-6-fluorobenzaldehyde oxime

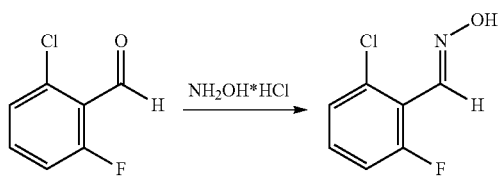 [SMILES: O=Cc1c(F)cccc1Cl ; O/N=C/c1c(F)cccc1Cl]

To a stirred mixture of 2-chloro-6-fluorobenzaldehyde (5 g, 31.5 mmol), ethanol (10 mL), ice and water (30 mL) and hydroxylamine hydrochloride (2.8 g, 40.3 mmol), an aqueous solution of NaOH (3.6 g, 90 mmol in 5 mL of water) was added. The mixture was stirred for an hour and extracted with 40 mL of ether to remove impurities.

The aqueous layer was neutralized with HCl and extracted with ether (2×50 mL). Extracts were dried over Na$_2$SO$_4$ and evaporated to give 5.19 g of the aldoxime (yield 93%).

Synthesis of ethyl 3-(2-chloro-6-fluorophenyl)-5-methylisoxazole-4-carboxylate

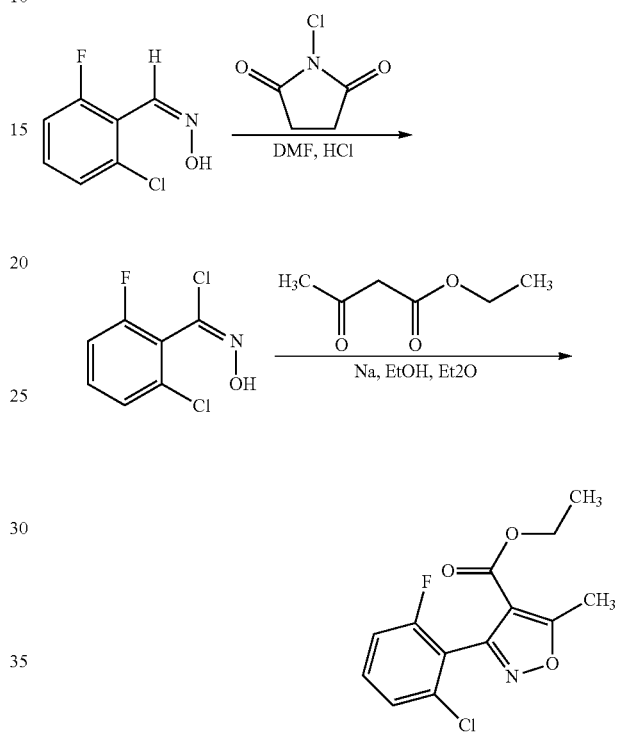

To a solution of (E)-2-chloro-6-fluorobenzaldehyde oxime (2 g) in 10 mL Dimethylformamide (DMF) at room temperature 0.23 g N-Chlorosuccinimide (NCS) were added. Dry hydrogen chloride was bubbled into the DMF solution until the reaction temperature rise up to 35° C. Then 1.21 g N-chloro-succinimide were added in portions, the temperature was kept at 35-45° C. The reaction mixture was cooled to room temperature and poured into 30 mL ice and extracted with ether. Combined extracts were dried and evaporated to give 2.5 g of 2-chloro-6-fluoro-N-hydroxybenzimidoyl chloride as a yellow oil.

A solution of ethyl sodium acetoacetate [from sodium (0.33 g), dry ethanol (10 mL) and ethyl acetoacetate (1.75 g)] was added slowly to a stirred solution of the hydroxamoyl chloride (2.5 g) in 20 mL ether at 0-3° C. The mixture was allowed to warm to room temperature overnight, and the solvent was evaporated in vacuo. The residue was shaken with water and ether, ether extract was evaporated and the product was purified by column chromatography (hexane) to give 2.2 g of ethyl 3-(2-chloro-6-fluorophenyl)-5-methylisoxazole-4-carboxylate as a colorless oil. Result of LC/MS [M+H]$^+$: 283.95; $^1$H NMR (DMSO-d$_6$; CCl$_4$): 0.98-1.03 (3H, t, CH$_3$), 2.77 (3H, s, CH$_3$), 4.05-4.12 (2H, q, CH$_2$), 7.39-7.67 (3H, m, CH-arom.)

Synthesis of methyl 3-(2,6-dichlorophenyl)-5-methylisoxazole-4-carboxylate

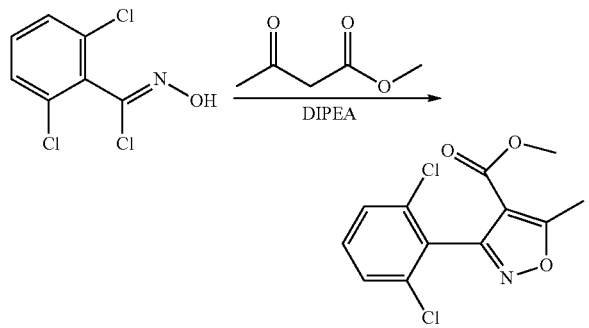

To a solution of 0.1 g (0.4455 mmol) alpha-Chloro-2,6-dichlorobenzaldoxime in 5 mL methyl 3-oxobutanoate, 0.11 mL (1.5 eq) diisopropylethlamine were added. The mixture was stirred for 24 h then ethylacetate was removed in the vacuo. The residue was dried under high vacuo and the crude product was triturated in water until it became solid. The solid was filtered off and further purified by recrystallization from a water-methanol mixture. The crystals were filtered off, washed with water and dried under reduced pressure to afford 248 mg (87%) of methyl 3-(2,6-dichlorophenyl)-5-methylisoxazole-4-carboxylate. Result of LC/MS [M+H]$^+$: 286.12; $^1$H NMR (DMSO-d$_6$; CCl$_4$): 2.77 (3H, s, CH$_3$-isooxazole), 3.28 (3H, s, CH$_3$-methoxy), 7.54-7.65 (3H, m, aromatic)

Starting from either unsubstituted benzaldehyde, 4-chlorobenzaldehyde, 2-fluorobenzaldehyde, 2-chlorobenzaldehyde, 2,4-dichlorobenzaldehyde, 4-methoxybenzaldehyde, 3-fluorobenzaldehyde, 2,6-dichlorobenzaldehyde, 2,4-dichlorobenzaldehyde, 3-fluoroisonicotinaldehyde or 3,5-dichloroisonicotinaldehyde and using either methyl or ethyl 3-oxobutanoate, the aforementioned synthetic routes were used to synthesize all differently substituted methyl or ethyl 5-methyl-3-phenylisoxazole-4-carboxylate building blocks required for the preparation of the respective examples of this invention, e.g:

Ethyl 3-(2,4-dichlorophenyl)-5-methylisoxazole-4-carboxylate, oil, yield 82%

$^1$H NMR (DMSO-D$_6$, CCl$_4$): 1.10 (3H, t, CH$_3$), 2.74 (3H, s, CH$_3$), 4.10 (2H, q, CH$_2$), 7.42 (1H, d, CH-arom.), 7.47 (1H dd, CH-arom.), 7.59 (1H, d, CH-arom.).

Methyl 3-(4-methoxyphenyl)-5-methylisoxazole-4-carboxylate yield 65%

$^1$H NMR (DCCl$_3$): 2.71 (3H, s, CH$_3$), 3.79 (3H, s, OCH$_3$), 3.85 (3H, s, OCH$_3$), 6.97 (2H, AB-syst., CH-arom.), 7.60 (2H AB-syst., CH-arom.).

Synthesis of methyl 3-(2-chloro-6-fluorophenyl)-5-(2-(dimethylamino)vinyl)isoxazole-4-carboxylate

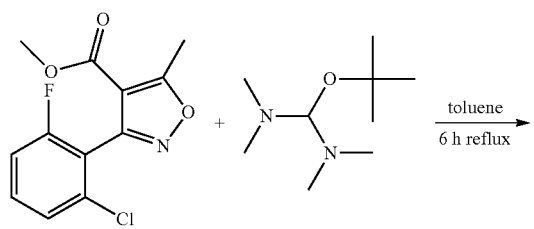

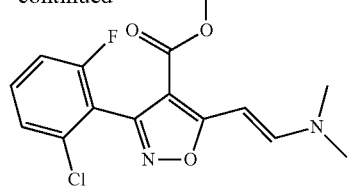

To a solution of 0.1 g (0.3708 mmol) methyl 3-(2-chloro-6-fluorophenyl)-5-methylisoxazole-4-carboxylate in 10 mL dry toluene, was added 0.15 mL (0.7417 mmol) tert-Butoxy-bis(dimethylamino)methane. The reaction mixture was heated under reflux for 6 h.

The mixture was concentrated in vacuo and was dried in high vacuum. Petroleum ether was added to the oily residue and crystalline product developed. The product was collected by filtration and 0.070 g (yield of theory: 58%) of clean product were obtained. Result of LC/MS [M+H]$^+$: 325.0; $^1$H NMR (DMSO-d$_6$; CCl$_4$): 3.02 (6H, s, N—CH$_3$), 3.53 (3H, s, CH$_3$), 5.54-5.58 (1H, d, CH), 7.72-7.76 (1H, d, CH), 7.32-7.38 (1H, dd, CH-arom.), 7.44-7.47 (1H, d, CH-arom.), 7.56-7.58 (1H, d, CH-arom.)

Synthesis of methyl 3-(2-chloro-6-fluorophenyl)-5-(1-(dimethylamino)-4,4,4-trifluoro-3-oxobut-1-en-2-yl)isoxazole-4-carboxylate

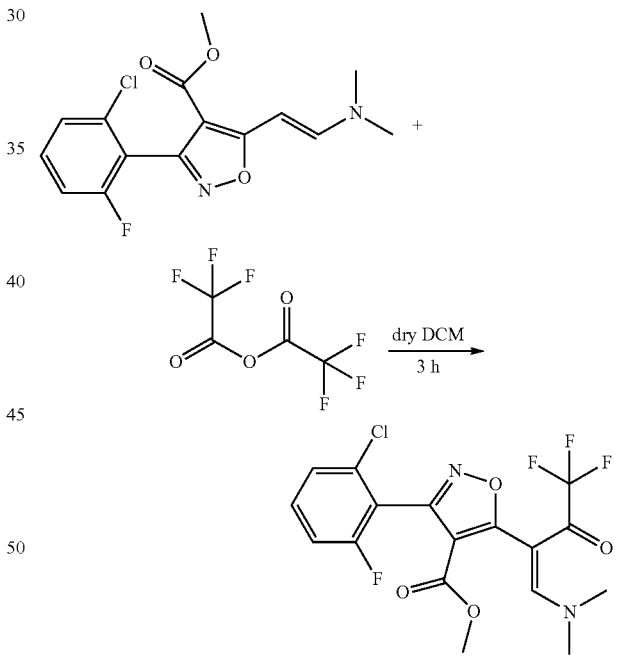

To a solution of 0.5 g (1.5397 mmol) methyl 3-(2-chloro-6-fluorophenyl)-5-[2-(dimethylamino)vinyl]isoxazole-4-carboxylate in 20 mL dry dichloromethane, was added dropwise under ice-bath cooling 0.32 mL (2.309 mmol) trifluoroacetic anhydride. The reaction mixture was stirred for 3 h at room temperature. Afterwards the mixture was concentrated in vacuo and was dried in the high vacuum. The oily residue crystallized with petroleum ether and the product was collected by filtration to obtain 0.604 g (yield of theory: 94%) of clean product. Result of LC/MS [M+H]$^+$: 420.9; $^1$H NMR (DMSO-d$_6$; CCl$_4$): 2.63 (3H, s, N—CH$_3$), 3.40 (3H, s, N—CH$_3$), 3.59 (3H, s, CH$_3$), 7.40-7.46 (1H, dd, CH-arom.), 7.51-7.55 (1H, d, CH-arom.), 7.64-7.66 (1H, d, CH-arom.), 8.12 (1H, s, CH).

Synthesis of methyl 3-(2-chloro-6-fluorophenyl)-5-(1-(3-chlorophenyl)-5-(trifluoromethyl)-1H-pyrazol-4-yl)isoxazole-4-carboxylate (Example I-11)

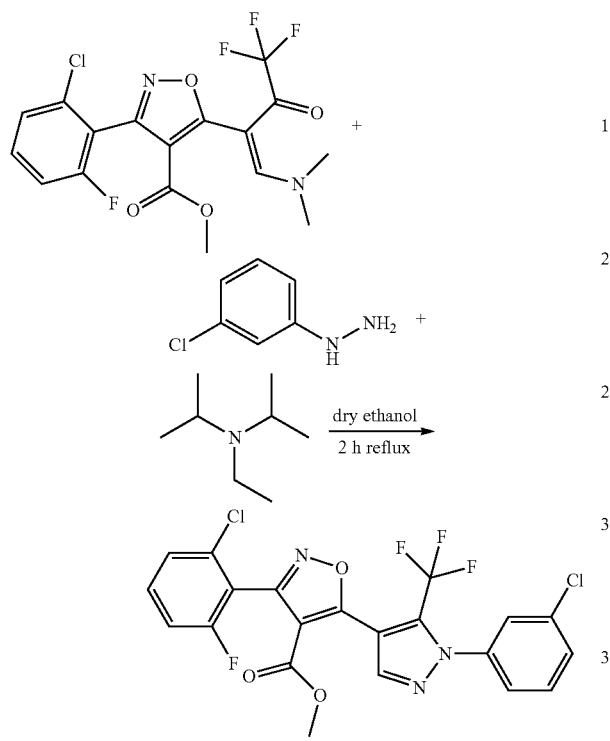

To a solution of 0.5047 g (1.1994 mmol) methyl 3-(2-chloro-6-fluorophenyl)-5-(1-(dimethylamino)-4,4,4-trifluoro-3-oxobut-1-en-2-yl)isoxazole-4-carboxylate in dry ethanol, were added 0.1790 g (0.9995 mmol) 3-Chlorophenylhydrazine and 0.17 mL (0.9995 mmol) N,N-Diisopropylethylamine (DIPEA). The reaction mixture was heated under reflux for 2 h.

The product was isolated by using column chromatography (Petroleum ether:Diethyl ether 80:20) and 0.305 g (yield of theory: 61%) of clean product (example I-11) was obtained. Result of LC/MS [M+H]$^+$: 499.8; $^1$H NMR (DMSO-d$_6$; CCl$_4$): 3.66 (3H, s, CH$_3$), 7.45-7.50 (1H, dd, CH-arom.), 7.55-7.58 (1H, d, CH-arom.), 7.65-7.77 (1H, d, CH-arom.), 7.65-7.77 (1H, dd, CH-arom. phenylhydrazine), 7.65-7.77 (1H, d, CH-arom. phenylhydrazine), 7.85 (1H, s, CH-arom phenylhydrazine), 8.56 (1H, s, 1-pyrazole)

The synthesis of the methyl ester compounds of examples I-1, I-3, I-4, I-5, I-7, I-12, I-14, I-33, I-46, I-47, I-48, I-50, I-51, I-52, I-53, I-54, I-61, I-67, I-68, I-69, I-70, I-73, I-74, I-79, I-80, I-81, I-82, I-84, I-85, I-86, I-87, I-88, I-92, I-95, I-96, I-97, I-106, I-107, I-109, I-111, I-116, I-119, IB-20 and IB-30 was conducted in analogy to the above synthesis of the compound of example I-11, using the appropriately substituted methyl 5-(1-(dimethylamino)-4,4,4-trifluoro-3-oxobut-1-en-2-yl)-3-phenylisoxazole-4-carboxylate building blocks and the appropriately substituted arylhydrazine derivatives.

The following examples were synthesized in analogy but using a non-aryl hydrazine: examples I-28, I-65, I-66, I-102, I-103 and I-104, incorporating isobutylhydrazine, (2,2,2-trifluoroethyl)hydrazine, isopropylhydrazine, (2-methoxyethyl)hydrazine and 3-hydrazinyltetrahydrothiophene 1,1-dioxide and 1-(2-hydrazinylethyl)piperidine respectively.

Synthesis of methyl 3-(2-chloro-6-fluorophenyl)-5-(1-(2-hydroxyethyl)-5-(trifluoromethyl)-1H-pyrazol-4-yl)isoxazole-4-carboxylate (Example I-83)

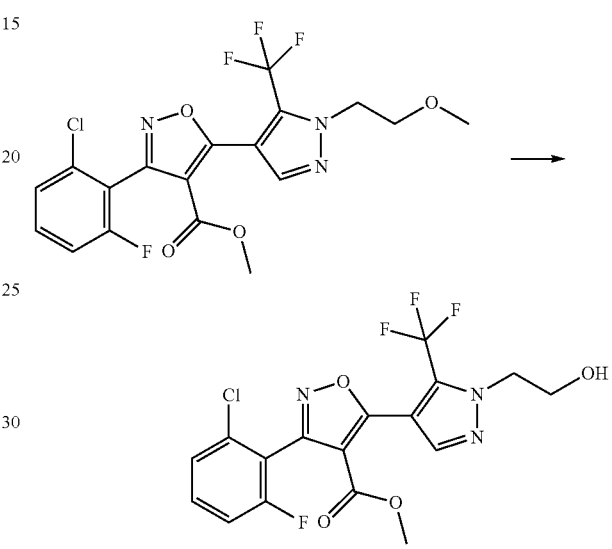

To a solution of methyl 3-(2-chloro-6-fluorophenyl)-5-(1-(2-methoxyethyl)-5-(trifluoromethyl)-1H-pyrazol-4-yl)isoxazole-4-carboxylate (example I-102) (27 mg, 0.06 mmol) in CH$_2$Cl$_2$ (1 mL) was added Bortribromide (0.06 mmol). The mixture was stirred at 0° C. for 1 h. The mixture was poured into iced water and extracted with ethyl acetate. The organic layer was dried over sodium sulfate, filtered and concentrated under reduced pressure. The resulting oil was purified by pTLC (PE:EE 1:1) to yield example I-83 as an oil (10 mg, 34%).

Synthesis of ethyl 3-(2-chloro-6-fluorophenyl)-5-(1-(2-chlorophenyl)-5-(trifluoromethyl)-1H-pyrazol-4-yl)isoxazole-4-carboxylate (Example IB-33)

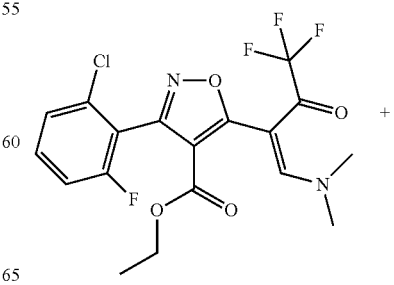

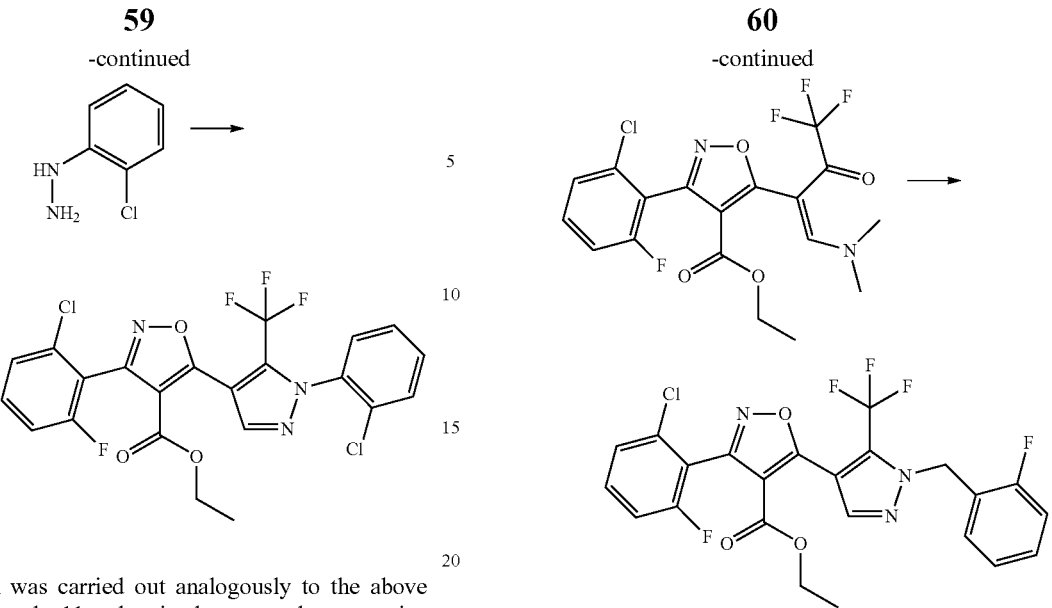

The reaction was carried out analogously to the above reaction of example 11, wherein, however, the respective methyl ester was replaced by an ethyl ester building block and 3-Chlorophenylhydrazine was replaced by 2-Chlorophenylhydrazine.

The synthesis of the ethyl ester compounds of examples I-42, IB-3, IB-4, IB-5, IB-6, IB-7, IB-8, IB-9, IB-10, IB-11, IB-12, IB-13, IB-14, IB-15, IB-16, IB-17, IB-32, IB-37, IB-38, IB-40, IB-41, IB-43, IB-44, IB-45, IB-46, IB-47, IB-70, IB-72, IB-84, IB-90, IB-94, IB-95, IB-99 and IB-103 was conducted in analogy to the above synthesis of the compound of example IB-33, using the appropriately substituted ethyl 5-(1-(dimethylamino)-4,4,4-trifluoro-3-oxobut-1-en-2-yl)-3-phenylisoxazole-4-carboxylate building blocks and the appropriately substituted arylhydrazine derivatives.

Example IB-2 and IB-81 were synthesized in analogy but using (2-methoxyethyl)hydrazine and ((tetrahydro-2H-pyran-4-yl)methyl)hydrazine, respectively, instead of an aryl hydrazine.

Synthesis of ethyl 3-(2-chloro-6-fluorophenyl)-5-(1-(2-fluorobenzyl)-5-(trifluoromethyl)-1H-pyrazol-4-yl)isoxazole-4-carboxylate (Example IB-80)

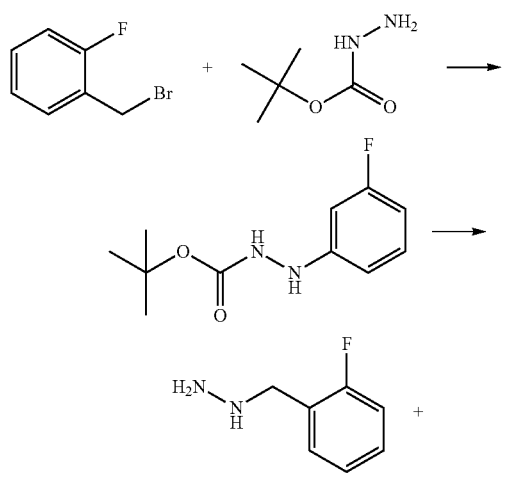

To a solution of tert-Butyl carbazate (Hydrazinecarboxylic acid tert-butyl ester) (0.3 g 2.3 mmol) and 2-Fluorobenzyl bromide (0.4 g, 2.3 mmol) in dichloromethane (4 mL) was added triethylamine (0.3 mL, 2.3 mmol). The mixture was stirred at 70° C. for 4 h. The mixture was then diluted in ethyl acetate and washed with water (3×), dried over sodium sulfate, filtered and concentrated under reduced pressure to give 380 mg as a white solid (yield 76%). $^1$H NMR (CDCl$_3$): 1.45 (s, 9H), 4.052 (s, 2H), 7.00-7.40 (m, 4H)

Tert-butyl 2-(2-fluorobenzyl)hydrazinecarboxylate (0.5 g, 2.27 mmol) dissolved in dichloromethane (4 mL) was treated with HCl 4M in dioxane (0.8 mL, 22.7 mmol). The mixture was stirred at room temperature for 1.5 h. The solvent was concentrated under reduced pressure. The product was lyophillized to give the unprotected benzylhydrazine as a white solid (200 mg, yield 66%). The last step (formation of the N-substituted pyrazole unit) was performed as described for example I-11 and gave 489 mg of the product as a pale yellow solid (yield 81%). Result of LC/MS [M+H]$^+$: 512.04; $^1$H NMR (CDCl$_3$): 1.03 (t, 3H), 4.12 (q, 2H), 5.61 (s, 2H), 7.10 (m, 4H), 7.38-7.48 (m, 3H), 8.04 (s, 1H).

The synthesis of the compounds of examples I-101, IB-85, IB-96, IB-97 and IB-104 was conducted in analogy to the above synthesis of the compound of example IB-80.

Synthesis of 3-(2-chloro-6-fluorophenyl)-5-(1-(3-chlorophenyl)-5-(trifluoromethyl)-1H-pyrazol-4-yl)-N-methoxy-N-methylisoxazole-4-carboxamide (Example I-63)

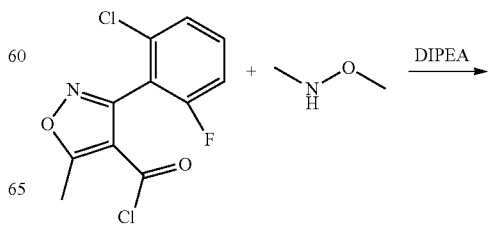

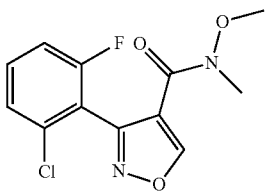

N,O-Dimethylhydroxylamine (1.780 g, 18.243 mmol) was dissolved in dry THF (100 mL). The solution was cooled to 0° C. and DIPEA (3.0 ml, 18.2427 mmol) was added. 3-(2-Chloro-6-fluorophenyl)-5-methylisoxazole-4-carbonyl chloride was then added in portions and the mixture was stirred at room temperature overnight. The solvent was evaporated. Water was added and the flask was placed in the refrigerator for 2 days. The obtained white solid was filtered, washed with a 5% aqueous solution of NaHCO₃, and dried to give 5.2 g of the Weinreb amide as a white solid (yield 95%).

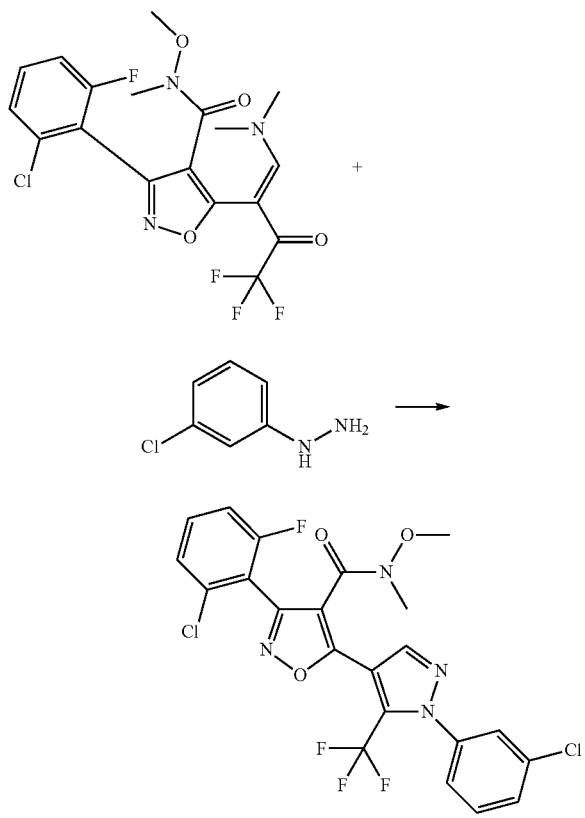

Conversion of the Weinreb amide 3-(2-chloro-6-fluorophenyl)-N-methoxy-N,5-dimethylisoxazole-4-carboxamide into 3-(2-chloro-6-fluorophenyl)-5-(1-(dimethylamino)-4,4,4-trifluoro-3-oxobut-1-en-2-yl)-N-methoxy-N-methylisoxazole-4-carboxamide and subsequently into the final product of example I-63 was carried out analogously to the aforementioned synthesis of example I-11.

The synthesis of the compound of example I-135 was conducted in analogy to the above synthesis of the compound of example I-63.

Saponification, Esterification and Amidation Procedures

Synthesis of 3-(2-chloro-6-fluorophenyl)-5-(1-(2-fluorophenyl)-5-(trifluoromethyl)-1H-pyrazol-4-yl)-N-methylisoxazole-4-carboxamide (Example I-19)

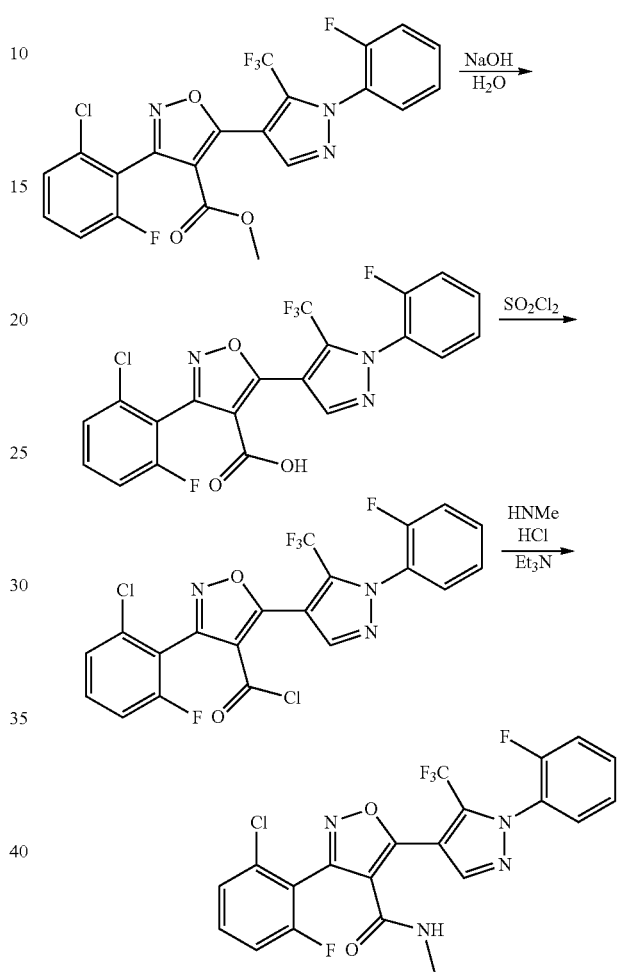

Saponification:

100 mg (0.27 mmol) of compound of example I-1 were dissolved in a mixture of 10 mL ethanol/water 1:1 and a solution of 100 mg NaOH (2.5 mmol) in 5 mL of water was added. The mixture was heated under reflux for 30 minutes. The ethanol was evaporated in the vacuum and water was added to adjust the volume to 10 mL. The mixture was filtered to remove unsoluble material and the solution adjusted to pH 1 with concentrated HCl. The precipitate which developed was collected by filtration, washed with water, and dried in the vacuum to yield 91 mg (93%) of 3-(2-chloro-6-fluorophenyl)-5-(1-(2-fluorophenyl)-5-(trifluoromethyl)-1H-pyrazol-4-yl)isoxazole-4-carboxylic acid.

Amidation:

A solution of 91 mg 3-(2-chloro-6-fluorophenyl)-5-(1-(2-fluorophenyl)-5-(trifluoromethyl)-1H-pyrazol-4-yl)isoxazole-4-carboxylic acid (0.197 mmol) in 5 mL SO₂Cl₂ was heated under reflux for 2 hours. The solution was concentrated in the vacuum and dried in the high vacuum. The residue 3-(2-chloro-6-fluorophenyl)-5-(1-(2-fluorophenyl)-5-(trifluoromethyl)-1H-pyrazol-4-yl)isoxazole-4-carbonyl chloride was, without further purification, dissolved in 3 mL dry dioxane. To this solution 60 mg (0.88 mmol) methylamine hydrochloride and 1.96 mL triethylamine was added. The reaction mixture was stirred at room temperature for 2 hours. The reaction mixture was concentrated in the vacuum and the residue triturated with hexane. The precipitate collected by filtration and 30 mg (31%) of example I-19 were obtained. Result of LC/MS [M+H]$^+$: 482.9; $^1$H NMR (DMSO-$d_6$; CCl$_4$): 2.609-2.619 (3H, s, CH$_3$), 7.419-7.737 (7H, m, arom.), 8.161 (1H, s, NH), 8.472 (CH-pyrazole)

The synthesis of the N-methyl carboxamides of examples I-32, I-37, I-55, I-56, I-57, I-58, I-59, I-60, I-62, I-75, I-93, I-96, I-98, I-105, I-110, and I-113, was conducted in analogy to the above synthesis of the compound of example 19.

The following acid compounds were obtained using the saponification protocol described above for the production of 3-(2-chloro-6-fluorophenyl)-5-(1-(2-fluorphenyl)-5-(trifluoromethyl)-1H-pyrazol-4-yl)isoxazole-4-carboxylic acid: examples I-91, I-108, I-114, IB-18, IB-19, IB-42, and IB-86.

Synthesis of 3-(2-chloro-6-fluorophenyl)-5-(1-(3-chlorophenyl)-5-(trifluoromethyl)-1H-pyrazol-4-yl)isoxazole-4-carboxamide (Example I-121)

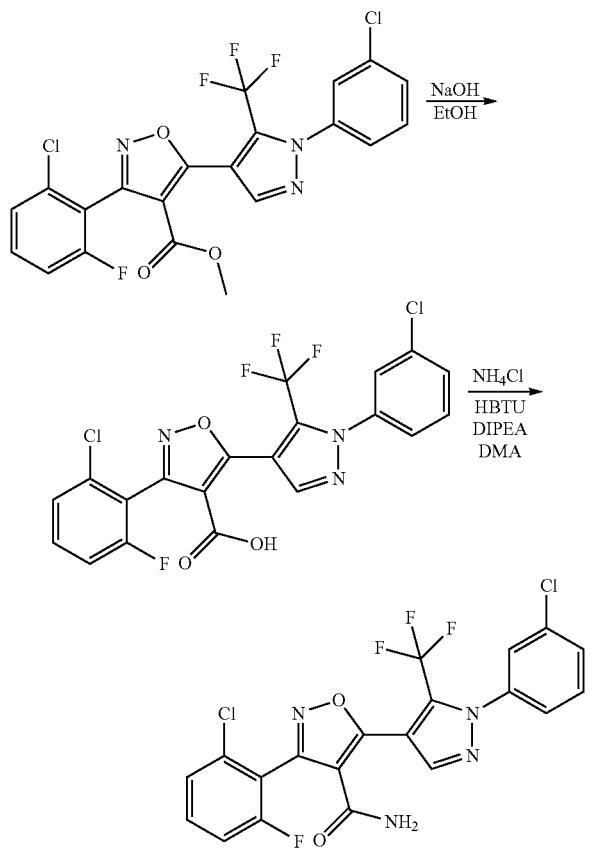

Saponification of the ester of example I-11 was achieved following the description for example I-19, first step, to give 3-(2-chloro-6-fluorophenyl)-5-(1-(3-chlorophenyl)-5-(trifluoromethyl)-1H-pyrazol-4-yl)isoxazole-4-carboxylic acid in 89% yield. To a solution of 6.0 g (12.34 mmol) 3-(2-chloro-6-fluorophenyl)-5-(1-(3-chlorophenyl)-5-(trifluoromethyl)-1H-pyrazol-4-yl)isoxazole-4-carboxylic acid and 1.98 g (37.021 mmol) ammoniumchlorid in 20 mL dry DMA 9.36 g (24.681 mmol) HBTU and 6.45 mL (37.021 mmol) DIPEA were added. The mixture was stirred 3 hours at r.t. Ethylacetate was added to the reaction mixture and it was washed twice with sodium hydrogen carbonate (5%, aq) and citric acid (5%, aq). The organic layer was dried over anhydrous magnesium sulfate and the solvent was removed in the vacuum. The oily residue became solid by drying in the vacuum. The solid was washed with petroleum ether, filtrated and dried in the vacuum to yield 5.37 g (90%) of example I-121. Result of LC/MS MH+: 484.83; $^1$H NMR (DMSO-$d_6$; CCl$_4$): 7.39-7.78 (7H, m, CH-arom./2H NH$_2$), 8.43 (1H, s, CH-pyraz.)

The synthesis of the carboxamide of example I-124 was conducted in analogy to the above synthesis of the compound of example I-121.

Furthermore, the synthesis of the following differently N-substituted carboxamides was conducted in analogy to the above synthesis of the compound of example I-121, in each case using the appropriate amine: examples I-2, I-16, I-17, I-18, I-20, I-21, I-22, I-23, I-24, I-118, I-127, and I-132.

Synthesis of (3-(2-chloro-6-fluorophenyl)-5-(1-(3-chlorophenyl)-5-(trifluoromethyl)-1H-pyrazol-4-yl)isoxazol-4-yl)(morpholino)methanone (Example IB-35)

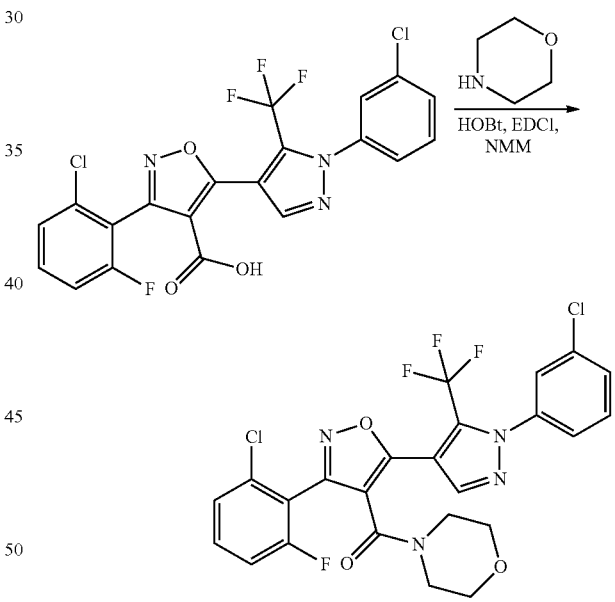

3-(2-chloro-6-fluorophenyl)-5-(1-(3-chlorophenyl)-5-(trifluoromethyl)-1H-pyrazol-4-yl)isoxazole-4-carboxylic acid (50 mg, 0.0001 mmol), Morpholine (9 mg, 0.0001 mmol), HOBt (14 mg, 0.0001 mmol) and EDCI (19 mg 0.00012 mmol) were dissolved in 1 mL dry DMF. N-Methylmorpholine (100 µL, 0.001 mmol) was added and the reaction mixture was stirred at room temperature overnight. Morpholine, HOBt, EDCI and N-Methylmorpholine were added again in the aforementioned ratios. The mixture was stirred at room temperature for 24 h. DMF was removed by evaporation. An aqueous solution of 5% citric acid was added. The precipitate was filtered and dried. The product (example IB-35) was purified by pTLC (PE/EE 5/5) to give 26 mg of a yellow oil (yield 45%). Result of LC/MS MH+: 554.7; $^1$H NMR (CDCl$_3$): 8.15 (1H, s, CH-pyraz.), 7.35-7.6 (6H, m, CH-arom), 7.15 (1H, t, CH-arom), 3.6 (4H, m, CH$_2$-morpholine), 3.18 (4H, m, CH$_2$-morpholine).

Further amide compounds were obtained as described above for compound IB-35, in each case by using the appropriate amine: examples IB-34, IB-49, IB-50, IB-51, IB-52, IB-53, IB-54, IB-55, IB-56, IB-57, IB-58, IB-59, IB-62, IB-63, IB-64, IB-65, IB-66, IB-74, IB-87, IB-88, IB-91, IB-93, and IB-100 (in the latter case, the amide formation was applied to the substituent at the aryl unit of the N-aryl-pyrazole moiety).

Synthesis of 3-(2-chloro-6-fluorophenyl)-5-(1-(3-chlorophenyl)-5-(trifluoromethyl)-1H-pyrazol-4-yl)-N-methoxy-N-methylisoxazole-4-carbxamide (Example I-63)

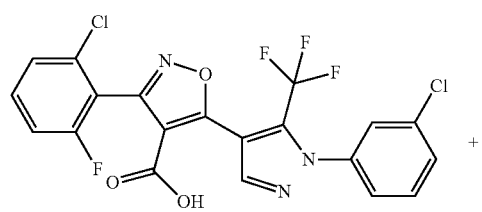

+

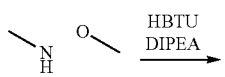

HBTU
DIPEA
→

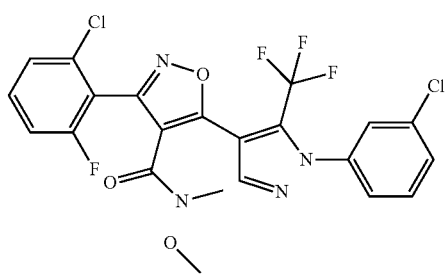

To a solution of 10.8 g (22.2 mmol) 3-(2-chloro-6-fluorophenyl)-5-(1-(3-chlorophenyl)-5-(trifluoromethyl)-1H-pyrazol-4-yl)isoxazole-4-carboxylic acid, 2.17 g (1 eq) N,O-Dimethylhydroxylamine and 8.42 g (1 eq) HBTU in dimethylhydroxylamine 3.68 mL DIPEA were added. The mixture was stirred overnight at r.t. The solvent was removed in the vacuum. The residue was resolved in ethylacetate and extracted with sodium hydrogen carbonate (5%, aq) and citric acid (5%, aq). The organic layer was dried over anhydrous magnesium sulfate and the solvent was removed in the vacuum. TLC (6:4 petrolether:ethylacetate) showed residual educt. The product was isolated by column chromatoghraphy (6:4 petrolether:ethylacetate). The product (example I-63) was dried under vacuum to yield 2.28 g (19%). Result of LC/MS MH+: 528.8; $^1$H NMR (DMSO-d$_6$; CCl$_4$): 3.08 (3H, s, CH$_3$), 3.36 (3H, s, CH$_3$), 7.40-7.81 (7H, m, CH-arom.), 8.39 (1H, s, CH-pyraz.)

Compound of example I-94 was obtained in analogy to the protocol of compound I-63.

Esterification

Synthesis of Ethyl 3-(2-chloro-6-fluorophenyl)-5-[1-(2-fluorophenyl)-5-(trifluoromethyl)-1H-pyrazol-4-yl]isoxazole-4-carboxylate (Example I-42)

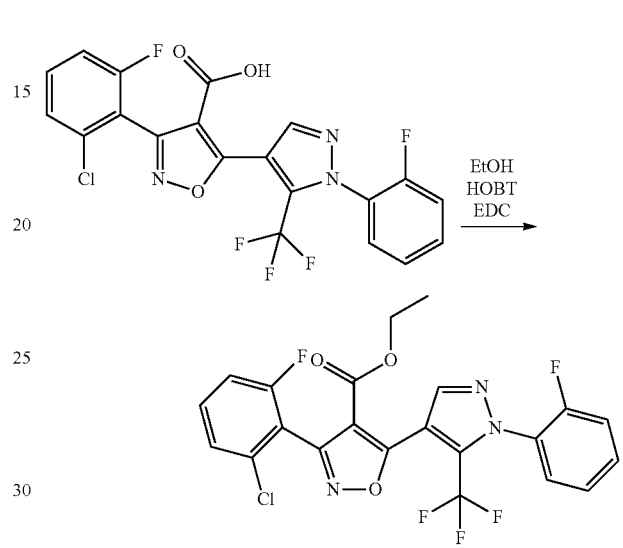

To a suspension of 3-(2-chloro-6-fluorophenyl)-5-(1-(2-fluorophenyl)-5-(trifluoromethyl)-1H-pyrazol-4-yl)isoxazole-4-carbonyl chloride (0.1 g) and ethanol (0.04 mL) in CH$_2$Cl$_2$ (1 mL) Hydroxybenzotriazole (HOBT) (50 mg) and 1-ethyl-3-(3-dimethylaminopropyl) carbodiimide (EDC) (45 mg) were added, the reaction mixture was stirred occasionally until a clear solution was formed and allowed to stay overnight. The solution was diluted with water and the separated organic layer was purified by column chromatography (CHCl$_3$) to give ester compound of example I-42 (yield 75%). Result of LC/MS M+H$^+$: 497.8; $^1$H NMR (DMSO-d$_6$, CCl$_4$): 1.03 (3H, t, CH$_3$), 4.10 (2H, q, CH$_2$), 7.32 (1H, t, CH-arom.), 7.42-7.71 (6H m, CH-arom.), 8.43 (1H, s, CH-pyraz.).

The synthesis of the compounds of examples I-77, I-78, I-90, I-99, I-100, and I-112 was conducted in analogy to the above synthesis of the compound of example I-42.

Synthesis of i-Propyl 3-(2-chloro-6-fluorophenyl)-5-[1-(2-fluorophenyl)-5-(trifluoromethyl)-1H-pyrazol-4-yl]isoxazole-4-carboxylate (Example I-43)

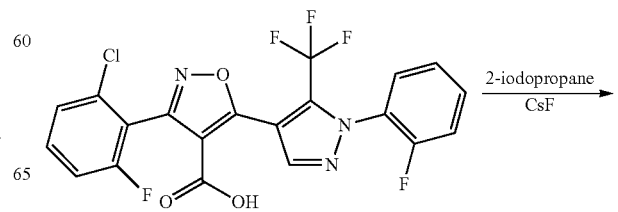

-continued

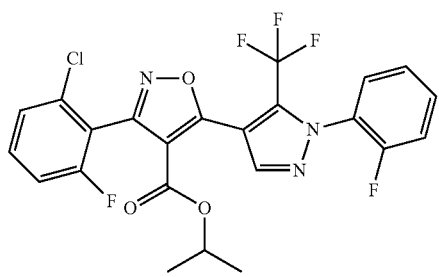

3-(2-chloro-6-fluorophenyl)-5-(1-(2-fluorophenyl)-5-(trifluoromethyl)-1H-pyrazol-4-yl)isoxazole-4-carboxylic acid (30 mg, 0.064 mmol), cesium fluoride (12 mg, 0.077 mmol) and 2-iodopropane (0.008 mL, 0.077 mmol) were dissolved in dried acetonitrile (1 mL) and the mixture was refluxed for 20 h. The mixture was diluted with dichloromethane and washed with water. The organic phase was dried over $Na_2SO_4$, filtered and the solvent was solvent removed under reduced pressure. The product was purified by pTLC (PE/EE 9/1) to give 26 mg of a yellow oil (yield 79%). Result of LC/MS [M+H]+: 511.8; $^1$H NMR ($CDCl_3$): 1.02 (6H, d, 2×$CH_3$), 5.02 (1H, m, CH-propyl), 7.18 (1H, t, CH-arom.), 7.28-7.61 (6H m, CH-arom.), 8.31 (1H, s, CH-pyraz.).

The synthesis of the compounds of examples IB-31, IB-60, IB-61, IB-73; IB-78, IB-79, and IB-82 was conducted in analogy to the above synthesis of the compound of example I-43.

Synthesis of 5-(1-(3-acetamidophenyl)-5-(trifluoromethyl)-1H-pyrazol-4-yl)-3-(2-chloro-6-fluorophenyl)isoxazole-4-carboxylate (Example IB-89)

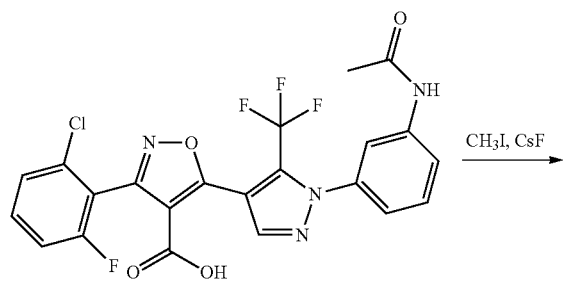

The same esterification procedure as described above for example I-43 was applied, replacing 2-iodopropane by iodomethane to give methyl ester of example IB-89 as a yellow oil (yield 15%).

Synthesis of methyl 3-(2-chloro-6-fluorophenyl)-5-(1-(pyridin-3-yl)-5-(trifluoromethyl)-1H-pyrazol-4-yl)isoxazole-4-carboxylate (Example IB-67)

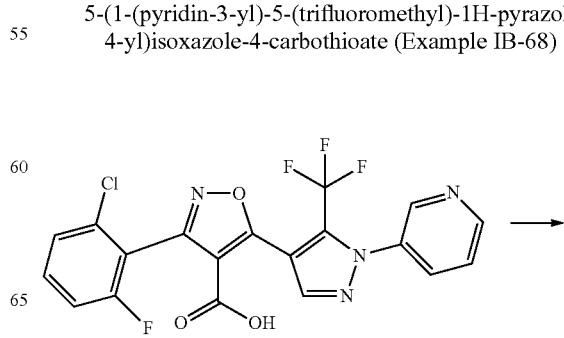

To a mixture of 3-(2-chloro-6-fluorophenyl)-5-(1-(pyridin-3-yl)-5-(trifluoromethyl)-1H-pyrazol-4-yl)isoxazole-4-carboxylic acid (30 mg, 0.1 mmol) in methanol (1.5 mL) was added thionylchloride (5 μL, 0.1 mmol). The mixture was stirred at room temperature for 60 h and for 5 h at reflux. The mixture was diluted with dichloromethane and washed with water (3×), dried over sodium sulfate, filtered and concentrated under reduced pressure. The product (example IB-67) was purified by pTLC (1:1 EE/PE) to give 3 mg of a white solid (yield 9%).

Result of LC/MS MH+: 466.76; $^1$H NMR ($CDCl_3$): 3.19 (s, 3H), 7.15 (t, 0.1H), 7.33-7.55 (m, 6H), 8.25 (s, 1H)

The synthesis of the compounds of examples IB-69, IB-71, IB-75, IB-76, IB-77, IB-92 was conducted in analogy to the above synthesis of the compound of example IB-67.

Synthesis of S-methyl 3-(2-chloro-6-fluorophenyl)-5-(1-(pyridin-3-yl)-5-(trifluoromethyl)-1H-pyrazol-4-yl)isoxazole-4-carbothioate (Example IB-68)

-continued

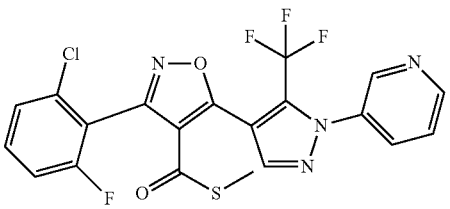

3-(2-chloro-6-fluorophenyl)-5-(1-(pyridin-3-yl)-5-(trifluoromethyl)-1H-pyrazol-4-yl)isoxazole-4-carboxylic acid (30 mg, 0.066 mmol) was treated with thionylchloride (1.5 mL) and stirred at reflux for 2 h. The mixture was concentrated under reduced pressure. The intermediate was treated with benzene (3×) and the benzene was evaporated to remove water. Then, the obtained mixture was dissolved in benzene (1.5 mL) and sodium methanethiolate (32.5 mg, 0.46 mmol) was added. The reaction mixture was stirred at reflux for 5 h. The mixture was diluted with dichloromethane and washed with water (3×), dried over sodium sulfate, filtered and concentrated under reduced pressure. The product (example IB-68) was purified by pTLC (1:1 EE/PE) to give 3 mg of a white solid (yield 9%). Result of LC/MS MH+: 482.76; $^1$H NMR (CDCl$_3$): 2.33 (t, 3H), 7.19 (t, 1H), 7.33-7.55 (m, 6H), 8.23 (s, 1H)

Synthesis of S-methyl 3-(2-chloro-6-fluorophenyl)-5-(1-(3-chlorophenyl)-5-(trifluoromethyl)-1H-pyrazol-4-yl)isoxazole-4-carbothioate (ample I-126)

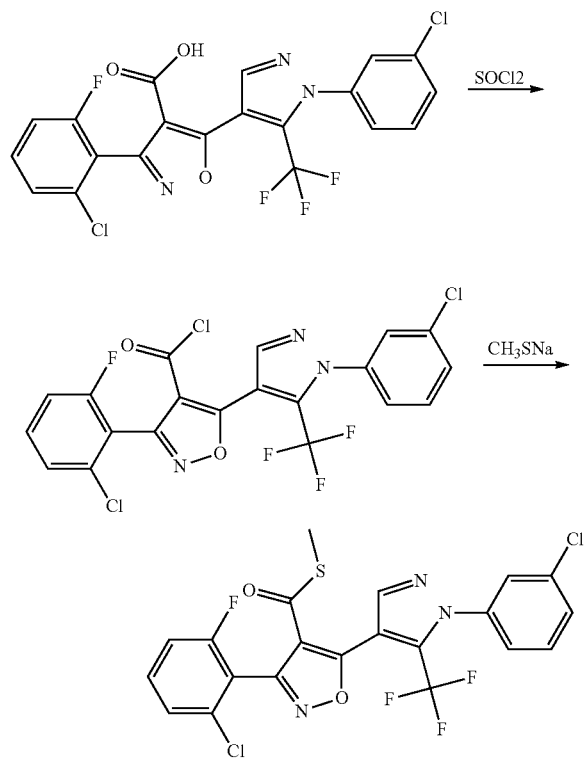

Carboxylic acid 3-(2-chloro-6-fluorophenyl)-5-(1-(3-chlorophenyl)-5-(trifluoromethyl)-1H-pyrazol-4-yl)isoxazole-4-carboxylic acid (60 mg, 0.123 mmol) was refluxed in SOCl$_2$ (5 mL) for 2 hours and an excess of thionyl chloride was evaporated. The residue was dissolved in dry dioxane (5 mL), sodium thiomethoxide (60 mg, 0.86 mmol) was added and the mixture was stirred for 1 day. After evaporation of the solvent, water (5 mL) was added to the residue. The mixture was stirred for 30 min at r.t. and the supernatant was poured off the resulting resin. The product was isolated from this resin by column chromatography (silica gel 0.040-0.100 mm, eluent-chloroform:hexane=1:1). Yield of example I-126: 45 mg (71%) of a slightly grayish resin. Result of LC/MS MH+: 515.9; $^1$H NMR (DMSO-d$_6$; CCl$_4$): 2.30 (s, 3H) 7.37 (t, J=8.66 Hz, 1H) 7.49 (d, J=8.03 Hz, 1H) 7.53-7.61 (m, 1H) 7.61-7.73 (m, 4H) 8.36 (s, 1H)

The synthesis of the compounds of examples I-128 and I-130 was conducted in analogy to the above synthesis of the compound of example I-126.

Synthesis of 3-(2-chloro-6-fluorophenyl)-5-(1-(3-chlorophenyl)-5-(trifluoromethyl)-1H-pyrazol-4-yl)-N-methylisoxazole-4-carbothioamide (Example I-72)

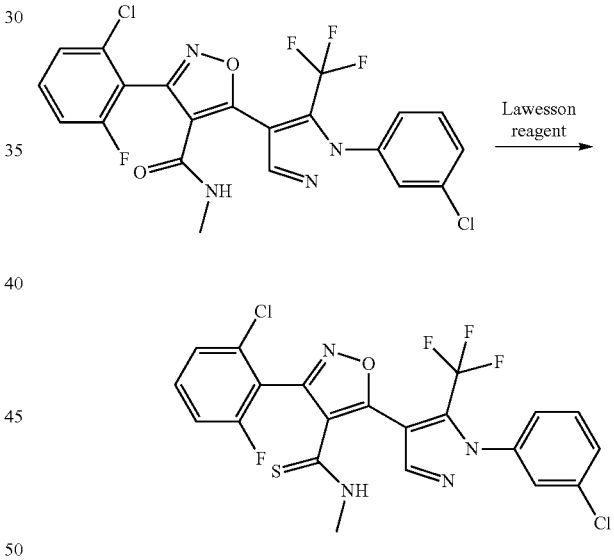

A mixture of compound of example I-19 0.37 g, 0.74 mmol, Lawesson reagent (0.30 g, 0.74 mmol) and dry dioxane (10 mL) was refluxed for 1.5 hours. The solvent was evaporated in vacuum to dryness and the residue crystallized from ethanol (20 mL).

Yield of compound I-72: 0.28 g (73%), yellowish crystals. Result of LC/MS MH+: 516.3; $^1$H NMR (DMSO-d$_6$; CCl$_4$): 3.03 (d, J=4.52 Hz, 3H) 7.25 (t, J=8.53 Hz, 1H) 7.38 (d, J=8.03 Hz, 1H) 7.48-7.57 (m, 2H) 7.58-7.67 (m, 3H) 8.05 (s, 1H) 10.31 (d, J=4.52 Hz, 1H)

The synthesis of the compounds of examples I-76, I-122, I-123, v125, I-129, IB-101 and IB-102 was conducted in analogy to the above synthesis of the compound of example I-72. Result of LC/MS MH+: 502.3

Synthesis of 3-(2-chloro-6-fluorophenyl)-5-(1-(4-fluorophenyl)-5-(trifluoromethyl)-1H-pyrazol-4-yl)isoxazole (Example I-25)

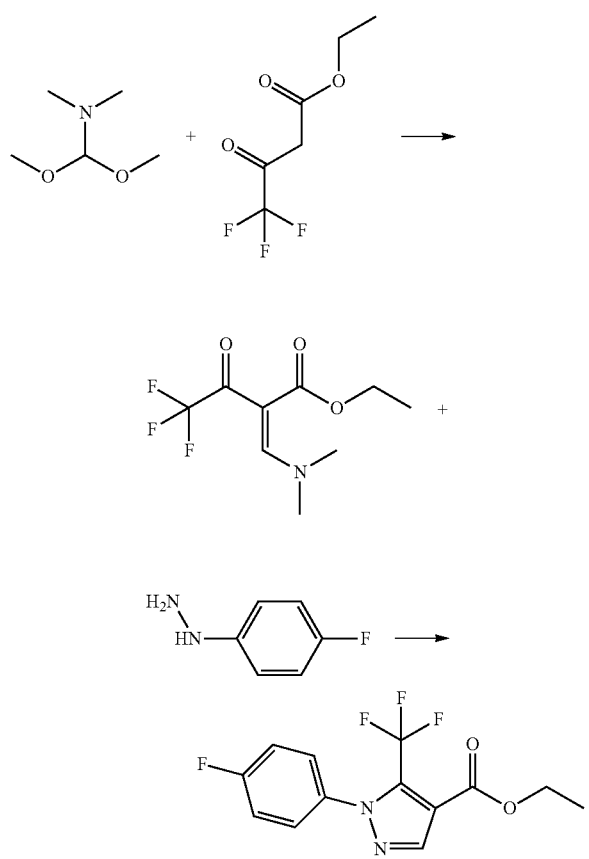

Ethyl 1-(4-fluorophenyl)-5-(trifluoromethyl)-1H-pyrazole-4-carboxylate

Ethyl 4,4,4-trifluoroacetoacetate (18.5 g, 77.34 mmol) and N,N-Dimethylformamide dimethyl acetal (9.21 g, 77.34 mmol) were dissolved in benzene (10 mL). The mixture was heated under reflux for 1 h. The solvent was evaporated and distilled with a Kugelrohr apparatus to give 12 g of ethyl 2-((dimethylamino)methylene)-4,4,4-trifluoro-3-oxobutanoate (yield 65%).

Phenylhydrazine (2.62 g, 20.82 mmol) was dissolved in anhydrous THF (100 mL) and triethylamine (2.9 mL, 20.82 mmol) was added. The solution was cooled to −10° C. A solution of ethyl 2-((dimethylamino)methylene)-4,4,4-trifluoro-3-oxobutanoate (5 g, 20.82 mmol) in 20 mL THF was added dropwise in 1 h. The mixture was then stirred 30 min at −10° C. and then 16 h at room temperature. The solvent was evaporated. The obtained oil was dissolved in ethylacetate and washed with a solution of sodium hydrogencarbonate and citric acid. The organic phase was dried over magnesium sulfate, filtered and evaporated. The product was purified by column chromatography (80:20 PE:EE) to give 2.8 g of ethyl 1-(4-fluorophenyl)-5-(trifluoromethyl)-1H-pyrazole-4-carboxylate (yield 44%).

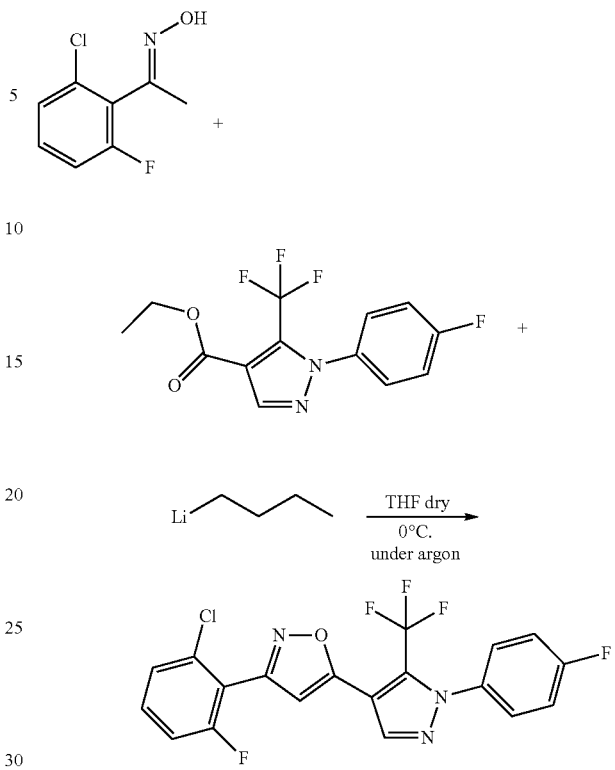

To a solution of 1.9243 g (10.2571 mmol) (E)-1-(2-chloro-6-fluorophenyl)ethanone oxime in 30 mL dry THF 8 mL (2 eq.) n-Butyllithium were added dropwise under argon and icebath cooling. 1.55 g (0.5 eq.) of ethyl 1-(4-fluorophenyl)-5-(trifluoromethyl)-1H-pyrazole-4-carboxylate were dissolved in 5 mL dry THF and also added within 5 minutes. The solution was stirred for 15 minutes at 0° C.

To this reaction mixture 40 mL hydrochloric acid (10% solution in water) were added. The mixture was heated under reflux for 1 h. The aqueous solution was extracted three times with ethyl acetate. The organic layer was dried over anhydrous magnesium sulfate and the solvent was removed in vacuo, TLC (4:1 hexane:ethyl acetate) showed several spots of impurities.

The product was purified by flash chromatography on silica gel with hexane:ethyl acetate 4:1 and 355 mg (yield of theory 48%) of compound I-25 were obtained. LC/MS MH+: 426.0; $^1$H NMR (DMSO-d$_6$; CCl$_4$): 7.17 (1H, s, isooxazole); 7.42-7.71 (7H, m, arom.); 8.48 (1H, s, pyrazole)

Synthesis of (E)-3-(2-chloro-6-fluorophenyl)-5-(2-(dimethylamino)vinyl)isoxazole-4-carbonitrile

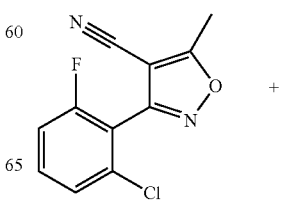

-continued

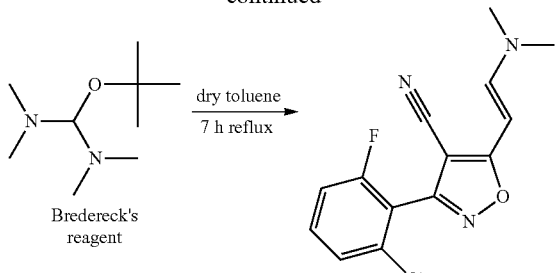

Bredereck's reagent

To a solution of 1.5 g (6.3389 mmol) 3-(2-chloro-6-fluorophenyl)-5-methylisoxazole-4-carbonitrile in 100 mL dry toluene, were added 2.10 g (12.6779 mmol) tert-Butoxy-bis(dimethylamino)methane. The reaction mixture was heated under reflux for 12 h. The mixture was concentrated in vacuo and was dried in the high vacuum. Petroleum ether was added to the crystallized residue. The product was collected by filtration and 1.791 g (yield of theory: 95.9%) of clean product were obtained. Result of LC/MS MH+: 292.0; $^1$H NMR (DMSO-d$_6$; CCl$_4$): 2.93 (3H, s, N—CH$_3$), 3.17 (3H, s, N—CH$_3$), 5.15-5.20 (1H, d, C$_2$H$_2$), 7.74-7.78 (1H, d, C$_2$H$_2$), 7.45-7.52 (1H, dd, CH-arom.), 7.57-7.59 (1H, d, CH-arom.), 7.65-7.71 (1H, d, CH-arom.)

Synthesis of (Z)-3-(2-chloro-6-fluorophenyl)-5-(1-(dimethylamino)-4,4,4-trifluoro-3-oxobut-1-en-2-yl)isoxazole-4-carbonitrile

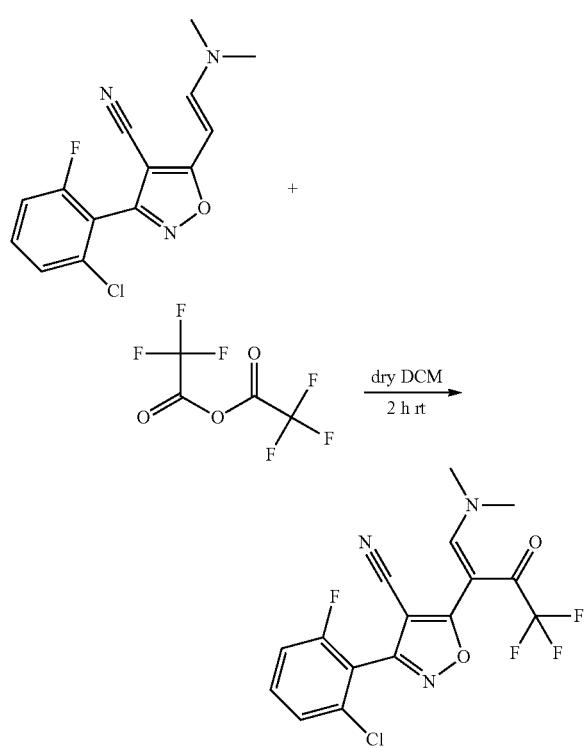

To a solution of 0.5 g (1.7140 mmol) (E)-3-(2-chloro-6-fluorophenyl)-5-(2-(dimethylamino)vinyl)isoxazole-4-carbonitrile in 20 mL dry dichloromethane, were added dropwise under ice-bath cooling 0.36 mL (2.5710 mmol) trifluoroacetic anhydride. The reaction mixture was stirred for 2 h at r.t. Afterwards the mixture was concentrated in vacuo and was dried in the high vacuum, Petroleum ether was added to the crystallized product and was collected by filtration to obtain 0.625 g (yield of theory: 94%) of clean product. Result of LC/MS MH+: 388.0; $^1$H NMR (DMSO-d$_6$; CCl$_4$): 2.75 (3H, s, N—CH$_3$), 3.46 (3H, s, N—CH$_3$), 7.53-7.59 (1H, dd, CH-arom.), 7.64-7.67 (1H, d, CH-arom.), 7.73-7.81 (1H, d, CH-arom.), 8.23 (1H, s, CH)

Synthesis of 3-(2-chloro-6-fluorophenyl)-5-(1-(3-chlorophenyl)-5-(trifluoromethyl)-1H-pyrazol-4-yl)isoxazole-4-carbonitrile (Example I-49)

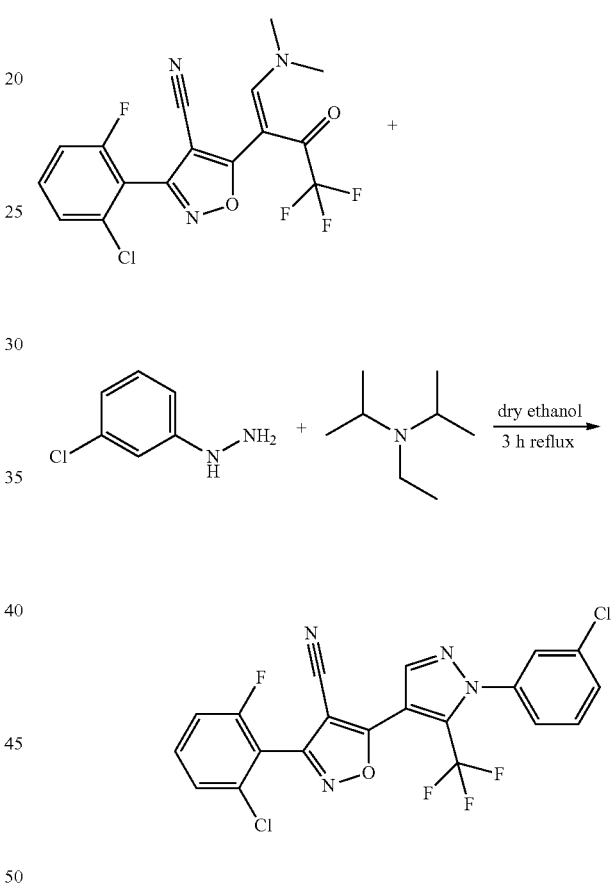

To a solution of 0.1 g (0.2579 mmol) (Z)-3-(2-chloro-6-fluorophenyl)-5-O-(dimethylamino)-4,4,4-trifluoro-3-oxobut-1-en-2-yl)isoxazole-4-carbonitrile in dry ethanol, were added 0.0462 g (0.2579 mmol) 3-Chlorophenylhydrazine and 0.78 mL (0.2579 mmol) DIPEA. The reaction mixture was heated under reflux for 3 h. The mixture was concentrated in vacuo and was dried in the high vacuum. The upper spot was isolated by using the preparative thin-layer chromatography and 0.0037 g (yield of theory: 3.0%) of clean product compound I-49 were obtained. Result of LC/MS MH+: 466.9; $^1$H NMR (DMSO-d$_6$; CCl$_4$): 7.73-7.97 (6H, m, CH-arom.), 8.04 (1H, s, CH-arom.), 8.81 (1H, s, CH-pyraz.)

The synthesis of the compound of example I-120 was conducted in analogy to the above synthesis of the compound of example I-49.

Synthesis of Synthesis of 3-(2-chloro-6-fluorophenyl)-5-(1-(3-chlorophenyl)-5-(trifluoromethyl)-1H-pyrazol-4-yl)-N-methylisoxazole-4-carbothioamide (Example I-64)

Synthesis of methyl 3-(2-chloro-6-fluorophenyl)-5-(1-(3-fluorophenyl)-5-(trifluoromethyl)-1H-pyrazol-4-yl)isothiazole-4-carboxylate (Example I-137)

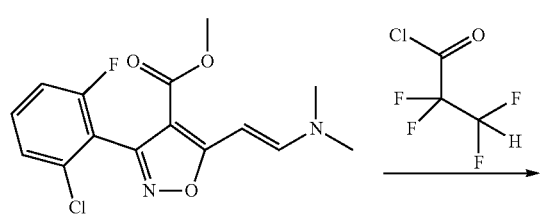

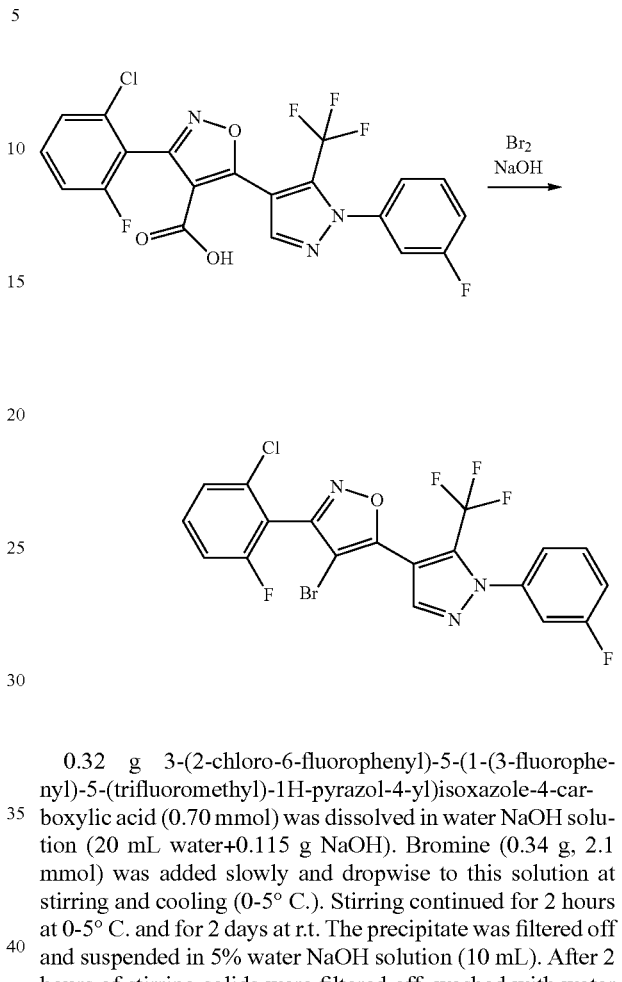

To a cooled (frozen) solution of (E)-methyl 3-(2-chloro-6-fluorophenyl)-5-(2-(dimethylamino)vinyl)isoxazole-4-carboxylate (85 mg, 0.26 mmol) a mixture of absolute dioxane (2.3 g) and Hünig's base (156 mg, 1.20 mmol) 2,2,3,3-tetrafluoropropanoyl chloride (129 mg, 0.76 mmol) was added. Reaction mixture (solution) was left to melt and kept for 1.5 h at r.t. TLC in EtOAc/C$_7$H$_{16}$ 9/1 showed no starting material and a single product. Solution was evaporated to dryness, oily residue was treated by boiling hexane which was concentrated to give pure (E)-methyl 3-(2-chloro-6-fluorophenyl)-5-(1-(dimethylamino)-4,4,5,5-tetrafluoro-3-oxopent-1-en-2-yl)isoxazole-4-carboxylate. The Residual oily (E)-methyl 3-(2-chloro-6-fluorophenyl)-5-(1-(dimethylamino)-4,4,5,5-tetrafluoro-3-oxopent-1-en-2-yl)isoxazole-4-carboxylate was used for further reactions without additional purification. Treating raw (E)-methyl 3-(2-chloro-6-fluorophenyl)-5-O-(dimethylamino)-4,4,5,5-tetrafluoro-3-oxopent-1-en-2-yl)isoxazole-4-carboxylate (116 mg) by 3-fluorophenyl hydrazine hydrochloride (42 mg) in ethanol by standard procedure gave 96 mg (73%) of pure compound I-64. Result of LC/MS MH+: 516.8; $^1$H NMR (400 MHz, DMSO-d$_6$) δppm 3.55-3.78 (m, 13H) 6.55-6.95 (m, 5H) 7.24-7.53 (m, 20H) 7.55-7.73 (m, 8H) 8.33 (s, 4H)

0.32 g 3-(2-chloro-6-fluorophenyl)-5-(1-(3-fluorophenyl)-5-(trifluoromethyl)-1H-pyrazol-4-yl)isoxazole-4-carboxylic acid (0.70 mmol) was dissolved in water NaOH solution (20 mL water+0.115 g NaOH). Bromine (0.34 g, 2.1 mmol) was added slowly and dropwise to this solution at stirring and cooling (0-5° C.). Stirring continued for 2 hours at 0-5° C. and for 2 days at r.t. The precipitate was filtered off and suspended in 5% water NaOH solution (10 mL). After 2 hours of stirring solids were filtered off, washed with water and dried on air to a yield of 0.15 g (0.30 mmol, 42%) of compound I-137 as white crystals. Result of LC/MS MH+: 505.7; $^1$H NMR (DMSO-d$_6$; CCl$_4$): 7.35-7.48 (m, 4H) 7.52 (d, J=8.28 Hz, 1H) 7.61-7.74 (m, 2H) 8.4 (s, 1H)

Further examples which were obtained in analogy to the protocol of example I-137 are: I-140, I-144, I-145, IB-23, IB-24, IB-25, IB-26, IB-27, IB-28, and IB-83.

Synthesis of methyl 3-(2-chloro-6-fluorophenyl)-5-(1-(3-fluorophenyl)-5-(trifluoromethyl)-1H-pyrazol-4-yl)isothiazole-4-carboxylate (Example I-133)

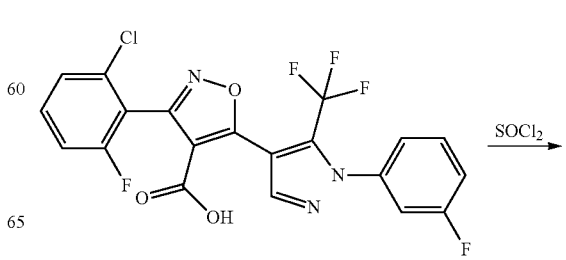

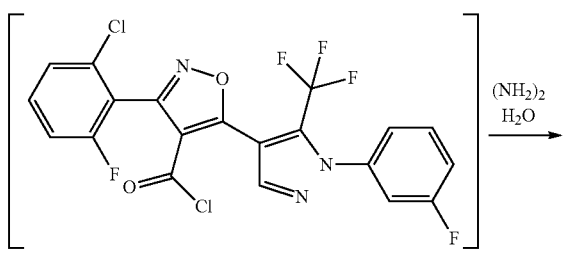
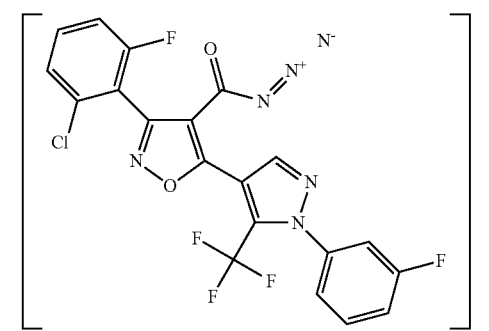

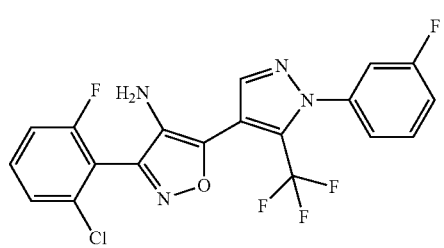

Solution of 102 mg (0.217 mmol) of 3-(2-chloro-6-fluorophenyl)-5-(1-(3-fluorophenyl)-5-(trifluoromethyl)-1H-pyrazol-4-yl)isoxazole-4-carboxylic acid in 8 mL SOCl$_2$ was refluxed for 3 h. Volatiles were evaporated in vacuum thoroughly. The residue was dissolved in 8 mL absolute dioxane and added at stirring dropwise to a mixture of 825 mg N$_2$H$_4$*H$_2$O and 6 mL absolute dioxane. TLC of reaction mixture showed new product with R$_f$ less that starting acid in EtOAc/heptane, 1/1 and greater—in EtOAc/Et$_3$N. Volatiles were evaporated, water was added to residue to precipitate an oily pink solid. Water was removed, residue was washed by water, than treated by 5 mL water with 10 drops of AcOH and finally washed by water.

Product was partially extracted by boiling heptane (38 mg) and partially extracted by ether with further treatment of the ether solution by heptane (39 mg). Total yield: 77 mg (73%) of compound I-133. Result of LC/MS MH+: 484.8; $^1$H NMR (DMSO-d$_6$; CCl$_4$): 4.49 (2H, s, NH$_2$), 7.44-7.79 (7H, m, CH-arom.), 8.44 (1H, s, CH-pyraz.), 9.54 (1H, s, NH)

Example I-134 was synthesized according to the protocol described for example I-133.

Synthesis of 3-(2-chloro-6-fluorophenyl)-5-(1-(3-fluorophenyl)-5-(trifluoromethyl)-1H-pyrazol-4-yl)isoxazol-4-amine (Example I-117)

Compound I-133 (0.60 g, 1.24 mmol) was dissolved in the mixture of dioxane (20 mL), H$_2$O (5 mL), HCl conc. (1 mL). A solution of NaNO$_2$ (0.532 g) in water (10 mL) was added dropwise at stirring and cooling (0-5° C.). After 30 min of stirring at this temperature the mixture was poured onto ice (approx. 50 g). A resinous residue of crude azide formed. After staying overnight in a refrigerator the supernatant was decanted. The residue was dissolved in the mixture of dioxane (20 mL) and water (6 mL) and refluxed for 30 min. The solvent was evaporated to dryness in vacuum. The residue was dissolved in a minimal amount of chloroform and pure product was isolated by column chromatography (silica gel 0.040-0.100 mm, eluent-chloroform, Rf≈0.3). Yield of compound I-117: 0.324 g (0.73 mmol, 59%) of a yellowish solid. Result of LC/MS MH+: 440.94; 1H NMR (DMSO-d6; CCl4): 4.56 (2H, s, NH2), 7.36-7.68 (7H, m, CH-arom.), 8.36 (1H, s, CH-pyraz.)

Example IB-36 was synthesized according to the protocol described for example I-117.

Synthesis of N-(3-(2-chloro-6-fluorophenyl)-5-(1-(3-fluorophenyl)-5-(trifluoromethyl)-1H-pyrazol-4-yl)isoxazol-4-yl)acetamide (Example I-139)

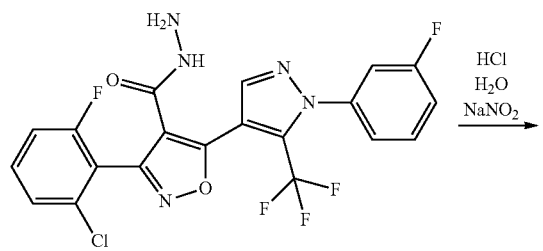
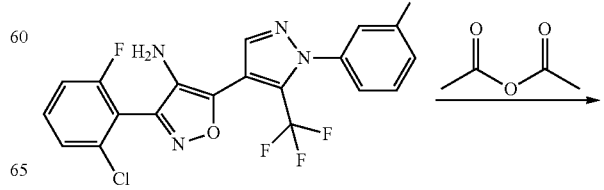

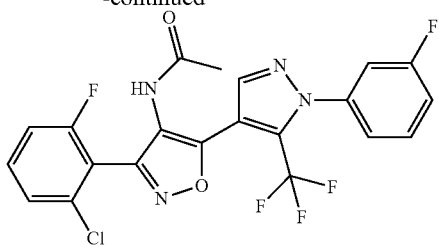

A mixture of compound I-117 (0.167 g, 0.38 mmol) and acetic anhydride (3 mL) was refluxed for 2 hours (until absence of starting amine by TLC). After cooling, water (15 mL) was added and the reaction mixture was stirred for 1 hour. The supernatant was removed from the oily precipitate of crude product. Purification by column chromatography (silica gel 0.040-0.100 mm, eluent-chloroform, $R_f$=0.25) gave an oil, which solidified after treatment with hexane. Yield of compound I-139: 0.112 g (0.23 mmol, 61%) of a yellowish solid. Result of LC/MS MH+: 483.8; $^1$H NMR (DMSO-d$_6$; CCl$_4$): 1.90 (s, 3H) 7.28 (t, J=8.66 Hz, 1H) 7.33-7.46 (m, 4H) 7.50-7.59 (m, 1H) 7.59-7.68 (m, 1H) 8.22 (s, 1H) 9.55 (s, 1H)

Example IB-39 was synthesized according to the protocol described for example I-139.

Synthesis of N-(3-(2-chloro-6-fluorophenyl)-5-(1-(3-chlorophenyl)-5-(trifluoromethyl)-1H-pyrazol-4-yl)isoxazol-4-yl)formamide (Example IB-48)

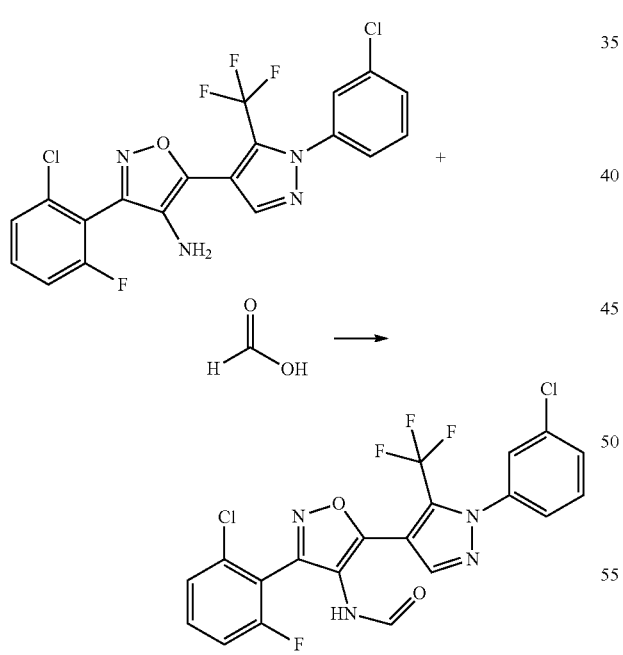

3-(2-chloro-6-fluorophenyl)-5-(1-(3-chlorophenyl)-5-(trifluoromethyl)-1H-pyrazol-4-yl)isoxazol-4-amine (example IB-36) (40 mg, 0.1 mmol) was dissolved in formic acid (3 mL). The mixture was stirred at room temperature overnight. The resulting precipitate was collected, washed with water and dried under vacuum. The product was purified by pTLC (EE/PE 2:1) to give 32 mg of the desired product (example IB-48) (yield 75%). Result of LC/MS MH+: 484.82; $^1$H NMR (CDCl$_3$): 6.63 (t, 1H), 7.22 (m, 1H), 7.38-7.59 (m, 6H), 8.02 (s, 1H) 8.22 (s, 1H)

Synthesis of 3-(2-chloro-6-fluorophenyl)-5-[1-(3-fluorophenyl)-3-(trifluoromethyl)-1H-pyrazol-4-yl]isoxazol-4-ylformamide (Example I-141)

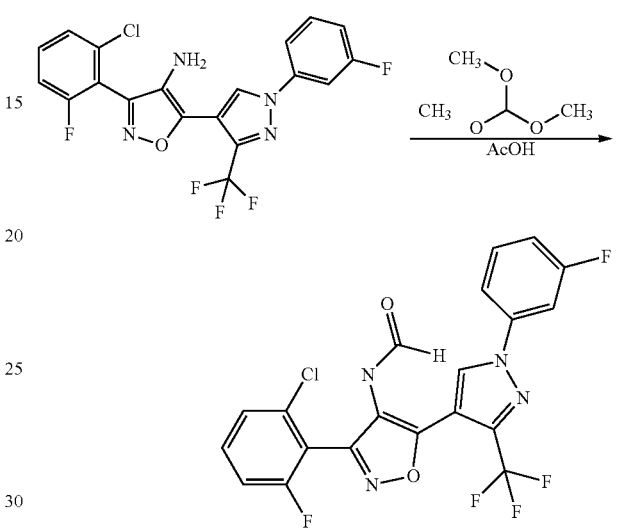

A solution of 130 mg (0.295 mmol) 3-(2-chloro-6-fluorophenyl)-5-[1-(3-fluorophenyl)-3-(trifluoromethyl)-1H-pyrazol-4-yl]isoxazol-4-amine (example I-117) in a mixture of 1847 mg (17.4 mmol) trimethylorthoether and 1660 mg (27.7 mmol) acetic acid was stirred at r.t. for 1 h. The suspension was filtered, and the obtained white solid salts were washed on the filter with hexane. Filtrates were combined and evaporated to dryness. The residue was treated by hexane, and the extract was purified by CC on silica gel, (eluent EtOAc/hexane 1/1). The obtained fraction of the pure product (example I-141) was evaporated to give 50 mg of a light greenish oil (yield 36%). Result of LC/MS MH+: 469.04; $^1$H NMR (400 MHz, methanol-d$_4$): 7.29-7.35 (m, 1H) 7.44 (s, 3H) 7.46-7.50 (m, 1H) 7.57-7.67 (m, 2H) 7.72 (s, 1H) 8.26 (s, 1H)

N-{3-(2-chloro-6-fluorophenyl)-5-[1-(3-fluorophenyl)-5-(trifluoromethyl)-1H-pyrazol-4-yl]-1,2-oxazol-4-yl}-2,2,2-trifluoroacetamide (Example IB-22)

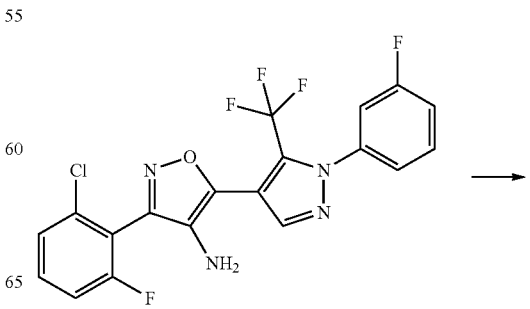

-continued

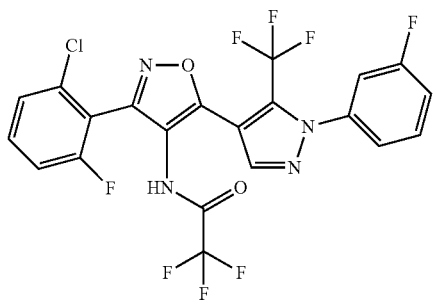

A mixture of 3-(2-chloro-6-fluorophenyl)-5-(1-3-fluorophenyl)-5-(trifluoromethyl)-1H-pyrazol-4-yl)isoxazol-4-amine (example I-117) (70 mg, 0.159 mmol), dioxane (5 ml) and trifluoroacetic anhydride (50 mg) was stirred at r.t. overnight. The solvent was evaporated in vacuum and water (5 ml) was added to the residue. The precipitate was filtered off, washed with water and dried to give 77 mg of example IB-22 (yield 90.2%). $^1$H NMR (DMSO-D6, CCl$_4$): 7.37 (m, 4H), 7.57 (m 2H), 8.26 (s, 1H), 11.29 (s, 1H).

Synthesis of (Z)-methyl N-(3-(2-chloro-6-fluorophenyl)-5-(1-(3-fluorophenyl)-5-(trifluoromethyl)-1H-pyrazol-4-yl)isoxazol-4-yl)-2,2,2-trifluoroacetimidate (Example I-136)

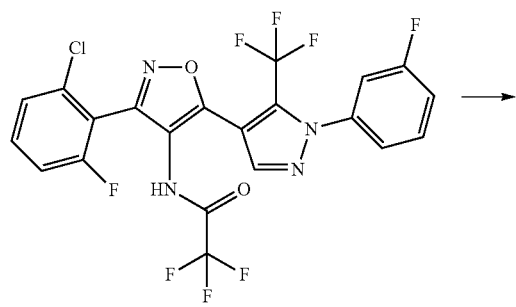

A mixture of example IB-22 (30 mg, 0.056 mmol), acetone (5 ml), anhydrous K$_2$CO$_3$ (100 mg) and CH$_3$I (100 mg) was stirred at r.t. overnight. Inorganic salts were filtered off and washed with acetone. The filtrate and rinse were combined and the solvent was evaporated in vacuum to give example I-136 as viscous resin (27 mg, 0.049 mmol, 87.5%) as a mixture of Z and E isomers (According to $^1$H NMR data). $^1$H NMR (DMSO-D6, CCl$_4$): 3.24-3.36 (m, 3H), 7.31-7.57 (m, 6H), 7.58-7.75 (m 2H), 8.23 (s, 1H).

Synthesis of N'-acetyl-3-(2-chloro-6-fluorophenyl)-5-(1-(2-fluorophenyl)-5-(trifluoromethyl)-1H-pyrazol-4-yl)isoxazole-4-carbohydrazide (Example I-142)

To a solution of 190 mg (0.393 mmol) 3-(2-chloro-6-fluorophenyl)-5-(1-(2-fluorophenyl)-5-(trifluoromethyl)-1H-pyrazol-4-yl)isoxazole-4-carbohydrazide (which was synthesized in analogy to the procedure described for example I-133) in 5.8 ml absolute dioxane, 148 mg (1.885 mmol) acetyl chloride were added. The conversion is complete within minutes. Volatiles were evaporated, residue was re-evaporated with ethanol. Residue was crystallized from EtOAc-heptane to give 175 mg (85%) of compound I-142 as a pale yellow powder. Result of LC/MS MH+: 526.06; $^1$H-NMR (400 MHz, methanol-d$_4$) δ ppm: 1.98 (3H, s, CH$_3$), 7.25-7.32 (1H, m, CH-arom.), 7.41-7.48 (3H, m, CH-arom.), 7.54-7.61 (1H, m, CH-arom), 7.64-7.74 (1H, m, CH-arom.), 8.63 (1H, s, CH-pyraz.)

Synthesis of 5-(1-(2-aminophenyl)-5-(trifluoromethyl)-1H-pyrazol-4-yl)-3-(2-chloro-6-fluorophenyl)isoxazole-4-carboxylate (Example IB-98)

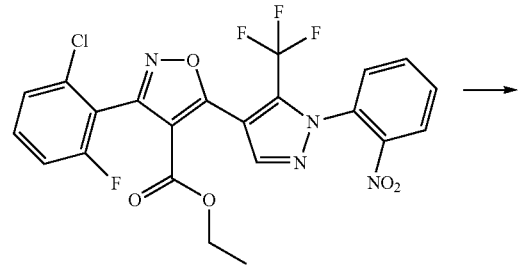

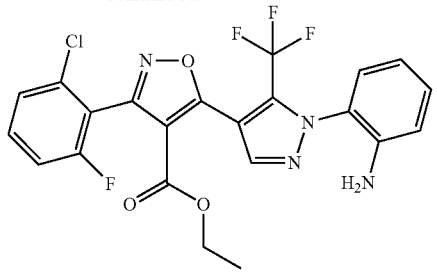

3-(2-chloro-6-fluorophenyl)-5-(1-(2-nitrophenyl)-5-(trifluoromethyl)-1H-pyrazol-4-yl)isoxazole-4-carboxylate (example IB-95) (100 mg, 0.19 mmol) was placed in a vial in the presence of acetic acid (1.5 mL) in tetrahydrofuran (2 mL). The solution was stirred and concentrated hydrochloric acid (0.03 mL, 0.19 mmol) and zinc (80.9 mg, 1.24 mmol) were added successively under ice-cooling. The mixture was allowed to stir at room temperature for 12 h. An aqueous solution of ammonia (25%) was added to the reaction mixture to alkalify. The mixture was then extracted with ethyl acetate and the organic layer was washed with brine, dried over MgSO₄, filtered and the solvent was removed under reduced pressure.

The product (example IB-98) was purified by pTLC (CH₂Cl₂/MeOH 100/5) to give 25 mg as a brown/yellow oil (yield 27%). Result of LC/MS MH+: 494.70; ¹H NMR (CDCl₃): 1.05 (t, 3H), 3.80 (s, 2H), 4.18 (q, 2H), 6.85 (m, 2H), 7.11-7.45 (m, 5H), 8.23 (s, 1H)

Synthesis of 5-(1-(2-acetamidophenyl)-5-(trifluoromethyl)-1H-pyrazol-4-yl)-3-(2-chloro-6-fluorophenyl)isoxazole-4-carboxylate (Example IB-1)

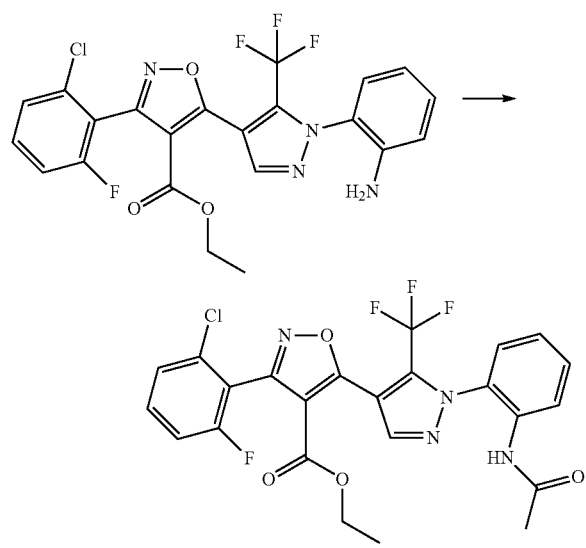

To a solution of ethyl 5-(1-(2-aminophenyl)-5-(trifluoromethyl)-1H-pyrazol-4-yl)-3-(2-chloro-6-fluorophenyl)isoxazole-4-carboxylate (example IB-98) (21 mg, 0.04 mmol) in acetic acid (1 mL) was added acetic anhydride (4 μL, 0.04 mmol). The mixture was stirred over night at room temperature. The mixture was diluted with dichloromethane and washed with water (3×), dried over sodium sulfate, filtered and concentrated under reduced pressure. The resulting oil was purified by TLC (DCM:MeOH 100:5) to give 3 mg of example IB-1 as a yellowish oil (yield 13%). Result of LC/MS MH+: 536.10; ¹H NMR (CDCl₃): 1.05 (t, 3H), 2.11 (s, 3H), 4.18 (q, 2H), 7.11-7.60 (m, 7H), 8.33 (s, 1H)

Synthesis of methyl 3-(2-chloro-6-fluorophenyl)-5-[1-(3-fluorophenyl)-5-(trifluoromethyl)-1H-pyrazol-4-yl]isoxazol-4-ylcarbamate (Example I-138)

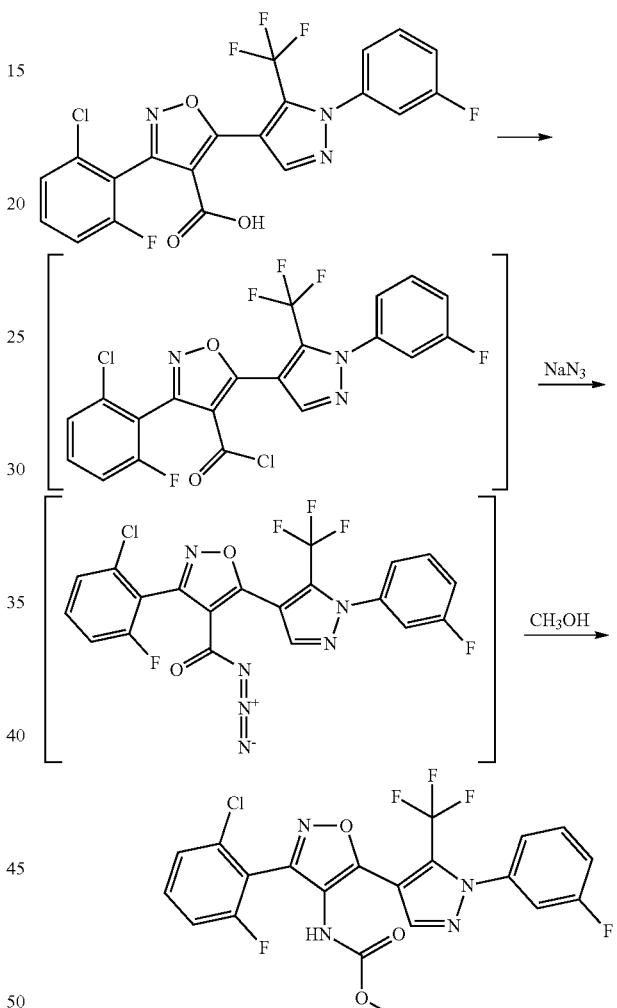

3-(2-chloro-6-fluorophenyl)-5-[1-(3-fluorophenyl)-5-(trifluoromethyl)-1H-pyrazol-4-yl]isoxazole-4-carboxylic acid (103 mg, 0.219 mmol) was dissolved in thionyl chloride (6 mL) and refluxed for 3 h. Volatiles were evaporated in vacuum, the residue was dissolved in absolute benzene (~5 mL), and sodium azide (281 mg, 4.322) and 10 drops of triethylamine were added to the solution (pH<7). The suspension was stirred for 3 h. Volatiles were evaporated in vacuum, and the residue was treated with 2×10 mL ether. Ethereal extracts were evaporated to give a viscous brown oil. Methanol (~5 mL) was added to the oil and the solution was kept at r.t. for 1 day. Volatiles were evaporated in vacuum, the residue was treated with 2×10 mL boiling heptane followed by evaporation of the solvent, giving 55 mg crude product. Column chromatography on silica gel (eluent EtOAc/heptane, 1/1 v/v) gave pure methyl 3-(2-chloro-6-fluorophenyl)-5-[1-(3-fluorophenyl)-5-(trifluoromethyl)-1H-pyrazol-4-yl]isoxazol-4-ylcarbamate (example I-138) (45 mg, 41%). Result of LC/MS MH+: 498

Methyl 3-(2-chloro-6-fluorophenyl)-5-[1-(2-fluorophenyl)-1H-pyrazol-4-yl]isoxazole-4-carboxylate (Example I-89)

A) methyl 3-(2-chloro-6-fluorophenyl)-5-(1-(dimethylamino)-3-oxoprop-1-en-2-yl)isoxazole-4-carboxylate

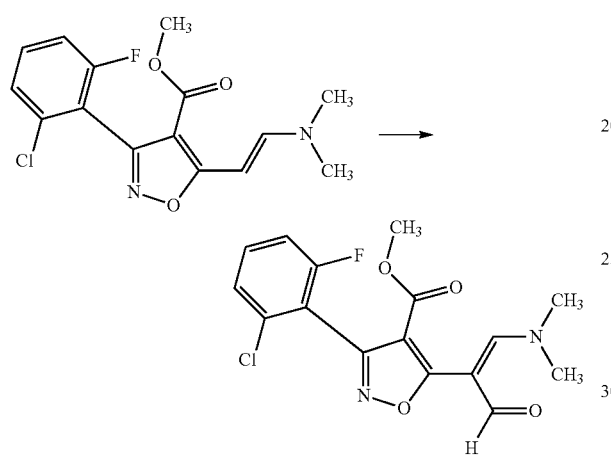

Methyl 3-(2-chloro-6-fluorophenyl)-5-(1-(dimethylamino)-3-oxoprop-1-en-2-yl)isoxazole-4-carboxylate was synthesized from methyl 3-(2-chloro-6-fluorophenyl)-5-(2-(dimethylamino)vinyl)isoxazole-4-carboxylate using a Vilsmeier formulation in analogy to *Tetrahedron Lett.* 1988, 29, 2339.

B)

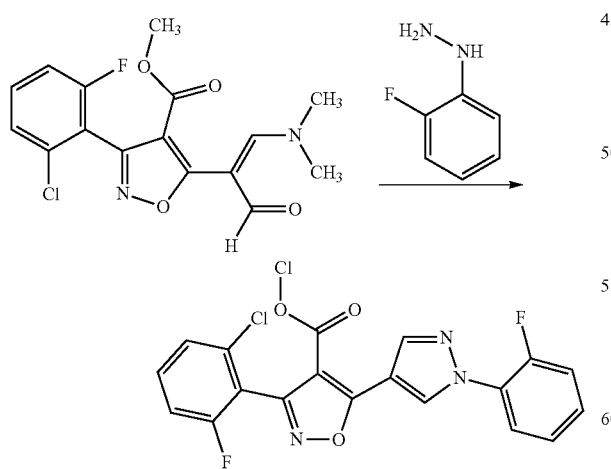

To a solution of raw methyl 3-(2-chloro-6-fluorophenyl)-5-[2-(dimethylamino)-1-formylvinyl]isoxazole-4-carboxylate (36 mg, 0.102 mmol) in ethanol (460 mg), 2-fluorophenyl hydrazine hydrochloride (16 mg, 0.100 mmol) was added. The mixture was warmed to 55-60° C. until a TLC sample showed no starting enamine. The solution was evaporated to dryness in vacuum, the reside was extracted with 3×10 ml of boiling hexane, and the hexane extracts were combined and concentrated and cooled to room temperature. Crystallization gave 25 mg of desired product (example I-89) (yield 60%). Result of LC/MS MH+: 416.05; $^1$H NMR (CDCl$_3$): 3.67 (s, 3H), 7.30 (t, 1H), 7.45 (m, 4H), 7.57 (m, 1H), 7.93 (t, 1H), 8.50 (s, 1H), 9.13 (s, 1H).

Further examples which were obtained in analogy to the protocol of example I-89 are: I-115, and IB-21.

Synthesis of methyl 3-(2-chloro-6-fluorophenyl)-5-{[1-(4-methoxycarbonyl-3-(4-chlorophenyl)isoxazol-5-yl)-5-trifluoromethyl-1H-pyrazol-4-yl]}-isoxazole-4-carboxylate (Example I-131)

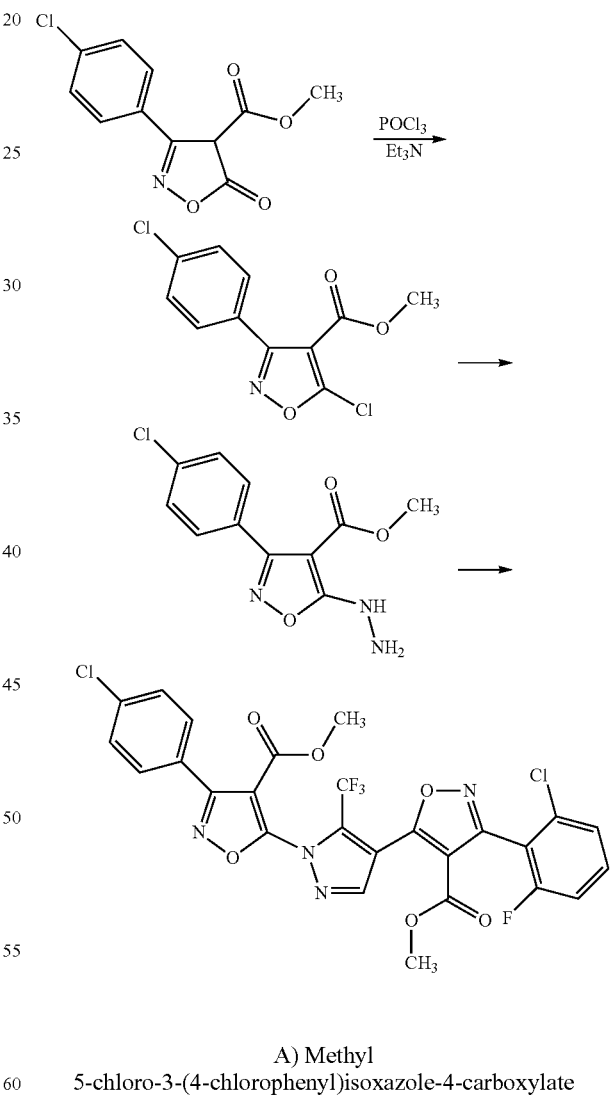

A) Methyl 5-chloro-3-(4-chlorophenyl)isoxazole-4-carboxylate

A suspension of methyl 3-(4-chlorophenyl)-5-oxo-4,5-dihydroisoxazole-4-carboxylate (518 mg, 2.04 mmol; building block is commercially available) in POCl$_3$ (3 mL) was cooled to 0-5° C., and upon stirring, Et$_3$N (0.3 mL) was added dropwise. The resulting mixture was heated to 100-110° C. and stirred at this temperature for 2-2.5 h, cooled to room temperature, poured into iced water and neutralized with aqueous NaOH (10%). The product was extracted with ether and purified by column chromatography (hexane:EtOAc 25:2) to give 320 mg of a yellow solid. Yield 57%. $^1$H NMR (DMSO-D6, CCl4): 3.79 (3H, s, OCH3), 7.50 (2H, AB-syst., CH-arom.), 7.65 (2H, AB-syst., CH-arom.).

B) Methyl 3-(4-chlorophenyl)-5-hydrazinoisoxazole-4-carboxylate

To an ice cooled solution of hydrazine hydrate in MeOH (0.3 mL in 5 mL) methyl 5-chloro-3-(4-chlorophenyl)isoxazole-4-carboxylate (0.3 g, 1.1 mmol) dissolved in CH$_2$Cl$_2$ (2 mL) was added dropwise. The reaction mixture was stirred for 2 h and half of the solvent was evaporated. The product was filtered off, washed with cold methanol and dried to give 227 mg (77%) of 5-hydrazinoisoxazole. $^1$H NMR (DMSO-D6, CCl4): 3.1 (3H, bs, NH+H2O), 3.64 (3H, s, OCH3), 4.65 (2H, bs, NH2), 7.43 (2H, AB-syst., CH-arom.), 7.60 (2H, AB-syst., CH-arom.).

C) Methyl 3-(2-chloro-6-fluorophenyl)-5-{[1-(4-methoxycarbonyl-3-(4-chlorophenyl)isoxazol-5-yl)-5-trifluoromethyl-1H-pyrazol-4-yl]}-isoxazole-4-carboxylate (Example I-131)

The mixture of methyl 3-(2-chloro-6-fluorophenyl)-5-(1-(dimethylamino)-4,4,4-trifluoro-3-oxobut-1-en-2-yl)isoxazole-4-carboxylate (157 mg, 0.37 mmol) and methyl 3-(4-chlorophenyl)-5-hydrazinoisoxazole-4-carboxylate (0.1 g, 0.37 mmol) in ethanol (1 mL) was heated at 60° C. for 5 h, the solution was evaporated and the product was crystallized from methanol to give 86 mg (37%) of example I-131. $^1$H NMR (DMSO-D6, CCl4): 3.69 (3H, s, OCH3), 3.71 (3H, s, OCH3), 7.35 (1H, dd, CH-arom.), 7.47 (1H, d, CH-arom.), 7.57 (2H, AB-syst., CH-arom.), 7.63 (1H, m, CH-arom.), 7.84 (2H, AB-syst., CH-arom.), 8.74 (1H, s, CH pyrazol.).

Synthesis of methyl 3-(2-chloro-6-fluorophenyl)-5-(5-(ethoxycarbonyl)-1-phenyl-1H-pyrazol-4-yl)isoxazole-4-carboxylate derivatives: examples I-6, I-8, I-9, I-10, I-13, I-15, I-26, I-29, I-34, I-35, I-38, I-39, I-40, I-41 and I-45

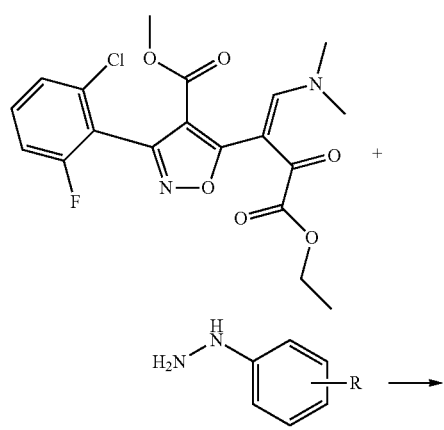

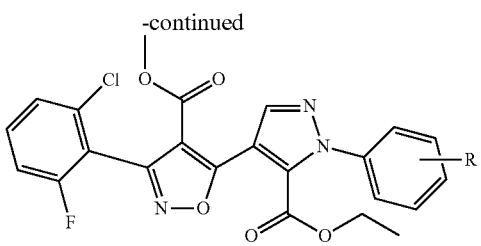

Starting from methyl 3-(2-chloro-6-fluorophenyl)-5-(1-(dimethylamino)-4-ethoxy-3,4-dioxobut-1-en-2-yl)isoxazole-4-carboxylate, which is commercially available from *Bionet Research Intermediates*, the pyrazole ring was constructed using differently substituted arylhydrazines as described for example I-11.

Analytic:

Abbreviations: min, minute(s); h, hour(s); r.t., room temperature; R$_f$ retention time; Ψ, pseudo; s, singlet; t, triplet, quint, quintet; br., broad; J, coupling constant; pTLC, preparative thin layer chromatography; DMAP, 4-dimethylaminopyridine.

Analytical TLC: Merck aluminium sheets, silica gel 60 F$_{254}$.

Preparative TLC: Merck PLC plates, silica gel 60 F$_{254}$, 0.5 mm, 1.0 mm or 2.0 mm.

Flash chromatography: Acros silica gel 60A, 0.035-0.070 mm. Flash Master Personal or Flash Master II, Jones Chromatography, UK.

NMR spectra: Bruker Avance 300 MHz. The $^1$H NMR spectra were recorded at 300 MHz; concentration, 1 to 5 mg/mL; temperature, 305 K. The $^{13}$C NMR spectra at 75.5 MHz; concentration, 5 to 20 mg/mL; temperature, 305 K. The residual solvent peaks were used as the internal standards (DMSO-d$_6$: δ$_H$ 2.49, δ$_C$ 39.5; CDCl$_3$: δ$_H$ 7.24, δ$_C$ 77.0; CD$_3$OD: δ$_H$ 3.30, δ$_C$ 49.0). Alternatively, TMS was used as a standard (indicated with TMS).

Analytical LC/ESI-MS: Waters 2700 Autosampler. 2× Waters 600 Multisolvent Delivery System, Waters 600 Controller. 50 µL sample loop. Column, Chromolith Speed ROD RP18e (Merck, Darmstadt), 50×4.6 mm, with 2 µm prefilter (Merck). Eluent A, H$_2$O+0.1% HCO$_2$H; eluent B, MeCN. Gradient, 2% B to 100% B within 4 min, then isocratic for 0.90 min, then back to 2% B within 0.15 min, then isocratic for 0.50 min; flow, 3 mL/min. Waters LCZ single quadrupol mass spectrometer with electrospray source. MS method, MS8minPM-80-800-20V; positive/negative ion mode scanning, m/z 80-800 or 80-900 in 1 s; capillary, 3.5 kV; cone voltage, 20 V; multiplier voltage, 400 V; probe and desolvation gas temperature, 120° C. and 350° C., respectively. Waters 2487 Dual λ Absorbance Detector, set to 254 nm. Software, Waters Masslynx V 4.0. Values for [M+H]$^+$ given in the Tables 1 and 2 are calculated exact mass values for the specific compound upon protonation, values found within the corresponding LC/MS chromatogram were all within tolerable margins of +/−0.3.

Preparative HPLC-MS: Waters 2700 Autosampler, Waters 600 Multisolvent Delivery System with preparative pump heads, Waters 600 Controller, 5000 µL Sample loop. At-column dilution: Waters 600 Multisolvent Delivery System with analytical pump heads; Waters 600 Controller; solvent, MeCN-MeOH 80:20 (v/v); flow rate, 0.20 or 1 mL/min. Column, Waters X-Terra RP18, 7 µm, 19×150 mm with X-Terra RP18 guard cartridge 7 µm, 19×10 mm, used at flow rate 20 mL/min. Eluent A, H$_2$O containing 0.1% (v/v) HCO$_2$H or H$_2$O containing 0.1% (v/v) NEt$_3$; eluent B, MeCN. Different linear gradients, individually adapted to sample. Injection volume, 0.5 mL-5 mL, depending on sample. Make-up solvent, MeOH-MeCN—H$_2$O—HCO$_2$H 80:15:4.95:0.05 (v/v/v/v). Make-up pump, Waters Reagent Manager, flow rate 0.5 mL/min. Waters ZQ single quadrupol mass spectrometer with electrospray source. Positive or negative ion mode scanning m/z 105-950 in 1 s; capillary, 4 kV; cone voltage, 20 V; multiplier voltage, 600 V; probe and desolvation gas temperature, 120° C. and 250° C., respectively. Waters Fraction Collector II with mass-triggered fraction collection. Waters 2487 Dual λ Absorbance Detector, set to 254 nm. Software, Waters Masslynx V 4.0.

Analysis of Proliferation of and Cytokine Production by Human PBMC Stimulated with PHA Peripheral blood mononuclear cells (PBMC) from healthy human donors were purified using Accuspin™ System-Histopaque-1077 (Sigma) according to the protocol recommended by the manufacturer. Purified PBMC were then washed twice with phosphate-buffered saline (PBS) and resuspended in RPMI1640 culture medium supplemented with 10% dialyzed heat inactivated fetal calf serum, 1.5 mM L-glutamine, 100 U penicillin/ml, and 100 mg streptomycin/ml (all from PAN Biotech, Aidenbach, Germany). For stimulation, PBMC were seeded at 1×10$^5$ cells/well, activated with 2 µg/ml phytohaemagglutinin (PHA, Sigma) and incubated with the test compounds for 48 hours. IL-17A, IL-17F and INF-γ were then determined in the culture supernatant using a Luminex BioPlex system, following the manufacturer's instructions (BioRad, Munich, Germany). For screening, compounds were used at 10, 1, 0.1 and 0.01 µM. To determine the IC$_{50}$, compounds were titrated semilogarithmically.

Cell proliferation was analysed using the BrdU based cell proliferation ELISA from Roche (Mannheim, Germany) according to the manufacturer's instructions.

Cytokines were determined in the aforementioned culture supernatant using the following methods: IL-17AA/AF was measured using the Luminex BioPlex system (BioRad, Munich, Germany); IL-17AA using the human homodimer IL-17A ELISA Ready Set Go Kit from eBioscience (Frankfurt, Germany); IL-17FF using the human IL-17F ELI-Pair from Hölzel DiagnosticaGmBH (Köln, Germany); and IFN-γ using the OptEIA human IFN-g ELISA from BD Bioscience (Heidelberg, Germany), all following the manufacturer's instructions.

T Cell Proliferation Assay

Peripheral blood mononuclear cells (PBMC) from healthy human donors were isolated by centrifugation over Ficoll-Hypaque (Sigma-Aldrich, Germany) according to manufacturer's instructions. Purified PBMC were washed twice with PBS and resuspended in RPMI1640 culture medium supplemented with 10% dialyzed heat inactivated fetal calf serum, 1.5 mM L-glutamine, 100 U penicillin/ml, and 100 mg streptomycin/ml (all from PAN Biotech, Aidenbach, Germany). For stimulation, PBMC were seeded at 1×105 cells/well, activated with 2 µg/ml phytohaemagglutinin (PHA, Sigma) and incubated with the test compound. After 48 hours proliferation was measured using the BrdU based cell proliferation ELISA from Roche (Mannheim, Germany) according to the manual.

TABLE 1

Exemplary compounds of formula (I) of the present invention include, but not limited to the following:

| No. | Formula | Name | HPLC/MS [M + H]+ | A | B | C | D |
|---|---|---|---|---|---|---|---|
| 1 | | 3-(2-chloro-6-fluorophenyl)-5-(1-isobutyl-5-(trifluoromethyl)-1H-pyrazol-4-yl)-4-(1H-tetrazol-5-yl)isoxazole | 456.09 | | | | 1 |
| 2 | | 3-(2-chloro-6-fluorophenyl)-5-(1-(3-fluorophenyl)-5-(trifluoromethyl)-1H-pyrazol-4-yl)-4-(1H-tetrazol-5-yl)isoxazole | 494.05 | 1 | 1 | 1 | |
| 3 | | 3-(2-chloro-6-fluorophenyl)-5-(1-(3-chlorophenyl)-5-(trifluoromethyl)-1H-pyrazol-4-yl)-4-(1H-tetrazol-5-yl)isoxazole | 510.02 | 1 | 1 | 1 | |

TABLE 1-continued

Exemplary compounds of formula (I) of the present invention include, but not limited to the following:

| No. | Formula | Name | HPLC/MS [M + H]+ | A | B | C | D |
|---|---|---|---|---|---|---|---|
| 4 | 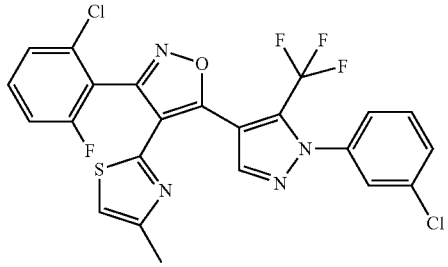 [SMILES: Cc1csc(-c2c(-c3c(F)cccc3Cl)noc2-c2cnn(-c3cccc(Cl)c3)c2C(F)(F)F)n1] | 3-(2-chloro-6-fluorophenyl)-5-(1-(3-chlorophenyl)-5-(trifluoromethyl)-1H-pyrazol-4-yl)-4-(4-methylthiazol-2-yl)isoxazole | 539.00 | | 4 | 4 | 4 |
| 5 | 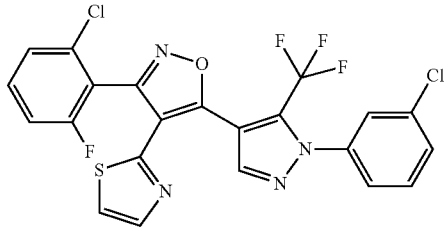 [SMILES: Fc1cccc(Cl)c1-c1noc(-c2cnn(-c3cccc(Cl)c3)c2C(F)(F)F)c1-c1nccs1] | 3-(2-chloro-6-fluorophenyl)-5-(1-(3-chlorophenyl)-5-(trifluoromethyl)-1H-pyrazol-4-yl)-4-(thiazol-2-yl)isoxazole | 524.99 | 4 | 4 | 4 | 4 |
| 6 | 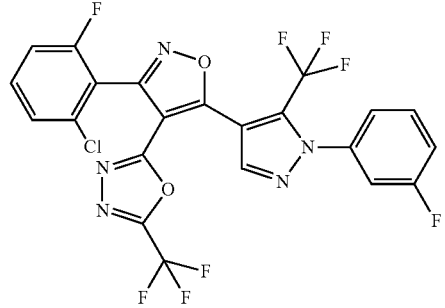 [SMILES: Fc1cccc(-n2ncc(-c3onc(-c4c(F)cccc4Cl)c3-c3nnc(C(F)(F)F)o3)c2C(F)(F)F)c1] | 2-(3-(2-chloro-6-fluorophenyl)-5-(1-(3-fluorophenyl)-5-(trifluoromethyl)-1H-pyrazol-4-yl)isoxazol-4-yl)-5-(trifluoromethyl)-1,3,4-oxadiazole | 562.02 | | 3 | 3 | 3 |
| 7 | 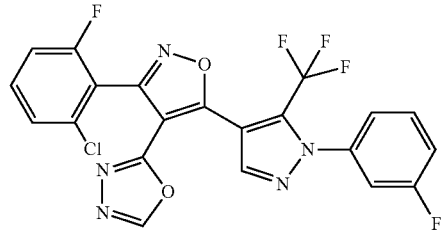 [SMILES: Fc1cccc(-n2ncc(-c3onc(-c4c(F)cccc4Cl)c3-c3nnco3)c2C(F)(F)F)c1] | 2-(3-(2-chloro-6-fluorophenyl)-5-(1-(3-fluorophenyl)-5-(trifluoromethyl)-1H-pyrazol-4-yl)isoxazol-4-yl)-1,3,4-oxadiazole | 494.04 | | 4 | 4 | 3 |
| 8 | 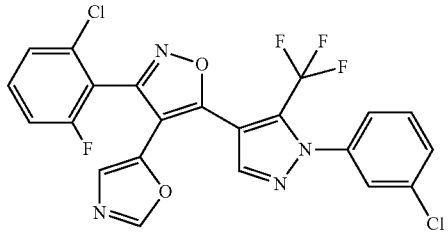 [SMILES: Fc1cccc(Cl)c1-c1noc(-c2cnn(-c3cccc(Cl)c3)c2C(F)(F)F)c1-c1cnco1] | 3-(2-chloro-6-fluorophenyl)-5-(1-(3-chlorophenyl)-5-(trifluoromethyl)-1H-pyrazol-4-yl)-4-(oxazol-5-yl)isoxazole | 509.01 | | 4 | 4 | 4 |

TABLE 1-continued

Exemplary compounds of formula (I) of the present invention include, but not limited to the following:

| No. | Formula | Name | HPLC/MS [M + H]+ | A | B | C | D |
|---|---|---|---|---|---|---|---|
| 9 | | 2-(3-(2-chloro-6-fluorophenyl)-5-(1-(3-fluorophenyl)-5-(trifluoromethyl)-1H-pyrazol-4-yl)isoxazol-4-yl)thiazol-4-ol | 525.01 | | 2 | 2 | 2 |
| 10 | | 3-(2-chloro-6-fluorophenyl)-5-(1-(3-fluorophenyl)-5-(trifluoromethyl)-1H-pyrazol-4-yl)-4-(4-methoxythiazol-2-yl)isoxazole | 539.03 | | 2 | 3 | 3 |
| 11 | | 2-(3-(2-chloro-6-fluorophenyl)-5-(1-(2-fluorophenyl)-5-(trifluoromethyl)-1H-pyrazol-4-yl)isoxazol-4-yl)-5-methyl-1,3,4-oxadiazole | 508.05 | 1 | 2 | 3 | 2 |
| 12 | | 3-(2-chloro-6-fluorophenyl)-5-(1-(2-fluorophenyl)-5-(trifluoromethyl)-1H-pyrazol-4-yl)-4-(5-methyl-1,3,4-thiadiazol-2-yl)isoxazole | 524.03 | 2 | 3 | 3 | 2 |
| 13 | | 3-(2-chloro-6-fluorophenyl)-5-(1-(3-fluorophenyl)-5-(trifluoromethyl)-1H-pyrazol-4-yl)-4-(furan-3-yl)isoxazole | 492.05 | 1 | 2 | 1 | 1 |

TABLE 1-continued

Exemplary compounds of formula (I) of the present invention include, but not limited to the following:

| No. | Formula | Name | HPLC/MS [M + H]⁺ | A | B | C | D |
|-----|---------|------|------------------|---|---|---|---|
| 14 | | 3-(2-chloro-6-fluorophenyl)-5-(1-(3-fluorophenyl)-5-(trifluoromethyl)-1H-pyrazol-4-yl)-4-phenylisoxazole | 502.07 | | 2 | 3 | 2 |
| 15 | | 2-(3-(2-chloro-6-fluorophenyl)-5-(1-(2-fluorophenyl)-5-(trifluoromethyl)-1H-pyrazol-4-yl)isoxazol-4-yl)-1,3,4-oxadiazole | 494.04 | | 2 | 2 | 2 |
| 16 | | 3-(2-chloro-6-fluorophenyl)-5-(1-(3-fluorophenyl)-5-(trifluoromethyl)-1H-pyrazol-4-yl)-4-(thiophen-3-yl)isoxazole | 508.02 | | 2 | 4 | 4 |
| 17 | | 3-(2-chloro-6-fluorophenyl)-5-(1-(3-fluorophenyl)-5-(trifluoromethyl)-1H-pyrazol-4-yl)-4-(furan-2-yl)isoxazole | 492.05 | | 4 | 4 | 4 |
| B-1 | | ethyl 2-(3-(2-chloro-6-fluorophenyl)-5-(1-(3-fluorophenyl)-5-(trifluoromethyl)-1H-pyrazol-4-yl)isoxazol-4-yl)thiazole-4-carboxylate | 581.04 | | 2 | 2 | 2 |

TABLE 1-continued

Exemplary compounds of formula (I) of the present invention include, but not limited to the following:

| No. | Formula | Name | HPLC/MS [M + H]+ | A | B | C | D |
|---|---|---|---|---|---|---|---|
| B-2 | | methyl 2-(3-(2-chloro-6-fluorophenyl)-5-(1-(3-fluorophenyl)-5-(trifluoromethyl)-1H-pyrazol-4-yl)isoxazol-4-yl)thiazole-4-carboxylate | 567.02 | 2 | 3 | 3 | 2 |
| B-3 | | 3-(2-chloro-6-fluorophenyl)-5-(1-(3-chlorophenyl)-5-(trifluoromethyl)-1H-pyrazol-4-yl)-4-(5-methyl-1,3,4-thiadiazol-2-yl)isoxazole | 540.00 | | 4 | 4 | 4 |
| B-4 | | 2-(3-(2-chloro-6-fluorophenyl)-5-(1-(3-chlorophenyl)-5-(trifluoromethyl)-1H-pyrazol-4-yl)isoxazol-4-yl)-5-methyl-1,3,4-oxadiazole | 524.02 | | 4 | 4 | 4 |
| B-5 | | 2-(3-(2-chloro-6-fluorophenyl)-5-(1-(3-chlorophenyl)-5-(trifluoromethyl)-1H-pyrazol-4-yl)isoxazol-4-yl)-1,3,4-oxadiazole | 510.00 | | 4 | 4 | 4 |

TABLE 1-continued

Exemplary compounds of formula (I) of the present invention include, but not limited to the following:

| No. | Formula | Name | HPLC/MS [M + H]+ | A | B | C | D |
|---|---|---|---|---|---|---|---|
| B-6 | | 3-(2-chloro-6-fluorophenyl)-5-(1-(3-chlorophenyl)-5-(trifluoromethyl)-1H-pyrazol-4-yl)-4-(furan-2-yl)isoxazole | 508.02 | | 4 | 4 | 4 |
| B-7 | | 3-(2-chloro-6-fluorophenyl)-5-(1-(3-chlorophenyl)-5-(trifluoromethyl)-1H-pyrazol-4-yl)-4-(furan-3-yl)isoxazole | 508.02 | | 4 | 4 | 4 |
| B-8 | | 3-(2-chloro-6-fluorophenyl)-5-(1-(3-chlorophenyl)-5-(trifluoromethyl)-1H-pyrazol-4-yl)-4-(1,3,4-thiadiazol-2-yl)isoxazole | 525.98 | | 4 | 4 | 4 |
| B-9 | | 3-(2-chloro-6-fluorophenyl)-5-(1-(2-fluorophenyl)-5-(trifluoromethyl)-1H-pyrazol-4-yl)-4-(furan-3-yl)isoxazole | 492.05 | 2 | 3 | 2 | 2 |
| B-10 | | 2-(3-(2-chloro-6-fluorophenyl)-5-(1-(pyridin-3-yl)-5-(trifluoromethyl)-1H-pyrazol-4-yl)isoxazol-4-yl)-5-methyl-1,3,4-oxadiazole | 491.06 | | 2 | 3 | 2 |

TABLE 1-continued

Exemplary compounds of formula (I) of the present invention include, but not limited to the following:

| No. | Formula | Name | HPLC/MS [M + H]+ | A | B | C | D |
|---|---|---|---|---|---|---|---|
| B-11 | | N-(3-(4-(3-(2-chloro-6-fluorophenyl)-4-(5-methyl-1,3,4-oxadiazol-2-yl)isoxazol-5-yl)-5-(trifluoromethyl)-1H-pyrazol-1-yl)phenyl)acetamide | 547.08 | | 1 | 2 | |
| B-12 | | N-(3-(4-(3-(2-chloro-6-fluorophenyl)-4-(5-methyl-1,3,4-thiadiazol-2-yl)isoxazol-5-yl)-5-(trifluoromethyl)-1H-pyrazol-1-yl)phenyl)acetamide | 563.06 | | 1 | 2 | 1 |
| B-13 | | N-(3-(4-(3-(2-chloro-6-fluorophenyl)-4-(1,3,4-oxadiazol-2-yl)isoxazol-5-yl)-5-(trifluoromethyl)-1H-pyrazol-1-yl)phenyl)acetamide | 533.07 | | 1 | 1 | |
| B-14 | | 2-(3-(2-chloro-6-fluorophenyl)-5-(1-(2-chlorophenyl)-5-(trifluoromethyl)-1H-pyrazol-4-yl)isoxazol-4-yl)-1,3,4-oxadiazole | 510.01 | | | 1 | |

TABLE 1-continued

Exemplary compounds of formula (I) of the present invention include, but not limited to the following:

| No. | Formula | Name | HPLC/MS [M + H]+ | A | B | C | D |
|---|---|---|---|---|---|---|---|
| B-15 | 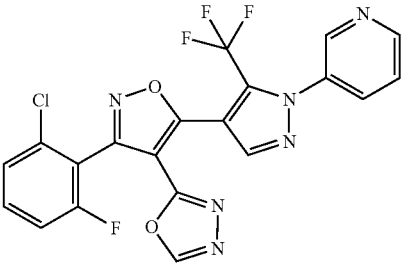 [SMILES: Fc1cccc(Cl)c1-c1noc(-c2cnn(-c3cccnc3)c2C(F)(F)F)c1-c1nnco1] | 2-(3-(2-chloro-6-fluorophenyl)-5-(1-(pyridin-3-yl)-5-(trifluoromethyl)-1H-pyrazol-4-yl)isoxazol-4-yl)-1,3,4-oxadiazole | 477.04 | | 2 | 2 | 2 |
| B-16 | 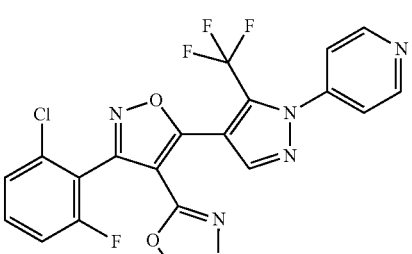 | 2-(3-(2-chloro-6-fluorophenyl)-5-(1-(pyridin-4-yl)-5-(trifluoromethyl)-1H-pyrazol-4-yl)isoxazol-4-yl)-1,3,4-oxadiazole | 477.04 | | 2 | 2 | 2 |
| B-17 | 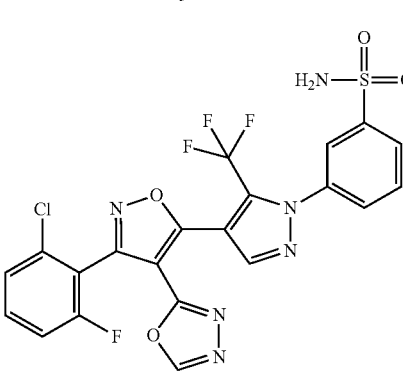 | 3-(4-(3-(2-chloro-6-fluorophenyl)-4-(1,3,4-oxadiazol-2-yl)isoxazol-5-yl)-5-(trifluoromethyl)-1H-pyrazol-1-yl)benzenesulfonamide | 555.02 | | 1 | 1 | 1 |
| B-18 | 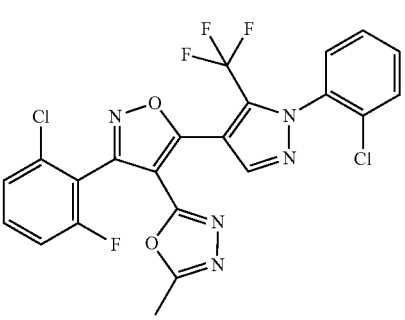 [SMILES: Cc1nnc(-c2c(-c3c(F)cccc3Cl)noc2-c2cnn(-c3ccccc3Cl)c2C(F)(F)F)o1] | 2-(3-(2-chloro-6-fluorophenyl)-5-(1-(2-chlorophenyl)-5-(trifluoromethyl)-1H-pyrazol-4-yl)isoxazol-4-yl)-5-methyl-1,3,4-oxadiazole | 524.02 | | 1 | 1 | 1 |
| B-19 | 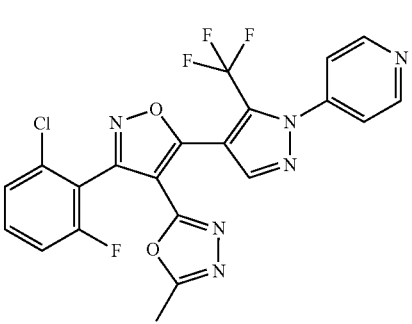 [SMILES: Cc1nnc(-c2c(-c3c(F)cccc3Cl)noc2-c2cnn(-c3ccncc3)c2C(F)(F)F)o1] | 2-(3-(2-chloro-6-fluorophenyl)-5-(1-(pyridin-4-yl)-5-(trifluoromethyl)-1H-pyrazol-4-yl)isoxazol-4-yl)-5-methyl-1,3,4-oxadiazole | 491.06 | | 2 | 2 | 2 |

TABLE 1-continued

Exemplary compounds of formula (I) of the present invention include, but not limited to the following:

| No. | Formula | Name | HPLC/MS [M + H]+ | A | B | C | D |
|---|---|---|---|---|---|---|---|
| B-20 | | 3-(2-chloro-6-fluorophenyl)-5-(1-(2-chlorophenyl)-5-(trifluoromethyl)-1H-pyrazol-4-yl)-4-(5-methyl-1,3,4-thiadiazol-2-yl)isoxazole | 540.00 | | 2 | 2 | 2 |
| B-21 | | 3-(2-chloro-6-fluorophenyl)-4-(5-methyl-1,3,4-thiadiazol-2-yl)-5-(1-(pyridin-3-yl)-5-(trifluoromethyl)-1H-pyrazol-4-yl)isoxazole | 507.03 | | 3 | 3 | 3 |
| B-22 | | 3-(2-chloro-6-fluorophenyl)-4-(5-methyl-1,3,4-thiadiazol-2-yl)-5-(1-(pyridin-4-yl)-5-(trifluoromethyl)-1H-pyrazol-4-yl)isoxazole | 507.03 | | 2 | 3 | 2 |
| B-23 | | 3-(4-(3-(2-chloro-6-fluorophenyl)-4-(5-methyl-1,3,4-thiadiazol-2-yl)isoxazol-5-yl)-5-(trifluoromethyl)-1H-pyrazol-1-yl)benzenesulfonamide | 585.01 | | 1 | 1 | 1 |

TABLE 1-continued

Exemplary compounds of formula (I) of the present invention include, but not limited to the following:

| No. | Formula | Name | HPLC/MS [M + H]⁺ | A | B | C | D |
|---|---|---|---|---|---|---|---|
| B-24 | | 3-(2-chloro-6-fluorophenyl)-4-(furan-3-yl)-5-(1-(pyridin-4-yl)-5-(trifluoromethyl)-1H-pyrazol-4-yl)isoxazole | 475.05 | | 3 | 3 | 3 |
| B-25 | | 2-(3-(2-chloro-6-fluorophenyl)-5-(1-(pyridin-2-yl)-5-(trifluoromethyl)-1H-pyrazol-4-yl)isoxazol-4-yl)-1,3,4-oxadiazole | 477.04 | | 2 | 3 | 3 |
| B-26 | | 2-(3-(2-chloro-6-fluorophenyl)-5-(1-(pyridin-2-yl)-5-(trifluoromethyl)-1H-pyrazol-4-yl)isoxazol-4-yl)-5-methyl-1,3,4-oxadiazole | 491.06 | | 3 | 3 | 2 |
| B-27 | | 3-(2-chloro-6-fluorophenyl)-4-(5-methyl-1,3,4-thiadiazol-2-yl)-5-(1-(pyridin-2-yl)-5-(trifluoromethyl)-1H-pyrazol-4-yl)isoxazole | 507.03 | | 3 | 3 | 3 |
| B-28 | | 3-(2-chloro-6-fluorophenyl)-5-(1-(2-fluorophenyl)-5-(trifluoromethyl)-1H-pyrazol-4-yl)-4-(oxazol-5-yl)isoxazole | 493.04 | | 2 | 2 | 2 |

TABLE 1-continued

Exemplary compounds of formula (I) of the present invention include, but not limited to the following:

| No. | Formula | Name | HPLC/MS [M + H]+ | A | B | C | D |
|---|---|---|---|---|---|---|---|
| B-29 | | 3-(2-chloro-6-fluorophenyl)-5-(1-(2-chlorophenyl)-5-(trifluoromethyl)-1H-pyrazol-4-yl)-4-(thiazol-2-yl)isoxazole | 524.99 | | 1 | 2 | 1 |
| B-30 | | 3-(2-chloro-6-fluorophenyl)-5-(1-(2-fluorophenyl)-5-(trifluoromethyl)-1H-pyrazol-4-yl)-4-(thiazol-2-yl)isoxazole | 509.02 | | 3 | 3 | 3 |
| B-31 | | 3-(2-chloro-6-methoxyphenyl)-4-(oxazol-5-yl)-5-(1-(pyridin-3-yl)-5-(trifluoromethyl)-1H-pyrazol-4-yl)isoxazole | 488.07 | | 1 | 2 | 1 |
| B-32 | | 3-(2-chloro-6-fluorophenyl)-4-(oxazol-5-yl)-5-(1-(pyridin-3-yl)-5-(trifluoromethyl)-1H-pyrazol-4-yl)isoxazole | 476.05 | | 1 | 2 | 1 |
| B-33 | | 3-(2-chloro-6-fluorophenyl)-4-(oxazol-5-yl)-5-(1-(pyridin-4-yl)-5-(trifluoromethyl)-1H-pyrazol-4-yl)isoxazole | 476.05 | | 1 | 2 | 1 |

TABLE 1-continued

Exemplary compounds of formula (I) of the present invention include, but not limited to the following:

| No. | Formula | Name | HPLC/MS [M + H]⁺ | A | B | C | D |
|---|---|---|---|---|---|---|---|
| B-34 | | 3-(2-chloro-6-methoxyphenyl)-5-(1-(2-chlorophenyl)-5-(trifluoromethyl)-1H-pyrazol-4-yl)-4-(oxazol-5-yl)isoxazole | 521.03 | | 2 | 2 | 2 | columns A, B, C and D specify: A: IC$_{50}$ (IL-17AA) [μM]-values marked with * were determined by Luminex assay on IL17AA/AF; B: IC$_{50}$ (IL-17FF) [μM]; C: IC$_{50}$ (IFNγ) [μM]; D: IC$_{50}$ (Tcell proliferation) [μM]

Activities: 1: >1 μM to 10 μM; 2: >100 nM to 1 μM; 3: >10 nM to 100 nM; 4: ≦10 nM

TABLE 2

Further illustrative examples, which further elucidate suitable substitution patterns on the central scaffold of formula (I) are enumerated as example I-1 to I-145 and IB-1 to IB-104 in the following:

| No. | Formula | Name | HPLC/MS [M + H]⁺ | A | B | C | D |
|---|---|---|---|---|---|---|---|
| I-1 | | methyl 3-(2-chloro-6-fluorophenyl)-5-(1-(2-fluorophenyl)-5-(trifluoromethyl)-1H-pyrazol-4-yl)isoxazole-4-carboxylate | 484.04 | 3 | 4 | 3 | |
| I-2 | | 3-(2-chloro-6-fluorophenyl)-5-(1-(2-fluorophenyl)-5-(trifluoromethyl)-1H-pyrazol-4-yl)-N-(2,4,6-trimethoxybenzyl)isoxazole-4-carboxamide | 649.12 | 1 | 1 | | |
| I-3 | | methyl 3-(2-chloro-6-fluorophenyl)-5-(1-(4-fluorophenyl)-5-(trifluoromethyl)-1H-pyrazol-4-yl)isoxazole-4-carboxylate | 484.04 | 4 | 4 | 3 | |

TABLE 2-continued

Further illustrative examples, which further elucidate suitable substitution patterns on the central scaffold of formula (I) are enumerated as example I-1 to I-145 and IB-1 to IB-104 in the following:

| No. | Formula | Name | HPLC/MS [M + H]+ | A | B | C | D |
|---|---|---|---|---|---|---|---|
| I-4 | | methyl 3-(2-chloro-6-fluorophenyl)-5-(1-(2,3-dichlorophenyl)-5-(trifluoromethyl)-1H-pyrazol-4-yl)isoxazole-4-carboxylate | 533.97 | | | | 1 |
| I-5 | | methyl 3-(2-chloro-6-fluorophenyl)-5-(1-(3-fluorophenyl)-5-(trifluoromethyl)-1H-pyrazol-4-yl)isoxazole-4-carboxylate | 484.04 | 4* | 4 | 4 | 4 |
| I-6 | | methyl 3-(2-chloro-6-fluorophenyl)-5-(1-(2,4-dichlorophenyl)-5-(ethoxycarbonyl)-1H-pyrazol-4-yl)isoxazole-4-carboxylate | 538.01 | | 1 | 1 | 1 |
| I-7 | | methyl 3-(2-chloro-6-fluorophenyl)-5-(1-(2,4-dichlorophenyl)-5-(trifluoromethyl)-1H-pyrazol-4-yl)isoxazole-4-carboxylate | 533.97 | | | | 1 |
| I-8 | | methyl 3-(2-chloro-6-fluorophenyl)-5-(5-(ethoxycarbonyl)-1-(3-fluorophenyl)-1H-pyrazol-4-yl)isoxazole-4-carboxylate | 488.07 | | 2 | 2 | 2 |
| I-9 | | methyl 3-(2-chloro-6-fluorophenyl)-5-(1-(2,3-dichlorophenyl)-5-(ethoxycarbonyl)-1H-pyrazol-4-yl)isoxazole-4-carboxylate | 538.01 | | 1 | | 1 |

TABLE 2-continued

Further illustrative examples, which further elucidate suitable substitution patterns on the central scaffold of formula (I) are enumerated as example I-1 to I-145 and IB-1 to IB-104 in the following:

| No. | Formula | Name | HPLC/MS [M + H]+ | A | B | C | D |
|---|---|---|---|---|---|---|---|
| I-10 | | methyl 3-(2-chloro-6-fluorophenyl)-5-(1-(3-chlorophenyl)-5-(ethoxycarbonyl)-1H-pyrazol-4-yl)isoxazole-4-carboxylate | 504.05 | | 2 | 3 | 3 |
| I-11 | | methyl 3-(2-chloro-6-fluorophenyl)-5-(1-(3-chlorophenyl)-5-(trifluoromethyl)-1H-pyrazol-4-yl)isoxazole-4-carboxylate | 500.01 | 4 | 4 | 4 | 4 |
| I-12 | | methyl 3-(2-chloro-6-fluorophenyl)-5-(1-(3-cyanophenyl)-5-(trifluoromethyl)-1H-pyrazol-4-yl)isoxazole-4-carboxylate | 491.05 | 2 | 3 | 3 | 3 |
| I-13 | | methyl 3-(2-chloro-6-fluorophenyl)-5-(1-(3-cyanophenyl)-5-(ethoxycarbonyl)-1H-pyrazol-4-yl)isoxazole-4-carboxylate | 495.08 | 2 | 2 | 2 | |
| I-14 | | methyl 3-(2-chloro-6-fluorophenyl)-5-(1-(2-(methoxycarbonyl)thiophen-3-yl)-5-(trifluoromethyl)-1H-pyrazol-4-yl)isoxazole-4-carboxylate | 530.01 | 3 | 2 | | |

TABLE 2-continued

Further illustrative examples, which further elucidate suitable substitution patterns on the central scaffold of formula (I) are enumerated as example I-1 to I-145 and IB-1 to IB-104 in the following:

| No. | Formula | Name | HPLC/MS [M + H]⁺ | A | B | C | D |
|---|---|---|---|---|---|---|---|
| I-15 | | methyl 3-(2-chloro-6-fluorophenyl)-5-(5-(ethoxycarbonyl)-1-(2-(methoxycarbonyl)thiophen-3-yl)-1H-pyrazol-4-yl)isoxazole-4-carboxylate | 534.05 | | | 1 | |
| I-16 | | (3-(2-chloro-6-fluorophenyl)-5-(1-(2-fluorophenyl)-5-(trifluoromethyl)-1H-pyrazol-4-yl)isoxazol-4-yl)(morpholino)methanone | 539.08 | | 2 | 2 | 1 |
| I-17 | | (3-(2-chloro-6-fluorophenyl)-5-(1-(2-fluorophenyl)-5-(trifluoromethyl)-1H-pyrazol-4-yl)isoxazol-4-yl)(4-methylpiperazin-1-yl)methanone | 552.11 | | 2 | 2 | 1 |
| I-18 | | 3-(2-chloro-6-fluorophenyl)-N-cyclohexyl-5-(1-(2-fluorophenyl)-5-(trifluoromethyl)-1H-pyrazol-4-yl)isoxazole-4-carboxamide | 551.12 | 1 | 2 | 2 | 1 |
| I-19 | | 3-(2-chloro-6-fluorophenyl)-5-(1-(2-fluorophenyl)-5-(trifluoromethyl)-1H-pyrazol-4-yl)-N-methylisoxazole-4-carboxamide | 483.06 | 1 | 1 | 1 | 1 |

TABLE 2-continued

Further illustrative examples, which further elucidate suitable substitution patterns on the central scaffold of formula (I) are enumerated as example I-1 to I-145 and IB-1 to IB-104 in the following:

| No. | Formula | Name | HPLC/MS [M + H]⁺ | A | B | C | D |
|---|---|---|---|---|---|---|---|
| I-20 | | 3-(2-chloro-6-fluorophenyl)-5-(1-(2-fluorophenyl)-5-(trifluoromethyl)-1H-pyrazol-4-yl)-N,N-dimethylisoxazole-4-carboxamide | 497.07 | | 1 | 1 | |
| I-21 | | (3-(2-chloro-6-fluorophenyl)-5-(1-(2-fluorophenyl)-5-(trifluoromethyl)-1H-pyrazol-4-yl)isoxazol-4-yl)(piperidin-1-yl)methanone | 537.10 | | | 3 | 3 |
| I-22 | | (3-(2-chloro-6-fluorophenyl)-5-(1-(2-fluorophenyl)-5-(trifluoromethyl)-1H-pyrazol-4-yl)isoxazol-4-yl)(pyrrolidin-1-yl)methanone | 523.09 | | | 2 | 2 |
| I-23 | | 3-(2-chloro-6-fluorophenyl)-5-(1-(2-fluorophenyl)-5-(trifluoromethyl)-1H-pyrazol-4-yl)-N-(2-(trifluoromethyl)benzyl)isoxazole-4-carboxamide | 627.08 | | 1 | 2 | 1 |
| I-24 | | (3-(2-chloro-6-fluorophenyl)-5-(1-(2-fluorophenyl)-5-(trifluoromethyl)-1H-pyrazol-4-yl)isoxazol-4-yl)(4-(3-chlorobenzyl)piperazin-1-yl)methanone | 662.11 | | | 1 | 2 |

TABLE 2-continued

Further illustrative examples, which further elucidate suitable substitution patterns on the central scaffold of formula (I) are enumerated as example I-1 to I-145 and IB-1 to IB-104 in the following:

| No. | Formula | Name | HPLC/MS [M + H]+ | A | B | C | D |
|---|---|---|---|---|---|---|---|
| I-25 | | 3-(2-chloro-6-fluorophenyl)-5-(1-(4-fluorophenyl)-5-(trifluoromethyl)-1H-pyrazol-4-yl)isoxazole | 426.04 | | | 1 | |
| I-26 | | methyl 3-(2-chloro-6-fluorophenyl)-5-(5-(ethoxycarbonyl)-1-(4-fluorophenyl)-1H-pyrazol-4-yl)isoxazole-4-carboxylate | 488.07 | | 1 | 1 | 1 |
| I-28 | | methyl 3-(2-chloro-6-fluorophenyl)-5-(1-isobutyl-5-(trifluoromethyl)-1H-pyrazol-4-carboxylate | 446.08 | | 3 | 3 | 2 |
| I-29 | | methyl 3-(2-chloro-6-fluorophenyl)-5-(5-(ethoxycarbonyl)-1-isobutyl-1H-pyrazole-4-carboxylate | 450.12 | | | | 1 |
| I-32 | | 3-(2-chloro-6-fluorophenyl)-5-(1-(3-chlorophenyl)-5-(trifluoromethyl)-1H-pyrazol-4-yl)-N-methylisoxazole-4-carboxamide | 499.03 | 2 | 3 | 2 | 3 |
| I-33 | | methyl 3-(2-chloro-6-fluorophenyl)-5-(1-(4-(trifluoromethoxy)phenyl)-5-(trifluoromethyl)-1H-pyrazol-4-yl)isoxazole-4-carboxylate | 550.03 | | | | 1 |

TABLE 2-continued

Further illustrative examples, which further elucidate suitable substitution patterns on the central scaffold of formula (I) are enumerated as example I-1 to I-145 and IB-1 to IB-104 in the following:

| No. | Formula | Name | HPLC/MS [M + H]+ | A | B | C | D |
|-----|---------|------|------------------|---|---|---|---|
| I-34 | | methyl 3-(2-chloro-6-fluorophenyl)-5-(5-(ethoxycarbonyl)-1-phenyl-1Hpyrazol-4-yl)isoxazole-4-carboxylate | 470.08 | | | | 1 |
| I-35 | | methyl 3-(2-chloro-6-fluorophenyl)-5-(1-(2,4-difluorophenyl)-5-(ethoxycarbonyl)-1H-pyrazol-4-yl)isoxazole-4-carboxylate | 506.07 | | 2 | 2 | 2 |
| I-37 | | 3-(2-chloro-6-fluorophenyl)-5-(1-isobutyl-5-(trifluoromethyl)-1H-pyrazol-4-yl)-N-methylisoxazole-4-carboxamide | 445.10 | | 2 | 1 | |
| I-38 | | methyl 3-(2-chloro-6-fluorophenyl)-5-(5(ethoxycarbonyl)-1-(2,3,5,6-tetrafluorophenyl)-1H-pyrazol-4-yl)isoxazole-4-carboxylate | 542.05 | | | 1 | |
| I-39 | | methyl 3-(2-chloro-6-fluorophenyl)-5-(1-(3,5-difluorophenyl)-5-(ethoxycarbonyl)-1-H-pyrazol-4-yl)isoxazole-4-carboxylate | 506.07 | | | | 1 |
| I-40 | | methyl 3-(2-chloro-6-phenyl)-5-(5-(ethoxycarbonyl)-1-(2-methoxyphenyl)-1H-pyrazol-4.-arboxylate | 500.09 | | | | 1 |

TABLE 2-continued

Further illustrative examples, which further elucidate suitable substitution patterns on the central scaffold of formula (I) are enumerated as example I-1 to I-145 and IB-1 to IB-104 in the following:

| No. | Formula | Name | HPLC/MS [M + H]+ | A | B | C | D |
|---|---|---|---|---|---|---|---|
| I-41 | | methyl 3-(2-chloro-6-phenyl)-5-(5-(ethoxycarbonyl)-1-(2-fluorophenyl)-1H-pyrazol-4-yl)isoxazole-4-carboxylate | 488.07 | | 2 | 2 | 2 |
| I-42 | | ethyl 3-(2-chloro-6-fluorophenyl)-5-(1-(2-fluorophenyl)-5-(trifluoromethyl)-1H-pyrazol-4-yl)isoxazole-4-carboxylate | 498.06 | | 3 | 4 | 3 |
| I-43 | | isopropyl 3-(2-chloro-6-fluorophenyl)-5-(1-(2-fluorophenyl)-5-(trifluoromethyl)-1H-pyrazol-4-yl)isoxazole--carboxylate | 512.07 | | 2 | 3 | 3 |
| I-45 | | methyl 3-(2-chloro-6-fluoro-phenyl)-5-(5-(ethoxycarbonyl)-1-(4-(trifluoromethoxy)phenyl)1H-pyrazol-4-yl)isoxazole-4-carboxylate | 554.07 | | | 1 | |
| I-46 | | methyl 3-(2-chlorophenyl-6-fluorophenyl)-5-(1-(3,5-dichlorophenyl)-5-1H-pyrrazol-4-carboxylate | 502.03 | | 2 | 2 | 2 |
| I-47 | | methyl 3-(2-chloro-6-fluorophenyl)-5-(1-(2,3,5,6-tetrafluorophenyl)-5-(trifluoromethyl)-1H-pyrazol-4-yl)isoxale-4-carboxylate | 538.01 | | 2 | 2 | 2 |

TABLE 2-continued

Further illustrative examples, which further elucidate suitable substitution patterns on the central scaffold of formula (I) are enumerated as example I-1 to I-145 and IB-1 to IB-104 in the following:

| No. | Formula | Name | HPLC/MS [M + H]⁺ | A | B | C | D |
|---|---|---|---|---|---|---|---|
| I-48 | | methyl 3-(2-chloro-6-fluorophenyl)-5-(1-phenyl-5-(trifluoromethyl)1H-pyrazol-4-yl)isoxazole-4-carboxylate | 466.05 | 2 | 3 | 3 | 3 |
| I-49 | | 3-(2-chloro-6-fluorophenyl)-5-(1-(3-chlorophenyl)-5-(trifluoromethyl)-1H pyrazol-4-yl)isoxazole-4-carbonitrile | 467.00 | | 2 | 2 | 2 |
| I-50 | | methyl 3-(2-chloro-6-fluorophenyl)-5-(1-(3,5-difluorophenyl)-5-(trifluoromethyl)-1H-pyrazol-4-yl)isoxazole-4-carboxylate | 502.03 | 4 | 4 | 4 | 4 |
| I-51 | | methyl 5-(1-(3-fluorophenyl)-5-(trifluoromethyl)-1H-pyrazol-4-yl)-3-phenylisoxazole-4-carboxylate | 432.09 | | | 1 | 1 |
| I-52 | | methyl 3-(2-chloro-6-fluorophenyl)-5-(1-(2-methoxyphenyl)-5-(trifluoromethyl)-1H-pyrazol-4-yl)isoxazole-4-carboxylate | 496.06 | | 2 | 2 | |

TABLE 2-continued

Further illustrative examples, which further elucidate suitable substitution patterns on the central scaffold of formula (I) are enumerated as example I-1 to I-145 and IB-1 to IB-104 in the following:

| No. | Formula | Name | HPLC/MS [M + H]+ | A | B | C | D |
|---|---|---|---|---|---|---|---|
| I-53 | | methyl 3-(2-chloro-6-fluorophenyl)-5-(1-(4-(ethoxycarbonyl)thiazol-2-yl)-5-(trifluoromethyl)-1H-pyrazol-4-yl)isoxazole-4-carboxylate | 545.02 | | 1 | 1 | |
| I-54 | | methyl 3-(2-chloro-6-fluorophenyl)-5-(1-(4-(4-fluorophenyl)thiazol-2-yl)-5-(trifluoromethyl)-1H-pyrazol-4-yl)isoxazole-4-carboxylate | 567.02 | | | | 1 |
| I-55 | | 3-(2-chloro-6-fluorophenyl)-5-(1-(4-fluorophenyl)-5-(trifluoromethyl)-1H-pyrazol-4-yl)-N-methylisoxazole-4-carboxamide | 483.06 | | 2 | 2 | 2 |
| I-56 | | 3-(2-chloro-6-fluorophenyl)-N-methyl-5-(1-(4-(trifluoromethoxy)phenyl)-5-(trifluoromethyl)-1H-pyrazol-4-yl)isoxazole-4-carboxamide | 549.05 | | 1 | | |
| I-57 | | 3-(2-chloro-6-fluorophenyl)-5-(1-(2,4-difluorophenyl)-5-(trifluoromethyl)-1H-pyrazol-4-yl)-N-methylisoxazole-4-carboxamide | 501.05 | 1 | 1 | 1 | 1 |
| I-58 | | 3-(2-chloro-6-fluorophenyl)-5-(1-(3,5-difluorophenyl)-5-(trifluoromethyl)-1H-pyrazol-4-yl)-N-methylisoxazole-4-carboxamide | 501.05 | | 1 | 2 | |

TABLE 2-continued

Further illustrative examples, which further elucidate suitable substitution patterns on the central scaffold of formula (I) are enumerated as example I-1 to I-145 and IB-1 to IB-104 in the following:

| No. | Formula | Name | HPLC/MS [M + H]+ | A | B | C | D |
|---|---|---|---|---|---|---|---|
| I-59 | | 3-(2-chloro-6-fluorophenyl)-N-methyl-5-(1-phenyl-5-(trifluoromethyl)-1H-pyrazol-4-yl)isoxazole-4-carboxamide | 465.07 | | 2 | 2 | 2 |
| I-60 | | 3-(2-chloro-6-fluorophenyl)-5-(1-(2-methoxyphenyl)-5-(trifluoromethyl)-1H-pyrazol-4-yl)-N-methylisoxazole-4-carboxamide | 495.08 | | 1 | 1 | |
| I-61 | | methyl 5-(1-(2-fluorophenyl)-5-(trifluoromethyl)-1H-pyrazol-4-yl)-3-phenylisoxazole-4-carboxylate | 432.09 | | 1 | 1 | 1 |
| I-62 | | 3-(2-chloro-6-fluorophenyl)-5-(1-(3-fluorophenyl)-5-(trifluoromethyl)-1H-pyrazol-4-yl)-N-methylisoxazole-4-carboxamide | 483.06 | 2* | 3 | 3 | 3 |
| I-63 | | 3-(2-chloro-6-fluorophenyl)-5-(1-(3-chlorophenyl)-5-(trifluoromethyl)-1H-pyrazol-4-yl)-N-methoxy-N-methylisoxazole-4-carboxamide | 529.04 | 2 | 3 | 2 | 2 |
| I-64 | | methyl 3-(2-chloro-6-fluorophenyl)-5-(1-(3-fluorophenyl)-5-(1,1,2,2-tetrafluoroethyl)-1H-pyrazol-4-yl)isoxazole-4-carboxylate | 516.05 | | | | 1 |

TABLE 2-continued

Further illustrative examples, which further elucidate suitable substitution patterns on the central scaffold of formula (I) are enumerated as example I-1 to I-145 and IB-1 to IB-104 in the following:

| No. | Formula | Name | HPLC/MS [M + H]+ | A | B | C | D |
|---|---|---|---|---|---|---|---|
| I-65 | | methyl 3-(2-chloro-6-fluorophenyl)-5-(1-(2,2,2-trifluoroethyl)-5-(trifluoromethyl)-1H-pyrazol-4-yl)isoxazole-4-carboxylate | 472.02 | | 3 | 3 | 3 |
| I-66 | | methyl 3-(2-chloro-6-fluorophenyl)-5-(1-isopropyl-5-(trifluoromethyl)-1H-pyrazol-4-yl)isoxazole-4-carboxylate | 432.07 | 1 | 2 | | 1 |
| I-67 | | methyl 3-(2-chloro-6-fluorophenyl)-5-(5-(trifluoromethyl)-1-(4-(trifluoromethyl)pyrimidin-2-yl)-1H-pyrazol-4-yl)isoxazole-4-carboxylate | 536.03 | | | | 2 |
| I-68 | | methyl 3-(2-chloro-6-fluorophenyl)-5-(1-(3,5-dichlorophenyl)-5-(trifluoromethyl)-1H-pyrazol-4-yl)isoxazole-4-carboxylate | 533.97 | 3 | 3 | | 3 |
| I-69 | | methyl 3-(2-chloro-6-fluorophenyl)-5-(1-(4-nitrophenyl)-5-(trifluoromethyl)-1H-pyrazol-4-yl)isoxazole-4-carboxylate | 511.04 | 1 | 1 | | |
| I-70 | | methyl 3-(2-chloro-6-fluorophenyl)-5-(1-(2,6-dichlorophenyl)-5-(trifluoromethyl)-1H-pyrazol-4-yl)isoxazole-4-carboxylate | 533.97 | 2 | 2 | 2 | |

TABLE 2-continued

Further illustrative examples, which further elucidate suitable substitution patterns on the central scaffold of formula (I) are enumerated as example I-1 to I-145 and IB-1 to IB-104 in the following:

| No. | Formula | Name | HPLC/MS [M + H]+ | A | B | C | D |
|---|---|---|---|---|---|---|---|
| I-72 | | 3-(2-chloro-6-fluorophenyl)-5-(1-(3-chlorophenyl)-5-(trifluoromethyl)-1H-pyrazol-4-yl)-N-methylisoxazole-4-carbothioamide | 515.00 | | | 2 | 2 |
| I-73 | | methyl 3-(4-chlorophenyl)-5-(1-(3-fluorophenyl)-5-(trifluoromethyl)-1H-pyrazol-4-yl)isoxazole-4-carboxylate | 466.05 | | | | 1 |
| I-74 | | methyl 3-phenyl-5-(1-(4-(trifluoromethoxy)phenyl)-5-(trifluoromethyl)-1H-pyrazol-4-yl)isoxazole-4-carboxylate | 498.08 | | | | 1 |
| I-75 | | 3-(4-chlorophenyl)-5-(1-(3-fluorophenyl)-5-(trifluoromethyl)-1H-pyrazol-4-yl)-N-methylisoxazole-4-carboxamide | 465.07 | | | | 1 |
| I-76 | | 3-(2-chloro-6-fluorophenyl)-5-(1-(4-fluorophenyl)-5-(trifluoromethyl)-1H-pyrazol-4-yl)-N-methylisoxazole-4-carbothioamide | 499.03 | 1 | | 2 | 1 |
| I-77 | | ethyl 3-(4-chlorophenyl)-5-(1-(3-chlorophenyl)-5-(trifluoromethyl)-1H-pyrazol-4-yl)isoxazole-4-carboxylate | 496.04 | 1 | | | 1 |

TABLE 2-continued

Further illustrative examples, which further elucidate suitable substitution patterns on the central scaffold of formula (I) are enumerated as example I-1 to I-145 and IB-1 to IB-104 in the following:

| No. | Formula | Name | HPLC/MS [M + H]+ | A | B | C | D |
|---|---|---|---|---|---|---|---|
| I-78 | | ethyl 3-(4-chlorophenyl)-5-(1-(4-fluorophenyl)-5-(trifluoromethyl)-1H-pyrazol-4-yl)isoxazole-4-carboxylate | 480.07 | 1 | | | |
| I-79 | | methyl 3-(2-chloro-6-fluorophenyl)-5-(1-(4-methoxyphenyl)-5-(trifluoromethyl)-1H-pyrazol-4 | 496.06 | | | 1 | |
| I-80 | | methyl 5-(1-(2-bromophenyl)-5-(trifluoromethyl)-1H-pyrazol-4-yl)-3-(2-chloro-6-fluorophenyl)isoxazole-4-carboxylate | 543.0 | | | 1 | |
| I-81 | | methyl 5-(1-(4-tert-butylphenyl)-5-(trifluoromethyl)-1H-pyrazol-4-yl)-3-(2-chloro-6-fluorophenyl)isoxazole-4-carboxylate | 522.11 | 1 | 2 | 1 | |
| I-82 | | methyl 3-(2-chloro-6-fluorophenyl)-5-(5-(trifluoromethyl)-1-(3-(trifluoromethyl)phenyl)-1H-pyrazol-4-yl)isoxazole-4-carboxylate | 534.04 | | | | 1 |
| I-83 | | methyl 3-(2-chloro-6-fluorophenyl)-5-(1-(2-hydroxyethyl)-5-(trifluoromethyl)-1H-pyrazol-4-yl)isoxazole-4-carboxylate | 434.05 | | | 1 | |

TABLE 2-continued

Further illustrative examples, which further elucidate suitable substitution patterns on the central scaffold of formula (I) are enumerated as example I-1 to I-145 and IB-1 to IB-104 in the following:

| No. | Formula | Name | HPLC/MS [M + H]+ | A | B | C | D |
|---|---|---|---|---|---|---|---|
| I-84 | | methyl 3-(2-chloro-6-fluorophenyl)-5-(1-(pyridin-2-yl)-5-(trifluoromethyl)-1H-pyrazol-4-yl)isoxazole-4-carboxylate | 467.05 | | 4 | 4 | 4 |
| I-85 | | methyl 3-(2-chloro-6-fluorophenyl)-5-(1-(4-(methylsulfonyl)phenyl)-5-(trifluoromethyl)-1H-pyrazol-4-yl)isoxazole-4-carboxylate | 544.03 | | 1 | 1 | 1 |
| I-86 | | methyl 3-(2-chloro-6-fluorophenyl)-5-(1-(4-sulfamoylphenyl)-5-(trifluoromethyl)-1H-pyrazol-4-yl)isoxazole-4-carboxylate | 545.02 | | 1 | 1 | |
| I-87 | | methyl 5-(1-(3-chloro-5-(trifluoromethyl)pyridin-2-yl)-5-(trifluoromethyl)-1H-pyrazol-4-yl)-3-(2 | 568.99 | | | | 1 |
| I-88 | | methyl 3-(2-chloro-6-fluorophenyl)-5-(1-(2-iodophenyl)-5-(trifluoromethyl)-1H-pyrazol-4-yl)isoxazole-4-carboxylate | 591.95 | | | | 1 |
| I-89 | | methyl 3-(2-chloro-6-fluorophenyl)-5-(1-(2-fluorophenyl)-1H-pyrazol-4-yl)isoxazole-4-carboxylate | 416.05 | | 3 | 2 | 2 |

TABLE 2-continued

Further illustrative examples, which further elucidate suitable substitution patterns on the central scaffold of formula (I) are enumerated as example I-1 to I-145 and IB-1 to IB-104 in the following:

| No. | Formula | Name | HPLC/MS [M + H]+ | A | B | C | D |
|---|---|---|---|---|---|---|---|
| I-90 | | ethyl 3-(2-fluorophenyl)-5-(1-(3-fluorophenyl)-5-(trifluoromethyl)-1H-pyrazol-4-yl)isoxazole-4-carboxylate | 464.10 | | 2 | 3 | 2 |
| I-91 | | 3-(2-fluorophenyl)-5-(1-(3-fluorophenyl)-5-(trifluoromethyl)-1H-pyrazol-4-yl)isoxazole-4-carboxylic acid | 436.06 | | | | 1 |
| I-92 | | methyl 3-(2-fluorophenyl)-5-(1-(3-fluorophenyl)-5-(trifluoromethyl)-1H-pyrazol-4-yl)isoxazole-4-carboxylate | 450.08 | | 2 | 2 | 2 |
| I-93 | | 3-(2-fluorophenyl)-5-(1-(3-fluorophenyl)-5-(trifluoromethyl)-1H-pyrazol-4-yl)-N-methylisoxazole-4-carboxamide | 449.10 | | 1 | | |
| I-94 | | 3-(2-fluorophenyl)-5-(1-(3-fluorophenyl)-5-(trifluoromethyl)-1H-pyrazol-4-yl)-N-methoxy-N-methylisoxazole-4-carboxamide | 479.11 | | 1 | 1 | 1 |
| I-95 | | methyl 3-(2-chlorophenyl)-5-(1-(3-fluorophenyl)-5-(trifluoromethyl)-1H-pyrazol-4-yl)isoxazole-4-carboxylate | 466.05 | | 4 | 4 | 4 |

TABLE 2-continued

Further illustrative examples, which further elucidate suitable substitution patterns on the central scaffold of formula (I) are enumerated as example I-1 to I-145 and IB-1 to IB-104 in the following:

| No. | Formula | Name | HPLC/MS [M + H]+ | A | B | C | D |
|---|---|---|---|---|---|---|---|
| I-96 | | 3-(2-chlorophenyl)-5-(1-(3-fluorophenyl)-5-(trifluoro-methyl)-1H-pyrazol-4-yl)-N-methylisoxazole-4-carboxamide | 465.07 | 2 | 2 | 2 | |
| I-97 | | methyl 3-(3,4-dichlorophenyl)-5-(1-(3-fluorophenyl)-5-(trifluoromethyl)-1H-pyrazol-4-yl)isoxazole-4-carboxylate | 500.01 | | | | 1 |
| I-98 | | 3-(3,4-dichlorophenyl)-5-(1-(3-fluorophenyl)-5-(trifluoromethyl)-1H-pyrazol-4-yl)-N-methylisoxazole-4-carboxamide | 499.03 | 1 | | | |
| I-99 | | ethyl 3-(3,4-dichlorophenyl)-5-(1-(3-fluorophenyl)-5-(trifluoromethyl)-1H-pyrazol-4-yl)isoxazole-4-carboxylate | 514.03 | | | | 1 |
| I-100 | | ethyl 5-(1-(3-fluorophenyl)-5-(trifluoromethyl)-1H-pyrazol-4-yl)-3-(4-methoxyphenyl)isoxazole-4-carboxylate | 476.12 | 1 | | 1 | |
| I-101 | | methyl 3-(2-chloro-6-fluorophenyl)-5-(1-(pyridin-2-ylmethyl)-5-(trifluoromethyl)-1H-pyrazol-4-yl)isoxazole-4-carboxylate | 481.06 | | 1 | | |

TABLE 2-continued

Further illustrative examples, which further elucidate suitable substitution patterns on the central scaffold of formula (I) are enumerated as example I-1 to I-145 and IB-1 to IB-104 in the following:

| No. | Formula | Name | HPLC/MS [M + H]+ | A | B | C | D |
|---|---|---|---|---|---|---|---|
| I-102 | | methyl 3-(2-chloro-6-fluorophenyl)-5-(1-(2-methoxyethyl)-5-(trifluoromethyl)-1H-pyrazol-4-yl)isoxazole-4-carboxylate | 448.06 | | 1 | 1 | 2 |
| I-103 | | methyl 3-(2-chloro-6-fluorophenyl)-5-(1-(3-hydrazinyltetrahydrothiophene 1,1-dioxide)-5-(trifluoromethyl)-1H-pyrazol-4-yl)isoxazole-4-carboxylate | 508.03 | | 2 | 2 | 2 |
| I-104 | | methyl 3-(2-chloro-6-fluorophenyl)-5-(1-(2-(piperidin-1-yl)ethyl)-5-(trifluoromethyl)-1H-pyrazol-4-yl)isoxazole-4-carboxylate | 501.12 | | | 1 | |
| I-105 | | 3-(3-fluorophenyl)-5-(1-(3-fluorophenyl)-5-(trifluoromethyl)-1H-pyrazol-4-yl)-N-methylisoxazole-4-carboxamide | 449.10 | | 1 | 1 | |
| I-106 | | methyl 3-(3-fluorophenyl)-5-(1-(3-fluorophenyl)-5-(trifluoromethyl)-1H-pyrazol-4-yl)isoxazole-4-carboxylate | 450.08 | | 1 | 1 | 1 |
| I-107 | | methyl 5-(1-(3-fluorophenyl)-5-(trifluoromethyl)-1H-pyrazol-4-yl)-3-(4-methoxyphenyl)isoxazole-4-carboxylate | 462.10 | | | | 1 |

TABLE 2-continued

Further illustrative examples, which further elucidate suitable substitution patterns on the central scaffold of formula (I) are enumerated as example I-1 to I-145 and IB-1 to IB-104 in the following:

| No. | Formula | Name | HPLC/MS [M + H]+ | A | B | C | D |
|---|---|---|---|---|---|---|---|
| I-108 | | 5-(1-(3-fluorophenyl)-5-(trifluoromethyl)-1H-pyrazol-4-yl)-3-(4-methoxyphenyl)isoxazole-4-carboxylic acid | 448.08 | | | | 1 |
| I-109 | | methyl 3-(2,6-dichlorophenyl)-5-(1-(3-fluorophenyl)-5-(trifluoromethyl)-1H-pyrazol-4-yl)isoxazole-4-carboxylate | 500.01 | 4 | 4 | 4 | |
| I-110 | | 3-(2,6-dichlorophenyl)-5-(1-(3-fluorophenyl)-5-(trifluoromethyl)-1H-pyrazol-4-yl)-N-methylisoxazole-4-carboxamide | 499.03 | 3 | 3 | 3 | |
| I-111 | | methyl 3-(2,4-dichlorophenyl)-5-(1-(3-fluorophenyl)-5-(trifluoromethyl)-1H-pyrazol-4-yl)isoxazole-4-carboxylate | 500.01 | 1 | 1 | 2 | |
| I-112 | | ethyl 3-(2,4-dichlorophenyl)-5-(1-(3-fluorophenyl)-5-(trifluoromethyl)-1H-pyrazol-4-yl)isoxazole-4-carboxylate | 514.03 | 2 | 3 | 2 | |
| I-113 | | 5-(1-(3,5-difluorophenyl)-5-(trifluoromethyl)-1H-pyrazol-4-yl)-N-methyl-3-phenylisoxazole-4-carboxamide | 449.10 | 1 | 1 | | |

TABLE 2-continued

Further illustrative examples, which further elucidate suitable substitution patterns on the central scaffold of formula (I) are enumerated as example I-1 to I-145 and IB-1 to IB-104 in the following:

| No. | Formula | Name | HPLC/MS [M + H]+ | A | B | C | D |
|---|---|---|---|---|---|---|---|
| I-114 | | 3-(3-fluorophenyl)-5-(1-(3-fluorophenyl)-5-(trifluoromethyl)-1H-pyrazol-4-yl)isoxazole-4-carboxylic acid | 436.06 | | | 1 | |
| I-115 | | methyl 3-(2-chloro-6-fluorophenyl)-5-(1-(3-chlorophenyl)-1H-pyrazol-4-yl)isoxazole-4-carboxylate | 432.02 | 1 | 1 | 1 | |
| I-116 | | methyl 3-(2-chloro-6-fluorophenyl)-5-(1-(6-ethoxypyrimidin-4-yl)-5-(trifluoromethyl)-1H-pyrazol-4-yl)isoxazole-4-carboxylate | 512.07 | | | | 1 |
| I-117 | | 3-(2-chloro-6-fluorophenyl)-5-(1-(3-fluorophenyl)-5-(trifluoromethyl)-1H-pyrazol-4-yl)isoxazol-4-amine | 441.05 | 2 | 2 | 2 | |
| I-118 | | (3-(2-chloro-6-fluorophenyl)-5-(1-(3-fluorophenyl)-5-(trifluoromethyl)-1H-pyrazol-4-yl)isoxazol-4-yl)(isoxazolidin-2-yl)methanone | 525.07 | 3 | 3 | 3 | |
| I-119 | | methyl 3-(2-chloro-6-fluorophenyl)-5-(1-(2,6-dimethylpyrimidin-4-yl)-5-(trifluoromethyl)-1H-pyrazol-4-yl)isoxazole-4-carboxylate | 496.07 | 2 | 2 | 2 | |

TABLE 2-continued

Further illustrative examples, which further elucidate suitable substitution patterns on the central scaffold of formula (I) are enumerated as example I-1 to I-145 and IB-1 to IB-104 in the following:

| No. | Formula | Name | HPLC/MS [M + H]+ | A | B | C | D |
|---|---|---|---|---|---|---|---|
| I-120 | | 3-(2-chloro-6-fluorophenyl)-5-(1-(3-fluorophenyl)-5-(trifluoromethyl)-1H-pyrazol-4-yl)isoxazole-4-carbonitrile | 451.03 | | 2 | 2 | 2 |
| I-121 | | 3-(2-chloro-6-fluorophenyl)-5-(1-(3-chlorophenyl)-5-(trifluoromethyl)-1H-pyrazol-4-yl)isoxazole-4-carboxamide | 485.01 | | 1 | 1 | 1 |
| I-122 | | 3-(2-chloro-6-fluorophenyl)-5-(1-(3-fluorophenyl)-5-(trifluoromethyl)-1H-pyrazol-4-yl)-N-methylisoxazole-4-carbothioamide | 499.03 | | 2 | 2 | 2 |
| I-123 | | (3-(2-chloro-6-fluorophenyl)-5-(1-(2-fluorophenyl)-5-(trifluoromethyl)-1H-pyrazol-4-yl)isoxazol-4-yl)(morpholino)methanethione | 555.06 | | | 1 | |
| I-124 | | 3-(2-chloro-6-fluorophenyl)-5-(1-(3-fluorophenyl)-5-(trifluoromethyl)-1H-pyrazol-4-yl)isoxazole-4-carboxamide | 469.04 | | | 1 | 1 |
| I-125 | | 3-(2-chloro-6-fluorophenyl)-5-(1-(3-chlorophenyl)-5-(trifluoromethyl)-1H-pyrazol-4-yl)isoxazole-4-carbothioamide | 500.99 | | 2 | 2 | 1 | ns

TABLE 2-continued

Further illustrative examples, which further elucidate suitable substitution patterns on the central scaffold of formula (I) are enumerated as example I-1 to I-145 and IB-1 to IB-104 in the following:

| No. | Formula | Name | HPLC/MS [M + H]⁺ | A | B | C | D |
|---|---|---|---|---|---|---|---|
| I-126 | | S-methyl 3-(2-chloro-6-fluorophenyl)-5-(1-(3-chlorophenyl)-5-(trifluoromethyl)-1H-pyrazol-4-yl)isoxazole-4-carbothioate | 515.99 | 3* | 4 | 4 | 4 |
| I-127 | | (3-(2-chloro-6-fluorophenyl)-5-(1-(3-fluorophenyl)-5-(trifluoromethyl)-1H-pyrazol-4-yl)isoxazol-4-yl)(morpholino)methanone | 539.08 | | 2 | 2 | 1 |
| I-128 | | S-methyl 3-(2-chloro-6-fluorophenyl)-5-(1-(3-fluorophenyl)-5-(trifluoromethyl)-1H-pyrazol-4-yl)isoxazole-4-carbothioate | 500.02 | 4* | 4 | 4 | 4 |
| I-129 | | (3-(2-chloro-6-fluorophenyl)-5-(1-(3-fluorophenyl)-5-(trifluoromethyl)-1H-pyrazol-4-yl)isoxazol-4-yl)(morpholino)methanethione | 555.06 | | 1 | | |
| I-130 | | S-methyl 3-(2-chloro-6-fluorophenyl)-5-(1-(2-fluorophenyl)-5-(trifluoromethyl)-1H-pyrazol-4-yl)isoxazole-4-carbothioate | 500.02 | | 4 | 4 | 4 |
| I-131 | | methyl 3-(2-chloro-6-fluorophenyl)-5-(1-(3-(4-chlorophenyl)-4-(methoxycarbonyl)isoxazol-5-yl)-5-(trifluoromethyl)-1H-pyrazol-4-yl)isoxazole-4-carboxylate | 625.02 | | | | 1 |

TABLE 2-continued

Further illustrative examples, which further elucidate suitable substitution patterns on the central scaffold of formula (I) are enumerated as example I-1 to I-145 and IB-1 to IB-104 in the following:

| No. | Formula | Name | HPLC/MS [M + H]+ | A | B | C | D |
|---|---|---|---|---|---|---|---|
| I-132 | 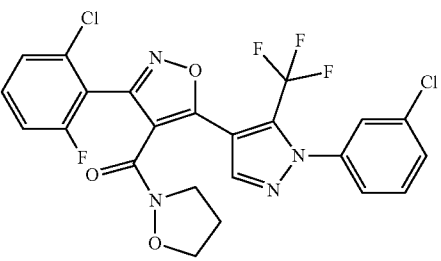 [SMILES: O=C(c1c(-c2c(F)cccc2Cl)noc1-c1cnn(-c2cccc(Cl)c2)c1C(F)(F)F)N1CCCO1] | (3-(2-chloro-6-fluorophenyl)-5-(1-(3-chlorophenyl)-5-(trifluoromethyl)-1H-pyrazol-4-yl)isoxazol-4-yl)(isoxazolidin-2-yl)methanone | 541.04 | | 3 | 4 | 3 |
| I-133 | 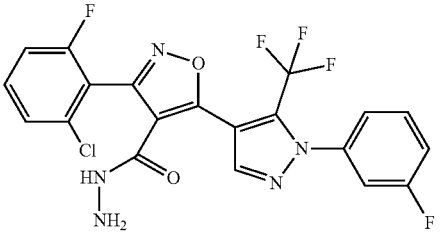 [SMILES: NNC(=O)c1c(-c2c(F)cccc2Cl)noc1-c1cnn(-c2cccc(F)c2)c1C(F)(F)F] | 3-(2-chloro-6-fluorophenyl)-5-(1-(3-fluorophenyl)-5-(trifluoromethyl)-1H-pyrazol-4-yl)isoxazole-4-carbohydrazide | 484.05 | | 1 | 1 | 1 |
| I-134 | 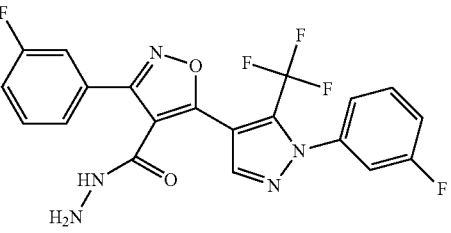 | 3-(3-fluorophenyl)-5-(1-(3-fluorophenyl)-5-(trifluoromethyl)-1H-pyrazol-4-yl)isoxazole-4-carbohydrazide | 450.09 | | | | 1 |
| I-135 | 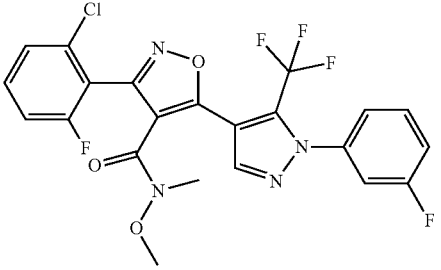 [SMILES: CON(C)C(=O)c1c(-c2c(F)cccc2Cl)noc1-c1cnn(-c2cccc(F)c2)c1C(F)(F)F] | 3-(2-chloro-6-fluorophenyl)-5-(1-(3-fluorophenyl)-5-(trifluoromethyl)-1H-pyrazol-4-yl)-N-methoxy-N-methylisoxazole-4-carboxamide | 513.07 | | 2 | 2 | 2 |
| I-136 | 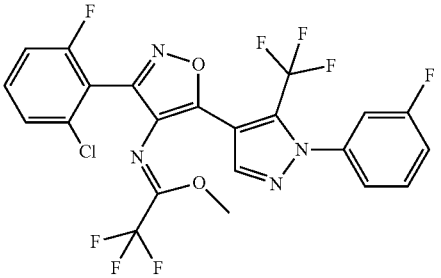 [SMILES: CO/C(=N\c1c(-c2c(F)cccc2Cl)noc1-c1cnn(-c2cccc(F)c2)c1C(F)(F)F)C(F)(F)F] | (Z)-methyl N-(3-(2-chloro-6-fluorophenyl)-5-(1-(3-fluorophenyl)-5-(trifluoromethyl)-1H-pyrazol-4-yl)isoxazol-4-yl)-2,2,2-trifluoroacetimidate | 551.04 | | 2 | 3 | 2 |

TABLE 2-continued

Further illustrative examples, which further elucidate suitable substitution patterns on the central scaffold of formula (I) are enumerated as example I-1 to I-145 and IB-1 to IB-104 in the following:

| No. | Formula | Name | HPLC/MS [M + H]⁺ | A | B | C | D |
|---|---|---|---|---|---|---|---|
| I-137 | | 4-bromo-3-(2-chloro-6-fluorophenyl)-5-(1-(3-fluorophenyl)-5-(trifluoromethyl)-1H-pyrazol-4-yl)isoxazole | 503.95 | | 2 | 2 | 3 |
| I-138 | | methyl (3-(2-chloro-6-fluorophenyl)-5-(1-(3-fluorophenyl)-5-(trifluoromethyl)-1H-pyrazol-4-yl)isoxazol-4-yl)carbamate | 499.05 | | 2 | 2 | 2 |
| I-139 | | N-(3-(2-chloro-6-fluorophenyl)-5-(1-(3-fluorophenyl)-5-(trifluoromethyl)-1H-pyrazol-4-yl)isoxazol-4-yl)acetamide | 483.06 | | 1 | 1 | 1 |
| I-140 | | 4-bromo-3-(2-chloro-6-fluorophenyl)-5-(1-(3-chlorophenyl)-5-(trifluoromethyl)-1H-pyrazol-4-yl)isoxazole | 519.92 | | 4 | 4 | 3 |
| I-141 | | N-(3-(2-chloro-6-fluorophenyl)-5-(1-(3-fluorophenyl)-5-(trifluoromethyl)-1H-pyrazol-4-yl)isoxazol-4-yl)formamide | 469.04 | | 1 | 1 | 1 |

| No. | Formula | Name | HPLC/MS [M + H]+ | A | B | C | D |
|---|---|---|---|---|---|---|---|
| I-142 | | N'-acetyl-3-(2-chloro-6-fluorophenyl)-5-(1-(2-fluorophenyl)-5-(trifluoromethyl)-1H-pyrazol-4-yl)isoxazole-4-carbohydrazide | 526.06 | | | 1 | |
| I-144 | | 4-bromo-3-(2-chloro-6-fluorophenyl)-5-(1-(2,3,5,6-tetrafluorophenyl)-5-(trifluoromethyl)-1H-pyrazol-4-yl)isoxazole | 557.92 | | 1 | 1 | |
| I-145 | | 4-bromo-3-(2-chloro-6-fluorophenyl)-5-(1-phenyl-5-(trifluoromethyl)-1H-pyrazol-4-yl)isoxazole | 485.96 | 3 | 4 | 3 | |
| IB-1 | | ethyl 5-(1-(2-acetamidophenyl)-5-(trifluoromethyl)-1H-pyrazol-4-yl)-3-(2-chloro-6-fluorophenyl)isoxazole-4-carboxylate | 537.09 | 1 | 2 | 1 | |
| IB-2 | | ethyl 3-(2-chloro-6-fluorophenyl)-5-(1-(2-methoxyethyl)-5-(trifluoromethyl)-1H-pyrazol-4-yl)isoxazole-4-carboxylate | 462.08 | 2 | 2 | 1 | |

TABLE 2-continued

Further illustrative examples, which further elucidate suitable substitution patterns on the central scaffold of formula (I) are enumerated as example I-1 to I-145 and IB-1 to IB-104 in the following:

| No. | Formula | Name | HPLC/MS [M + H]⁺ | A | B | C | D |
|---|---|---|---|---|---|---|---|
| IB-3 | | ethyl 3-(3-fluoropyridin-4-yl)-5-(1-(pyridin-4-yl)-5-(trifluoromethyl)-1H-pyrazol-4-yl)isoxazole-4-carboxylate | 448.10 | | 2 | 3 | 2 |
| IB-4 | | ethyl 5-(1-(3-chlorophenyl)-5-(trifluoromethyl)-1H-pyrazol-4-yl)-3-(3-fluoropyridin-4-yl)isoxazole-4-carboxylate | 481.06 | | 2 | 2 | 1 |
| IB-5 | | ethyl 3-(3,5-dichloropyridin-4-yl)-5-(1-(pyridin-2-yl)-5-(trifluoromethyl)-1H-pyrazol-4-yl)isoxazole-4-carboxylate | 498.03 | | 1 | 2 | 1 |
| IB-6 | | ethyl 5-(1-(3-acetamidophenyl)-5-(trifluoromethyl)-1H-pyrazol-4-yl)-3-(3-fluoropyridin-4-yl)isoxazole-4-carboxylate | 504.12 | | 3 | 4 | 2 |
| IB-7 | | ethyl 5-(1-(3-chlorophenyl)-5-(trifluoromethyl)-1H-pyrazol-4-yl)-3-(3,5-dichloropyridin-4-yl)isoxazole-4-carboxylate | 530.99 | | 1 | 2 | 1 |

TABLE 2-continued

Further illustrative examples, which further elucidate suitable substitution patterns on the central scaffold of formula (I) are enumerated as example I-1 to I-145 and IB-1 to IB-104 in the following:

| No. | Formula | Name | HPLC/MS [M + H]+ | A | B | C | D |
|---|---|---|---|---|---|---|---|
| IB-8 | | ethyl 3-(3-fluoropyridin-4-yl)-5-(1-(pyridin-2-yl-5-(trifluoromethyl)-1H-pyrazol-4-yl)isoxazole-4-carboxylate | 448.10 | | 1 | 1 | 1 |
| IB-9 | | ethyl 3-(3,5-dichloropyridin-4-yl)-5-(1-(2-fluorophenyl)-5-(trifluoromethyl)-1H-pyrazol-4-yl)isoxazole-4-carboxylate | 515.02 | | 3 | 3 | 3 |
| IB-10 | | ethyl 3-(3,5-dichloropyridin-4-yl)-5-(1-(pyridin-4-yl)-5-(trifluoromethyl)-1H-pyrazol-4-yl)isoxazole-4-carboxylate | 498.03 | | 2 | 2 | 2 |
| IB-11 | | ethyl 5-(1-(3-acetamidophenyl)-5-(trifluoromethyl)-1H-pyrazol-4-yl)-3-(3,5-dichloropyridin-4-yl)isoxazole-4-carboxylate | 554.05 | | 3 | 3 | 2 |
| IB-12 | | ethyl 3-(3,5-dichloropyridin-4-yl)-5-(1-(pyridin-3-yl)-5-(trifluoromethyl)-1H-pyrazol-4-yl)isoxazole-4-carboxylate | 498.03 | | 3 | 2 | 2 |

TABLE 2-continued

Further illustrative examples, which further elucidate suitable substitution patterns on the central scaffold of formula (I) are enumerated as example I-1 to I-145 and IB-1 to IB-104 in the following:

| No. | Formula | Name | HPLC/MS [M + H]+ | A | B | C | D |
|---|---|---|---|---|---|---|---|
| IB-13 | | ethyl 5-(1-(2-chlorophenyl)-5-(trifluoromethyl)-1H-pyrazol-4-yl)-3-(3-fluoropyridin-4-yl)isoxazole-4-carboxylate | 481.06 | | 3 | 3 | 3 |
| IB-14 | | ethyl 5-(1-(3-fluorophenyl)-5-(trifluoromethyl)-1H-pyrazol-4-yl)-3-(3-fluoropyridin-4-yl)isoxazole-4-carboxylate | 465.09 | | 2 | 1 | 1 |
| IB-15 | | ethyl 5-(1-(2-fluorophenyl)-5-(trifluoromethyl)-1H-pyrazol-4-yl)-3-(3-fluoropyridin-4-yl)isoxazole-4-carboxylate | 465.09 | | 1 | 2 | 2 |
| IB-16 | | ethyl 5-(1-(2-chlorophenyl)-5-(trifluoromethyl)-1H-pyrazol-4-yl)-3-(3,5-dichloropyridin-4-yl)isoxazole-4-carboxylate | 530.99 | | 2 | 1 | 1 |
| IB-17 | | ethyl 3-(3-fluoropyridin-4-yl)-5-(1-(pyridin-3-yl)-5-(trifluoromethyl)-1H-pyrazol-4-yl)isoxazole-4-carboxylate | 448.10 | | 2 | 1 | 1 |

TABLE 2-continued

Further illustrative examples, which further elucidate suitable substitution patterns on the central scaffold of formula (I) are enumerated as example I-1 to I-145 and IB-1 to IB-104 in the following:

| No. | Formula | Name | HPLC/MS [M + H]⁺ | A | B | C | D |
|---|---|---|---|---|---|---|---|
| IB-18 | | 3-(2-chloro-6-fluorophenyl)-5-(1-(3-chlorophenyl)-5-(trifluoromethyl)-1H-pyrazol-4-yl)isoxazole-4-carboxylic acid | 486.00 | | 1 | | |
| IB-19 | | 3-(2-chloro-6-fluorophenyl)-5-(1-isobutyl-5-(trifluoromethyl)-1H-pyrazol-4-yl)isoxazole-4-carboxylic acid | 432.07 | | 1 | | |
| IB-20 | | methyl 3-(2-chloro-6-fluorophenyl)-5-(1-(2-chlorophenyl)-5-(trifluoromethyl)-1H-pyrazol-4-yl)isoxazole-4-carboxylate | 500.01 | | 1 | 1 | 1 |
| IB-21 | | methyl 3-(2-chloro-6-fluorophenyl)-5-(1-(3-fluorophenyl)-1H-pyrazol-4-yl)isoxazole-4-carboxylate | 416.05 | | 2 | 2 | 2 |
| IB-22 | | N-(3-(2-chloro-6-fluorophenyl)-5-(1-(3-fluorophenyl)-5-(trifluoromethyl)-1H-pyrazol-4-yl)isoxazol-4-yl)-2,2,2-trifluoroacetamide | 537.03 | | 1 | 1 | 1 |
| IB-23 | | 4-bromo-3-(2-chloro-6-fluorophenyl)-5-(1-(2-methoxyphenyl)-5-(trifluoromethyl)-1H-pyrazol-4-yl)isoxazole | 515.97 | | | 1 | |

TABLE 2-continued

Further illustrative examples, which further elucidate suitable substitution patterns on the central scaffold of formula (I) are enumerated as example I-1 to I-145 and IB-1 to IB-104 in the following:

| No. | Formula | Name | HPLC/MS [M + H]+ | A | B | C | D |
|---|---|---|---|---|---|---|---|
| IB-24 | | 4-bromo-3-(2-chloro-6-fluorophenyl)-5-(1-(2,4-difluorophenyl)-5-(trifluoromethyl)-1H-pyrazol-4-yl)isoxazole | 521.94 | | 1 | 1 | 1 |
| IB-25 | | 4-bromo-3-(2-chloro-6-fluorophenyl)-5-(1-(4-(trifluoromethoxy)phenyl)-5-(trifluoromethyl)-1H-pyrazol-4-yl)isoxazole | 569.94 | | 1 | | |
| IB-26 | | 4-bromo-3-(2-chloro-6-fluorophenyl)-5-(1-(2-fluorophenyl)-5-(trifluoromethyl)-1H-pyrazol-4-yl)isoxazole | 503.95 | | | 2 | 1 |
| IB-27 | | 4-bromo-3-(2-chloro-6-fluorophenyl)-5-(1-(3,5-difluorophenyl)-5-(trifluoromethyl)-1H-pyrazol-4-yl)isoxazole | 521.94 | | 2 | 2 | 2 |
| IB-28 | | 4-bromo-3-(2-chloro-6-fluorophenyl)-5-(1-(4-fluorophenyl)-5-(trifluoromethyl)-1H-pyrazol-4-yl)isoxazole | 503.95 | | 2 | 2 | 2 |
| IB-29 | | 3-(2-chloro-6-fluorophenyl)-5-(1-(3-fluorophenyl)-1H-pyrazol-4-yl)-N'-(propan-2-ylidene)isoxazole-4-carbohydrazide | 456.10 | | 1 | 1 | |

TABLE 2-continued

Further illustrative examples, which further elucidate suitable substitution patterns on the central scaffold of formula (I) are enumerated as example I-1 to I-145 and IB-1 to IB-104 in the following:

| No. | Formula | Name | HPLC/MS [M + H]+ | A | B | C | D |
|---|---|---|---|---|---|---|---|
| IB-30 | | methyl 5-(1-(3-chlorophenyl)-5-(trifluoromethyl)-1H-pyrazol-4-yl)-3-phenylisoxazole-4-carboxylate | 448.06 | | 2 | 2 | 2 |
| IB-31 | | isopropyl 3-(2-chloro-6-fluorophenyl)-5-(1-(3-chlorophenyl)-5-(trifluoromethyl)-1H-pyrazol-4-yl)isoxazole-4-carboxylate | 528.04 | | 4 | 4 | 4 |
| IB-32 | | ethyl 3-(2-chloro-6-fluorophenyl)-5-(1-(3-cyanophenyl)-5-(trifluoromethyl)-1H-pyrazol-4-yl)isoxazole-4-carboxylate | 505.06 | | 4 | 4 | 3 |
| IB-33 | | ethyl 3-(2-chloro-6-fluorophenyl)-5-(1-(2-chlorophenyl)-5-(trifluoromethyl)-1H-pyrazol-4-yl)isoxazole-4-carboxylate | 514.03 | | 2 | 2 | 2 |
| IB-34 | | (3-(2-chloro-6-fluorophenyl)-5-(1-(3-chlorophenyl)-5-(trifluoromethyl)-1H-pyrazol-4-yl)-isoxazol-4-yl)(4-methylpiperazin-1-yl)methanone | 568.09 | | | 2 | 2 |

TABLE 2-continued

Further illustrative examples, which further elucidate suitable substitution patterns on the central scaffold of formula (I) are enumerated as example I-1 to I-145 and IB-1 to IB-104 in the following:

| No. | Formula | Name | HPLC/MS [M + H]+ | A | B | C | D |
|---|---|---|---|---|---|---|---|
| IB-35 | | (3-(2-chloro-6-fluorophenyl)-5-(1-(3-chlorophenyl)-5-(trifluoromethyl)-1H-pyrazol-4-yl)-isoxazol-4-yl)(morpholino)methanone | 555.05 | | 2 | 2 | 1 |
| IB-36 | | 3-(2-chloro-6-fluorophenyl)-5-(1-(3-chlorophenyl)-5-(trifluoromethyl)-1H-pyrazol-4-yl)-isoxazol-4-amine | 457.02 | | 2 | 2 | 2 |
| IB-37 | | ethyl 3-(2-chloro-6-fluorophenyl)-5-(1-(pyridin-3-yl)-5-(trifluoromethyl)-1H-pyrazol-4-yl)-isoxazole-4-carboxylate | 481.06 | | 4 | 4 | 4 |
| IB-38 | | ethyl 3-(2-chloro-6-fluorophenyl)-5-(1-(pyridin-4-yl)-5-(trifluoromethyl)-1H-pyrazol-4-yl)-isoxazole-4-carboxylate | 481.06 | | 4 | 4 | 4 |
| IB-39 | | N-(3-(2-chloro-6-fluorophenyl)-5-(1-(3-chlorophenyl)-5-(trifluoromethyl)-1H-pyrazol-4-yl)-isoxazol-4-yl)acetamide | 499.03 | | | 1 | 1 |

TABLE 2-continued

Further illustrative examples, which further elucidate suitable substitution patterns on the central scaffold of formula (I) are enumerated as example I-1 to I-145 and IB-1 to IB-104 in the following:

| No. | Formula | Name | HPLC/MS [M + H]+ | A | B | C | D |
|---|---|---|---|---|---|---|---|
| IB-40 | | ethyl 3-(2-chloro-6-fluorophenyl)-5-(1-(4-cyanophenyl)-5-(trifluoromethyl)-1H-pyrazol-4-yl)-isoxazole-4-carboxylate | 505.06 | | | 1 | 1 |
| IB-41 | | ethyl 3-(2-chlorophenyl)-5-(1-(3-chlorophenyl)-5-(trifluoromethyl)-1H-pyrazol-4-yl)-isoxazole-4-carboxylate | 496.04 | | 4 | 4 | 3 |
| IB-42 | | 3-(2-chlorophenyl)-5-(1-(3-chlorophenyl)-5-(trifluoromethyl)-1H-pyrazol-4-yl)-isoxazole-4-carboxylic acid | 468.01 | | 1 | 1 | 1 |
| IB-43 | | ethyl 3-(2-chloro-6-fluorophenyl)-5-(1-(3-sulfamoylphenyl)-5-(trifluoromethyl)-1H-pyrazol-4-yl)-isoxazole-4-carboxylate | 559.04 | | 2 | 1 | 1 |
| IB-44 | | ethyl 3-(2-chloro-6-fluorophenyl)-5-(1-(2-cyanophenyl)-5-(trifluoromethyl)-1H-pyrazol-4-yl)-isoxazole-4-carboxylate | 505.06 | | 1 | 1 | 1 |

TABLE 2-continued

Further illustrative examples, which further elucidate suitable substitution patterns on the central scaffold of formula (I) are enumerated as example I-1 to I-145 and IB-1 to IB-104 in the following:

| No. | Formula | Name | HPLC/MS [M + H]+ | A | B | C | D |
|---|---|---|---|---|---|---|---|
| IB-45 | | ethyl 5-(1-(3-chlorophenyl)-5-(trifluoromethyl)-1H-pyrazol-4-yl)-3-(2,6-dichlorophenyl)-isoxazole-4-carboxylate | 530.00 | | 4 | 4 | 4 |
| IB-46 | | ethyl 5-(1-(3-chlorophenyl)-5-(trifluoromethyl)-1H-pyrazol-4-yl)-3-(2,4-dichlorophenyl)-isoxazole-4-carboxylate | 530.00 | | 2 | 2 | 2 |
| IB-47 | | ethyl 5-(1-(3-chlorophenyl)-5-(trifluoromethyl)-1H-pyrazol-4-yl)-3-(2-fluorophenyl)isoxazole-4-carboxylate | 480.07 | | 3 | 3 | 3 |
| IB-48 | | N-(3-(2-chloro-6-fluorophenyl)-5-(1-(3-chlorophenyl)-5-(trifluoromethyl)-1H-pyrazol-4-yl)isoxazol-4-yl)formamide | 485.01 | | 1 | | 1 |
| IB-49 | | (3-(2-chloro-6-fluorophenyl)-5-(1-(2-chlorophenyl)-5-(trifluoromethyl)-1H-pyrazol-4-yl)isoxazol-4-yl)(isoxazolidin-2-yl)methanone | 541.04 | | 2 | 1 | 1 |

TABLE 2-continued

Further illustrative examples, which further elucidate suitable substitution patterns on the central scaffold of formula (I) are enumerated as example I-1 to I-145 and IB-1 to IB-104 in the following:

| No. | Formula | Name | HPLC/MS [M + H]+ | A | B | C | D |
|---|---|---|---|---|---|---|---|
| IB-50 | | 3-(2-chloro-6-fluorophenyl)-5-(1-(2-chlorophenyl)-5-(trifluoromethyl)-1H-pyrazol-4-yl)-N-methylisoxazole-4-carboxamide | 499.03 | | 1 | | |
| IB-51 | | 3-(2-chloro-6-fluorophenyl)-5-(1-(2-chlorophenyl)-5-(trifluoromethyl)-1H-pyrazol-4-yl)-N-methoxy-N-methylisoxazole-4-carboxamide | 529.04 | | 1 | 1 | 1 |
| IB-52 | | (3-(2-chloro-6-fluorophenyl)-5-(1-(2-fluorophenyl)-5-(trifluoromethyl)-1H-pyrazol-4-yl)isoxazol-4-yl)(isoxazolidin-2-yl)methanone | 525.07 | | 1 | 1 | 1 |
| IB-53 | | 3-(2-chloro-6-fluorophenyl)-5-(1-(2-fluorophenyl)-5-(trifluoromethyl)-1H-pyrazol-4-yl)-N-methoxy-N-methylisoxazole-4-carboxamide | 51.07 | | 2 | 2 | 2 |
| IB-54 | | (3-(2-chloro-6-fluorophenyl)-5-(1-(pyridin-3-yl)-5-(trifluoromethyl)-1H-pyrazol-4-yl)isoxazol-4-yl)(isoxazolidin-2-yl)methanone | 508.07 | | 1 | 1 | 1 |
| IB-55 | | 3-(2-chloro-6-fluorophenyl)-N-methyl-5-(1-(pyridin-3-yl)-5-(trifluoromethyl)-1H-pyrazol-4-yl)isoxazole-4-carboxamide | 466.06 | | 1 | 1 | 1 |

TABLE 2-continued

Further illustrative examples, which further elucidate suitable substitution patterns on the central scaffold of formula (I) are enumerated as example I-1 to I-145 and IB-1 to IB-104 in the following:

| No. | Formula | Name | HPLC/MS [M + H]+ | A | B | C | D |
|---|---|---|---|---|---|---|---|
| IB-56 | | 3-(2-chloro-6-fluorophenyl)-N-methoxy-N-methyl-5-(1-(pyridin-3-yl)-5-(trifluoromethyl)-1H-pyrazol-4-yl)isoxazole-4-carboxamide | 496.07 | | 1 | 1 | 1 |
| IB-57 | | (3-(2-chloro-6-fluorophenyl)-5-(1-(pyridin-4-yl)-5-(trifluoromethyl)-1H-pyrazol-4-yl)isoxazol-4-yl)(isoxazolidin-2-yl)methanone | 508.07 | | 1 | 1 | 1 |
| IB-58 | | 3-(2-chloro-6-fluorophenyl)-N-methyl-5-(1-(pyridin-4-yl)-5-(trifluoromethyl)-1H-pyrazol-4-yl)isoxazole-4-carboxamide | 466.06 | | 1 | 1 | |
| IB-59 | | 3-(2-chloro-6-fluorophenyl)-N-methoxy-N-methyl-5-(1-(pyridin-4-yl)-5-(trifluoromethyl)-1H-pyrazol-4-yl)isoxazole-4-carboxamide | 496.07 | | 1 | 1 | 1 |
| IB-60 | | isopropyl 3-(2-chloro-6-fluorophenyl)-5-(1-(o-tolyl)-5-(trifluoromethyl)-1H-pyrazol-4-yl)isoxazole-4-carboxylate | 528.04 | | 1 | 1 | 1 |

TABLE 2-continued

Further illustrative examples, which further elucidate suitable substitution patterns on the central scaffold of formula (I) are enumerated as example I-1 to I-145 and IB-1 to IB-104 in the following:

| No. | Formula | Name | HPLC/MS [M + H]+ | A | B | C | D |
|---|---|---|---|---|---|---|---|
| IB-61 | | isopropyl 3-(2-chloro-6-fluorophenyl)-5-(1-(pyridin-3-yl)-5-(trifluoromethyl)-1H-pyrazol-4-yl)isoxazole-4-carboxylate | 495.08 | | 3 | 4 | 3 |
| IB-62 | | (3-(2-chlorophenyl)-5-(1-(3-chlorophenyl)-5-(trifluoromethyl)-1H-pyrazol-4-yl)isoxazol-4-yl)(isoxazolidin-2-yl)methanone | 523.05 | | 3 | 3 | 3 |
| IB-63 | | 3-(2-chlorophenyl)-5-(1-(3-chlorophenyl)-5-(trifluoromethyl)-1H-pyrazol-4-yl)-N-methylisoxazole-4-carboxamide | 481.04 | | 2 | 2 | 2 |
| IB-64 | | 3-(2-chlorophenyl)-5-(1-(3-chlorophenyl)-5-(trifluoromethyl)-1H-pyrazol-4-yl)-N-methoxy-N-methylisoxazole-4-carboxamide | 511.05 | | 3 | 2 | 2 |
| IB-65 | | 3-(4-(3-(2-chloro-6-fluorophenyl)-4-(isoxazolidine-2-carbonyl)isoxazol-5-yl)-5-(trifluoromethyl)-1H-pyrazol-1-yl)benzenesulfonamide | 586.05 | | 1 | 1 | |

TABLE 2-continued

Further illustrative examples, which further elucidate suitable substitution patterns on the central scaffold of formula (I) are enumerated as example I-1 to I-145 and IB-1 to IB-104 in the following:

| No. | Formula | Name | HPLC/MS [M + H]+ | A | B | C | D |
|---|---|---|---|---|---|---|---|
| IB-66 | | 3-(2-chloro-6-fluorophenyl)-N-methoxy-N-methyl-5-(1-(3-sulfamoylphenyl)-5-(trifluoromethyl)-1H-pyrazol-4-yl)isoxazole-4-carboxamide | 574.05 | | 1 | 1 | |
| IB-67 | | methyl 3-(2-chloro-6-fluorophenyl)-5-(1-(pyridin-3-yl)-5-(trifluoromethyl)-1H-pyrazol-4-yl)isoxazole-4-carboxylate | 467.05 | | 3 | 3 | 3 |
| IB-68 | | S-methyl 3-(2-chloro-6-fluorophenyl)-5-(1-(pyridin-3-yl)-5-(trifluoromethyl)-1H-pyrazol-4-yl)isoxazole-4-carbothioate | 483.02 | | 4 | 4 | 3 |
| IB-69 | | methyl 3-(2-chloro-6-fluorophenyl)-5-(1-(pyridin-4-yl)-5-(trifluoromethyl)-1H-pyrazol-4-yl)isoxazole-4-carboxylate | 467.05 | | 3 | 3 | 3 |
| IB-70 | | ethyl 5-(1-(3-acetamidophenyl)-5-(trifluoromethyl)-1H-pyrazol-4-yl)-3-(2-chloro-6-fluorophenyl)isoxazole-4-carboxylate | 537.09 | 3 | 3 | 3 | 3 |

TABLE 2-continued

Further illustrative examples, which further elucidate suitable substitution patterns on the central scaffold of formula (I) are enumerated as example I-1 to I-145 and IB-1 to IB-104 in the following:

| No. | Formula | Name | HPLC/MS [M + H]⁺ | A | B | C | D |
|---|---|---|---|---|---|---|---|
| IB-71 | | methyl 3-(2-chlorophenyl)-5-(1-(3-chlorophenyl)-5-(trifluoromethyl)-1H-pyrazol-4-yl)isoxazole-4-carboxylate | 482.02 | | 4 | 4 | 4 |
| IB-72 | | ethyl 5-(1-(2-bromophenyl)-5-(trifluoromethyl)-1H-pyrazol-4-yl)-3-(2-chloro-6-fluorophenyl)isoxazole-4-carboxylate | 557.98 | | 2 | 2 | 2 |
| IB-73 | | isopropyl 3-(2-chloro-6-fluorophenyl)-5-(1-(3-sulfamoylphenyl)-5-(trifluoromethyl)-1H-pyrazol-4-yl)isoxazole-4-carboxylate | 573.05 | | | 1 | 1 |
| IB-74 | | 5-(1-(-2-bromophenyl)-5-(trifluoromethyl)-1H-pyrazol-4-yl)-3-(2-chloro-6-fluorophenyl)-N-methoxy-N-methylisoxazole-4-carboxamide | 572.99 | | | 1 | 1 |
| IB-75 | | methyl 5-(1-(3-chlorophenyl)-5-(trifluoromethyl)-1H-pyrazol-4-yl)-3-(2,6-dichlorophenyl)isoxazole-4-carboxylate | 515.98 | | 4 | 4 | 4 |
| IB-76 | | methyl 5-(1-(3-chlorophenyl)-5-(trifluoromethyl)-1H-pyrazol-4-yl)-3-(2,4-dichlorophenyl)isoxazole-4-carboxylate | 515.98 | | 3 | 2 | 2 |

TABLE 2-continued

Further illustrative examples, which further elucidate suitable substitution patterns on the central scaffold of formula (I) are enumerated as example I-1 to I-145 and IB-1 to IB-104 in the following:

| No. | Formula | Name | HPLC/MS [M + H]+ | A | B | C | D |
|---|---|---|---|---|---|---|---|
| IB-77 | | methyl 5-(1-(3-chlorophenyl)-5-(trifluoromethyl)-1H-pyrazol-4-yl)-3-(2-fluorophenyl)isoxazole-4-carboxylate | 466.05 | | 3 | 3 | 3 |
| IB-78 | | isopropyl 5-(1-(3-acetamidophenyl)-5-(trifluoromethyl)-1H-pyrazol-4-yl)-3-(2-chloro-6-fluorophenyl)isoxazole-4-carboxylate | 551.10 | | 3 | 2 | 2 |
| IB-79 | | isopropyl 3-(2-chloro-6-fluorophenyl)-5-(1-(3-(N-isopropylsulfamoyl)phenyl)-5-(trifluoromethyl)-1H-pyrazol-4-yl)isoxazole-4-carboxylate | 615.10 | | 2 | 2 | 2 |
| IB-80 | | ethyl 3-(2-chloro-6-fluorophenyl)-5-(1-(2-fluorobenzyl)-5-(trifluoromethyl)-1H-pyrazol-4-yl)isoxazole-4-carboxylate | 512.07 | | 1 | 1 | 1 |
| IB-81 | | ethyl 3-(2-chloro-6-fluorophenyl)-5-(1-((tetrahydro-2H-pyran-4-yl)methyl)-5-(trifluoromethyl)-1H-pyrazol-4-yl)isoxazole-4-carboxylate | 502.11 | | 2 | 2 | 2 |

TABLE 2-continued

Further illustrative examples, which further elucidate suitable substitution patterns on the central scaffold of formula (I) are enumerated as example I-1 to I-145 and IB-1 to IB-104 in the following:

| No. | Formula | Name | HPLC/MS [M + H]+ | A | B | C | D |
|---|---|---|---|---|---|---|---|
| IB-82 | | isopropyl 3-(2-chloro-6-fluorophenyl)-5-(1-(pyridin-4-yl)-5-(trifluoromethyl)-1H-pyrazol-4-yl)isoxazole-4-carboxylate | 495.08 | | 3 | 3 | 3 |
| IB-83 | | 4-bromo-3-(2-chloro-6-fluorophenyl)-5-(1-(pyridin-4-yl)-5-(trifluoromethyl)-1H-pyrazol-4-yl)isoxazole | 486.95 | | 2 | 1 | 1 |
| IB-84 | | ethyl 3-(2-chloro-6-fluorophenyl)-5-(1-(pyridin-2-yl)-5-(trifluoromethyl)-1H-pyrazol-4-yl)isoxazole-4-carboxylate | 481.06 | | 4 | 4 | 4 |
| IB-85 | | ethyl 3-(2-chloro-6-fluorophenyl)-5-(1-(pyridin-4-ylmethyl)-5-(trifluoromethyl)-1H-pyrazol-4-yl)isoxazole-4-carboxylate | 495.08 | | 1 | 1 | |
| IB-86 | | 3-(2-chloro-6-fluorophenyl)-5-(1-(2-fluorobenzyl)-5-(trifluoromethyl)-1H-pyrazol-4-yl)isoxazole-4-carboxylic acid | 484.04 | | | | 1 |

TABLE 2-continued

Further illustrative examples, which further elucidate suitable substitution patterns on the central scaffold of formula (I) are enumerated as example I-1 to I-145 and IB-1 to IB-104 in the following:

| No. | Formula | Name | HPLC/MS [M + H]+ | A | B | C | D |
|---|---|---|---|---|---|---|---|
| IB-87 | | 5-(1-(3-acetamidophenyl)-5-(trifluoromethyl)-1H-pyrazol-4-yl)-3-(2-chloro-6-fluorophenyl)-N-methoxy-N-methylisoxazole-4-carboxamide | 552.10 | | 1 | 1 | |
| IB-88 | | N-(3-(4-(3-(2-chloro-6-fluorophenyl)-4-(isoxazolidine-2-carbonyl)isoxazol-5-yl)-5-(trifluoromethyl)-1H-pyrazol-1-yl)phenyl)acetamide | 564.10 | | 1 | 1 | |
| IB-89 | | methyl 5-(1-(3-acetamidophenyl)-5-(trifluoromethyl)-1H-pyrazol-4-yl)-3-(2-chloro-6-fluorophenyl)isoxazole-4-carboxylate | 523.07 | | 3 | 3 | 2 |
| IB-90 | | ethyl 3-(2-chloro-6-fluorophenyl)-5-(1-(3-nitrophenyl)-5-(trifluoromethyl)-1H-pyrazol-4-yl)isoxazole-4-carboxylate | 525.05 | | 3 | 3 | 3 |

TABLE 2-continued

Further illustrative examples, which further elucidate suitable substitution patterns on the central scaffold of formula (I) are enumerated as example I-1 to I-145 and IB-1 to IB-104 in the following:

| No. | Formula | Name | HPLC/MS [M + H]+ | A | B | C | D |
|---|---|---|---|---|---|---|---|
| IB-91 | | 5-(1-(3-acetamidophenyl)-5-(trifluoromethyl)-1H-pyrazol-4-yl)-3-(2-chloro-6-fluorophenyl)-N-methylisoxazole-4-carboxamide | 522.09 | | 1 | | |
| IB-92 | | methyl 5-(1-(3-aminophenyl)-5-(trifluoromethyl)-1H-pyrazol-4-yl)-3-(2-chloro-6-fluorophenyl)isoxazole-4-carboxylate | 481.06 | | 3 | 3 | 3 |
| IB-93 | | 3-(2-chloro-6-fluorophenyl)-N-methyl-5-(1-(pyridin-2-yl)-5-(trifluoromethyl)-1H-pyrazol-4-yl)isoxazole-4-carboxamide | 466.06 | | 2 | 2 | 1 |
| IB-94 | | ethyl 3-(2-chloro-6-fluorophenyl)-5-(1-(4-nitrophenyl)-5-(trifluoromethyl)-1H-pyrazol-4-yl)isoxazole-4-carboxylate | 525.05 | | 1 | 1 | 1 |
| IB-95 | | ethyl 3-(2-chloro-6-fluorophenyl)-5-(1-(2-nitrophenyl)-5-(trifluoromethyl)-1H-pyrazol-4-yl)isoxazole-4-carboxylate | 525.05 | | 3 | 3 | 2 |

TABLE 2-continued

Further illustrative examples, which further elucidate suitable substitution patterns on the central scaffold of formula (I) are enumerated as example I-1 to I-145 and IB-1 to IB-104 in the following:

| No. | Formula | Name | HPLC/MS [M + H]+ | A | B | C | D |
|---|---|---|---|---|---|---|---|
| IB-96 | | ethyl 3-(2-chloro-6-fluorophenyl)-5-(1-((tetrahydrofuran-2-yl)methyl)-5-(trifluoromethyl)-1H-pyrazol-4-yl)isoxazole-4-carboxylate | 488.09 | | 3 | 3 | 3 |
| IB-97 | | ethyl 3-(2-chloro-6-fluorophenyl)-5-(1-(2-morpholinoethyl)-5-(trifluoromethyl)-1H-pyrazol-4-yl)isoxazole-4-carboxylate | 517.12 | | 2 | 2 | 1 |
| IB-98 | | ethyl 5-(1-(2-aminophenyl)-5-(trifluoromethyl)-1H-pyrazol-4-yl)-3-(2-chloro-6-fluorophenyl)isoxazole-4-carboxylate | 495.08 | | 3 | 3 | 3 |
| IB-99 | | ethyl 5-(1-(4-acetamidophenyl)-5-(trifluoromethyl)-1H-pyrazol-4-yl)-3-(2-chloro-6-fluorophenyl)isoxazole-4-carboxylate | 537.09 | | 1 | 1 | 1 |
| IB-100 | | ethyl 5-(1-(3-carbamoylphenyl)-5-(trifluoromethyl)-1H-pyrazol-4-yl)-3-(2-chloro-6-fluorophenyl)isoxazole-4-carboxylate | 523.07 | | 1 | 1 | 1 |

TABLE 2-continued

Further illustrative examples, which further elucidate suitable substitution patterns on the central scaffold of formula (I) are enumerated as example I-1 to I-145 and IB-1 to IB-104 in the following:

| No. | Formula | Name | HPLC/MS [M + H]+ | A | B | C | D |
|---|---|---|---|---|---|---|---|
| IB-101 | | 3-(2-chloro-6-fluorophenyl)-5-(1-(2-chlorophenyl)-5-(trifluoromethyl)-1H-pyrazol-4-yl)isoxazole-4-carbothioamide | 500.99 | 1 | 1 | 1 | |
| IB-102 | | 3-(2-chloro-6-fluorophenyl)-5-(1-(2-fluorophenyl)-5-(trifluoromethyl)-1H-pyrazol-4-yl)isoxazole-4-carbothioamide | 485.02 | 2 | 2 | 2 | |
| IB-103 | | ethyl 3-(3,5-dichloropyridin-4-yl)-5-(1-(3-fluorophenyl)-5-(trifluoromethyl)-1H-pyrazol-4-yl)isoxazole-4-carboxylate | 515.02 | 1 | | 1 | |
| IB-104 | | ethyl 3-(2-chloro-6-fluorophenyl)-5-(1-(pyridin-2-ylmethyl)-5-(trifluoromethyl)-1H-pyrazol-4-yl)isoxazole-4-carboxylate | 495.08 | 1 | | 1 | | columns A, B, C and D specify: A: IC$_{50}$ (IL-17AA) [μM]-values marked with * were determined by Luminex assay on IL17AA/AF; B: IC$_{50}$ (IL-17FF) [μM]; C: IC$_{50}$ (IFNγ) [μM]; D: IC$_{50}$ (Tcell proliferation) [μM]
Activities: 1: >1 μM to 10 μM; 2: >100 nM to 1 μM; 3: >10 nM to 100 nM; 4: ≦10 nM Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing and in the examples, all temperatures are set forth uncorrected in degrees Celsius and, all parts and percentages are by weight, unless otherwise indicated.

The entire disclosures of all applications, patents and publications, cited herein and of corresponding EP application No. 11152512.7, filed 2011 Jan. 28, and U.S. Provisional Application Ser. No. 61/437,080, filed 2011 Jan. 28, are incorporated by reference herein.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:
1. A compound of formula (I)

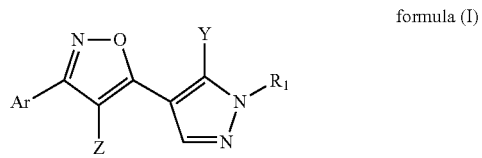

formula (I)

or a pharmaceutically acceptable salt thereof,
wherein
R$^1$ is aryl, heteroaryl, cycloalkyl, heterocyclyl or alkyl, which can be substituted by one or more substituents R'

Ar is aryl, cycloalkyl, heterocyclyl or heteroaryl, which can be substituted by one or more substituents R';

Z is aryl, heteroaryl, cycloalkyl or heterocyclyl, which can be substituted by one or more substituents R';

Y is H, halogen, haloalkyl, alkyl or an alkylester, which can be substituted by one or more substituents R';

R' independently represents H, —CO$_2$R", —CONHR", —CR"O, —SO$_2$N(R")$_2$, —SO$_2$NHR", —NR"—CO-haloalkyl, —NO$_2$, —NR"—SO$_2$-haloalkyl, —NR"—SO$_2$-alkyl, —SO$_2$-alkyl, —NR"—CO-alkyl, —CN, alkyl, cycloalkyl, aminoalkyl, alkylamino, alkoxy, —OH, —SH, alkylthio, hydroxyalkyl, hydroxyalkylamino, halogen, haloalkyl, haloalkoxy, amino, heterocyclyl, aryl, haloaryl, haloarylalkyl, arylalkyl or heteroaryl; and R" independently represents H, haloalkyl, hydroxyalkyl, amino, alkoxy, —N=C(R')$_2$, —NR'—CO—R', —CR'O, —CO$_2$R', alkyl, cycloalkyl, aryl, haloaryl, haloarylalkyl, heteroaryl, heterocyclyl, arylalkyl or aminoalkyl, which are optionally substituted by one or more substituents R', wherein R$^1$, Ar, Z and Y may not comprise more than three coupled substituents R' and/or R".

2. A compound according to claim 1, wherein

Ar is aryl or heteroaryl, which can be substituted by one or more substituents R'.

3. A compound according to claim 1, wherein

R$^1$ is aryl or heteroaryl, which can be substituted by one or more substituents R', and Ar is aryl or heteroaryl, which can be substituted by one or more substituents R'.

4. A compound according to claim 1, wherein

R$^1$ is aryl or heteroaryl, which can be substituted by one or more substituents R'

Ar is aryl or heteroaryl, which can be substituted by one or more substituents R';

Z is aryl, cycloalkyl, heterocyclyl or heteroaryl, which can be substituted by one or more substituents R';

Y is H, halogen, haloalkyl, or alkyl, which can be substituted by one or more substituents R';

R' independently represents H, —CO$_2$R", —CONHR", —CR"O, —SO$_2$N(R")$_2$, —SO$_2$NHR", —CN, alkyl, cycloalkyl, aminoalkyl, alkoxy, —OH, hydroxyalkyl, halogen, haloalkyl, haloalkoxy, amino, heterocyclyl, aryl, haloaryl, haloarylalkyl, arylalkyl or heteroaryl; and R" independently represents H, haloalkyl, hydroxyalkyl, amino, alkoxy, —N=C(R')$_2$, —NR'—CO—R', —CR'O, —CO$_2$R', alkyl, cycloalkyl, aryl, haloaryl, haloarylalkyl, heteroaryl, heterocyclyl, arylalkyl or aminoalkyl, which are optionally substituted by one or more substituents R'.

5. A compound according to claim 1, wherein

R$^1$ is aryl or heteroaryl, which can be substituted by one or more substituents R';

Ar is aryl or heteroaryl, which can be substituted by one or more substituents R';

Z is aryl, cycloalkyl, heterocyclyl or heteroaryl, which can be substituted by one or more substituents R';

Y is H, halogen, haloalkyl, or alkyl, which can be substituted by one or more substituents R';

R' independently represents H, —CO$_2$R", —SO$_2$N(R")$_2$, —SO$_2$NHR", —CN, alkyl, alkoxy, —OH, hydroxyalkyl, halogen, haloalkyl, haloalkoxy, heterocyclyl, aryl, haloaryl, haloarylalkyl, arylalkyl or heteroaryl; and R" independently represents H, haloalkyl, hydroxyalkyl, amino, alkoxy, —N=C(R')$_2$, —NR'—CO—R', —CR'O, —CO$_2$R', alkyl, cycloalkyl, aryl, haloaryl, haloarylalkyl, heteroaryl, heterocyclyl, arylalkyl or aminoalkyl, which are optionally substituted by one or more substituents R'.

6. A compound according to claim 1, wherein

R$^1$ is aryl or heteroaryl, which can be substituted by one or more substituents R';

Ar is aryl or heteroaryl, which can be substituted by one or more substituents R';

Z is aryl, cycloalkyl, heterocyclyl or heteroaryl, which can be substituted by one or more substituents R';

Y is H, halogen, haloalkyl, or alkyl, which can be substituted by one or more substituents R';

R' independently represents H, —CO$_2$R", —CONHR", —CR"O, —SO$_2$N(R")$_2$, —SO$_2$NHR", —CN, alkyl, alkoxy, —OH, halogen, haloalkyl or haloalkoxy; and R" independently represents H, haloalkyl, hydroxyalkyl, amino, alkoxy, —N=C(R')$_2$, —NR'—CO—R', —CR'O, —CO$_2$R', alkyl, cycloalkyl, aryl, haloaryl, haloarylalkyl, heteroaryl, heterocyclyl, arylalkyl or aminoalkyl, which are optionally substituted by one or more substituents R'.

7. A compound according to claim 1, wherein

R$^1$ is selected from the group consisting of phenyl, which is optionally substituted by one or more substituents individually selected from the group consisting of trifluoromethyl, fluorine, chlorine, bromine, nitro, NH$_2$, —CN, —NHCO—C$_{1-4}$-alkyl, methoxy, C$_{1-4}$-alkyl, —SO$_2$NH$_2$, and —SO$_2$NH—C$_{1-4}$-alkyl; pyridyl, which is optionally substituted by one or more of the aforementioned substituents for phenyl; pyrimidyl which is optionally substituted by one or more of the aforementioned substituents for phenyl; thienyl which is optionally substituted by one substituent —COO—C$_{1-4}$alkyl; 1,1-dioxo-tetrahydrothienyl, 2,2,2-trifluoroethyl, isopropyl, isobutyl, 2-methoxyethyl, tetrahydropyran-4-ylmethyl, 2-morpholinoethyl, pyridin-2-ylmethyl and tetrahydrofuran-2-ylmethyl;

Ar is selected from the group consisting of phenyl and pyridyl, which can be substituted by one or more substituents independently selected from the group consisting of fluorine, methoxy and chlorine;

Z is selected from the group consisting of phenyl and heteroaryl, which can be substituted by one or more substituents selected from the group consisting of C$_{1-4}$alkyl, C$_{1-4}$haloalkyl, hydrogen, hydroxyl, C$_{1-4}$alkoxy, and C$_{1-4}$alkoxycarbonyl; and Y is selected from the group consisting of H, trifluoromethyl and methoxycarbonyl.

8. A compound according to claim 1, wherein

R$^1$ is selected from the group consisting of phenyl, which is optionally substituted by one or more substituents individually selected from the group consisting of fluorine, chlorine, bromine, nitro, NH$_2$, —CN, —NHCO—C$_{1-4}$-alkyl, methoxy, t-butyl, —SO$_2$NH$_2$, and —SO$_2$NH-isopropyl; pyridyl; pyrimidyl, which is optionally substituted by one or more substituents selected from the group consisting of methyl and trifluoromethyl; thienyl, which is optionally substituted by one substituent —COO-methyl; 1,1-dioxo-tetrahydrothienyl, 2,2,2-trifluoroethyl, isopropyl, isobutyl, 2-methoxyethyl, tetrahydropyran-4-ylmethyl, 2-morpholinoethyl, pyridin-2-ylmethyl and tetrahydrofuran-2-ylmethyl;

Ar is selected from the group consisting of phenyl, 2,6-difluorophenyl, 2-chloro-6-fluorophenyl, 2-chloro-6-methoxyphenyl, 2-fluorophenyl, 2-chlorophenyl, 2,6- dichlorophenyl, 2,4-dichlorophenyl, 3-fluoropyridin-4-yl, 3,5-dichloropyridin-4-yl and 3,5-difluoropyridin-4-yl;

Z is selected from the group consisting of phenyl, tetrazolyl, thiazolyl, 1,3,4-oxadiazolyl, oxazolyl, 1,3,4-thiadiazolyl, furanyl, and thiophenyl, which can be substituted by one or more substituents selected from the group consisting of methyl, trifluoromethyl, hydrogen, hydroxyl, methoxy, methoxycarbonyl and ethoxyoxycarbonyl; and Y is selected from the group consisting of H, trifluoromethyl and methoxycarbonyl.

9. A compound according to claim 1, wherein $R^1$ is selected from the group consisting of phenyl, 2-fluorophenyl, 2methoxyphenyl, 2-chlorophenyl, 2-bromophenyl, 2-nitrophenyl, 2-aminophenyl, 4-fluorophenyl, 4-tertbutylphenyl, 3-fluorophenyl, 3-chlorophenyl, 3-cyanophenyl, 3-acetamido-phenyl, 2-acetamido-phenyl, 3-aminosulfonyl-phenyl, 3-(isopropylamino)sulfonyl-phenyl, 3-nitrophenyl, 3-aminophenyl, 2,4-difluorophenyl, 3,5-difluorophenyl, 3,5-dichlorophenyl, 2,3,5,6-tetrafluorophenyl, 2-pyridyl; 3-pyridyl; 4-pyridyl; 4-trifluoromethyl-pyrimid-2-yl, 2,6-dimethyl-pyrimid-4-yl, 2-methoxycarbonyl-thien-3-yl, 1,1-dioxo-tetrahydrothienyl, 2,2,2-trifluoroethyl, isopropyl, isobutyl, 2-methoxyethyl, tetrahydropyran-4-yl-methyl, 2-(morpholin-4-yl)-ethyl, and tetrahydrofuran-2-yl-methyl;

Ar is selected from the group consisting of phenyl, 2-chloro-6-fluorophenyl, 2-fluorophenyl, 2-chlorophenyl, 2,6-dichlorophenyl, 2,4-dichlorophenyl, 3-fluoropyridin-4-yl, and 3,5-difluoropyridin-4-yl;

Z is selected from the group consisting of 1H-tetrazol-5-yl, 4-methylthiazol-2-yl, thiazol-2-yl, 5-(trifluoromethyl)-1,3,4-oxadiazol-2-yl, 5-methyl-1,3,4-oxadiazol-2-yl, 1,3,4-oxadiazol-2-yl, oxazol-5-yl, 4-hydroxy-thiazol-2-yl, 4-methoxy-thiazol-2-yl, 5-methyl-1,3,4-thiadiazol-2-yl, 1,3,4-thiadiazol-2-yl, furan-3-yl, furan-2-yl, thiophen-3-yl, phenyl, 4-methoxycarbonyl-thiazol-2-yl, and 4-ethoxycarbonyl-thiazol-2-yl; and Y is selected from the group consisting of H, trifluoromethyl and methoxycarbonyl.

10. A compound according to claim 1, which is selected from the group consisting of 3-(2-chloro-6-fluorophenyl)-5-(1-(3-chlorophenyl)-5-(trifluoromethyl)-1H-pyrazol-4-yl)-4-(4-methylthiazol-2-yl)isoxazole;

3-(2-chloro-6-fluorophenyl)-5-(1-(3-chlorophenyl)-5-(trifluoromethyl)-1H-pyrazol-4-yl)-4-(thiazol-2-yl)isoxazole;

2-(3-(2-chloro-6-fluorophenyl-5-(1-(3-fluorophenyl)-5-(trifluoromethyl)-1H-pyrazol-4-yl)isoxazol-4-yl)-5-(trifluoromethyl)-1,3,4-oxadiazole;

2-(3-(2-chloro-6-fluorophenyl-5-(1-(3-fluorophenyl)-5-(trifluoromethyl)-1H-pyrazol-4-yl)isoxazol-4-yl)-1,3,4-oxadiazole;

3-(2-chloro-6-fluorophenyl-5-(1-(3-chlorophenyl)-5-(trifluoromethyl)-1H-pyrazol-4-yl)-4-(oxazol-5-yl)isoxazole;

3-(2-chloro-6-fluorophenyl)-5-(1-(3-fluorophenyl)-5-(trifluoromethyl)-1H-pyrazol-4-yl)-4-(4-methoxythiazol-2-yl)isoxazole;

2-(3-(2-chloro-6-fluorophenyl)-5-(1-(2-fluorophenyl)-5-(trifluoromethyl)-1H-pyrazol-4-yl)isoxazol-4-yl)-5-methyl-1,3,4-oxadiazole;

3-(2-chloro-6-fluorophenyl)-5-(1-(2-fluorophenyl)-5-(trifluoromethyl)-1H-pyrazol-4-yl)-4-(5-methyl-1,3,4-thiadiazol-2-yl)isoxazole;

3-(2-chloro-6-fluorophenyl)-5-(1-(3-fluorophenyl)-5-(trifluoromethyl)-1H-pyrazol-4-yl)-4-phenylisoxazole;

3-(2-chloro-6-fluorophenyl)-5-(1-(3-fluorophenyl)-5-(trifluoromethyl)-1H-pyrazol-4-yl)-4-(thiophen-3-yl)isoxazole;

3-(2-chloro-6-fluorophenyl)-5-(1-(3-fluorophenyl)-5-(trifluoromethyl)-1H-pyrazol-4-yl)-4-(furan-2-yl)isoxazole;

methyl 2-(3-(2-chloro-6-fluorophenyl)-5-(1-(3-fluorophenyl)-5-(trifluoromethyl)-1H-pyrazol-4-yl)isoxazol-4-yl)thiazole-4-carboxylate;

3-(2-chloro-6-fluorophenyl)-5-(1-(3-chlorophenyl)-5-(trifluoromethyl)-1H-pyrazol-4-yl)-4-(5-methyl-1,3,4-thiadiazol-2-yl)isoxazole;

2-(3-(2-chloro-6-fluorophenyl)-5-(1-(3-chlorophenyl)-5-(trifluoromethyl)-1H-pyrazol-4-yl)isoxazol-4-yl)-5-methyl-1,3,4-oxadiazole;

2-(3-(2-chloro-6-fluorophenyl)-5-(1-(3-chlorophenyl)-5-(trifluoromethyl)-1H-pyrazol-4-yl)isoxazol-4-yl)-1,3,4-oxadiazole;

3-(2-chloro-6-fluorophenyl)-5-(1-(3-chlorophenyl)-5-(trifluoromethyl)-1H-pyrazol-4-yl)-4-(furan-2-yl)isoxazole;

3-(2-chloro-6-fluorophenyl)-5-(1-(3-chlorophenyl)-5-(trifluoromethyl)-1H-pyrazol-4-yl)-4-(furan-3-yl)isoxazole;

3-(2-chloro-6-fluorophenyl)-5-(1-(3-chlorophenyl)-5-(trifluoromethyl)-1H-pyrazol-4-yl)-4-(1,3,4-thiadiazol-2-yl)isoxazole;

3-(2-chloro-6-fluorophenyl)-5-(1-(2-fluorophenyl)-5-(trifluoromethyl)-1H-pyrazol-4-yl)-4-(furan-3-yl)isoxazole;

2-(3-(2-chloro-6-fluorophenyl)-5-(1-(pyridin-3-yl)-5-(trifluoromethyl)-1H-pyrazol-4-yl)isoxazol-4-yl)-5-methyl-1,3,4-oxadiazole;

3-(2-chloro-6-fluorophenyl)-4-(5-methyl-1,3,4-thiadiazol-2-yl)-5-(1-(pyridin-3-yl)-5-(trifluoromethyl)-1H-pyrazol-4-yl)isoxazole;

3-(2-chloro-6-fluorophenyl)-4-(5-methyl-1,3,4-thiadiazol-2-yl)-5-(1-(pyridin-4-yl)-5-(trifluoromethyl)-1H-pyrazol-4-yl)isoxazole;

2-chloro-6-fluorophenyl)-4-(furan-3-yl)-5-(1-(pyridin-4-yl)-5-(trifluoromethyl)-1H-pyrazol-4-yl)isoxazole;

2-(3-(2-chloro-6-fluorophenyl)-5-(1-(pyridin-2-yl)-5-(trifluoromethyl)-1H-pyrazol-4-yl)isoxazol-4-yl)-1,3,4-oxadiazole;

2-(3-(2-chloro-6-fluorophenyl)-5-(1-(pyridin-2-yl)-5-(trifluoromethyl)-1H-pyrazol-4-yl)isoxazol-4-yl)-5-methyl-1,3,4-oxadiazole;

3-(2-chloro-6-fluorophenyl)-4-(5-methyl-1,3,4-thiadiazol-2-yl)-5-(1-(pyridin-2-yl)-5-(trifluoromethyl)-1H-pyrazol-4-yl)isoxazole; and 3-(2-chloro-6-fluorophenyl)-5-(1-(2-fluorophenyl)-5-(trifluoromethyl)-1H-pyrazol-4-yl)-4-(thiazol-2-yl)isoxazole.

11. A pharmaceutically acceptable salt of a compound according to claim 1, which compound is selected from the group consisting of 3-(2-chloro-6-fluorophenyl)-5-(1-(3-chlorophenyl)-5-(trifluoromethyl)-1H-pyrazol-4-yl)-4-(4-methylthiazol-2-yl)isoxazole;

3-(2-chloro-6-fluorophenyl)-5-(1-(3-chlorophenyl)-5-(trifluoromethyl)-1H-pyrazol-4-yl)-4-(thiazol-2-yl)isoxazole;

2-(3-(2-chloro-6-fluorophenyl)-5-(1-(3-fluorophenyl)-5-(trifluoromethyl)-1H-pyrazol-4-yl)isoxazol-4-yl)-5-(trifluoromethyl)-1,3,4-oxadiazole;

2-(3-(2-chloro-6-fluorophenyl)-5-(1-(3-fluorophenyl)-5-(trifluoromethyl)-1H-pyrazol-4-yl)isoxazol-4-yl)-1,3,4-oxadiazole;
3-(2-chloro-6-fluorophenyl)-5-(1-(3-chlorophenyl)-5-(trifluoromethyl)-1H-pyrazol-4-yl)-4-(oxazol-5-yl)isoxazole;
3-(2-chloro-6-fluorophenyl)-5-(1-(3-fluorophenyl)-5-(trifluoromethyl)-1H-pyrazol-4-yl)-4-(4-methoxythiazol-2-yl)isoxazole;
2-(3-(2-chloro-6-fluorophenyl)-5-(1-(2-fluorophenyl)-5-(trifluoromethyl)-1H-pyrazol-4-yl)isoxazol-4-yl)-5-methyl-1,3,4-oxadiazole;
3-(2-chloro-6-fluorophenyl)-5-(1-(2-fluorophenyl)-5-(trifluoromethyl)-1H-pyrazol-4-yl)-4-(5-methyl-1,3,4-thiadiazol-2-yl)isoxazole;
3-(2-chloro-6-fluorophenyl)-5-(1-(3-fluorophenyl)-5-(trifluoromethyl)-1H-pyrazol-4-yl)-4-phenylisoxazole;
3-(2-chloro-6-fluorophenyl)-5-(1-(3-fluorophenyl)-5-(trifluoromethyl)-1H-pyrazol-4-yl)-4-(thiophen-3-yl)isoxazole;
3-(2-chloro-6-fluorophenyl)-5-(1-(3-fluorophenyl)-5-(trifluoromethyl)-1H-pyrazol-4-yl)-4-(furan-2-yl)isoxazole;
methyl 2-(3-(2-chloro-6-fluorophenyl)-5-(1-(3-fluorophenyl)-5-(trifluoromethyl)-1H-pyrazol-4-yl)isoxazol-4-yl)thiazole-4-carboxylate;
3-(2-chloro-6-fluorophenyl)-5-(1-(3-chlorophenyl)-5-(trifluoromethyl)-1H-pyrazol-4-yl)-4-(5-methyl-1,3,4-thiadiazol-2-yl)isoxazole;
2-(3-(2-chloro-6-fluorophenyl)-5-(1-(3-chlorophenyl)-5-(trifluoromethyl)-1H-pyrazol-4-yl)isoxazol-4-yl)-5-methyl-1,3,4-oxadiazole;
2-(3-(2-chloro-6-fluorophenyl)-5-(1-(3-chlorophenyl)-5-(trifluoromethyl)-1H-pyrazol-4-yl)isoxazol-4-yl)-1,3,4-oxadiazole;
3-(2-chloro-6-fluorophenyl)-5-(1-(3-chlorophenyl)-5-(trifluoromethyl)-1H-pyrazol-4-yl)-4-(furan-2-yl)isoxazole;
3-(2-chloro-6-fluorophenyl)-5-(1-(3-chlorophenyl)-5-(trifluoromethyl)-1H-pyrazol-4-yl)-4-(furan-3-yl)isoxazole;
3-(2-chloro-6-fluorophenyl)-5-(1-(3-chlorophenyl)-5-(trifluoromethyl)-1H-pyrazol-4-yl)-4-(1,3,4-thiadiazol-2-yl)isoxazole;
3-(2-chloro-6-fluorophenyl)-5-(1-(2-fluorophenyl)-5-(trifluoromethyl)-1H-pyrazol-4-yl)-4-(furan-3-yl)isoxazole;
2-(3-(2-chloro-6-fluorophenyl)-5-(1-(pyridin-3-yl)-5-(trifluoromethyl)-1H-pyrazol-4-yl)isoxazol-4-yl)-5-methyl-1,3,4-oxadiazole;
3-(2-chloro-6-fluorophenyl)-4-(5-methyl-1,3,4-thiadiazol-2-yl)-5-(1-(pyridin-3-yl)-5-(trifluoromethyl)-1H-pyrazol-4-yl)isoxazole;
3-(2-chloro-6-fluorophenyl)-4-(5-methyl-1,3,4-thiadiazol-2-yl)-5-(1-(pyridin-4-yl)-5-(trifluoromethyl)-1H-pyrazol-4-yl)isoxazole;
3-(2-chloro-6-fluorophenyl)-4-(furan-3-yl)-5-(1-(pyridin-4-yl)-5-(trifluoromethyl)-1H-pyrazol-4-yl)isoxazole;
2-(3-(2-chloro-6-fluorophenyl)-5-(1-(pyridin-2-yl)-5-(trifluoromethyl)-1H-pyrazol-4-yl)isoxazol-4-yl)-1,3,4-oxadiazole;
2-(3-(2-chloro-6-fluorophenyl)-5-(1-(pyridin-2-yl)-5-(trifluoromethyl)-1H-pyrazol-4-yl)isoxazol-4-yl)-5-methyl-1,3,4-oxadiazole;
3-(2-chloro-6-fluorophenyl)-4-(5-methyl-1,3,4-thiadiazol-2-yl)-5-(1-(pyridin-2-yl)-5-(trifluoromethyl)-1H-pyrazol-4-yl)isoxazole; and
3-(2-chloro-6-fluorophenyl)-5-(1-(2-fluorophenyl)-5-(trifluoromethyl)-1H-pyrazol-4-yl)-4-(thiazol-2-yl)isoxazole.

12. A compound of formula (I)

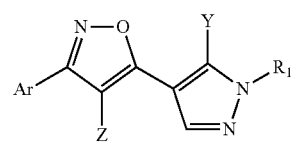

formula (I)

or a pharmaceutically acceptable salt thereof,
wherein
$R^1$ is aryl, heteroaryl, cycloalkyl, heterocyclyl or alkyl, which can be substituted by one or more substituents R';
Ar is aryl, cycloalkyl, heterocyclyl or heteroaryl, which can be substituted by one or more substituents R';
Z is aryl, heteroaryl, cycloalkyl or heterocyclyl, which can be substituted by one or more substituents R';
Y is H, halogen, haloalkyl, alkyl or an alkylester, which can be substituted by one or more substituents R';
R' independently represents H, —CO$_2$R", —CONHR", —CR"O, —SO$_2$N(R")$_2$, —SO$_2$NHR", —NR"—CO-haloalkyl, —NO$_2$, —NR"—SO$_2$-haloalkyl, —NR"—SO$_2$-alkyl, —SO$_2$-alkyl, —NR"—CO-alkyl, —CN, alkyl, cycloalkyl, aminoalkyl, alkylamino, alkoxy, —OH, —SH, alkylthio, hydroxyalkyl, hydroxyalkylamino, halogen, haloalkyl, haloalkoxy, amino, heterocyclyl, aryl, haloaryl, haloarylalkyl, arylalkyl or heteroaryl;
R" independently represents H, haloalkyl, hydroxyalkyl, amino, alkoxy, —N=C(R''')$_2$, —NR'''—CO—R''', —CR'''O, —CO$_2$R''', alkyl, cycloalkyl, aryl, haloaryl, haloarylalkyl, heteroaryl, heterocyclyl, arylalkyl or aminoalkyl, which are optionally substituted by one or more substituents R'''; and
R''' independently represents H, —NO$_2$, —CN, alkyl, cycloalkyl, aminoalkyl, alkylamino, alkoxy, —OH, —SH, alkylthio, hydroxyalkyl, hydroxyalkylamino, halogen, haloalkyl, haloalkoxy, amino, heterocyclyl, aryl, haloaryl, haloarylalkyl, arylalkyl or heteroaryl.

13. A pharmaceutical composition comprising a compound according to claim 1 and a pharmaceutically acceptable carrier.

14. A pharmaceutical composition comprising a compound according to claim 10 and a pharmaceutically acceptable carrier.

15. A pharmaceutical composition comprising a pharmaceutically acceptable salt according to claim 11 and a pharmaceutically acceptable carrier.

16. A pharmaceutical composition comprising a compound according to claim 12 and a pharmaceutically acceptable carrier.

17. A method for treating psoriasis, psoriatric arthritis, autoimmune thyroiditis, Grave's disease, rheumatoid arthritis, vitiligo, Crohn's disease, ulcerative colitis, inflammatory bowel disease, ankylosing spondylitis, diabetes type I, multiple sclerosis, celiac disease, systemic lupus erythematosus, uveitis, Behcet disease, atopic dermatitis, Lichen planus, Sjögren's syndrome, spinal disc herniation, acne, Graft-versus-Host-Reaction, Host-versus-Graft-Reaction or osteoarthritis, comprising administering to a subject in need thereof an effective amount of a compound according to claim 1.

18. A method for treating psoriasis, psoriatric arthritis, autoimmune thyroiditis, Grave's disease, rheumatoid arthritis, vitiligo, Crohn's disease, ulcerative colitis, inflammatory bowel disease, ankylosing spondylitis, diabetes type I, multiple sclerosis, celiac disease, systemic lupus erythematosus, uveitis, Behcet disease, atopic dermatitis, Lichen planus, Sjögren's syndrome, spinal disc herniation, acne, Graft-versus-Host-Reaction, Host-versus-Graft-Reaction or osteoarthritis, comprising administering to a subject in need thereof an effective amount of a compound according to claim 10.

19. A method for treating psoriasis, psoriatric arthritis, autoimmune thyroiditis, Grave's disease, rheumatoid arthritis, vitiligo, Crohn's disease, ulcerative colitis, inflammatory bowel disease, ankylosing spondylitis, diabetes type I, multiple sclerosis, celiac disease, systemic lupus erythematosus, uveitis, Behcet disease, atopic dermatitis, Lichen planus, Sjögren's syndrome, spinal disc herniation, acne, Graft-versus-Host-Reaction, Host-versus-Graft-Reaction or osteoarthritis, comprising administering to a subject in need thereof an effective amount of pharmaceutically acceptable salt according to claim 11.

20. A method for treating psoriasis, psoriatric arthritis, autoimmune thyroiditis, Grave's disease, rheumatoid arthritis, vitiligo, Crohn's disease, ulcerative colitis, inflammatory bowel disease, ankylosing spondylitis, diabetes type I, multiple sclerosis, celiac disease, systemic lupus erythematosus, uveitis, Behcet disease, atopic dermatitis, Lichen planus, Sjögren's syndrome, spinal disc herniation, acne, Graft-versus-Host-Reaction, Host-versus-Graft-Reaction or osteoarthritis, comprising administering to a subject in need thereof an effective amount of pharmaceutically acceptable salt according to claim 12.

* * * * *

UNITED STATES PATENT AND TRADEMARK OFFICE
CERTIFICATE OF CORRECTION

PATENT NO. : 8,354,436 B2
APPLICATION NO. : 13/360063
DATED : January 15, 2013
INVENTOR(S) : Johann Leban et al.

It is certified that error appears in the above-identified patent and that said Letters Patent is hereby corrected as shown below:

In the Specification:

On column 167, change the structure of compound IB-18 from

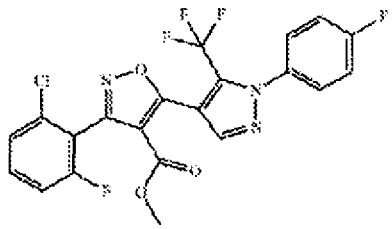 [SMILES: COC(=O)c1c(-c2c(F)cccc2Cl)noc1-c1cnn(-c2ccc(F)cc2)c1C(F)(F)F]

to

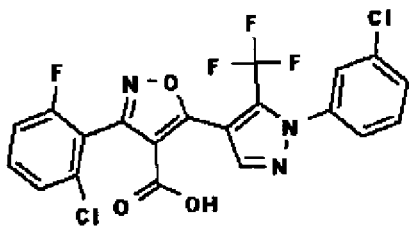

Signed and Sealed this
Seventeenth Day of June, 2014

Michelle K. Lee
*Deputy Director of the United States Patent and Trademark Office*